(12) United States Patent  
Frackenpohl et al.

(10) Patent No.: US 9,185,914 B2
(45) Date of Patent: Nov. 17, 2015

(54) SUBSTITUTED 5-(CYCLOHEX-2-EN-1-YL)-PENTA-2,4-DIENES AND 5-(CYCLOHEX-2-EN-1-YL)-PENT-2-EN-4-INES AS ACTIVE AGENTS AGAINST ABIOTIC STRESS IN PLANTS

(75) Inventors: Jens Frackenpohl, Frankfurt (DE); Thomas Müller, Frankfurt (DE); Ines Heinemann, Hofheim (DE); Pascal Von Koskull-Döring, Leverkusen (DE); Christopher Hugh Rosinger, Hofheim (DE); Isolde Häuser-Hahn, Leverkusen (DE); Martin Jeffrey Hills, Idstein (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 0 days.

(21) Appl. No.: 14/111,741

(22) PCT Filed: Mar. 28, 2012

(86) PCT No.: PCT/EP2012/055478
§ 371 (c)(1),
(2), (4) Date: Nov. 20, 2013

(87) PCT Pub. No.: WO2012/139890
PCT Pub. Date: Oct. 18, 2012

(65) Prior Publication Data
US 2014/0087949 A1    Mar. 27, 2014

Related U.S. Application Data

(60) Provisional application No. 61/475,854, filed on Apr. 15, 2011.

(30) Foreign Application Priority Data

Apr. 15, 2011 (EP) .................................. 11162596

(51) Int. Cl.
*A01N 43/40* (2006.01)
*A01N 35/06* (2006.01)
*A01N 33/24* (2006.01)
*A01N 55/00* (2006.01)
*A01N 37/42* (2006.01)
*A01N 43/30* (2006.01)
*C07C 403/20* (2006.01)
*C07D 317/72* (2006.01)
*C07F 7/22* (2006.01)
*C07F 7/18* (2006.01)
*C07F 17/00* (2006.01)
*C07F 7/30* (2006.01)

(52) U.S. Cl.
CPC ............... *A01N 55/00* (2013.01); *A01N 33/24* (2013.01); *A01N 35/06* (2013.01); *A01N 37/42* (2013.01); *A01N 43/30* (2013.01); *C07C 403/20* (2013.01); *C07D 317/72* (2013.01);

*C07F 7/1828* (2013.01); *C07F 7/1856* (2013.01); *C07F 7/2212* (2013.01); *C07F 7/30* (2013.01); *C07F 17/00* (2013.01); *C07C 2101/02* (2013.01); *C07C 2101/16* (2013.01)

(58) Field of Classification Search
CPC ....... A01N 33/24; A01N 35/06; A01N 43/30; A01N 55/00; A01N 37/42; C07C 403/20; C07C 2101/02; C07C 2101/16; C07F 17/00; C07F 7/1856; C07F 7/30; C07F 7/2212; C07F 7/1828; C07D 317/72
USPC .................. 504/193, 295, 344, 348; 556/436; 549/214, 341; 568/377; 564/256
See application file for complete search history.

(56) References Cited

U.S. PATENT DOCUMENTS 4,581,057 A    4/1986  Nooden
4,785,002 A   11/1988  Draber et al.
(Continued)

FOREIGN PATENT DOCUMENTS

DE    1793229    2/1972
DE    3534948    4/1987
(Continued)

OTHER PUBLICATIONS

Stille; Angew. Chem. Int. Ed. Engl., 1986, 25, 508-524.*
(Continued)

*Primary Examiner* — John Mabry
*Assistant Examiner* — Daniel Carcanague
(74) *Attorney, Agent, or Firm* — Miles and Stockbridge

(57) ABSTRACT

Substituted 5-(cyclohex-2-en-1-yl)-penta-2,4-dienes and 5-(cyclohex-2-en-1-yl)-pent-2-en-4-ynes as active agents against abiotic stress in plants
The invention relates to substituted 5-(cyclohex-2-en-1-yl) penta-2,4-dienes and 5-(cyclohex-2-en-1-yl)pent-2-en-4-ynes of the formula (I) and their salts

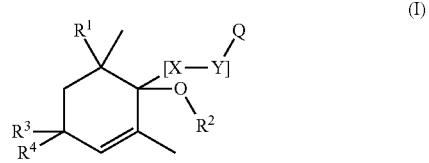

where the radicals $R^1$, $R^2$, $R^3$, $R^4$, [X—Y] and Q are each as defined in the description, to processes for preparation thereof and to the use thereof for enhancing stress tolerance in plants with respect to abiotic stress, and/or for increasing plant yield.

13 Claims, No Drawings

(56) References Cited

U.S. PATENT DOCUMENTS

| | | |
|---|---|---|
| 5,518,995 A | 5/1996 | Abrams et al. |
| 6,693,185 B2 | 2/2004 | Babiychuk et al. |
| 7,241,936 B2 | 7/2007 | Babiychuk et al. |
| 8,058,510 B2 | 11/2011 | Babiychuk et al. |
| 2001/0011381 A1 | 8/2001 | Babiychuk et al. |
| 2004/0128704 A1 | 7/2004 | Babiychuk et al. |
| 2009/0205069 A1 | 8/2009 | Babiychuk et al. |
| 2010/0160166 A1 | 6/2010 | Abrams et al. |
| 2012/0164650 A1 | 6/2012 | Babiychuk et al. |

FOREIGN PATENT DOCUMENTS

| | | |
|---|---|---|
| DE | 277832 | 12/1988 |
| DE | 277835 | 12/1988 |
| DE | 4103253 | 8/1992 |
| EP | 0 240 257 | 10/1987 |
| EP | 0 371 882 | 6/1990 |
| NL | 6811769 | 2/1969 |
| WO | 94/15467 | 7/1994 |
| WO | 9723441 | 7/1997 |
| WO | 00/04173 | 1/2000 |
| WO | 00/28055 | 5/2000 |
| WO | 2004/090140 | 10/2004 |
| WO | 2005/108345 | 11/2005 |

OTHER PUBLICATIONS

Dorwald; "Side Reactions in Organic Synthesis: A Guide to Successful Synthesis Design" 2005 Wiley-VCH Verlag GmbH & Co. KGaA, Wienheim, chapter 1.*

Asami; Biosci. Biotech. Biochem., 1992, 56, 2089-2090.*

International Search Report for PCT/EP2012/055478 Mailed Jul. 6, 2012.

Lamb et al., "Synthesis of Optically Active Cyclohexanone Analogs of the Plant Hormone Abscisi Acid," Canadian Journal of Chemistry, vol. 68, No. 7, pp. 1151-1162, (Jul. 1, 1990).

Smith et al., "Concise Enantioselective Synthesis of Abscisic Acid and a New Analogue," Organic & Biomolecular chemistry, vol. 4, No. 22, p. 4186, (Jan. 1, 2006).

European Search Report for EP 11 16 2596 Dated Aug. 11, 2011.

Lamb, Nancy et al., "Synthesis of optically active cyclohexanone analogs of the plant hormone abscisic acid", Plant Biotechnology Institute, National Research Council of Canada, 68, 1151 (1990).

Smith, Timothy et al., "Concise enantioselective synthesis of abscisic acid and a new analogue", Organic and Biomolecular Chemistry, The Society of Chemistry 2006, 4, 4186-4192 (2006).

* cited by examiner

SUBSTITUTED 5-(CYCLOHEX-2-EN-1-YL)-PENTA-2,4-DIENES AND 5-(CYCLOHEX-2-EN-1-YL)-PENT-2-EN-4-INES AS ACTIVE AGENTS AGAINST ABIOTIC STRESS IN PLANTS

CROSS REFERENCE TO RELATED APPLICATIONS

This application is a §371 National Stage Application of PCT/EP2012/055478, filed Mar. 28, 2012, which claims priority to European Application No. 11162596.8, filed Apr. 15, 2011, and U.S. Provisional Application 61/475,854, filed Apr. 15, 2011.

BACKGROUND OF THE INVENTION

1. Field of the Invention

The invention relates to substituted 5-(cyclohex-2-en-1-yl) penta-2,4-dienes and 5-(cyclohex-2-en-1-yl)pent-2-en-4-ynes, to processes for their preparation and their use for enhancing stress tolerance in plants to abiotic stress, and/or for increasing plant yield.

2. Description of Related Art

It is known that particular 5-(1,2-epoxy-2,6,6-trimethylcyclohexyl)-3-methylpenta-2,4-dienoic acids and derivatives thereof have properties which influence plant growth (cf. NL6811769). The growth-moderating effect of certain 1,2-epoxy analogs of abscisic acid on rice seedlings is also described in Agr. Biol. Chem. 1969, 33, 1357 and Agr. Biol. Chem. 1970, 34, 1393. The use of substituted 5-cyclohex-2-en-1-ylpenta-2,4-dienyl- and 5-cyclohex-2-en-1-ylpent-2-en-4-ynylols, 5-cyclohex-2-en-1-ylpenta-2,4-dienyl and 5-cyclohex-2-en-1-ylpent-2-en-4-ynyl thioethers and 5-cyclohex-2-en-1-ylpenta-2,4-dienyl- and 5-cyclohex-2-en-1-ylpent-2-en-4-ynylamines as inhibitors of epoxycarotenoid dioxygenase and as germination inhibitors is described in US2010/0160166. The preparation of particular abscisic acid derivatives with a 3-methyl substituent in the 2,4-pentadienoic acid unit and the use thereof for influencing germination and plant growth is described in U.S. Pat. No. 5,518,995 and EP0371882. It is additionally known that particular abscisic acid derivatives with a 3-methyl substituent can be used to increase tolerance of plants to low temperatures (cf. WO94/15467). The increase in the yield of soybean seeds through use of a mixture of abscisic acid and a suitable fertilizer is described in U.S. Pat. No. 4,581,057.

It is likewise known that 5-(cyclohex-2-en-1-yl)-3-methylpenta-2,4-dienoic acid derivatives having unsaturated substituents at position C6 of the 5-cyclohex-2-en-1-yl unit can influence the water balance and the germination of plants (cf. WO97/23441). Described are furthermore trifluoromethyl, alkyl and methoxymethyl substituents at position C6 of the 5-cyclohex-2-en-1-yl unit in 5-(cyclohex-2-en-1-yl)-3-methylpenta-2,4-dienoic acids (cf. Biosci. Biotech. Biochem. 1994, 58, 707; Biosci. Biotech. Biochem. 1995, 59, 699; Phytochem. 1995, 38, 561; Bioorg. Med. Chem. Lett. 1995, 5, 275). Bicyclic tetralone-based 3-methylpenta-2,4-dienoic acid derivatives are described in WO2005108345.

It is also known that abscisic acid and derivatives thereof can be used as pharmaceutically active compounds for regulation of calcium transport (cf. EP240257).

The preparation of an abscisic acid derivative having a 3-hydroxymethyl side chain, (2E,4E)-3-(hydroxymethyl)-5-(1-hydroxy-2,6,6-trimethyl-4-oxocyclohex-2-en-1-yl)penta-2,4-dienoic acid, is described in Org. Biomol. Chem. 2006, 4, 4186.

It is known that plants can react with specific or unspecific defense mechanisms to natural stress conditions, for example cold, heat, drought stress (stress caused by aridity and/or lack of water), injury, pathogenic attack (viruses, bacteria, fungi, insects) etc., but also to herbicides [Pflanzenbiochemie [Plant Biochemistry], p. 393-462, Spektrum Akademischer Verlag, Heidelberg, Berlin, Oxford, Hans W. Heldt, 1996; Biochemistry and Molecular Biology of Plants, S. 1102-1203, American Society of Plant Physiologists, Rockville, Md., eds. Buchanan, Gruissem, Jones, 2000].

In plants, there is knowledge of numerous proteins, and the genes which code for them, which are involved in defense reactions to abiotic stress (for example cold, heat, drought stress, salt, flooding). Some of these form part of signal transduction chains (for example transcription factors, kinases, phosphatases) or cause a physiological response of the plant cell (for example ion transport, deactivation of reactive oxygen species). The signaling chain genes of the abiotic stress reaction include inter alia transcription factors of the DREB and CBF classes (Jaglo-Ottosen et al., 1998, Science 280: 104-106). The reaction to salinity stress involves phosphatases of the ATPK and MP2C types. In addition, in the event of salinity stress, the biosynthesis of osmolytes such as proline or sucrose is often activated. This involves, for example, sucrose synthase and proline transporters (Hasegawa et al., 2000, Annu Rev Plant Physiol Plant Mol Biol 51: 463-499). The stress defense of the plants to cold and drought uses some of the same molecular mechanisms. There is a known accumulation of what are called late embryogenesis abundant proteins (LEA proteins), which include the dehydrins as an important class (Ingram and Bartels, 1996, Annu Rev Plant Physiol Plant Mol Biol 47: 277-403, Close, 1997, Physiol Plant 100: 291-296). These are chaperones which stabilize vesicles, proteins and membrane structures in stressed plants (Bray, 1993, Plant Physiol 103: 1035-1040). In addition, there is frequently induction of aldehyde dehydrogenases, which deactivate the reactive oxygen species (ROS) which form in the event of oxidative stress (Kirch et al., 2005, Plant Mol Biol 57: 315-332). Heat shock factors (HSF) and heat shock proteins (HSP) are activated in the event of heat stress and play a similar role here as chaperones to that of dehydrins in the event of cold and drought stress (Yu et al., 2005, Mol Cells 19: 328-333).

A number of signaling substances which are endogenous to plants and are involved in stress tolerance or pathogenic defense are already known. Examples here include salicylic acid, benzoic acid, jasmonic acid or ethylene [Biochemistry and Molecular Biology of Plants, p. 850-929, American Society of Plant Physiologists, Rockville, Md., eds. Buchanan, Gruissem, Jones, 2000]. Some of these substances or the stable synthetic derivatives and derived structures thereof are also effective on external application to plants or in seed dressing, and activate defense reactions which cause elevated stress tolerance or pathogen tolerance of the plant [Sembdner, and Parthier, 1993, Ann. Rev. Plant Physiol. Plant Mol. Biol. 44: 569-589].

It is additionally known that chemical substances can increase the tolerance of plants to abiotic stress. Such substances are applied either by seed dressing, by leaf spraying or by soil treatment. For instance, an increase in abiotic stress tolerance of crop plants by treatment with elicitors of systemic acquired resistance (SAR) or abscisic acid derivatives is described (Schading and Wei, WO200028055, Churchill et al., 1998, Plant Growth Regul 25: 35-45). In addition, effects of growth regulators on the stress tolerance of crop plants have been described (Morrison and Andrews, 1992, J Plant Growth Regul 11: 113-117, RD-259027). In this context, it is likewise known that a growth-regulating naphthylsulfonamide (4-bromo-N-(pyridin-2-ylmethyl)naphthalene-1-sulfonamide) influences the germination of plant seeds in the same way as abscisic acid (Park et al. Science 2009, 324, 1068-1071). It is also known that a further naphthylsulfonamide, N-(6-aminohexyl)-5-chloronaphthalene-1-sulfonamide, influences the calcium level in plants which have been exposed to cold shock (Cholewa et al. Can. J. Botany 1997, 75, 375-382).

Similar effects are also observed on application of fungicides, especially from the group of the strobilurins or of the succinate dehydrogenase inhibitors, and are frequently also accompanied by an increase in yield (Draber et al., DE3534948, Bartlett et al., 2002, Pest Manag Sci 60: 309). It is likewise known that the herbicide glyphosate in low dosage stimulates the growth of some plant species (Cedergreen, Env. Pollution 2008, 156, 1099).

In the event of osmotic stress, a protective effect has been observed as a result of application of osmolytes, for example glycine betaine or the biochemical precursors thereof, e.g. choline derivatives (Chen et al., 2000, Plant Cell Environ 23: 609-618, Bergmann et al., DE4103253). The effect of antioxidants, for example naphthols and xanthines, to increase abiotic stress tolerance in plants has also already been described (Bergmann et al., DD277832, Bergmann et al., DD277835). However, the molecular causes of the antistress action of these substances are substantially unknown.

It is additionally known that the tolerance of plants to abiotic stress can be increased by a modification of the activity of endogenous poly-ADP-ribose polymerases (PARP) or poly-(ADP-ribose) glycohydrolases (PARG) (de Block et al., The Plant Journal, 2004, 41, 95; Levine et al., FEBS Lett. 1998, 440, 1; WO0004173; WO04090140).

It is thus known that plants possess several endogenous reaction mechanisms which can bring about effective defense against a wide variety of different harmful organisms and/or natural abiotic stress.

Since the ecologic and economic demands on modern plant treatment compositions are increasing constantly, for example with respect to toxicity, selectivity, application rate, formation of residues and favorable manufacture, there is a constant need to develop novel plant treatment compositions which have advantages over those known, at least in some areas.

SUMMARY

It was therefore an object of the present invention to provide further compounds which increase tolerance to abiotic stress in plants, in particular bring about invigoration of plant growth and/or contribute to an increase in plant yield.

Accordingly, the present invention provides substituted 5-(cyclohex-2-en-1-yl)penta-2,4-dienes and 5-(cyclohex-2-en-1-yl)pent-2-en-4-ynes of the formula (I) or salts thereof

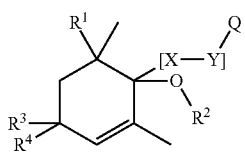
(I)

where
[X—Y] represents the moieties

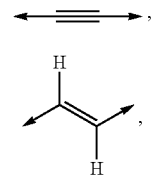
[X-Y]$^1$

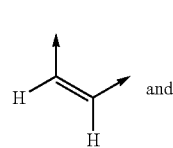
[X-Y]$^2$

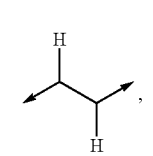
and
[X-Y]$^3$

[X-Y]$^4$

Q represents the moieties Q-1 to Q-4

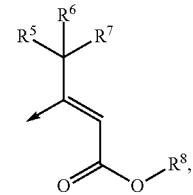
Q-1

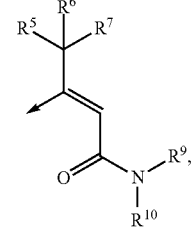
Q-2

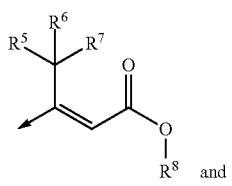
Q-3 and

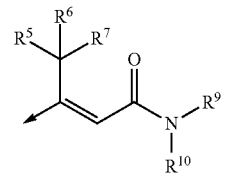
Q-4 where $R^5$, $R^6$, $R^7$, $R^8$, $R^9$ and $R^{10}$ are each as defined below and where the arrow represents a bond to the respective [X—Y] grouping;

$R^1$ represents alkyl, alkenyl, alkynyl, alkenylalkyl, alkynylalkyl, alkoxyalkyl, hydroxyalkyl, haloalkyl, haloalkenyl, haloalkynyl, haloalkoxyalkyl, alkoxyhaloalkyl, haloalkoxyhaloalkyl, alkylthioalkyl, $R^2$ represents hydrogen, alkyl, alkenyl, alkenylalkyl, alkoxyalkyl, alkylcarbonyl, arylcarbonyl, heteroarylcarbonyl, cycloalkylcarbonyl, alkoxycarbonyl, alkenyloxycarbonyl, aryloxyalkyl, arylalkoxycarbonyl, arylalkoxyalkyl, arylalkyl, alkoxyalkoxyalkyl, alkylthioalkyl, trialkylsilyl, alkyl(bisalkyl)silyl, alkyl(bisaryl)silyl, aryl(bisalkyl)silyl, cycloalkyl(bisalkyl)silyl, halo(bisalkyl)silyl, trialkylsilylalkoxyalkyl, trialkylsilylalkyl, $R^3$ and $R^4$ independently of one another represent alkoxy, alkoxyalkoxy, cycloalkylalkoxy, haloalkoxy, alkylthio, haloalkylthio, arylalkoxy, arylalkylthio or together with the atom to which they are attached form an oxo group, hydroxyimino group, alkoxyimino group, cycloalkoxyimino group, cycloalkylalkoximino group, arylalkoxyimino group or a 5- to 7-membered heterocyclic ring which may optionally be substituted further, $R^5$ and $R^6$ independently of one another represent hydrogen, halogen, alkyl, haloalkyl, $R^7$ represents halogen, alkyl, haloalkyl, haloalkoxy, haloalkoxyalkyl, haloalkoxyhaloalkyl, alkoxyhaloalkyl, alkynyloxyhaloalkyl, alkenyloxyhaloalkyl, alkylthio, haloalkylthio, aryl, arylalkyl, heteroaryl, heteroarylalkyl, $R^6$ and $R^7$ with the atoms to which they are bonded form a fully saturated 3- to 6-membered ring optionally interrupted by heteroatoms and optionally with further substitution, $R^8$ represents hydrogen, alkyl, alkoxyalkyl, cycloalkyl, cycloalkylalkyl, aryl, arylalkyl, heteroarylalkyl, bisarylalkyl, trisarylalkyl, alkenyl, alkenylalkyl, cycloalkenylalkyl, alkynylalkyl, trialkylsilylal koxyalkyl, alkoxyalkoxyalkyl, alkylthioalkyl, haloalkyl, arylsulfonylalkyl, trialkylsilyl, alkyl(bisaryl)silyl, alkyl(bisalkyl)silyl, bisalkylaminoalkyl, $R^9$ represents hydrogen, alkyl, cycloalkyl, halogen, alkenylalkyl, alkynylalkyl, haloalkyl, alkynyl, alkenyl, cyanoalkyl, cycloalkylalkyl, arylalkyl, heteroarylalkyl, alkylcarbonyl, alkoxycarbonyl, alkenyloxycarbonyl, alkenylalkyloxycarbonyl, arylalkyloxycarbonyl, cycloalkoxycarbonyl, cycloalkylalkoxycarbonyl, alkylsulfonyl, arylsulfonyl, cycloalkylsulfonyl, alkylsulfinyl, arylsulfinyl, cycloalkylsulfinyl, alkoxycarbonylalkyl, hydroxycarbonylalkyl, arylalkoxycarbonylalkyl, cycloalkylalkoxycarbonylalkyl, alkoxycarbonylcycloalkyl, hydroxycarbonylcycloalkyl, arylalkoxycarbonylcycloalkyl, alkenyloxycarbonylcycloalkyl, aminocarbonylcycloalkyl, alkylaminocarbonylcycloalkyl, cycloalkylaminocarbonylcycloalkyl, alkoxycarbonylcycloalkenyl, hydroxycarbonylcycloalkenyl, bisalkylaminoalkyl, hydroxycarbonylheterocyclyl, alkoxycarbonylheterocyclyl, alkenyloxycarbonylheterocyclyl, alkenylalkoxycarbonylheterocyclyl, arylalkoxycarbonylheterocyclyl, cycloalkoxycarbonylheterocyclyl, cycloalkylalkoxycarbonylheterocyclyl, aminocarbonylheterocyclyl, alkylaminocarbonylheterocyclyl, bisalkylaminocarbonylheterocyclyl, cycloalkylaminocarbonylheterocyclyl, arylalkylaminocarbonylheterocyclyl, alkenylaminocarbonylheterocyclyl, hydroxycarbonylheterocyclylalkyl, alkoxycarbonylheterocyclylalkyl, hydroxycarbonylcycloalkylalkyl, alkoxycarbonylcycloalkylalkyl, hydroxy, alkoxy, $R^{10}$ represents hydrogen, alkyl, cycloalkyl, halogen, alkylalkenyl, halogenalkyl, alkynyl, alkenyl, cyanoalkyl, arylalkyl, heteroarylalkyl, alkylcarbonyl, alkoxycarbonyl, alkylsulfonyl, arylsulfonyl, cycloalkylsulfonyl, alkylsulfinyl, arylsulfinyl, cycloalkylsulfinyl, alkoxycarbonylalkyl or $R^9$ and $R^{10}$ with the nitrogen to which they are attached form an optionally halogen-, alkyl-, haloalkyl-, alkoxy-, alkoxycarbonyl-, cycloalkoxycarbonyl-, cycloalkylalkoxycarbonyl-, alkenyloxycarbonyl-, hydroxycarbonyl-, aminocarbonyl-, alkylaminocarbonyl-, cycloalkylaminocarbonyl-, arylalkylaminocarbonyl-substituted three- to eight-membered ring which is optionally interrupted by O, S or N or $R^9$ and $R^{10}$ together are part of an optionally substituted sulfilimine or amidine group or form an iminophosphorane.

DETAILED DESCRIPTION OF A PREFERRED EMBODIMENT

The compounds of the formula (I) are capable of forming salts. Salts can be formed by the action of a base on those compounds of the formula (I) which bear an acidic hydrogen atom, for example in the case that $R^1$ contains a COOH group or a sulfonamide group —NHSO$_2$—. Suitable bases are, for example, organic amines such as trialkylamines, morpholine, piperidine or pyridine, and also ammonium, alkali metal or alkaline earth metal hydroxides, carbonates and hydrogencarbonates, especially sodium and potassium hydroxide, sodium and potassium carbonate and sodium and potassium hydrogencarbonate. These salts are compounds in which the acidic hydrogen is replaced by an agriculturally suitable cation, for example metal salts, especially alkali metal salts or alkaline earth metal salts, especially sodium and potassium salts, or else ammonium salts, salts with organic amines or quaternary ammonium salts, for example with cations of the formula [NRR'R''R''']$^+$ in which R to R''' are each independently of one another an organic radical, especially alkyl, aryl, aralkyl or alkylaryl. Also useful are alkylsulfonium and alkylsulfoxonium salts, such as ($C_1$-$C_4$)trialkylsulfonium and ($C_1$-$C_4$)trialkylsulfoxonium salts.

The compounds of the formula (I) according to the invention and salts thereof and/or those used in accordance with the invention are also referred to hereinafter as "compounds of the formula (I)" for short.

Preference is given to compounds of the formula (I) in which

[X—Y] represents the moieties

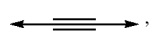

[X-Y]$^1$

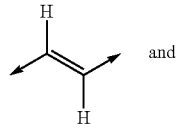 and

[X-Y]$^2$

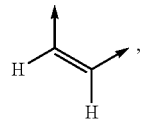,

[X-Y]$^3$

Q represents the moieties Q-1 to Q-4

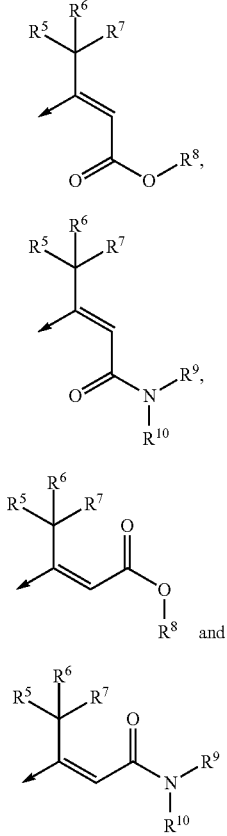

where $R^5$, $R^6$, $R^7$, $R^8$, $R^9$ and $R^{10}$ are each as defined below and where the arrow represents a bond to the respective [X—Y] grouping;

$R^1$ represents $(C_1-C_8)$-alkyl, $(C_2-C_8)$-alkenyl, $(C_2-C_8)$-alkynyl, $(C_2-C_8)$-alkenyl-$(C_1-C_8)$-alkyl, $(C_2-C_8)$-alkynyl-$(C_1-C_8)$-alkyl, $(C_1-C_8)$-alkoxy-$(C_1-C_8)$-alkyl, hydroxy-$(C_1-C_8)$-alkyl, $(C_1-C_8)$-haloalkyl, $(C_2-C_8)$-haloalkenyl, $(C_2-C_8)$-haloalkynyl, $(C_1-C_8)$-haloalkoxy-$(C_1-C_8)$-alkyl, $(C_3-C_8)$-cycloalkyl, $(C_1-C_8)$-alkoxy-$(C_1-C_8)$-haloalkyl, $(C_1-C_8)$-haloalkoxy-$(C_1-C_8)$-haloalkyl, $(C_1-C_8)$-alkylthio-$(C_1-C_8)$-alkyl, $R^2$ represents hydrogen, $(C_1-C_8)$-alkyl, $(C_2-C_8)$-alkenyl, $(C_2-C_8)$-alkenyl-$(C_1-C_8)$-alkyl, $(C_1-C_8)$-alkoxy-$(C_1-C_8)$-alkyl, $(C_1-C_8)$-alkylcarbonyl, arylcarbonyl, heteroarylcarbonyl, $(C_3-C_8)$-cycloalkylcarbonyl, $(C_1-C_8)$-alkoxycarbonyl, $(C_2-C_8)$-alkenyloxycarbonyl, aryl-$(C_1-C_8)$-alkoxycarbonyl, aryl-$(C_1-C_8)$-alkoxy-$(C_1-C_8)$-alkyl, aryloxy-$(C_1-C_8)$-alkyl, aryl-$(C_1-C_8)$-alkyl, $(C_1-C_8)$-alkoxy-$(C_1-C_8)$-alkoxy-$(C_1-C_8)$-alkyl, $(C_1-C_8)$-alkylthio-$(C_1-C_8)$-alkyl, tri-$(C_1-C_8)$-alkylsilyl, $(C_1-C_8)$-alkyl-(bis-$(C_1-C_8)$-alkyl)silyl, $(C_1-C_8)$-alkyl(bisaryl)silyl, aryl(bis-$(C_1-C_8)$-alkyl)silyl, $(C_3-C_8)$-cycloalkyl(bis-$(C_1-C_6)$-alkyl)silyl, halo(bis-$(C_1-C_8)$-alkyl)silyl, tri-$(C_1-C_8)$-alkylsilyl-$(C_1-C_8)$-alkoxy-$(C_1-C_8)$-alkyl, tri-$(C_1-C_8)$-alkylsilyl-$(C_1-C_8)$-alkyl, $R^3$ and $R^4$ independently of one another represent $(C_1-C_8)$-alkoxy, $(C_1-C_8)$-alkoxy-$(C_1-C_8)$-alkoxy, $(C_3-C_8)$-cycloalkyl-$(C_1-C_8)$-alkoxy, $(C_1-C_8)$-haloalkoxy, $(C_1-C_8)$-alkylthio, $(C_1-C_8)$-haloalkylthio, aryl-$(C_1-C_8)$-alkoxy, aryl-$(C_1-C_8)$-alkylthio or together with the atom to which they are attached form an oxo group, hydroxyimino group, $(C_1-C_8)$-alkoxyimino group, $(C_3-C_8)$-cycloalkoxyimino group, $(C_3-C_8)$-cycloalkyl-$(C_1-C_8)$-alkoximino group, aryl-$(C_1-C_8)$-alkoxyimino group or a 5- to 7-membered heterocyclic ring which may optionally be substituted further, $R^5$ and $R^6$ independently of one another represent hydrogen, halogen, $(C_1-C_8)$-alkyl, $(C_1-C_8)$-haloalkyl, $R^7$ represents halogen, $(C_1-C_8)$-alkyl, $(C_1-C_8)$-haloalkyl, $(C_1-C_8)$-haloalkoxy, $(C_1-C_8)$-haloalkoxy-$(C_1-C_8)$-alkyl, $(C_1-C_8)$-haloalkoxy-$(C_1-C_8)$-haloalkyl, $(C_1-C_8)$-alkoxy-$(C_1-C_8)$-haloalkyl, $(C_1-C_8)$-alkynyloxy-$(C_1-C_8)$-haloalkyl, $(C_1-C_8)$-alkenyloxy-$(C_1-C_8)$-haloalkyl, $(C_1-C_8)$-alkylthio, $(C_1-C_8)$-haloalkylthio, optionally substituted phenyl, aryl-$(C_1-C_8)$-alkyl, heteroaryl, heteroaryl-$(C_1-C_8)$-alkyl, $R^6$ and $R^7$ with the atoms to which they are bonded form a fully saturated 3- to 6-membered ring optionally interrupted by heteroatoms and optionally with further substitution, $R^8$ represents hydrogen, $(C_1-C_8)$-alkyl, $(C_1-C_8)$-alkoxy-$(C_1-C_8)$-alkyl, $(C_3-C_8)$-cycloalkyl, $(C_3-C_8)$-cycloalkyl-$(C_1-C_8)$-alkyl, optionally substituted phenyl, aryl-$(C_1-C_8)$-alkyl, heteroaryl-$(C_1-C_8)$-alkyl, bisaryl-$(C_1-C_8)$-alkyl, trisaryl-$(C_1-C_8)$-alkyl, $(C_2-C_8)$-alkenyl, $(C_2-C_8)$-alkenyl-$(C_1-C_8)$-alkyl, $(C_4-C_8)$-cycloalkenyl-$(C_1-C_8)$-alkyl, $(C_2-C_8)$-alkynyl-$(C_1-C_8)$-alkyl, tri-$(C_1-C_8)$-alkylsilyl-$(C_1-C_8)$-alkoxy-$(C_1-C_8)$-alkyl, $(C_1-C_8)$-alkoxy-$(C_1-C_8)$-alkoxy-$(C_1-C_8)$-alkyl, $(C_1-C_8)$-alkylthio-$(C_1-C_8)$-alkyl, $(C_1-C_8)$-haloalkyl, arylsulfonyl-$(C_1-C_8)$-alkyl, tri-$(C_1-C_8)$-alkylsilyl, $(C_1-C_8)$-alkyl-(bisaryl)silyl, $(C_1-C_8)$-alkyl-(bis-$(C_1-C_8)$-alkyl)silyl, bis-$(C_1-C_8)$-alkylamino-$(C_1-C_8)$-alkyl, $R^9$ represents hydrogen, $(C_1-C_8)$-alkyl, $(C_3-C_8)$-cycloalkyl, halogen, $(C_2-C_8)$-alkenyl-$(C_1-C_8)$-alkyl, $(C_2-C_8)$-alkynyl-$(C_1-C_8)$-alkyl, $(C_1-C_8)$-haloalkyl, $(C_2-C_8)$-alkynyl, $(C_2-C_8)$-alkenyl, cyano-$(C_1-C_8)$-alkyl, $(C_3-C_8)$-cycloalkyl-$(C_1-C_8)$-alkyl, aryl-$(C_1-C_8)$-alkyl, heteroaryl-$(C_1-C_8)$-alkyl, $(C_1-C_8)$-alkylcarbonyl, $(C_1-C_8)$-alkoxycarbonyl, $(C_2-C_8)$-alkenyloxycarbonyl, $(C_2-C_8)$-alkenyl-$(C_1-C_8)$-alkyloxycarbonyl, aryl-$(C_1-C_8)$-alkyloxycarbonyl, $(C_3-C_8)$-cycloalkoxycarbonyl, $(C_3-C_8)$-cycloalkyl-$(C_1-C_8)$-alkoxycarbonyl, $(C_1-C_8)$-alkylsulfonyl, arylsulfonyl, $(C_3-C_8)$-cycloalkylsulfonyl, $(C_1-C_8)$-alkylsulfinyl, arylsulfinyl, $(C_3-C_8)$-cycloalkylsulfinyl, $(C_1-C_8)$-alkoxycarbonyl-$(C_1-C_8)$-alkyl, hydroxycarbonyl-$(C_1-C_8)$-alkyl, aryl-$(C_1-C_8)$-alkoxycarbonyl-$(C_1-C_8)$-alkyl, $(C_3-C_8)$-cycloalkyl-$(C_1-C_8)$-alkoxycarbonyl-$(C_1-C_8)$-alkyl, $(C_1-C_8)$-alkoxycarbonyl-$(C_3-C_8)$-cycloalkyl, hydroxycarbonyl-$(C_3-C_8)$-cycloalkyl, aryl-$(C_1-C_8)$-alkoxycarbonyl-$(C_3-C_8)$-cycloalkyl, $(C_2-C_8)$-alkenyloxycarbonyl-$(C_3-C_8)$-cycloalkyl, aminocarbonyl-$(C_3-C_8)$-cycloalkyl, $(C_1-C_8)$-alkylaminocarbonyl-$(C_3-C_8)$-cycloalkyl, $(C_3-C_8)$-cycloalkylaminocarbonyl-$(C_3-C_8)$-cycloalkyl, $(C_1-C_8)$-alkoxycarbonyl-$(C_4-C_8)$-cycloalkenyl, hydroxycarbonyl-$(C_4-C_8)$-cycloalkenyl, bis-$(C_1-C_8)$-alkylamino-$(C_1-C_8)$-alkyl, hydroxycarbonylheterocyclyl, $(C_1-C_8)$-alkoxycarbonylheterocyclyl, $(C_2-C_8)$-alkenyloxycarbonylheterocyclyl, $(C_2-C_8)$-alkenyl-$(C_1-C_8)$-alkoxycarbonylheterocyclyl, aryl-$(C_1-C_8)$-alkoxycarbonylheterocyclyl, $(C_3-C_8)$-cycloalkoxycarbonylheterocyclyl, $(C_3-C_8)$-cycloalkyl-$(C_1-C_8)$-alkoxycarbonylheterocyclyl, aminocarbonylheterocyclyl, $(C_1-C_8)$-alkylaminocarbonylheterocyclyl, bis-$(C_1-C_8)$-alkylaminocarbonylheterocyclyl, $(C_3-C_8)$-cycloalkylaminocarbonylheterocyclyl, aryl-$(C_1-C_8)$-alkylaminocarbonylheterocyclyl, $(C_2-C_8)$- alkenylaminocarbonylheterocyclyl, hydroxycarbonylheterocyclyl-($C_1$-$C_8$)-alkyl, ($C_1$-$C_8$)-alkoxycarbonylheterocyclyl-($C_1$-$C_8$)-alkyl, hydroxycarbonyl-($C_3$-$C_8$)-cycloalkyl-($C_1$-$C_8$)-alkyl, ($C_1$-$C_8$)-alkoxycarbonyl-($C_3$-$C_8$)-cycloalkyl-($C_1$-$C_8$)-alkyl, hydroxy, ($C_1$-$C_8$)-alkoxy, $R^{10}$ represents hydrogen, ($C_1$-$C_8$)-alkyl, ($C_3$-$C_8$)-cycloalkyl, halogen, ($C_1$-$C_8$)-alkyl-($C_1$-$C_8$)-alkenyl, ($C_1$-$C_8$)-haloalkyl, ($C_2$-$C_8$)-alkynyl, ($C_2$-$C_8$)-alkenyl, cyano-($C_1$-$C_8$)-alkyl, aryl-($C_1$-$C_8$)-alkyl, heteroaryl-($C_1$-$C_8$)-alkyl, ($C_1$-$C_8$)-alkylcarbonyl, ($C_1$-$C_8$)-alkoxycarbonyl, ($C_1$-$C_8$)-alkylsulfonyl, arylsulfonyl, ($C_3$-$C_8$)-cycloalkylsulfonyl, ($C_1$-$C_8$)-alkylsulfinyl, arylsulfinyl, ($C_3$-$C_8$)-cycloalkylsulfinyl, ($C_1$-$C_8$)-alkoxycarbonyl-($C_1$-$C_8$)-alkyl, $R^9$ and $R^{10}$ with the nitrogen to which they are attached form an optionally halogen-, ($C_1$-$C_8$)-alkyl-, ($C_1$-$C_8$)-haloalkyl-, ($C_1$-$C_8$)-alkoxy-, ($C_1$-$C_8$)-alkoxycarbonyl-, ($C_3$-$C_8$)-cycloalkoxycarbonyl-, ($C_3$-$C_8$)-cycloalkyl-($C_1$-$C_8$)-alkoxycarbonyl-, ($C_2$-$C_8$)-alkenyloxycarbonyl-, hydroxycarbonyl-, aminocarbonyl-, ($C_1$-$C_8$)-alkylaminocarbonyl-, ($C_3$-$C_8$)-cycloalkylaminocarbonyl-, aryl-($C_1$-$C_8$)-alkylaminocarbonyl-substituted three- to eight-membered ring which is optionally interrupted by O, S or N or $R^9$ and $R^{10}$ together form an N-(bis-($C_1$-$C_6$)-alkyl)sulfanylidene, N-(aryl-($C_1$-$C_6$)-alkyl)sulfanylidene, N-(bis-($C_3$-$C_7$)-cycloalkyl)sulfanylidene, N—(($C_1$-$C_6$)-alkyl-($C_3$-$C_7$)-cycloalkyl)sulfanylidene group or an N,N-di-($C_1$-$C_6$)-alkylformylidene group.

Particular preference is given to compounds of the formula (I) in which

[X—Y] represents the moieties

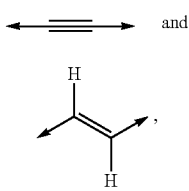

Q represents the moieties Q-1 to Q-3

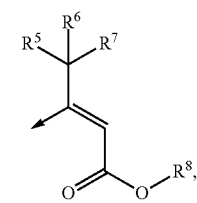

Q-1

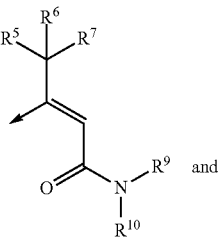

Q-2

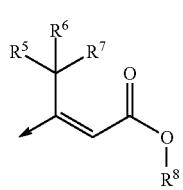

Q-3 where $R^5$, $R^6$, $R^7$, $R^8$, $R^9$ and $R^{10}$ are each as defined below and where the arrow represents a bond to the respective [X—Y] grouping;

$R^1$ represents ($C_1$-$C_6$)-alkyl, ($C_2$-$C_6$)-alkenyl, ($C_2$-$C_6$)-alkynyl, ($C_2$-$C_6$)-alkenyl-($C_1$-$C_6$)-alkyl, ($C_2$-$C_6$)-alkynyl-($C_1$-$C_6$)-alkyl, ($C_1$-$C_6$)-alkoxy-($C_1$-$C_6$)-alkyl, hydroxy-($C_1$-$C_6$)-alkyl, ($C_1$-$C_6$)-haloalkyl, ($C_2$-$C_6$)-haloalkenyl, ($C_2$-$C_6$)-haloalkynyl, ($C_1$-$C_6$)-haloalkoxy-($C_1$-$C_6$)-alkyl, ($C_3$-$C_7$)-cycloalkyl, ($C_1$-$C_6$)-alkoxy-($C_1$-$C_6$)-haloalkyl, ($C_1$-$C_6$)-haloalkoxy-($C_1$-$C_6$)-haloalkyl, ($C_1$-$C_6$)-alkylthio-($C_1$-$C_6$)-alkyl, $R^2$ represents hydrogen, tri-($C_1$-$C_6$)-alkylsilyl, ($C_1$-$C_6$)-alkyl-(bis-($C_1$-$C_6$)-alkyl)silyl, ($C_1$-$C_6$)-alkyl(bis-aryl)silyl, aryl(bis-($C_1$-$C_6$)-alkyl)silyl, ($C_3$-$C_7$)-cycloalkyl(bis-($C_1$-$C_6$)-alkyl)silyl, halo(bis-($C_1$-$C_6$)-alkyl)silyl, tri-($C_1$-$C_6$)-alkylsilyl-($C_1$-$C_6$)-alkoxy-($C_1$-$C_6$)-alkyl, tri-($C_1$-$C_6$)-alkylsilyl-($C_1$-$C_6$)-alkyl, $R^3$ and $R^4$ independently of one another represent ($C_1$-$C_6$)-alkoxy, ($C_1$-$C_6$)-alkylthio or together with the atom to which they are attached form an oxo group, hydroxyimino group, ($C_1$-$C_6$)-alkoxyimino group, ($C_3$-$C_6$)-cycloalkoxyimino group, ($C_3$-$C_6$)-cycloalkyl-($C_1$-$C_6$)-alkoximino group, aryl-($C_1$-$C_6$)-alkoxyimino group or a 5- to 7-membered heterocyclic ring which may optionally be substituted further, $R^5$ and $R^6$ independently of one another represent hydrogen, halogen, ($C_1$-$C_8$)-alkyl, ($C_1$-$C_6$)-haloalkyl, $R^7$ represents halogen, ($C_1$-$C_8$)-alkyl, ($C_1$-$C_8$)-haloalkyl, ($C_1$-$C_8$)-haloalkoxy, ($C_1$-$C_8$)-haloalkoxy-($C_1$-$C_8$)-alkyl, ($C_1$-$C_8$)-haloalkoxy-($C_1$-$C_8$)-haloalkyl, ($C_1$-$C_8$)-alkoxy-($C_1$-$C_8$)-haloalkyl, ($C_1$-$C_8$)-alkynyloxy-($C_1$-$C_8$)-haloalkyl, ($C_1$-$C_8$)-alkenyloxy-($C_1$-$C_8$)-haloalkyl, ($C_1$-$C_6$)-alkylthio, ($C_1$-$C_6$)-haloalkylthio, optionally substituted phenyl, aryl-($C_1$-$C_6$)-alkyl, heteroaryl, heteroaryl-($C_1$-$C_6$)-alkyl, $R^6$ and $R^7$ with the atoms to which they are bonded form a fully saturated 3- to 6-membered ring optionally interrupted by heteroatoms and optionally with further substitution, $R^8$ represents hydrogen, ($C_1$-$C_6$)-alkyl, ($C_1$-$C_6$)-alkoxy-($C_1$-$C_6$)-alkyl, ($C_3$-$C_7$)-cycloalkyl, ($C_3$-$C_7$)-cycloalkyl-($C_1$-$C_6$)-alkyl, optionally substituted phenyl, aryl-($C_1$-$C_6$)-alkyl, heteroaryl-($C_1$-$C_6$)-alkyl, bisaryl-($C_1$-$C_6$)-alkyl, trisaryl-($C_1$-$C_6$)-alkyl, ($C_2$-$C_6$)-alkenyl, ($C_2$-$C_6$)-alkenyl-($C_1$-$C_6$)-alkyl, ($C_4$-$C_7$)-cycloalkenyl-($C_1$-$C_6$)-alkyl, ($C_2$-$C_6$)-alkynyl-($C_1$-$C_6$)-alkyl, tri-($C_1$-$C_6$)-alkylsilyl-($C_1$-$C_6$)-alkoxy-($C_1$-$C_6$)-alkyl, ($C_1$-$C_6$)-alkoxy-($C_1$-$C_6$)-alkoxy-($C_1$-$C_6$)-alkyl, ($C_1$-$C_6$)-alkylthio-($C_1$-$C_6$)-alkyl, ($C_1$-$C_6$)-haloalkyl, arylsulfonyl-($C_1$-$C_6$)-alkyl, tri-($C_1$-$C_6$)-alkylsilyl, ($C_1$-$C_6$)-alkyl-(bisaryl)silyl, ($C_1$-$C_6$)-alkyl-(bis-($C_1$-$C_6$)-alkyl)silyl, bis-($C_1$-$C_6$)-alkylamino-($C_1$-$C_6$)-alkyl, $R^9$ represents hydrogen, ($C_1$-$C_6$)-alkyl, ($C_3$-$C_7$)-cycloalkyl, halogen, ($C_2$-$C_6$)-alkenyl-($C_1$-$C_6$)-alkyl, ($C_2$-$C_6$)-alkynyl-($C_1$-$C_6$)-alkyl, ($C_1$-$C_6$)-haloalkyl, ($C_2$-$C_6$)-alkynyl, ($C_2$-$C_6$)-alkenyl, cyano-($C_1$-$C_6$)-alkyl, ($C_3$-$C_7$)-cycloalkyl-($C_1$-$C_6$)-alkyl, aryl-($C_1$-$C_6$)-alkyl, heteroaryl-($C_1$-$C_6$)- alkyl, (C₁-C₆)-alkylcarbonyl, (C₁-C₆)-alkoxycarbonyl, (C₂-C₆)-alkenyloxycarbonyl, (C₂-C₆)-alkenyl-(C₁-C₆)-alkyloxycarbonyl, aryl-(C₁-C₆)-alkyloxycarbonyl, (C₃-C₇)-cycloalkoxycarbonyl, (C₃-C₆)-cycloalkyl-(C₁-C₆)-alkoxycarbonyl, (C₁-C₆)-alkylsulfonyl, arylsulfonyl, (C₃-C₇)-cycloalkylsulfonyl, (C₁-C₆)-alkylsulfinyl, arylsulfinyl, (C₃-C₇)-cycloalkylsulfinyl, (C₁-C₆)-alkoxycarbonyl-(C₁-C₆)-alkyl, hydroxycarbonyl-(C₁-C₆)-alkyl, aryl-(C₁-C₆)-alkoxycarbonyl-(C₁-C₆)-alkyl, (C₃-C₇)-cycloalkyl-(C₁-C₆)-alkoxycarbonyl-(C₁-C₆)-alkyl, (C₁-C₆)-alkoxycarbonyl-(C₃-C₆)-cycloalkyl, hydroxycarbonyl-(C₃-C₆)-cycloalkyl, aryl-(C₁-C₆)-alkoxycarbonyl-(C₁-C₆)-cycloalkyl, (C₂-C₆)-alkenyloxycarbonyl-(C₃-C₆)-cycloalkyl, aminocarbonyl-(C₃-C₇)-cycloalkyl, (C₁-C₆)-alkylaminocarbonyl-(C₃-C₇)-cycloalkyl, (C₃-C₇)-cycloalkylaminocarbonyl-(C₃-C₇)-cycloalkyl, (C₁-C₆)-alkoxycarbonyl-(C₄-C₇)-cycloalkenyl, hydroxycarbonyl-(C₄-C₇)-cycloalkenyl, bis-(C₁-C₆)-alkylamino-(C₁-C₆)-alkyl, hydroxycarbonylheterocyclyl, (C₁-C₆)-alkoxycarbonylheterocyclyl, (C₂-C₆)-alkenyloxycarbonylheterocyclyl, (C₂-C₆)-alkenyl-(C₁-C₆)-alkoxycarbonylheterocyclyl, aryl-(C₁-C₆)-alkoxycarbonylheterocyclyl, (C₃-C₇)-cycloalkoxycarbonylheterocyclyl, (C₃-C₇)-cycloalkyl-(C₁-C₆)-alkoxycarbonylheterocyclyl, aminocarbonylheterocyclyl, (C₁-C₆)-alkylaminocarbonylheterocyclyl, bis-(C₁-C₆)-alkylaminocarbonylheterocyclyl, (C₃-C₇)-cycloalkylaminocarbonylheterocyclyl, aryl-(C₁-C₆)-alkylaminocarbonylheterocyclyl, (C₂-C₆)-alkenylaminocarbonylheterocyclyl, hydroxycarbonylheterocyclyl-(C₁-C₆)-alkyl, (C₁-C₆)-alkoxycarbonylheterocyclyl-(C₁-C₆)-alkyl, hydroxycarbonyl-(C₃-C₇)-cycloalkyl-(C₁-C₆)-alkyl, (C₁-C₆)-alkoxycarbonyl-(C₃-C₇)-cycloalkyl-(C₁-C₆)-alkyl, hydroxy, (C₁-C₆)-alkoxy, $R^{10}$ represents hydrogen, (C₁-C₆)-alkyl, (C₃-C₇)-cycloalkyl, (C₁-C₆)-alkyl-(C₁-C₆)-alkenyl, (C₁-C₆)-haloalkyl, (C₂-C₆)-alkynyl, (C₂-C₆)-alkenyl, cyano-(C₁-C₆)-alkyl, aryl-(C₁-C₆)-alkyl, heteroaryl-(C₁-C₆)-alkyl, (C₁-C₆)-alkylcarbonyl, (C₁-C₆)-alkoxycarbonyl, (C₁-C₆)-alkylsulfonyl, arylsulfonyl, (C₃-C₇)-cycloalkylsulfonyl, (C₁-C₆)-alkylsulfinyl, arylsulfinyl, (C₃-C₇)-cycloalkylsulfinyl, (C₁-C₆)-alkoxycarbonyl-(C₁-C₆)-alkyl, $R^9$ and $R^{10}$ with the nitrogen to which they are attached form an optionally fluorine-, chlorine-, bromine-, iodine-, (C₁-C₆)-alkyl-, (C₁-C₆)-haloalkyl-, (C₁-C₆)-alkoxy-, (C₁-C₆)-alkoxycarbonyl-, (C₃-C₇)-cycloalkoxycarbonyl-, (C₃-C₇)-cycloalkyl-(C₁-C₆)-alkoxycarbonyl-, (C₂-C₆)-alkenyloxycarbonyl-, hydroxycarbonyl-, aminocarbonyl-, (C₁-C₆)-alkylaminocarbonyl-, (C₃-C₇)-cycloalkylaminocarbonyl-, aryl-(C₁-C₆)-alkylaminocarbonyl-substituted three- to eight-membered ring which is optionally interrupted by O, S or N or $R^9$ and $R^{10}$ together form an N-(bis-(C₁-C₆)-alkyl)sulfanylidene, N-(aryl-(C₁-C₆)-alkyl)sulfanylidene, N-(bis-(C₃-C₇)-cycloalkyl)sulfanylidene, N—((C₁-C₆)-alkyl-(C₃-C₇)-cycloalkyl)sulfanylidene group or an N,N-di-(C₁-C₆)-alkylformylidene group.

Very particular preference is given to compounds of the formula (I) in which

[X—Y] represents the moieties

  [X—Y]¹

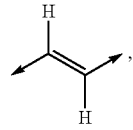  [X—Y]²

Q represents the moieties Q-1 to Q-3

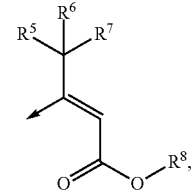  Q-1

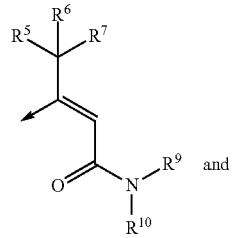  Q-2

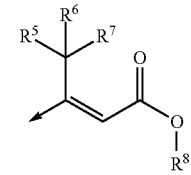  Q-3 where $R^5$, $R^6$, $R^7$, $R^8$, $R^9$ and $R^{10}$ are each as defined below and where the arrow represents a bond to the respective [X—Y] grouping;

$R^1$ represents methyl, ethyl, n-propyl, n-butyl, isobutyl, isopropyl, n-pentyl, n-hexyl, isopentyl, cyclopropyl, cyclobutyl, cyclopentyl, prop-1-yn-3-yl, prop-1-yn-1-yl, but-2-yn-3-yl, but-1-yn-1-yl, ethynyl, 1-methylprop-2-yn-1-yl, 2-butynyl, 2-pentynyl, 1-methylbut-3-yn-1-yl, ethenyl, prop-1-en-1-yl, but-1-en-1-yl, allyl, 1-methylprop-2-en-1-yl, 2-methylprop-2-en-1-yl, but-2-en-1-yl, 1-methylbut-3-en-1-yl and 1-methylbut-2-en-1-yl, 2-methylprop-1-en-1-yl, 1-methylprop-1-en-1-yl, 1-methylprop-2-en-1-yl, 2-methylprop-2-en-1-yl, but-2-en-1-yl, but-3-en-1-yl, 1-methylbut-3-en-1-yl or 1-methylbut-2-en-1-yl, pentenyl, 2-methylpentenyl or hexenyl, 2-bromoethyn-1-yl, 2-chloroethyn-1-yl, 2-iodoethyn-1-yl, 2,2,3,3,3-pentafluoropropyl, 3,3,2,2-tetrafluoropropyl, 4,4,4-trifluorobutyl, 1-fluoroethyl, 2-fluoroethyl, fluoromethyl, difluoromethyl, trifluoromethyl, pentafluoroethyl, heptafluoro-n-propyl, heptafluoroisopropyl, chlorodifluoromethyl, 2,2-difluoroethyl, 2,2,2-trifluoroethyl, 2,2-dichloro-2-fluoroethyl, 2-chloro-2,2-difluoroethyl, difluoro-tert-butyl, 2-bromo-1,1,2-trifluoroethyl, 1,1,2,2-tetrafluoroethyl, 1,2,2,2-tetrafluoroethyl, 2-chloro-1,1,2-trifluoroethyl, 2-chloro-1,1,2,2-tetrafluoroethyl, 1,2,2,3,3,3-hexafluoropropyl, 1-methyl-2,2,2-trifluoroethyl, 1-chloro-2,2,2-trifluoroethyl, 1,2,2,3,3,4,4,4-octafluorobutyl, 1-fluoro-1-methylethyl, n-propoxydifluoromethyl, methoxydifluoromethyl, ethoxydifluoromethyl, methylthiomethyl, ethylthiomethyl, n-propylthiomethyl, chloromethyl, bromomethyl, $R^2$ represents hydrogen, tert-butyldimethylsilyl, trimethylsilyl, triethylsilyl, tri(isopropyl)silyl, tri-(n-propyl)silyl, tert-butyldiphenylsilyl, diethylisopropylsilyl, isopropyldimethylsilyl, tert-hexyldimethylsilyl, 2-(trimethylsilyl)ethoxymethyl, 2-(trimethylsilyl)ethyl, dimethyl(phenyl)silyl, $R^3$ and $R^4$ independently of one another represent methoxy, ethoxy, n-propoxy, isopropoxy, n-butyloxy, isobutyloxy, methylthio, ethylthio, n-propylthio, isopropylthio, n-butylthio, isobutylthio or together with the atom to which they are attached form an oxo group, hydroxyimino group, $(C_1$-$C_6)$-alkoxyimino group, $(C_3$-$C_6)$-cycloalkoxyimino group, $(C_3$-$C_6)$-cycloalkyl-$(C_1$-$C_6)$-alkoximino group, aryl-$(C_1$-$C_6)$-alkoxyimino group or a 5- to 7-membered heterocyclic ring, for example a 1,3-dioxolanyl, 1,3-dioxanyl, 1,3-dithiolanyl, 1,3-dithianyl, 1,3-oxathianyl, 5-alkyl-1,3,5-dithiazinyl, 1,3-oxazolidinyl ring, which may optionally be substituted further by $(C_1$-$C_6)$-alkyl, $(C_1$-$C_6)$-alkoxycarbonyl, $(C_3$-$C_6)$-cycloalkyl, spiro-$(C_3$-$C_6)$-cycloalkyl, spiro-oxetanyl, $R^5$ and $R^6$ independently of one another represent hydrogen, fluorine, chlorine, bromine, iodine, methyl, ethyl, n-propyl, n-butyl, isobutyl, isopropyl, n-pentyl, n-hexyl, isopentyl, trifluoromethyl, pentafluoroethyl, heptafluoropropyl, nonafluorobutyl, chlorodifluoromethyl, bromodifluoromethyl, dichlorofluoromethyl, bromofluoromethyl, 1-fluoroethyl, 2-fluoroethyl, fluoromethyl, difluoromethyl, 2,2-difluoroethyl, 2,2,2-trifluoroethyl, 2,2-dichloro-2-fluoroethyl, 2-chloro-2,2-difluoroethyl, difluoro-tert-butyl, $R^7$ represents fluorine, chlorine, bromine, iodine, $(C_1$-$C_8)$-alkyl, $(C_1$-$C_8)$-haloalkyl, $(C_1$-$C_8)$-haloalkoxy-$(C_1$-$C_8)$-alkyl, $(C_1$-$C_8)$-haloalkoxy-$(C_1$-$C_8)$-haloalkyl, $(C_1$-$C_8)$-alkoxy-$(C_1$-$C_8)$-haloalkyl, $(C_1$-$C_8)$-alkynyloxy-$(C_1$-$C_8)$-haloalkyl, $(C_1$-$C_8)$-alkenyloxy-$(C_1$-$C_8)$-haloalkyl, $(C_1$-$C_6)$-alkylthio, $(C_1$-$C_6)$-haloalkylthio, optionally substituted phenyl, aryl-$(C_1$-$C_6)$-alkyl, heteroaryl, heteroaryl-$(C_1$-$C_6)$-alkyl, $(C_3$-$C_7)$-cycloalkyl, $(C_3$-$C_7)$-cyclohaloalkyl, $R^6$ and $R^7$ with the atoms to which they are bonded form a fully saturated 3- to 6-membered ring optionally interrupted by heteroatoms and optionally with further substitution, $R^8$ represents hydrogen, $(C_1$-$C_6)$-alkyl, $(C_1$-$C_6)$-alkoxy-$(C_1$-$C_6)$-alkyl, $(C_3$-$C_7)$-cycloalkyl, $(C_3$-$C_7)$-cycloalkyl-$(C_1$-$C_6)$-alkyl, optionally substituted phenyl, aryl-$(C_1$-$C_6)$-alkyl, heteroaryl-$(C_1$-$C_6)$-alkyl, bisaryl-$(C_1$-$C_6)$-alkyl, trisaryl-$(C_1$-$C_6)$-alkyl, $(C_2$-$C_6)$-alkenyl, $(C_2$-$C_6)$-alkenyl-$(C_1$-$C_6)$-alkyl, $(C_4$-$C_6)$-cycloalkenyl-$(C_1$-$C_6)$-alkyl, $(C_2$-$C_6)$-alkynyl-$(C_1$-$C_6)$-alkyl, tri-$(C_1$-$C_6)$-alkylsilyl-$(C_1$-$C_6)$-alkoxy-$(C_1$-$C_6)$-alkyl, $(C_1$-$C_6)$-alkoxy-$(C_1$-$C_6)$-alkoxy-$(C_1$-$C_6)$-alkyl, $(C_1$-$C_6)$-alkylthio-$(C_1$-$C_6)$-alkyl, $(C_1$-$C_6)$-haloalkyl, arylsulfonyl-$(C_1$-$C_6)$-alkyl, tri-$(C_1$-$C_6)$-alkylsilyl, $(C_1$-$C_6)$-alkyl-(bisaryl)silyl, $(C_1$-$C_6)$-alkyl-(bis-$(C_1$-$C_6)$-alkyl)silyl, bis-$(C_1$-$C_6)$-alkylamino-$(C_1$-$C_6)$-alkyl, $R^9$ represents hydrogen, $(C_1$-$C_6)$-alkyl, $(C_3$-$C_6)$-cycloalkyl, chlorine, bromine, $(C_2$-$C_6)$-alkenyl-$(C_1$-$C_6)$-alkyl, $(C_2$-$C_6)$-alkynyl-$(C_1$-$C_6)$-alkyl, $(C_1$-$C_6)$-haloalkyl, $(C_2$-$C_6)$-alkynyl, $(C_2$-$C_6)$-alkenyl, cyano-$(C_1$-$C_6)$-alkyl, $(C_3$-$C_7)$-cycloalkyl-$(C_1$-$C_6)$-alkyl, aryl-$(C_1$-$C_6)$-alkyl, heteroaryl-$(C_1$-$C_6)$-alkyl, $(C_1$-$C_6)$-alkylcarbonyl, $(C_1$-$C_6)$-alkoxycarbonyl, $(C_2$-$C_6)$-alkenyloxycarbonyl, $(C_2$-$C_6)$-alkenyl-$(C_1$-$C_6)$-alkyloxycarbonyl, aryl-$(C_1$-$C_6)$-alkyloxycarbonyl, $(C_3$-$C_7)$-cycloalkoxycarbonyl, $(C_3$-$C_6)$-cycloalkyl-$(C_1$-$C_6)$-alkoxycarbonyl, $(C_1$-$C_6)$-alkylsulfonyl, arylsulfonyl, $(C_3$-$C_7)$-cycloalkylsulfonyl, $(C_1$-$C_6)$-alkylsulfinyl, arylsulfinyl, $(C_3$-$C_7)$-cycloalkylsulfinyl, $(C_1$-$C_6)$-alkoxycarbonyl-$(C_1$-$C_6)$-alkyl, hydroxycarbonyl-$(C_1$-$C_6)$-alkyl, aryl-$(C_1$-$C_6)$-alkoxycarbonyl-$(C_1$-$C_6)$-alkyl, $(C_3$-$C_7)$-cycloalkyl-$(C_1$-$C_6)$-alkoxycarbonyl-$(C_1$-$C_6)$-alkyl, $(C_1$-$C_6)$-alkoxycarbonyl-$(C_3$-$C_6)$-cycloalkyl, hydroxycarbonyl-$(C_3$-$C_6)$-cycloalkyl, aryl-$(C_1$-$C_6)$-alkoxycarbonyl-$(C_3$-$C_6)$-cycloalkyl, $(C_2$-$C_6)$-alkenyloxycarbonyl-$(C_3$-$C_6)$-cycloalkyl, aminocarbonyl-$(C_3$-$C_6)$-cycloalkyl, $(C_1$-$C_6)$-alkylaminocarbonyl-$(C_3$-$C_6)$-cycloalkyl, $(C_3$-$C_6)$-cycloalkylaminocarbonyl-$(C_3$-$C_6)$-cycloalkyl, $(C_1$-$C_6)$-alkoxycarbonyl-$(C_4$-$C_6)$-cycloalkenyl, hydroxycarbonyl-$(C_4$-$C_7)$-cycloalkenyl, bis-$(C_1$-$C_6)$-alkylamino-$(C_1$-$C_6)$-alkyl, hydroxycarbonylheterocyclyl, $(C_1$-$C_6)$-alkoxycarbonylheterocyclyl, $(C_2$-$C_6)$-alkenyloxycarbonylheterocyclyl, $(C_2$-$C_6)$-alkenyl-$(C_1$-$C_6)$-alkoxycarbonylheterocyclyl, aryl-$(C_1$-$C_6)$-alkoxycarbonylheterocyclyl, $(C_3$-$C_6)$-cycloalkoxycarbonylheterocyclyl, $(C_3$-$C_6)$-cycloalkyl-$(C_1$-$C_6)$-alkoxycarbonylheterocyclyl, aminocarbonylheterocyclyl, $(C_1$-$C_6)$-alkylaminocarbonylheterocyclyl, bis-$(C_1$-$C_6)$-alkylaminocarbonylheterocyclyl, $(C_3$-$C_6)$-cycloalkylaminocarbonylheterocyclyl, aryl-$(C_1$-$C_6)$-alkylaminocarbonylheterocyclyl, $(C_2$-$C_6)$-alkenylaminocarbonylheterocyclyl, hydroxycarbonylheterocyclyl-$(C_1$-$C_6)$-alkyl, $(C_1$-$C_6)$-alkoxycarbonylheterocyclyl-$(C_1$-$C_6)$-alkyl, hydroxycarbonyl-$(C_3$-$C_6)$-cycloalkyl-$(C_1$-$C_6)$-alkyl, $(C_1$-$C_6)$-alkoxycarbonyl-$(C_3$-$C_7)$-cycloalkyl-$(C_1$-$C_6)$-alkyl, hydroxy, $(C_1$-$C_6)$-alkoxy, $R^{10}$ represents hydrogen, $(C_1$-$C_6)$-alkyl, $(C_3$-$C_7)$-cycloalkyl, $(C_1$-$C_6)$-alkyl-$(C_1$-$C_6)$-alkenyl, $(C_1$-$C_6)$-haloalkyl, $(C_2$-$C_6)$-alkynyl, $(C_2$-$C_6)$-alkenyl, cyano-$(C_1$-$C_6)$-alkyl, aryl-$(C_1$-$C_6)$-alkyl, heteroaryl-$(C_1$-$C_6)$-alkyl, $(C_1$-$C_6)$-alkylcarbonyl, $(C_1$-$C_6)$-alkoxycarbonyl, $(C_1$-$C_6)$-alkylsulfonyl, arylsulfonyl, $(C_3$-$C_7)$-cycloalkylsulfonyl, $(C_1$-$C_6)$-alkylsulfinyl, arylsulfinyl, $(C_3$-$C_7)$-cycloalkylsulfinyl, $(C_1$-$C_6)$-alkoxycarbonyl-$(C_1$-$C_6)$-alkyl, $R^9$ and $R^{10}$ with the nitrogen to which they are attached form an optionally fluorine-, chlorine-, bromine-, iodine-, $(C_1$-$C_6)$-alkyl-, $(C_1$-$C_6)$-haloalkyl-, $(C_1$-$C_6)$-alkoxy-, $(C_1$-$C_6)$-alkoxycarbonyl-, $(C_3$-$C_7)$-cycloalkoxycarbonyl-, $(C_3$-$C_6)$-cycloalkyl-$(C_1$-$C_6)$-alkoxycarbonyl-, $(C_2$-$C_6)$-alkenyloxycarbonyl-, hydroxycarbonyl-, aminocarbonyl-, $(C_1$-$C_6)$-alkylaminocarbonyl-, $(C_3$-$C_7)$-cycloalkylaminocarbonyl-, aryl-$(C_1$-$C_6)$-alkylaminocarbonyl-substituted three- to seven-membered ring which is optionally interrupted by O, S or N or $R^9$ and $R^{10}$ together represent N-(di-n-butylsulfanylidene), N-(diisopropylsulfanylidene), N-(di-n-propylsulfanylidene), N-(di-n-pentylsulfanylidene), N-(diisobutylsulfanylidene), N-(cyclobutylisopropylsulfanylidene), N-(n-propylisopropylsulfanylidene),
N-(cyclopropylisopropylsulfanylidene), N-(isobutylisopropylsulfanylidene), N,N-dimethylformylidene, and Q is furthermore one of the Q-1.1 to Q-3.45 moieties described in the table below.

| | |
|---|---|
| 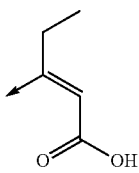 Q-1.1 | 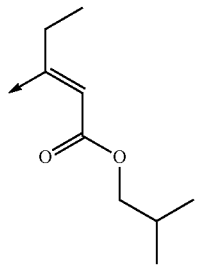 Q-1.8 |
| 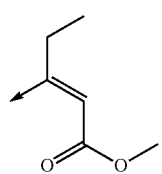 Q-1.2 | |
| 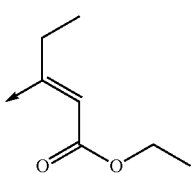 Q-1.3 | 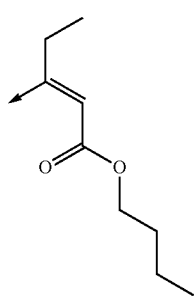 Q-1.9 |
| 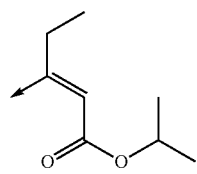 Q-1.4 | 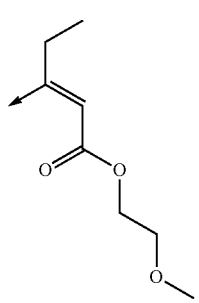 Q-1.10 |
| 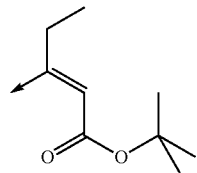 Q-1.5 | |
| 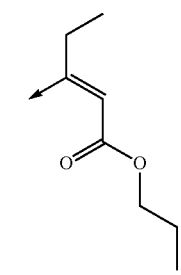 Q-1.6 | 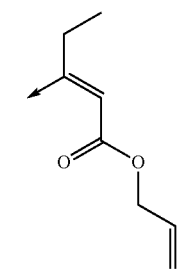 Q-1.11 |
| 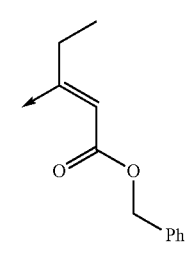 Q-1.7 | 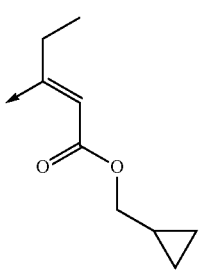 Q-1.12 |

| | |
|---|---|
| Q-1.13 | Q-1.19 |
| Q-1.14 | Q-1.20 |
| Q-1.15 | Q-1.21 |
| Q-1.16 | Q-1.22 |
| Q-1.17 | Q-1.23 |
| Q-1.18 | |

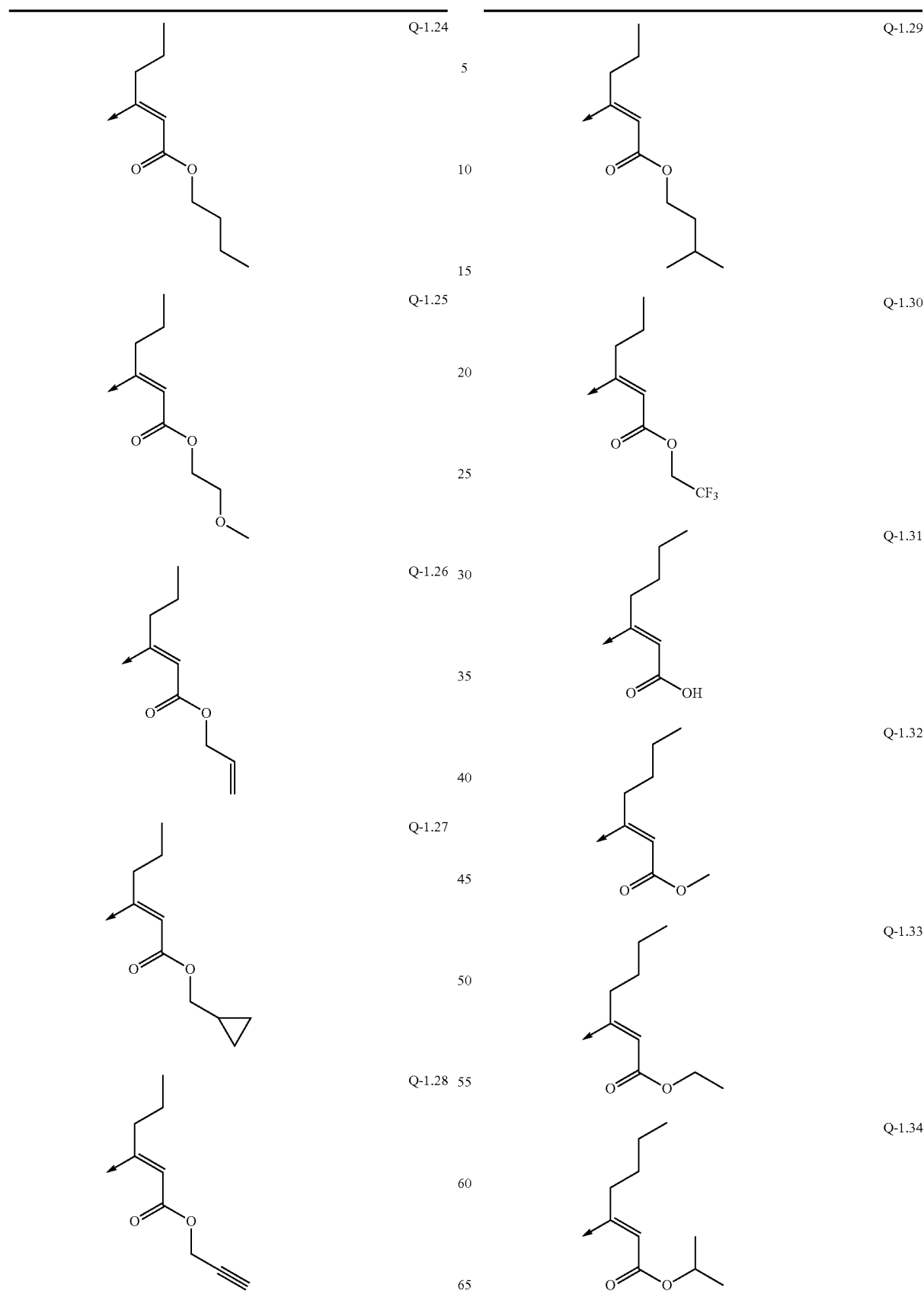

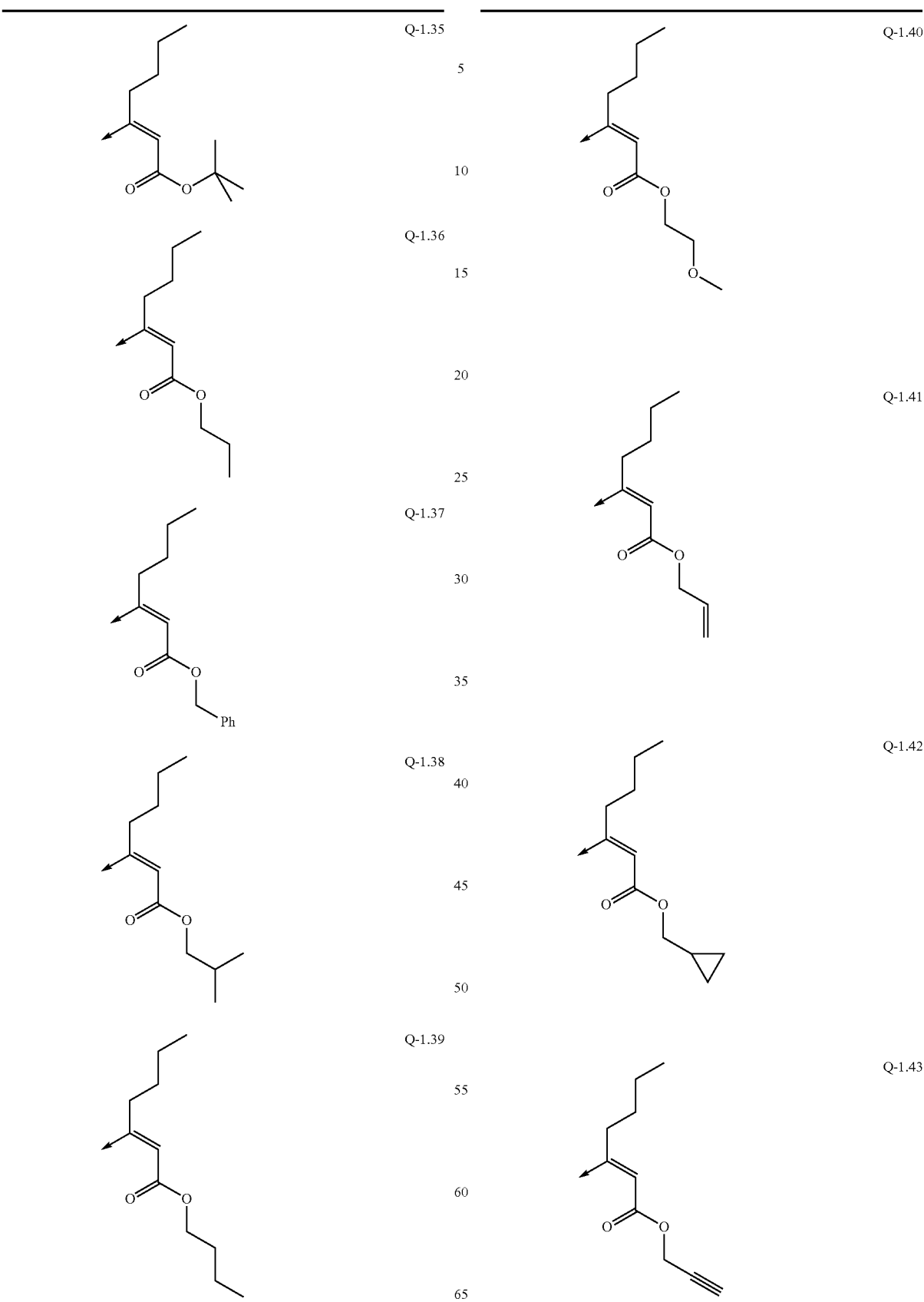

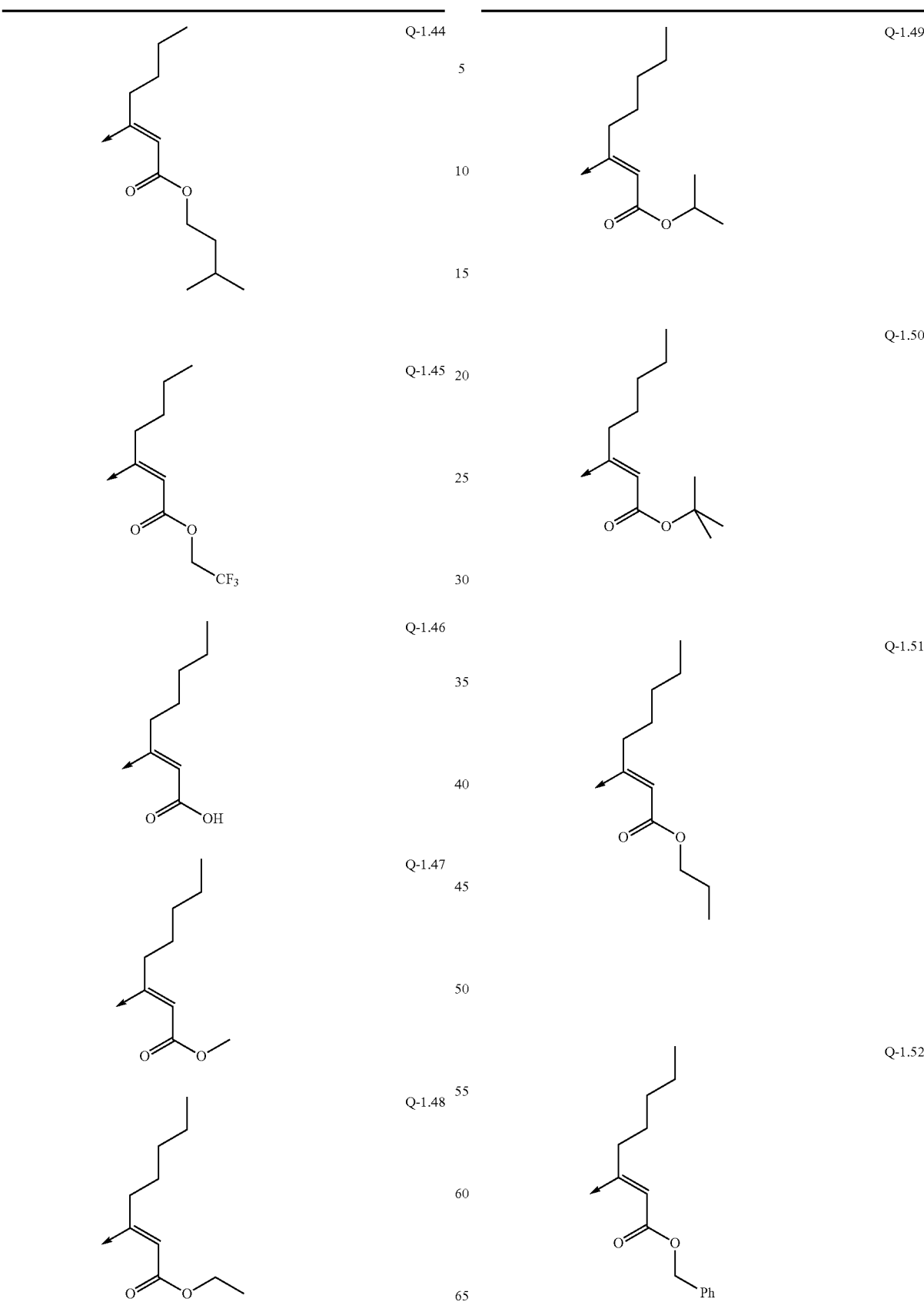

Q-1.53
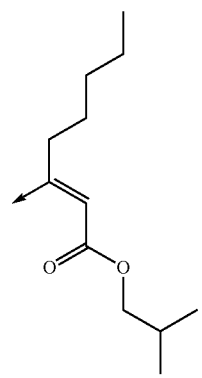
Q-1.54
Q-1.55
Q-1.56
Q-1.57
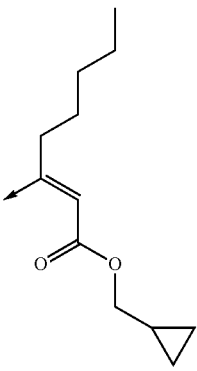
Q-1.58
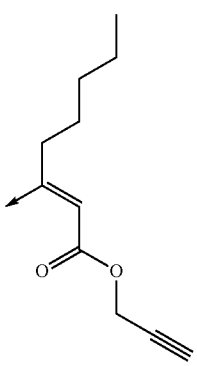
Q-1.59
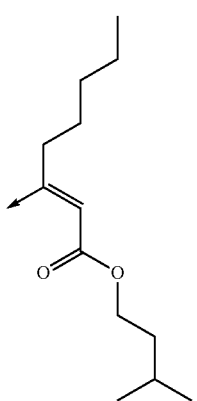
Q-1.60
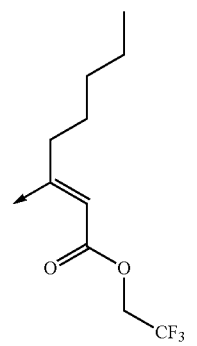

-continued
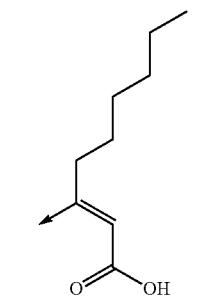
Q-1.61
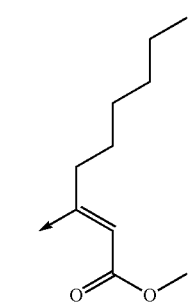
Q-1.62
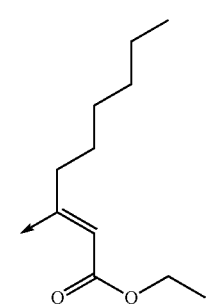
Q-1.63
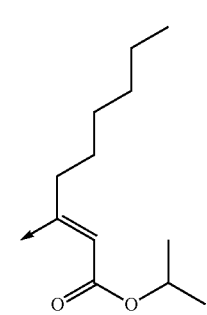
Q-1.64
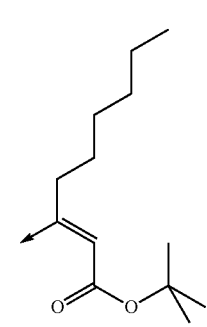
Q-1.65
-continued
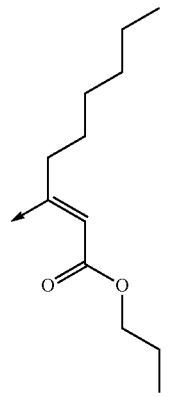
Q-1.66
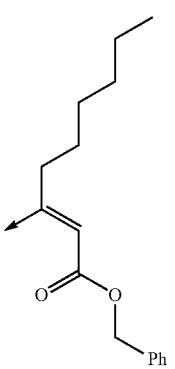
Q-1.67
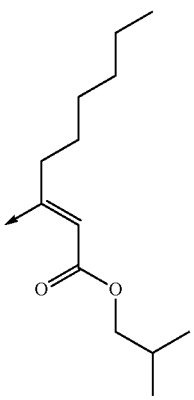
Q-1.68
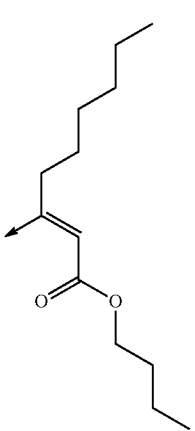
Q-1.69

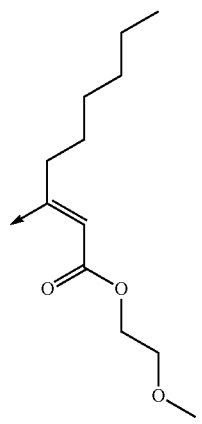
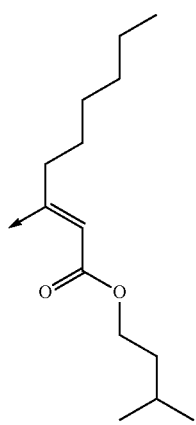

| 31 -continued | | 32 -continued | |
|---|---|---|---|
| 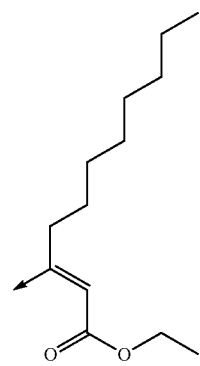 | Q-1.78 | 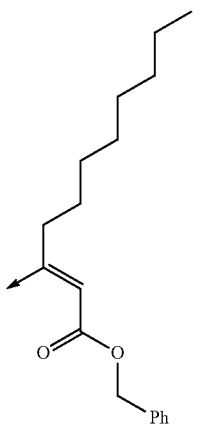 | Q-1.82 |
| 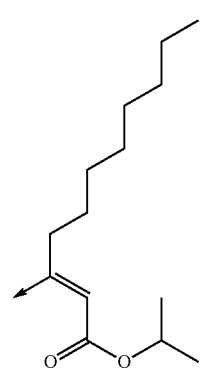 | Q-1.79 | 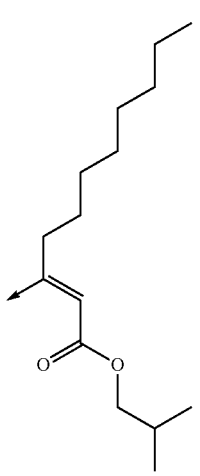 | Q-1.83 |
| 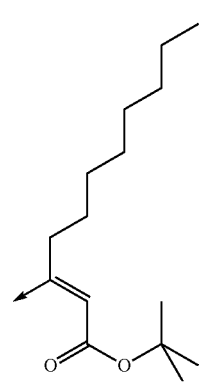 | Q-1.80 | | |
| 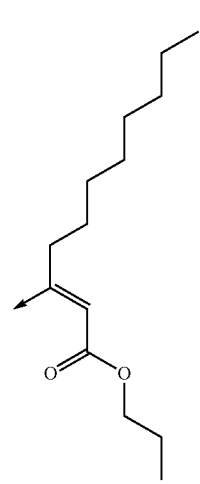 | Q-1.81 | 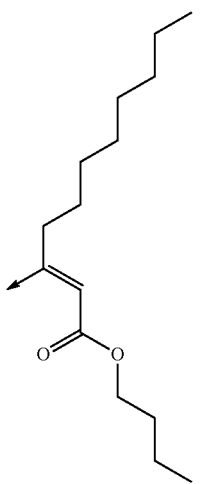 | Q-1.84 |

Q-1.85
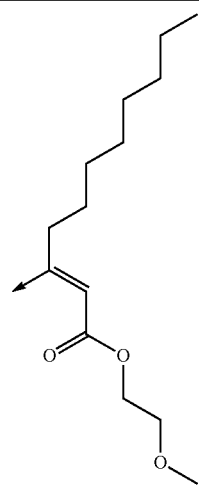
Q-1.86
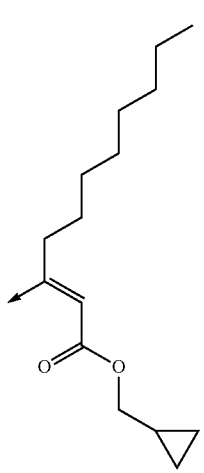
Q-1.87
Q-1.88
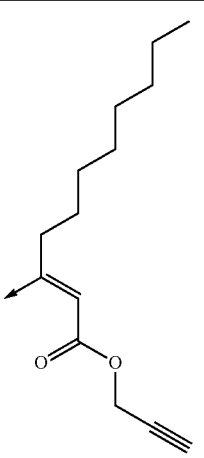
Q-1.89
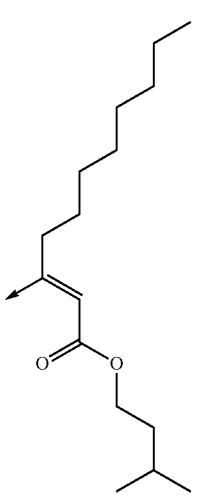
Q-1.90
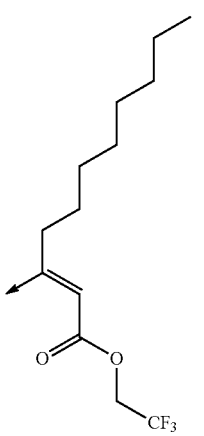
Q-1.91
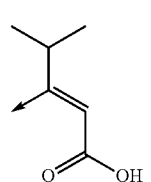

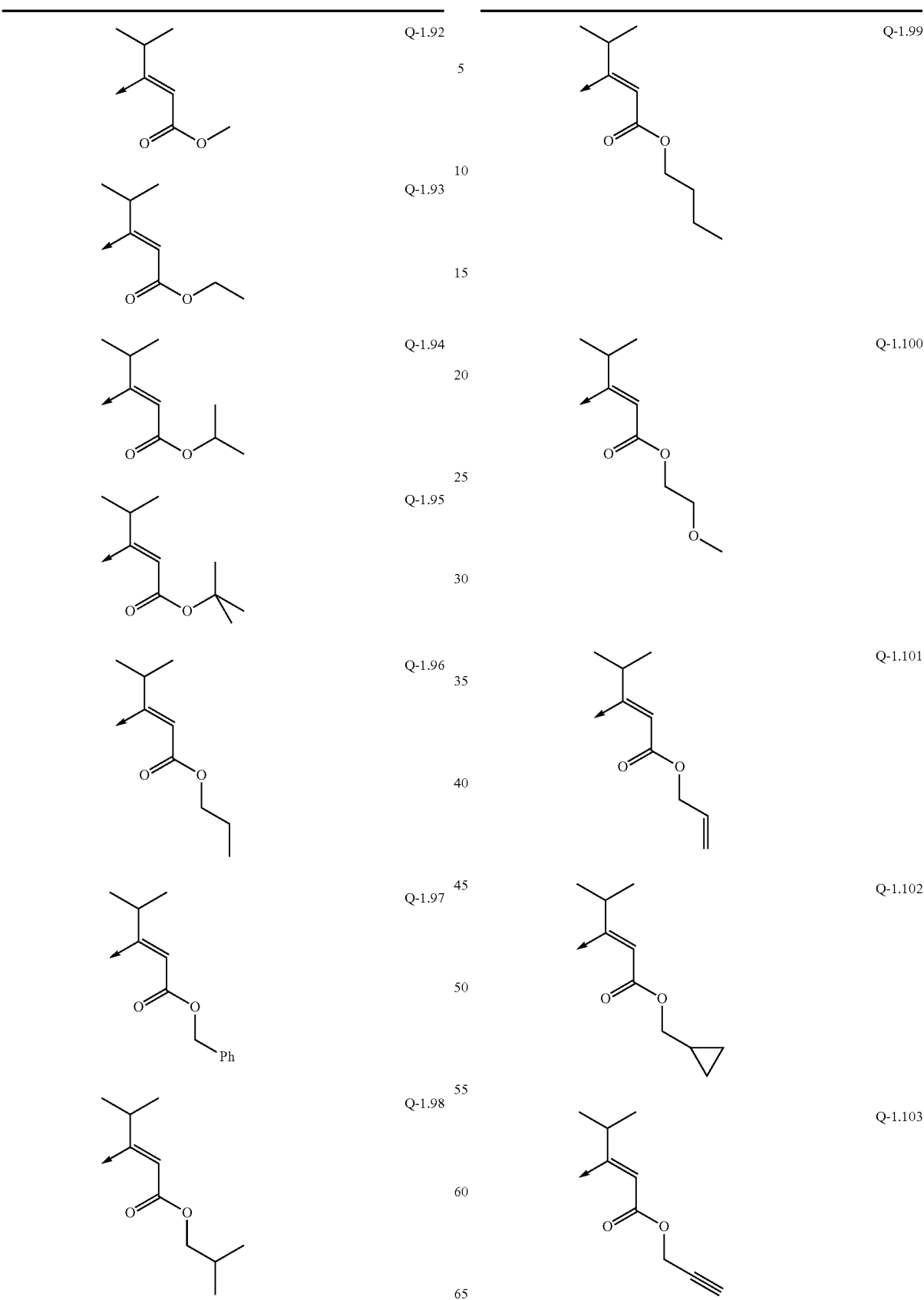

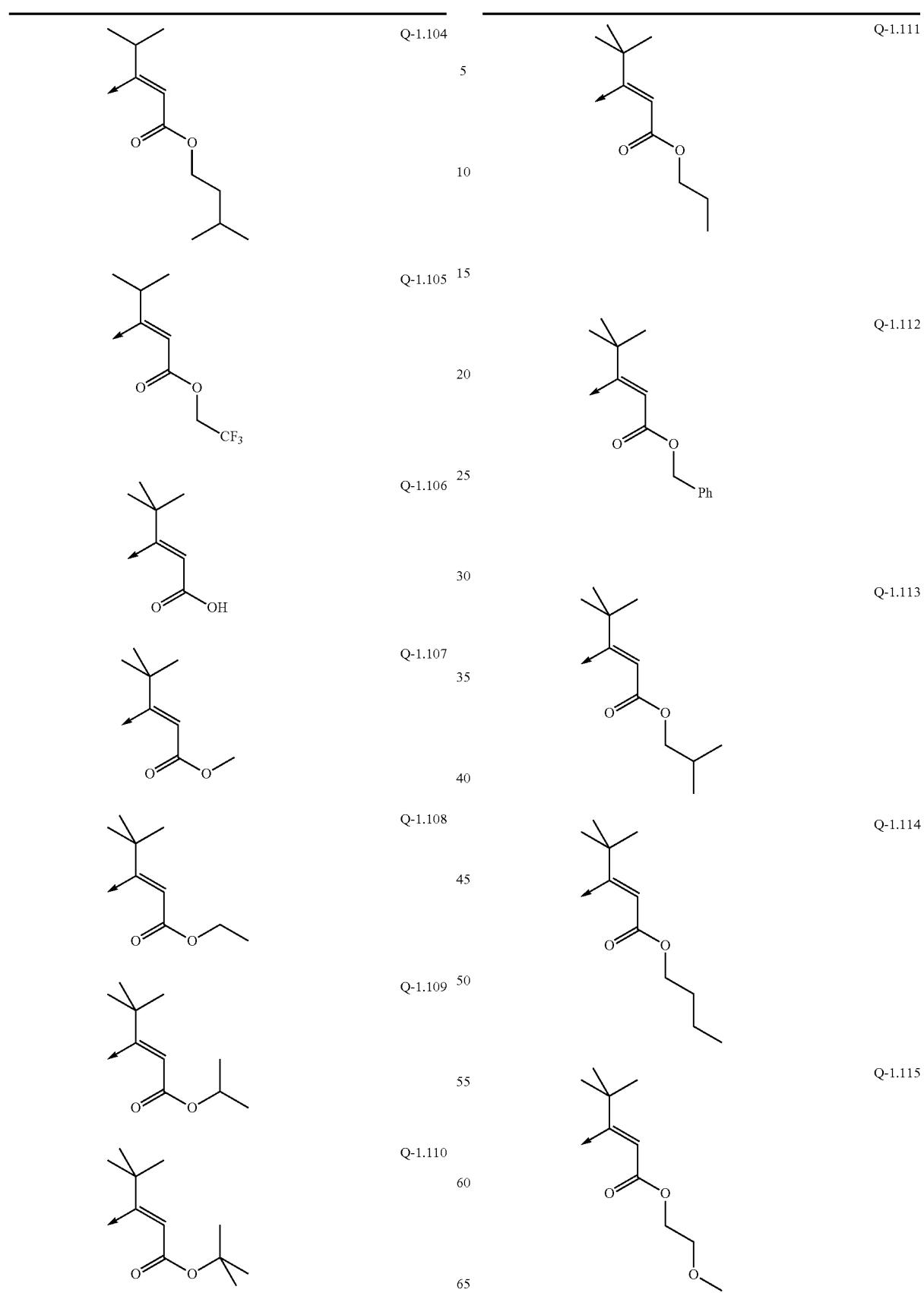

| | |
|---|---|
| 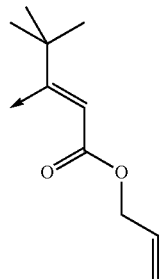 | Q-1.116 |
| 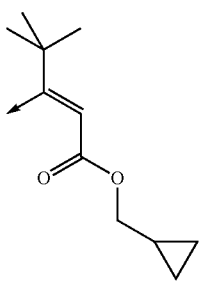 | Q-1.117 |
| 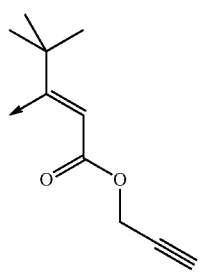 | Q-1.118 |
| 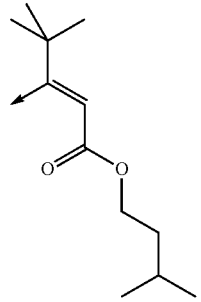 | Q-1.119 |
| 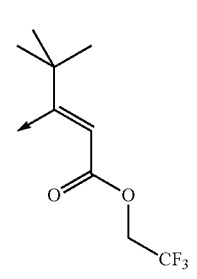 | Q-1.120 |
| 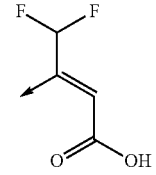 | Q-1.121 |
| 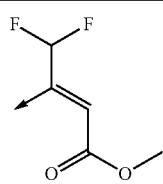 | Q-1.122 |
| 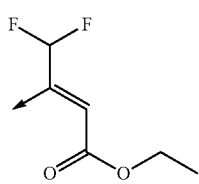 | Q-1.123 |
| 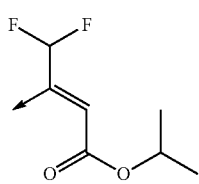 | Q-1.124 |
| 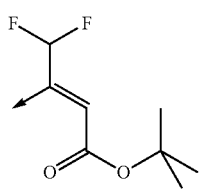 | Q-1.125 |
| 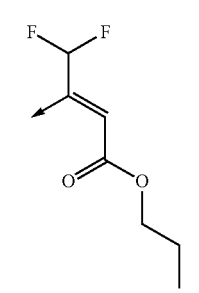 | Q-1.126 |
| 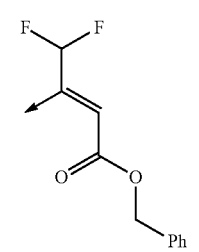 | Q-1.127 |
| 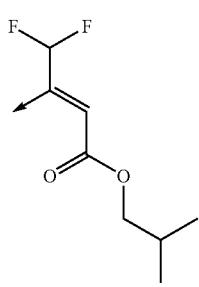 | Q-1.128 |

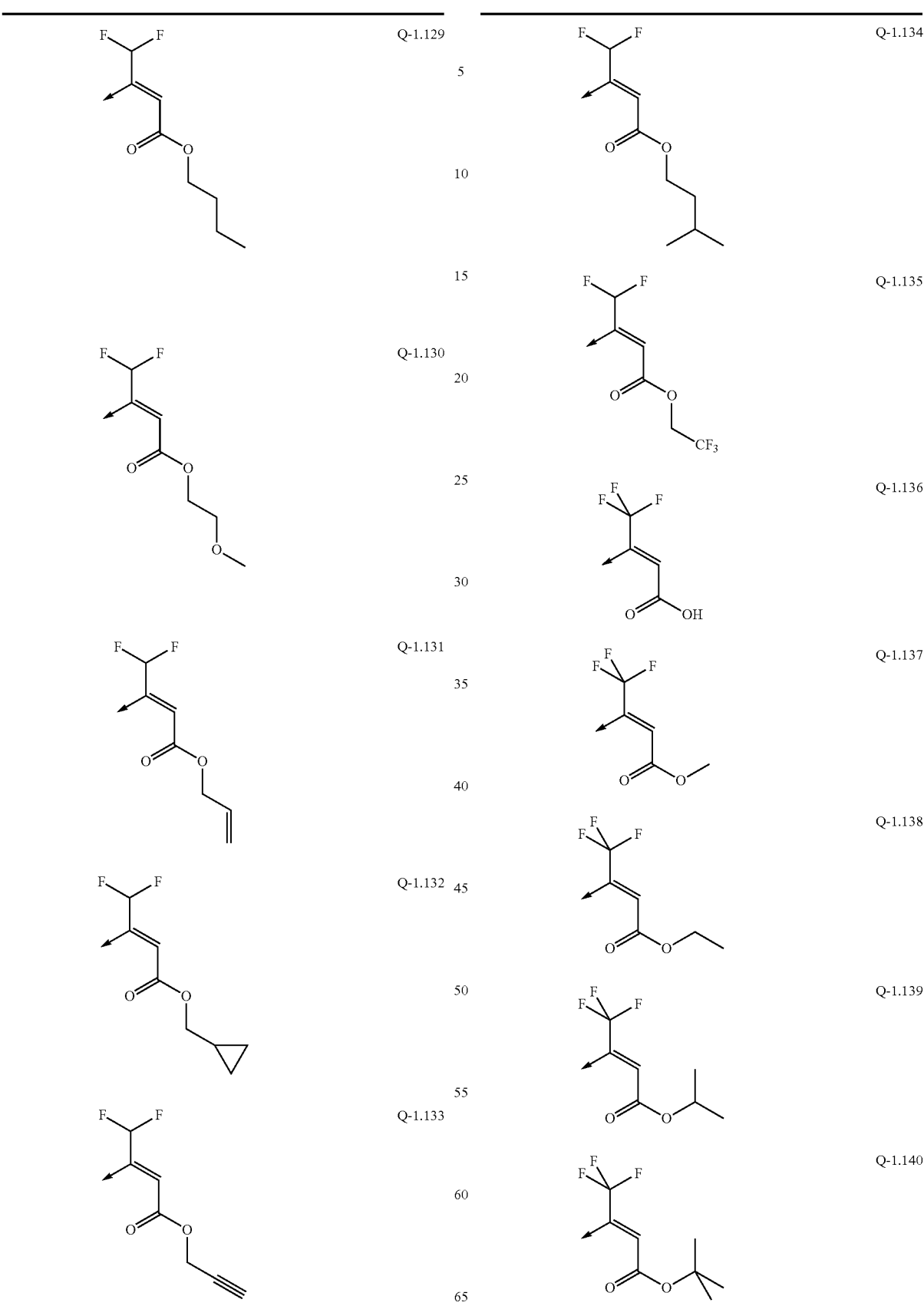

| | |
|---|---|
| 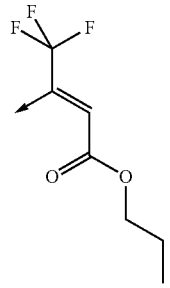 Q-1.141 | 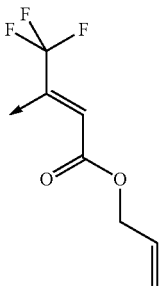 Q-1.146 |
| 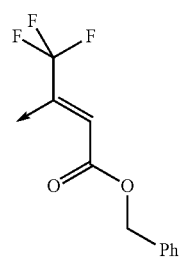 Q-1.142 | 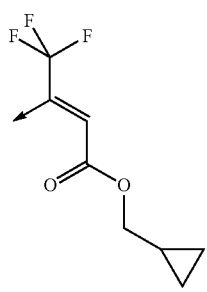 Q-1.147 |
| 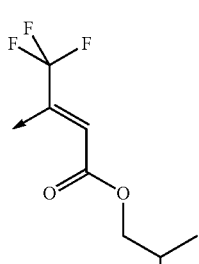 Q-1.143 | 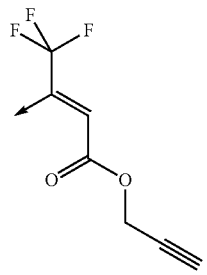 Q-1.148 |
| 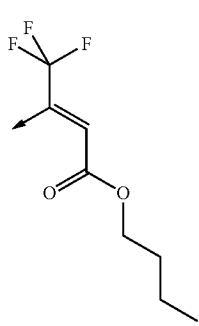 Q-1.144 | 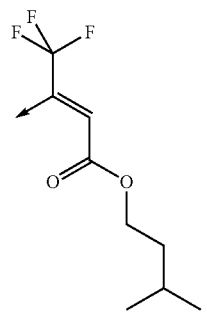 Q-1.149 |
| 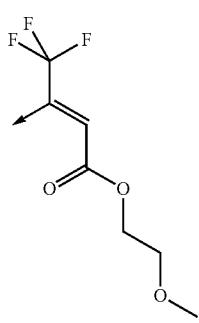 Q-1.145 | 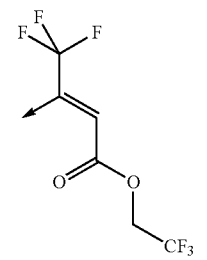 Q-1.150 |

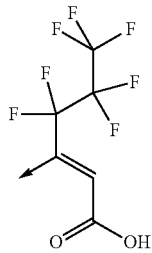 Q-1.151
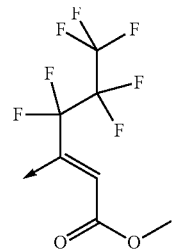 Q-1.152
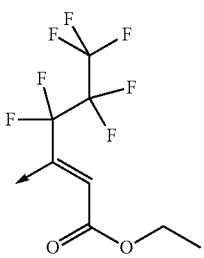 Q-1.153
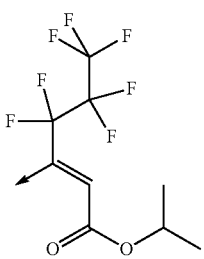 Q-1.154
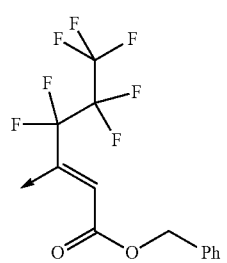 Q-1.155
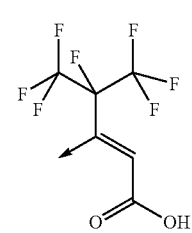 Q-1.156
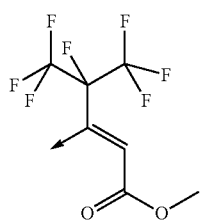 Q-1.157
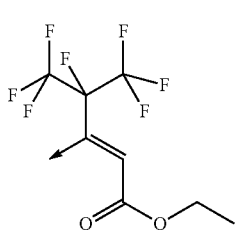 Q-1.158
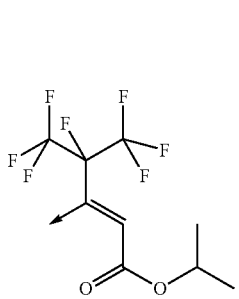 Q-1.159
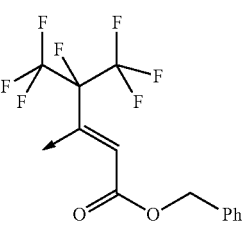 Q-1.160
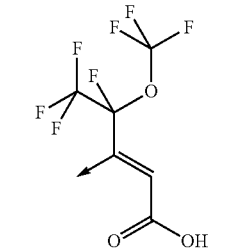 Q-1.161
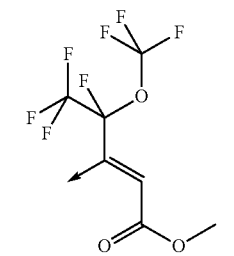 Q-1.162

| | |
|---|---|
| 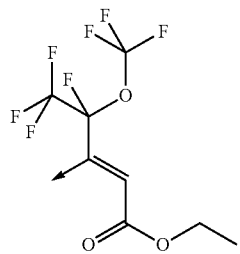 | Q-1.163 |
| 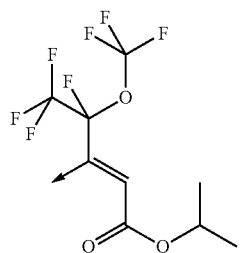 | Q-1.164 |
| 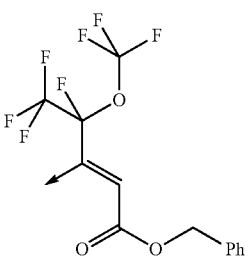 | Q-1.165 |
| 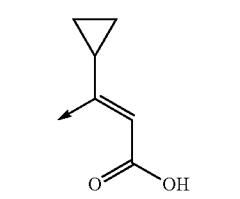 | Q-1.166 |
| 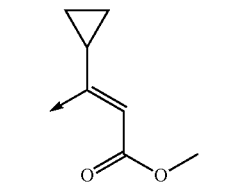 | Q-1.167 |
| 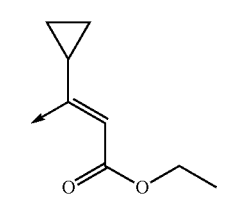 | Q-1.168 |
| 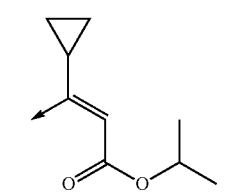 | Q-1.169 |
| 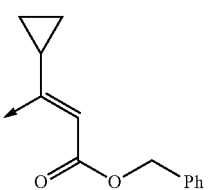 | Q-1.170 |
| 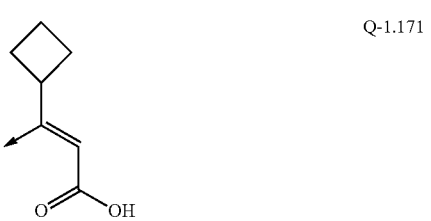 | Q-1.171 |
|  | Q-1.172 |
| 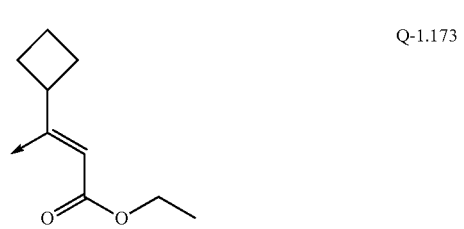 | Q-1.173 |
| 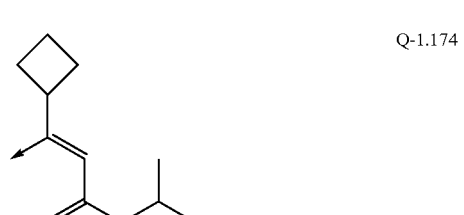 | Q-1.174 |
|  | Q-1.175 |
| 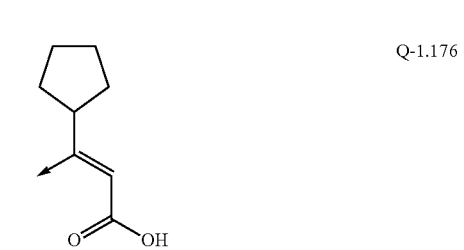 | Q-1.176 |

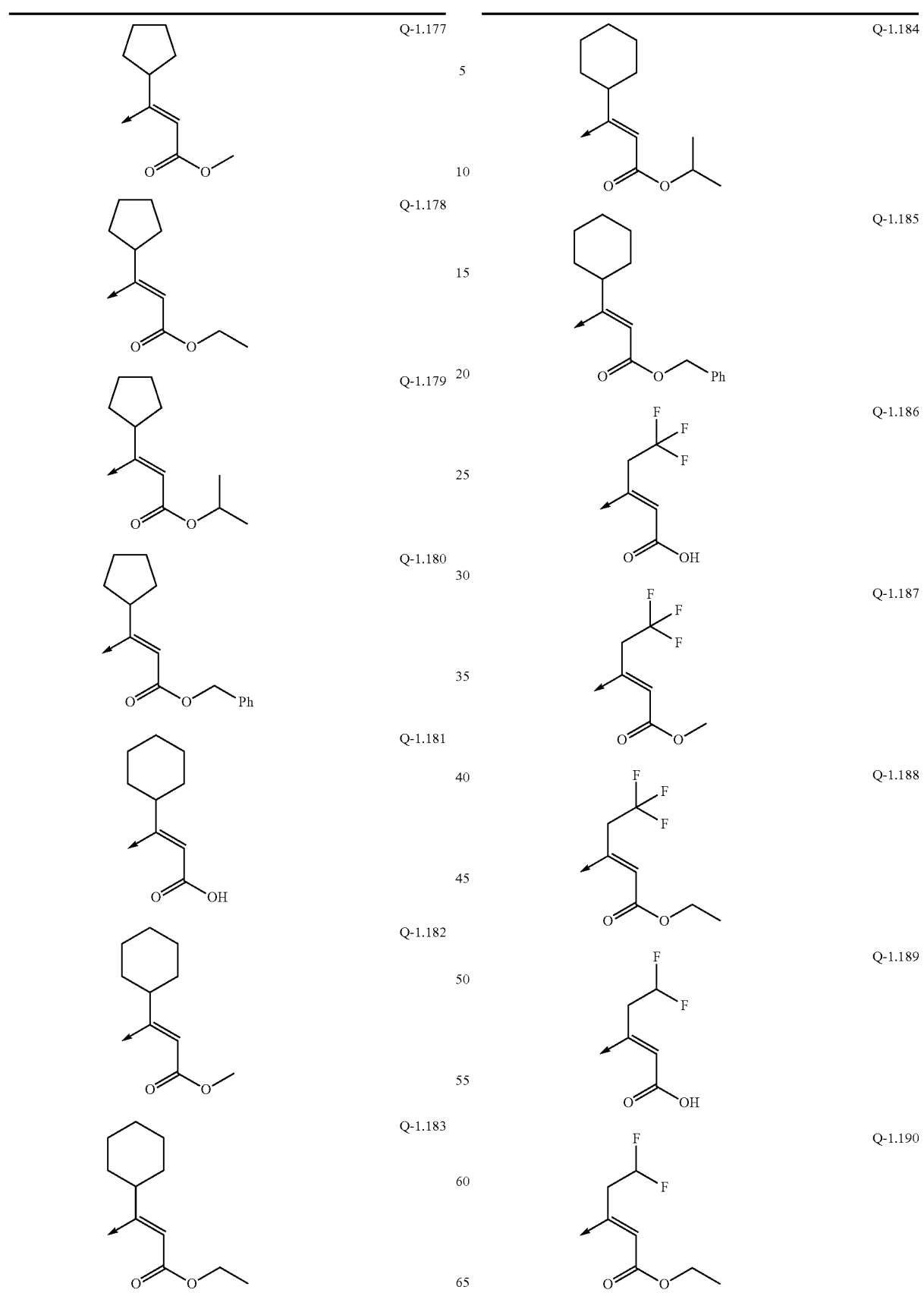

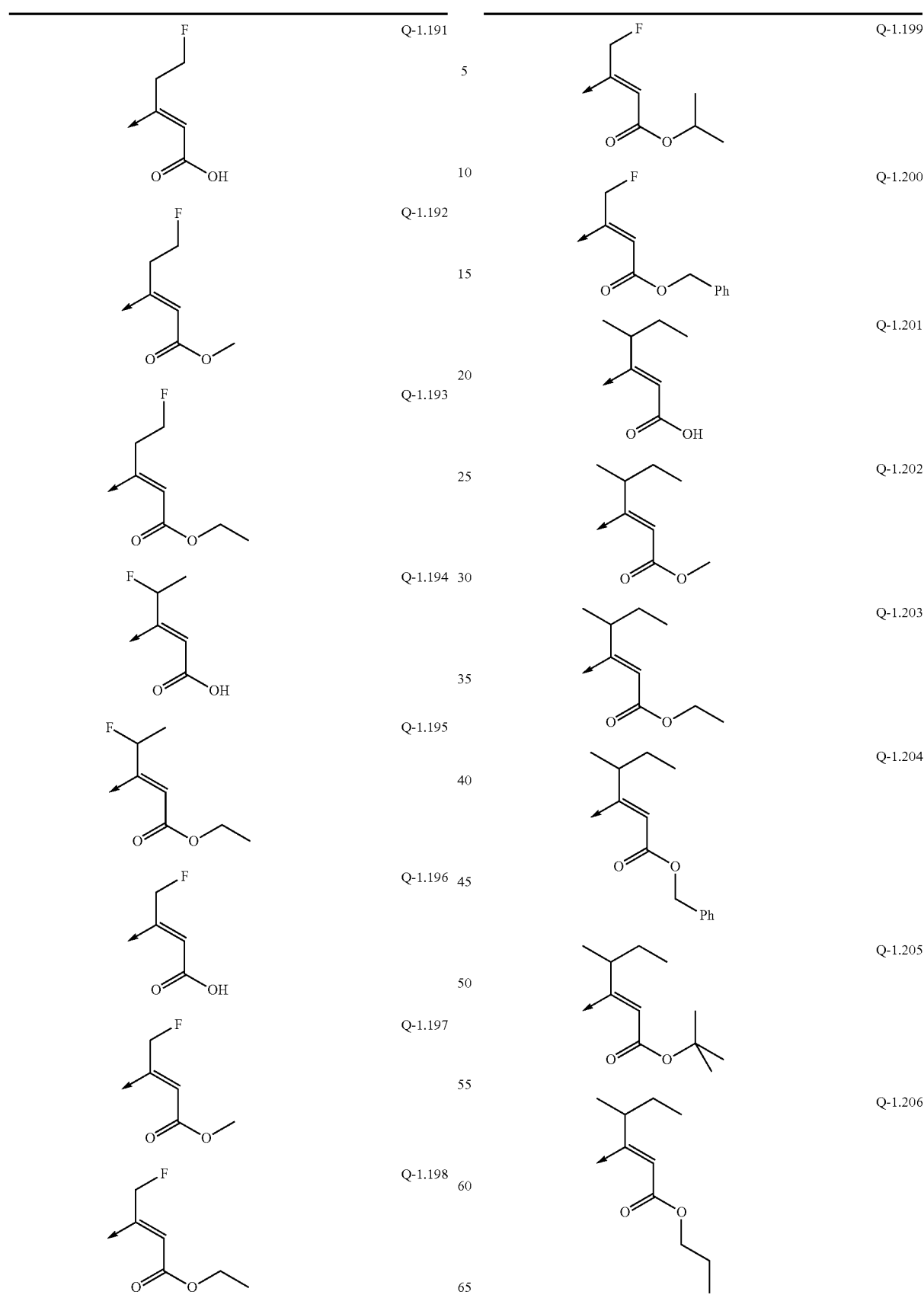

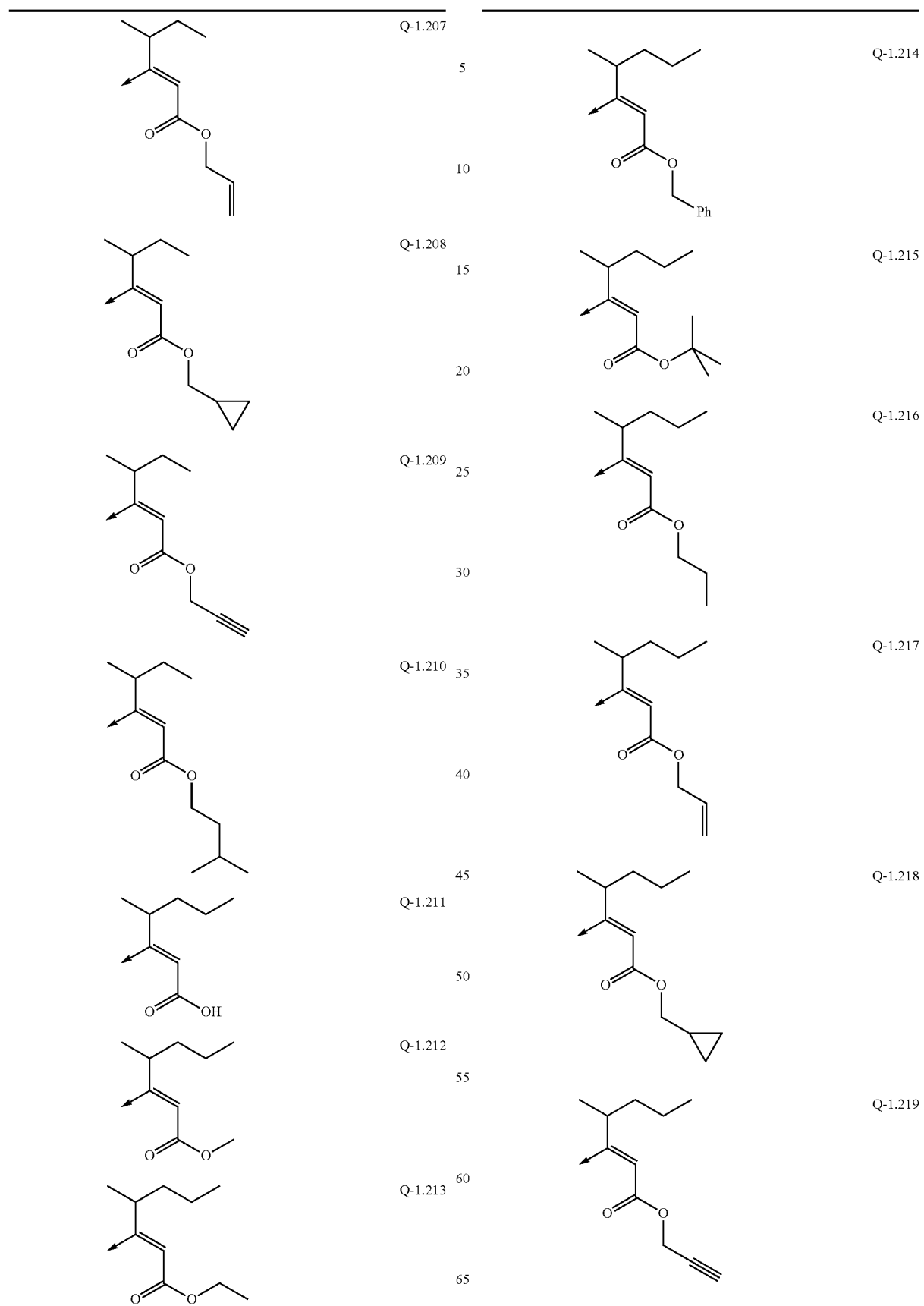

| | |
|---|---|
| 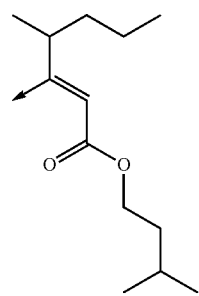 Q-1.220 | 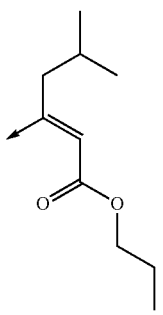 Q-1.226 |
| 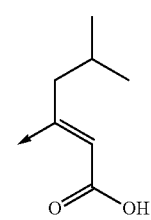 Q-1.221 | 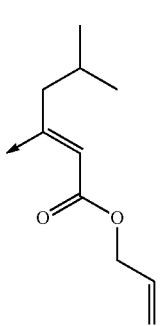 Q-1.227 |
| 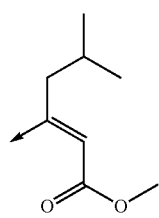 Q-1.222 | 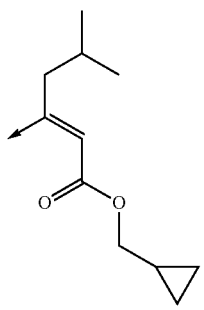 Q-1.228 |
| 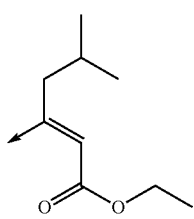 Q-1.223 | 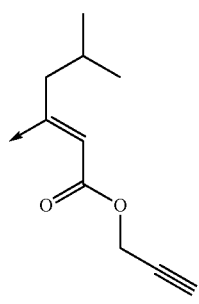 Q-1.229 |
| 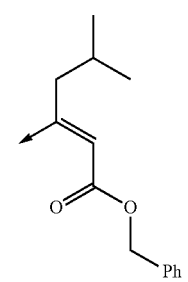 Q-1.224 | 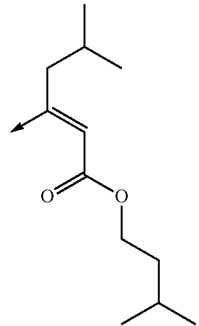 Q-1.230 |
| 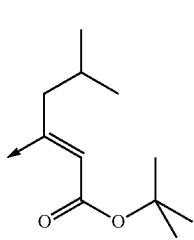 Q-1.225 | |

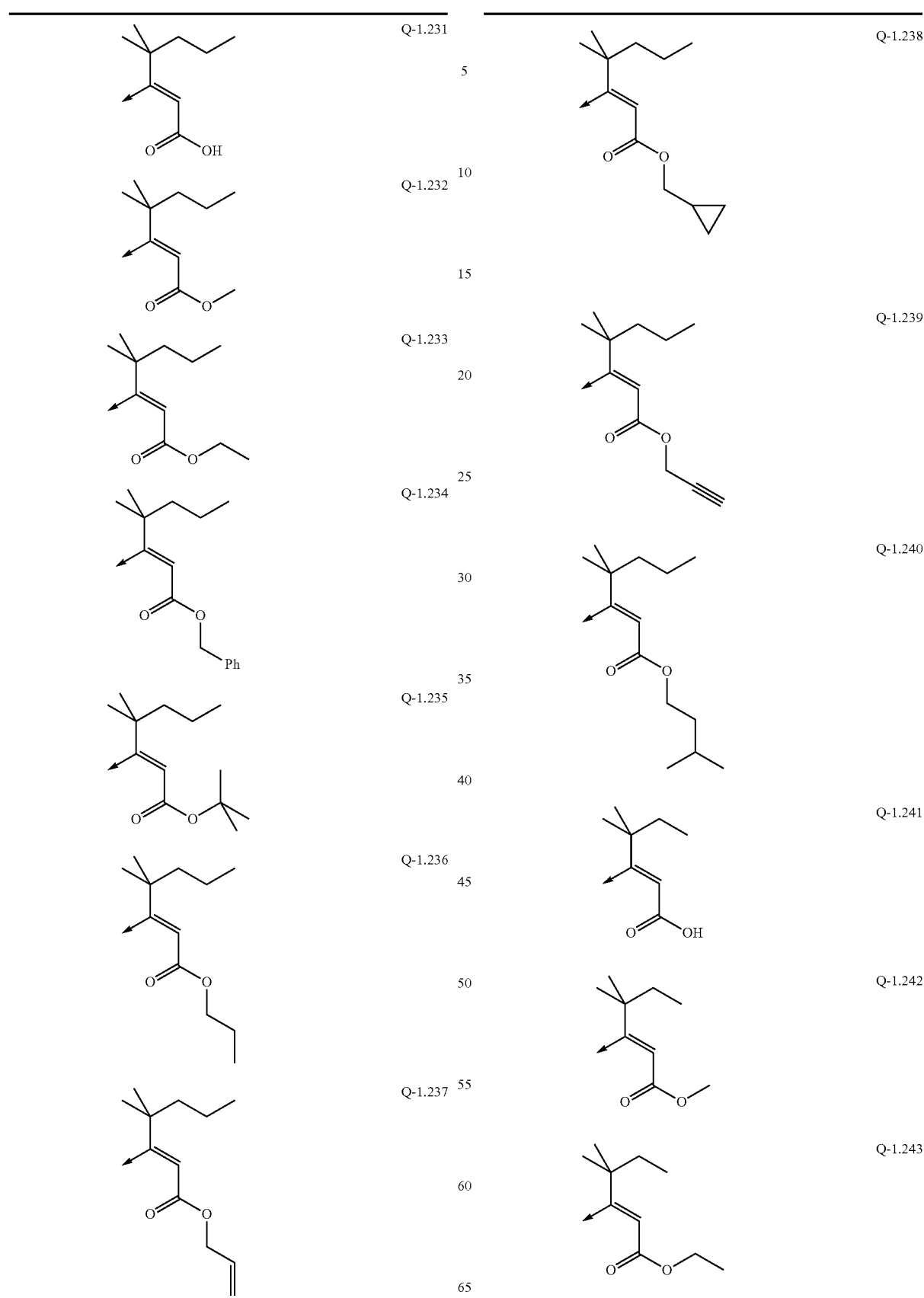

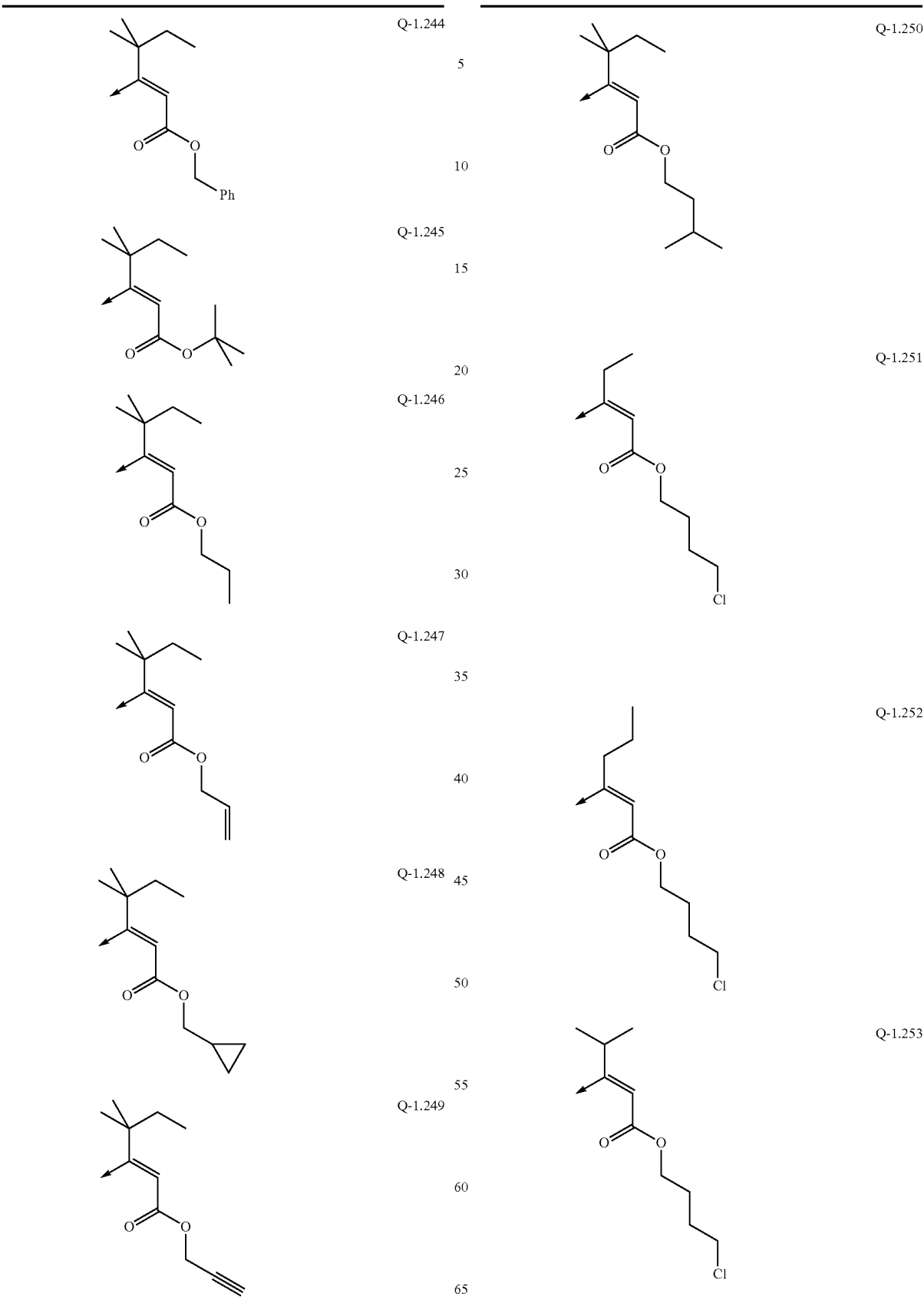

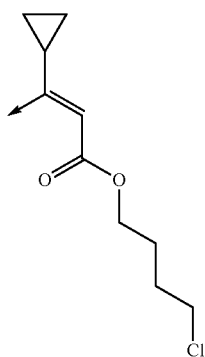
Q-1.254
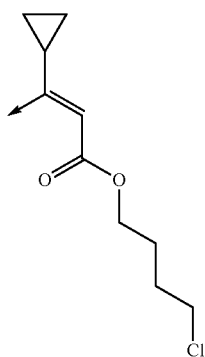
Q-1.255
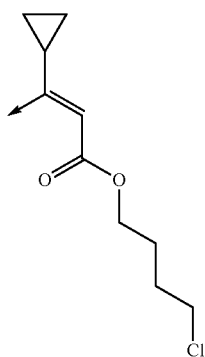
Q-2.1
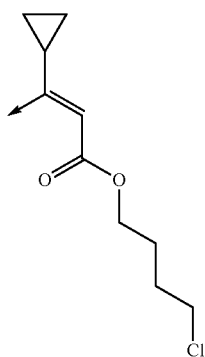
Q-2.2
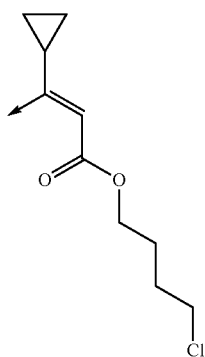
Q-2.3
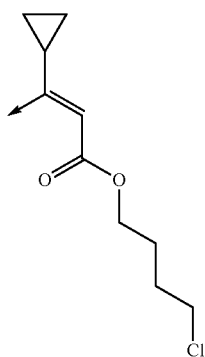
Q-2.4
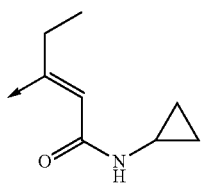
Q-2.5
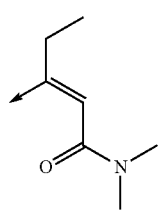
Q-2.6
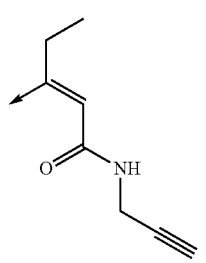
Q-2.7
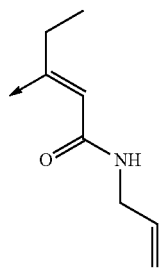
Q-2.8
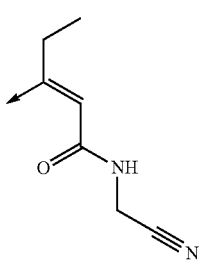
Q-2.9
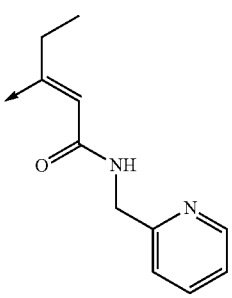
Q-2.10

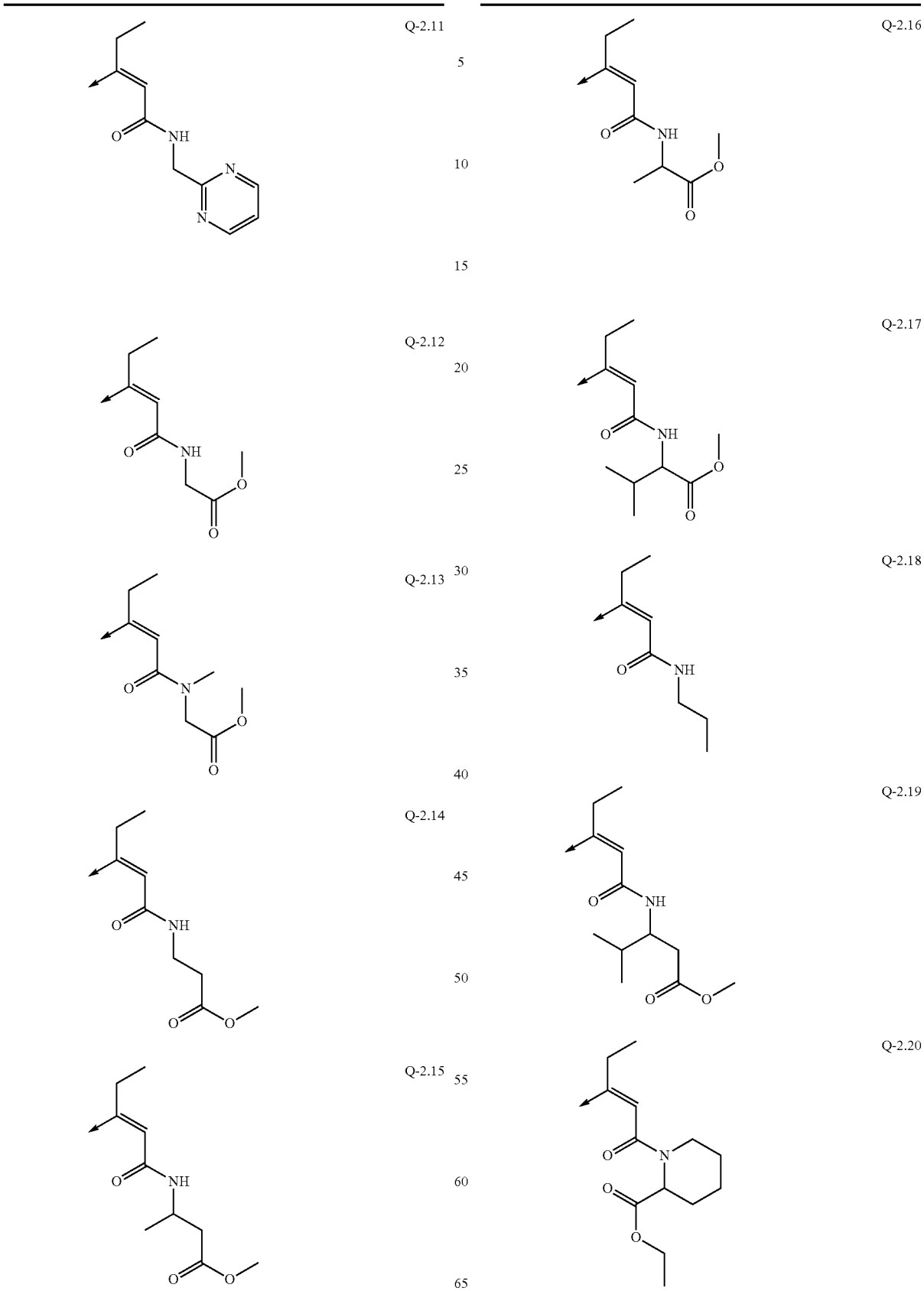

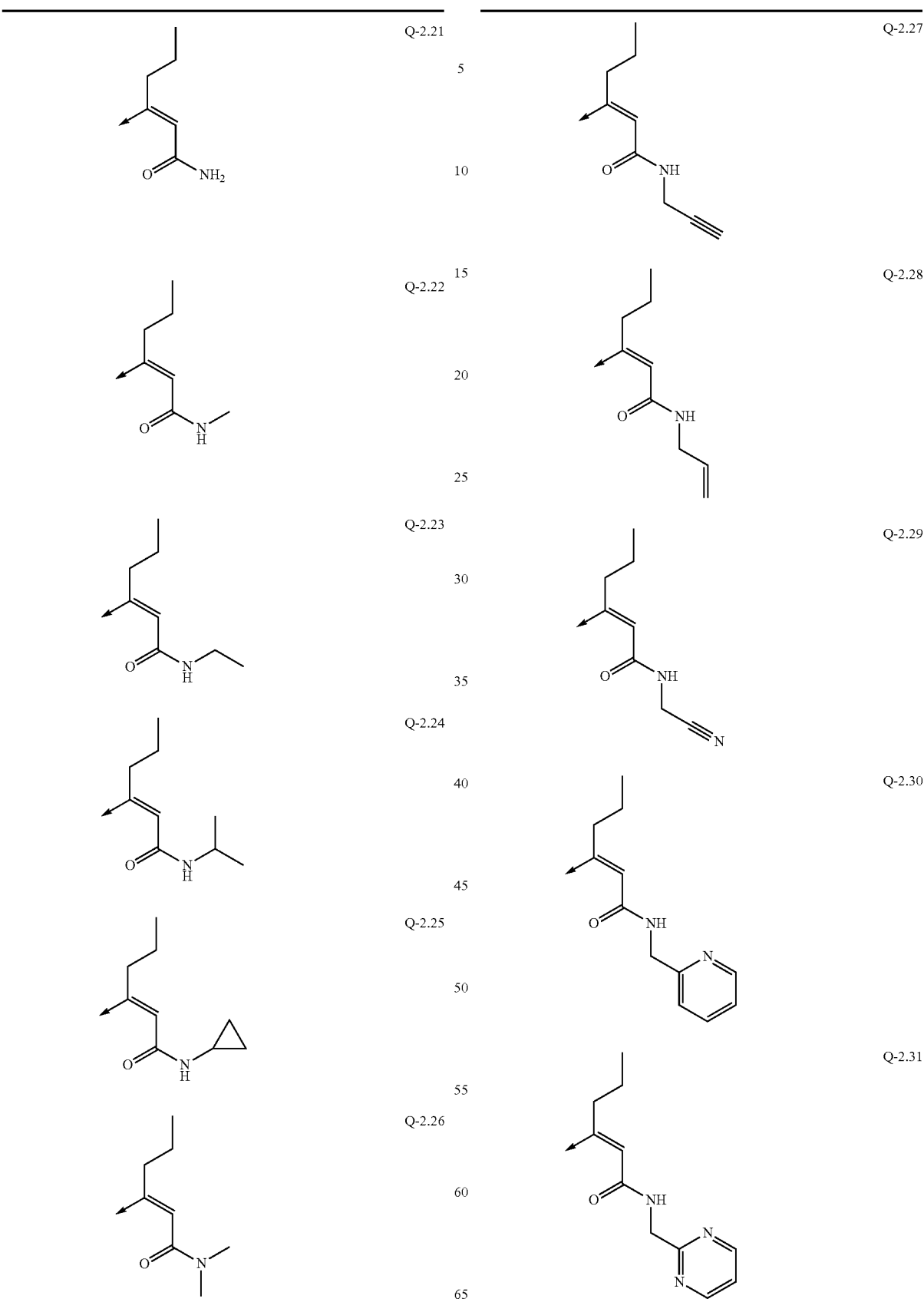

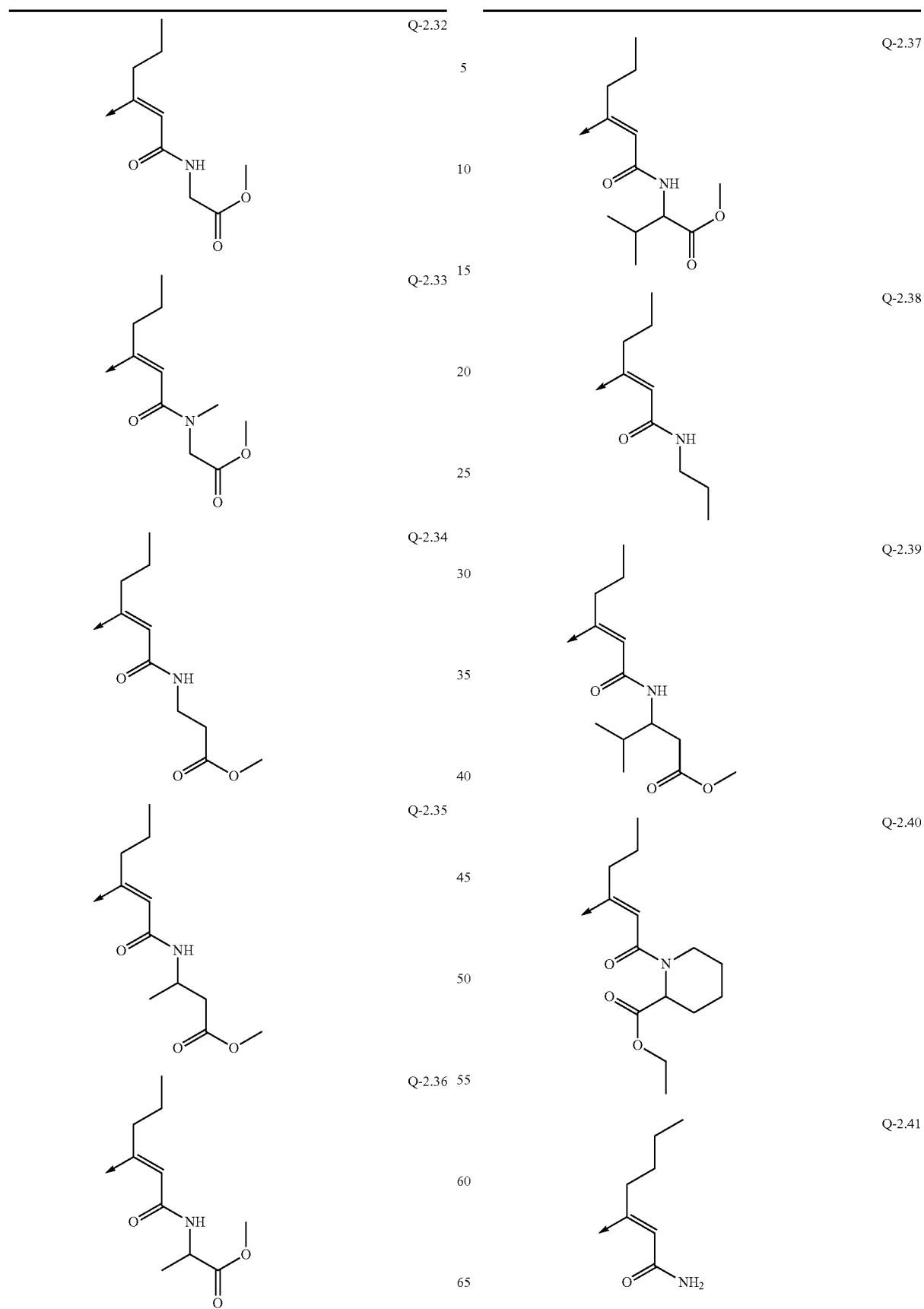

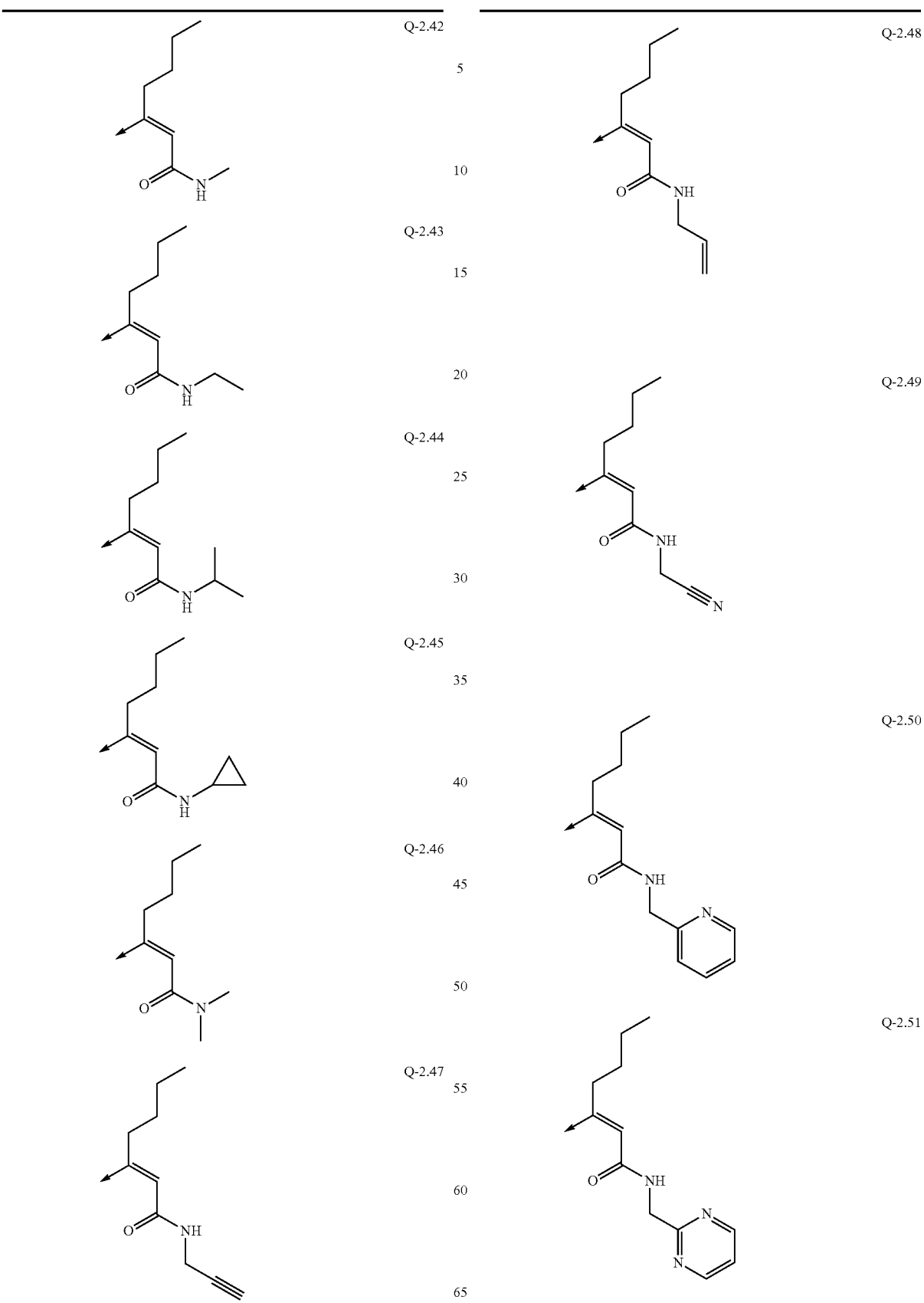

-continued
Q-2.52
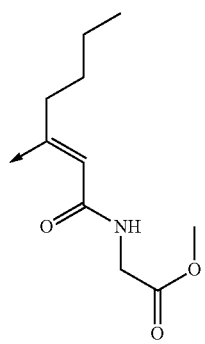
Q-2.53
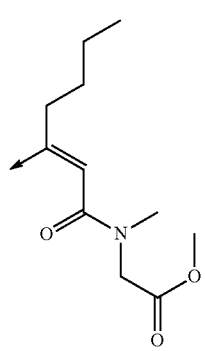
Q-2.54
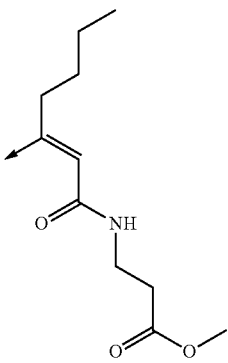
Q-2.55
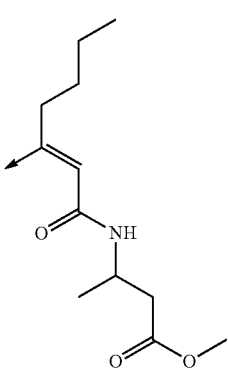
-continued
Q-2.56
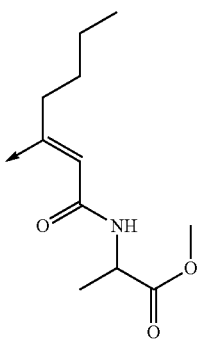
Q-2.57
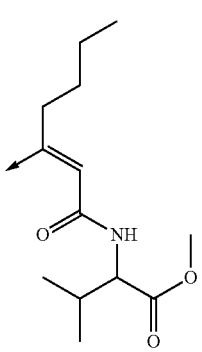
Q-2.58
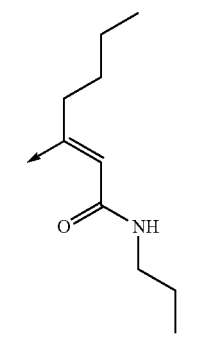
Q-2.59
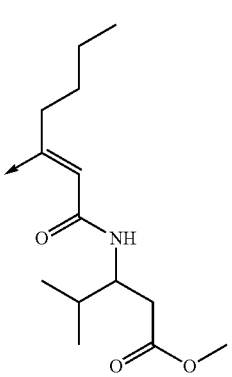

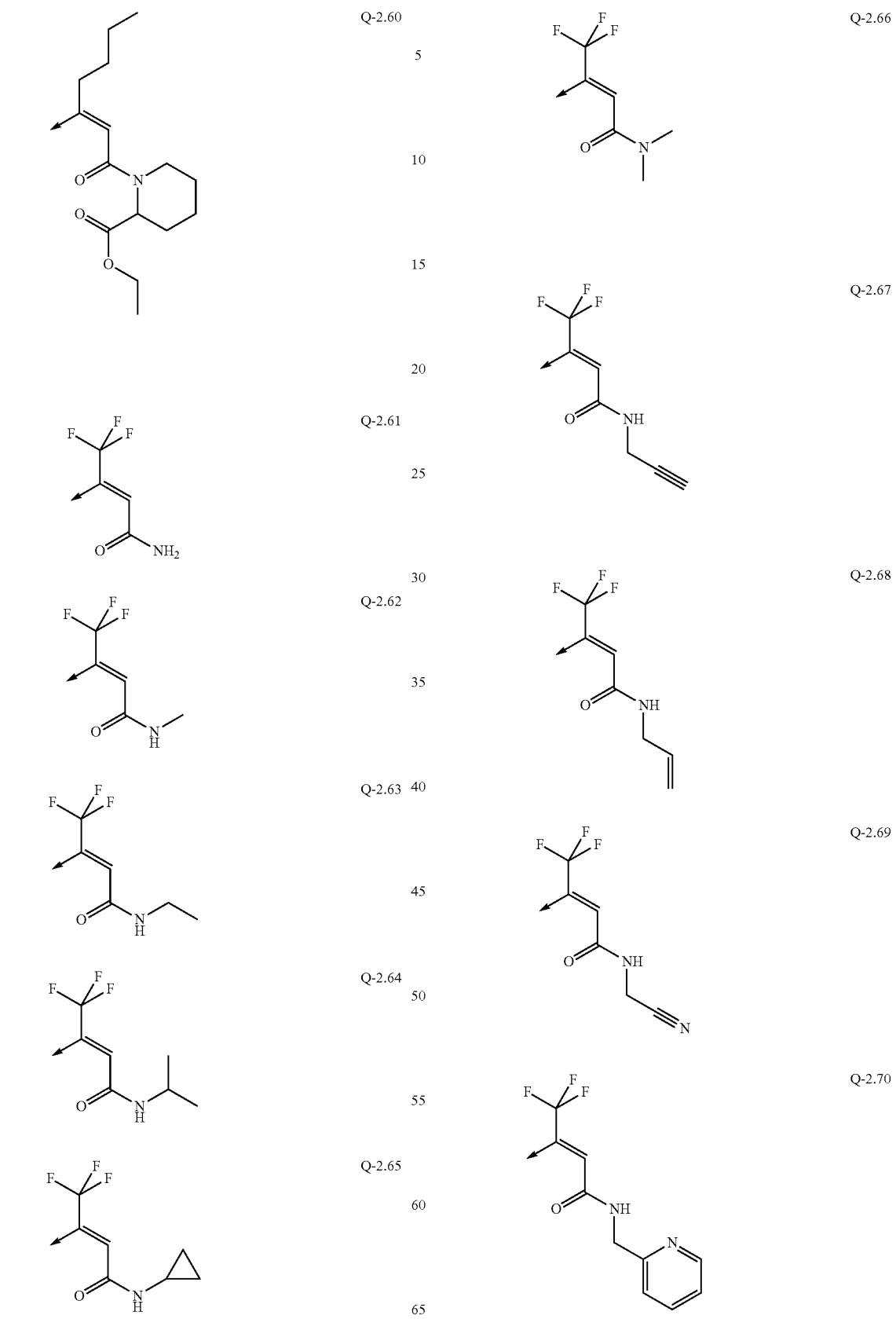

| | |
|---|---|
| 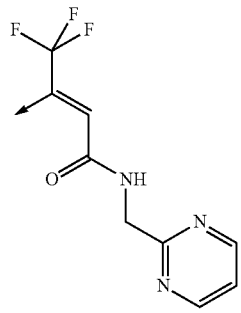 Q-2.71 | 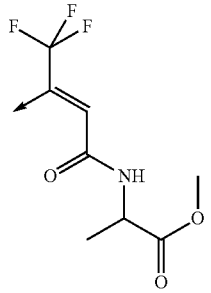 Q-2.76 |
| 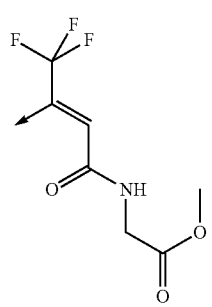 Q-2.72 | 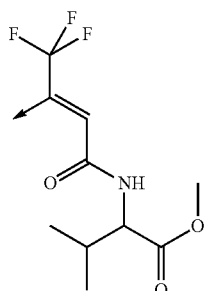 Q-2.77 |
| 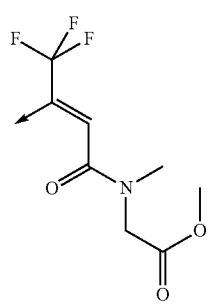 Q-2.73 | 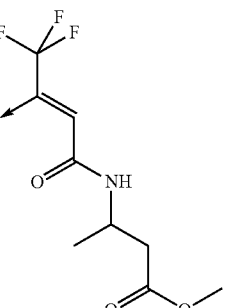 Q-2.78 |
| 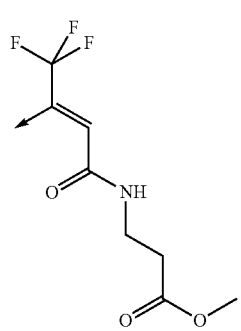 Q-2.74 | 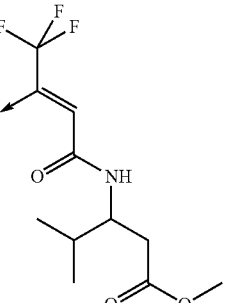 Q-2.79 |
| 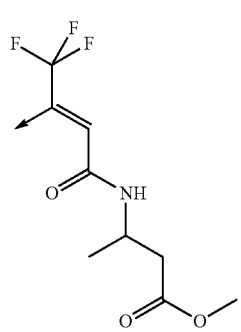 Q-2.75 | 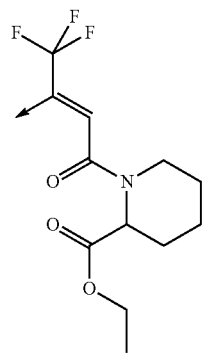 Q-2.80 |

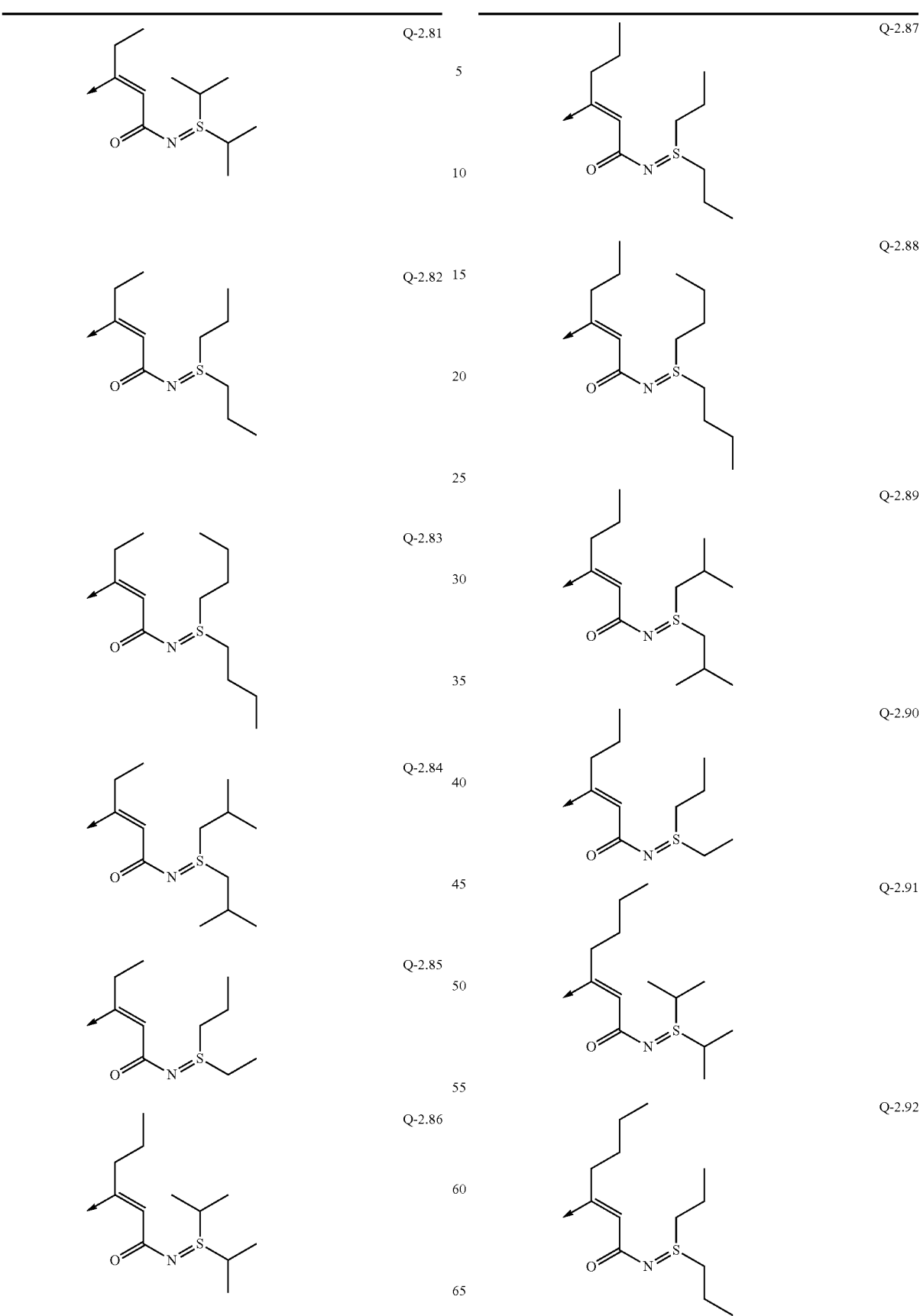

| | |
|---|---|
| 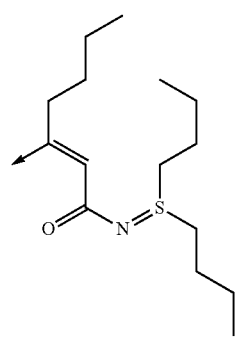 Q-2.93 | 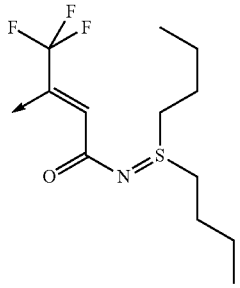 Q-2.98 |
| 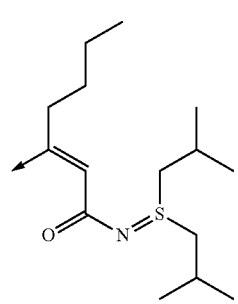 Q-2.94 | 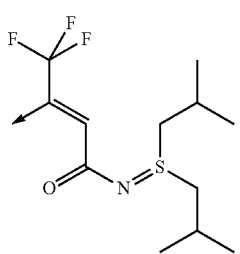 Q-2.99 |
| 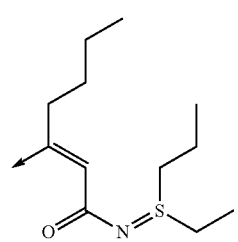 Q-2.95 | 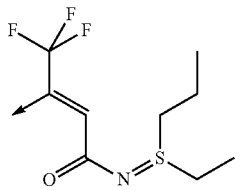 Q-2.100 |
| 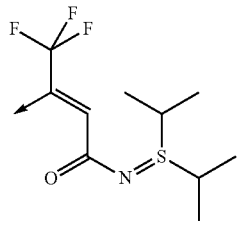 Q-2.96 | 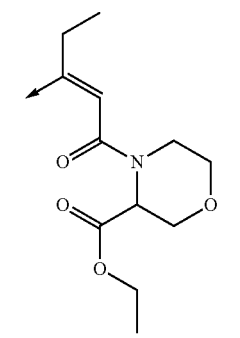 Q-2.101 |
| 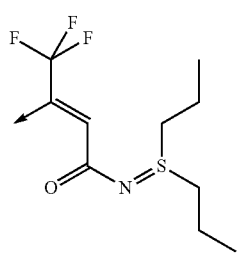 Q-2.97 | 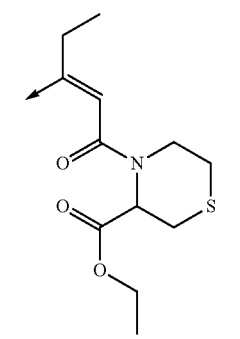 Q-2.102 |

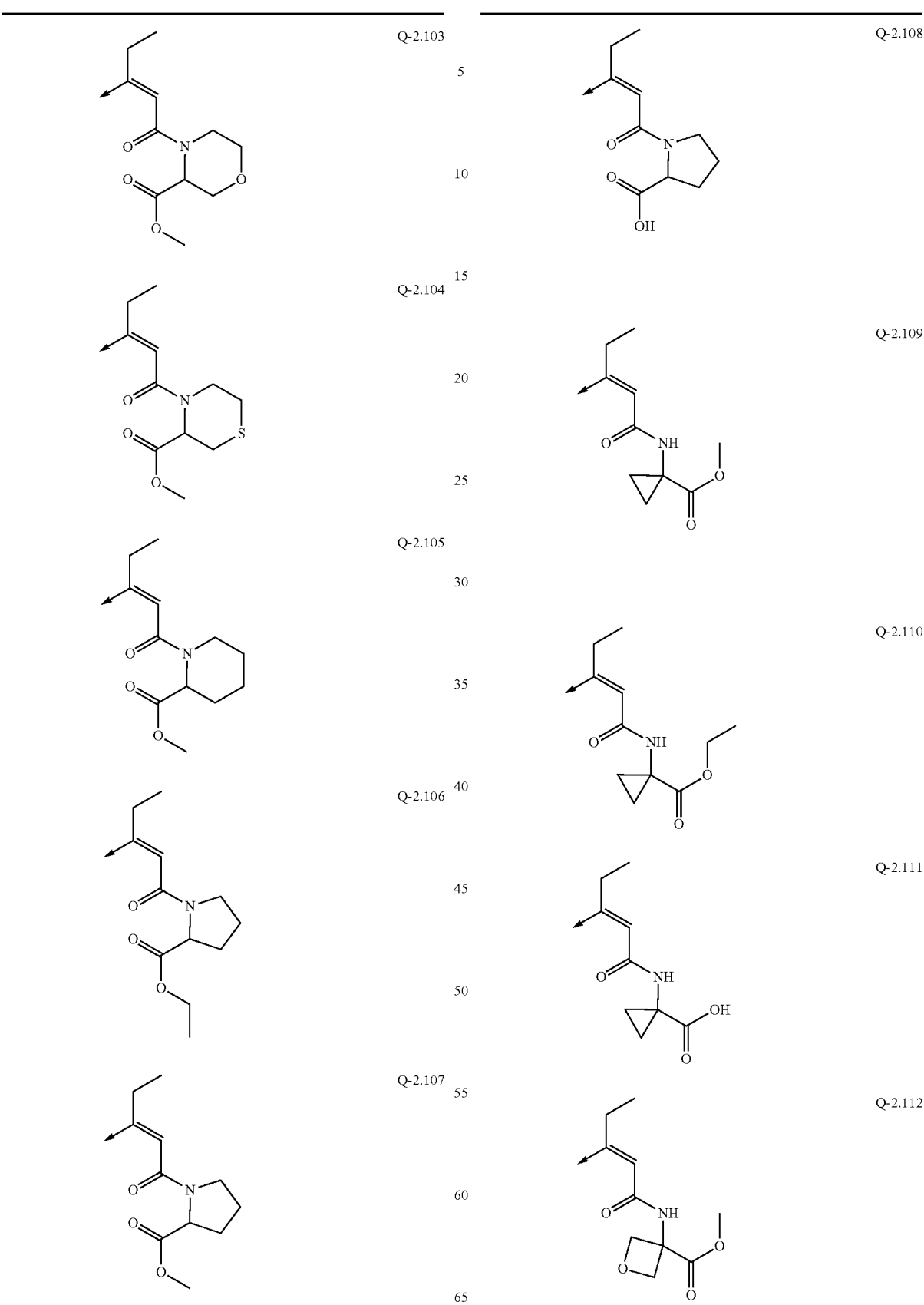

| 83 -continued | 84 -continued |
|---|---|
| 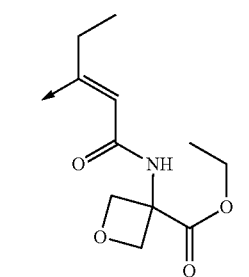 Q-2.113 | 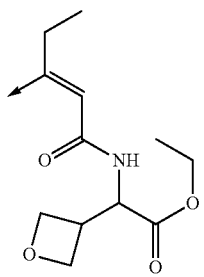 Q-2.118 |
| 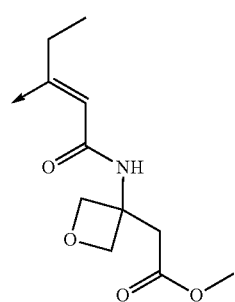 Q-2.114 | 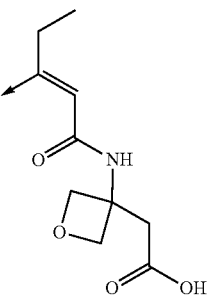 Q-2.119 |
| 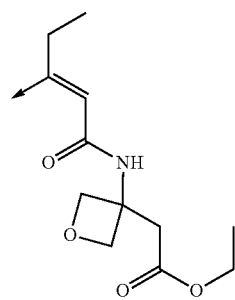 Q-2.115 | 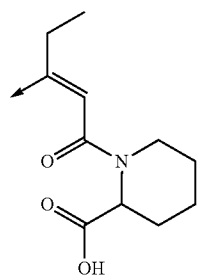 Q-2.120 |
| 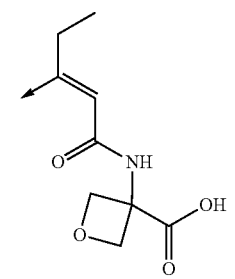 Q-2.116 | 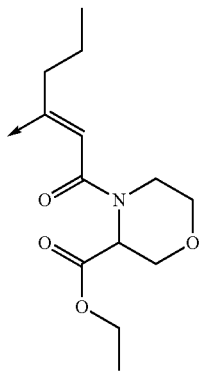 Q-2.121 |
| 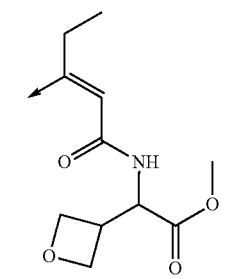 Q-2.117 | 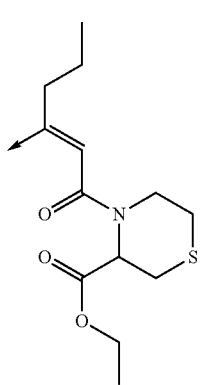 Q-2.122 |

| 85 -continued | 86 -continued |
|---|---|
| 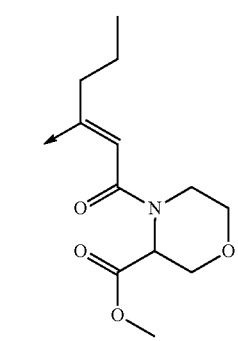 Q-2.123 | 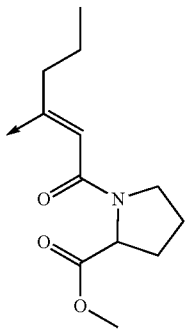 Q-2.127 |
| 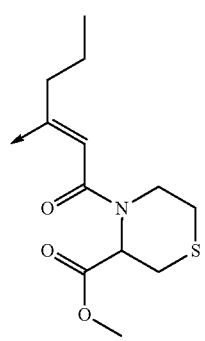 Q-2.124 | 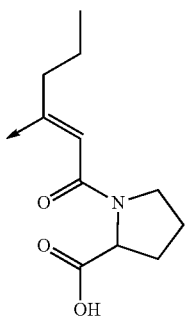 Q-2.128 |
| 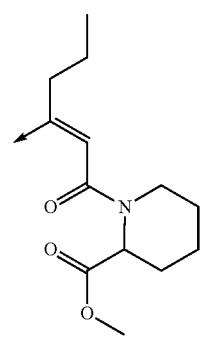 Q-2.125 | 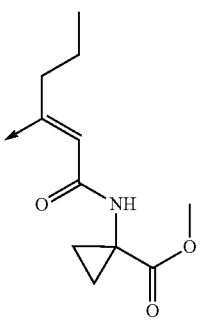 Q-2.129 |
| 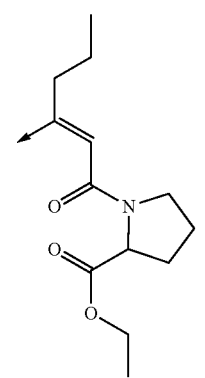 Q-2.126 | 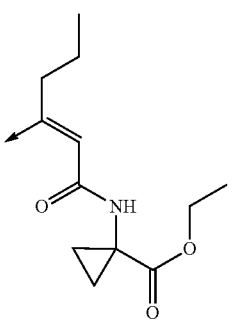 Q-2.130 |
| | 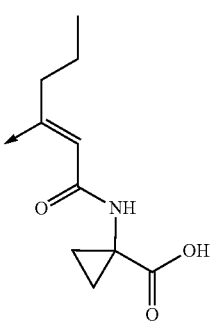 Q-2.131 |

| 87 -continued | | 88 -continued | |
|---|---|---|---|
| 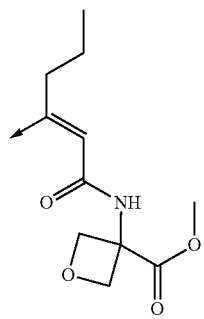 | Q-2.132 | 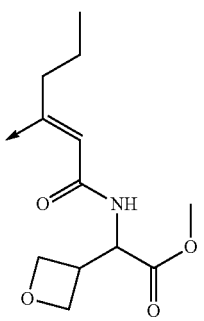 | Q-2.137 |
| 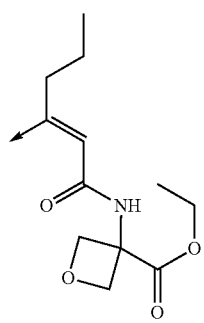 | Q-2.133 | 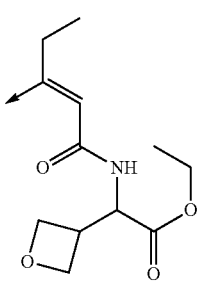 | Q-2.138 |
| 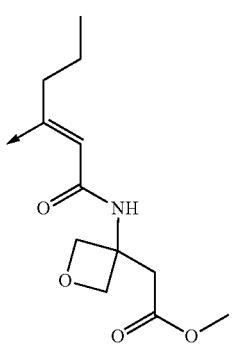 | Q-2.134 | 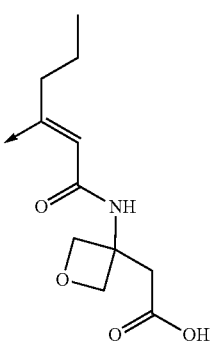 | Q-2.139 |
| 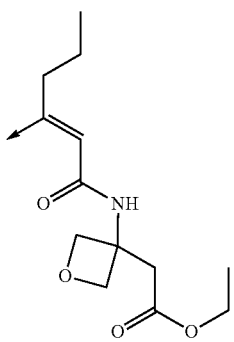 | Q-2.135 | 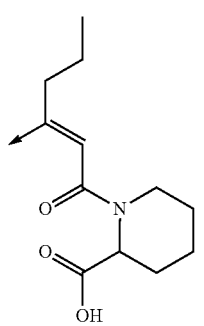 | Q-2.140 |
| 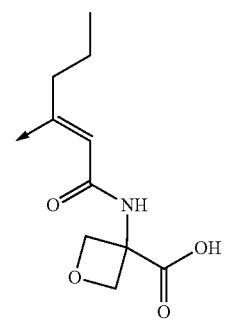 | Q-2.136 | 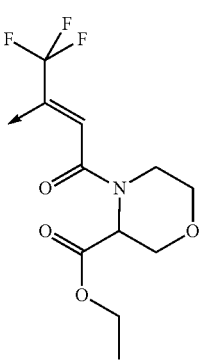 | Q-2.141 |

| | |
|---|---|
| 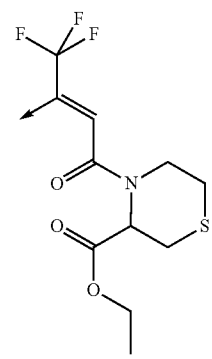 Q-2.142 | 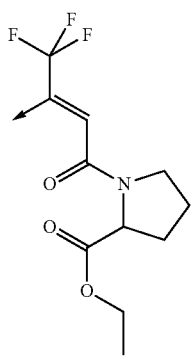 Q-2.146 |
| 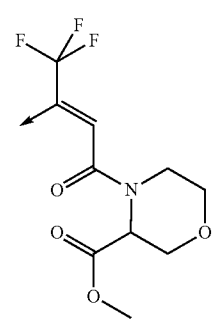 Q-2.143 | 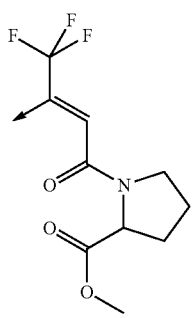 Q-2.147 |
| | 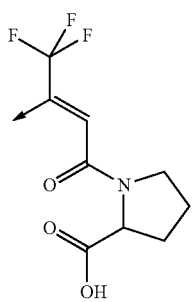 Q-2.148 |
| 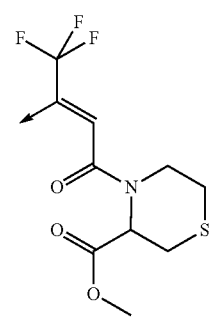 Q-2.144 | 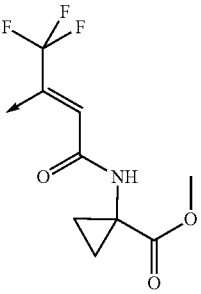 Q-2.149 |
| 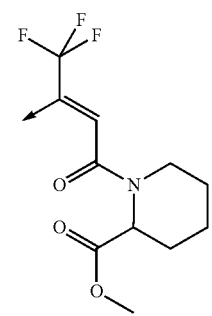 Q-2.145 | 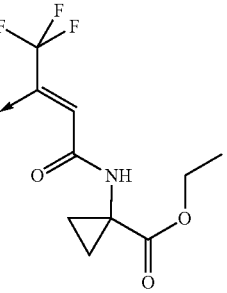 Q-2.150 |

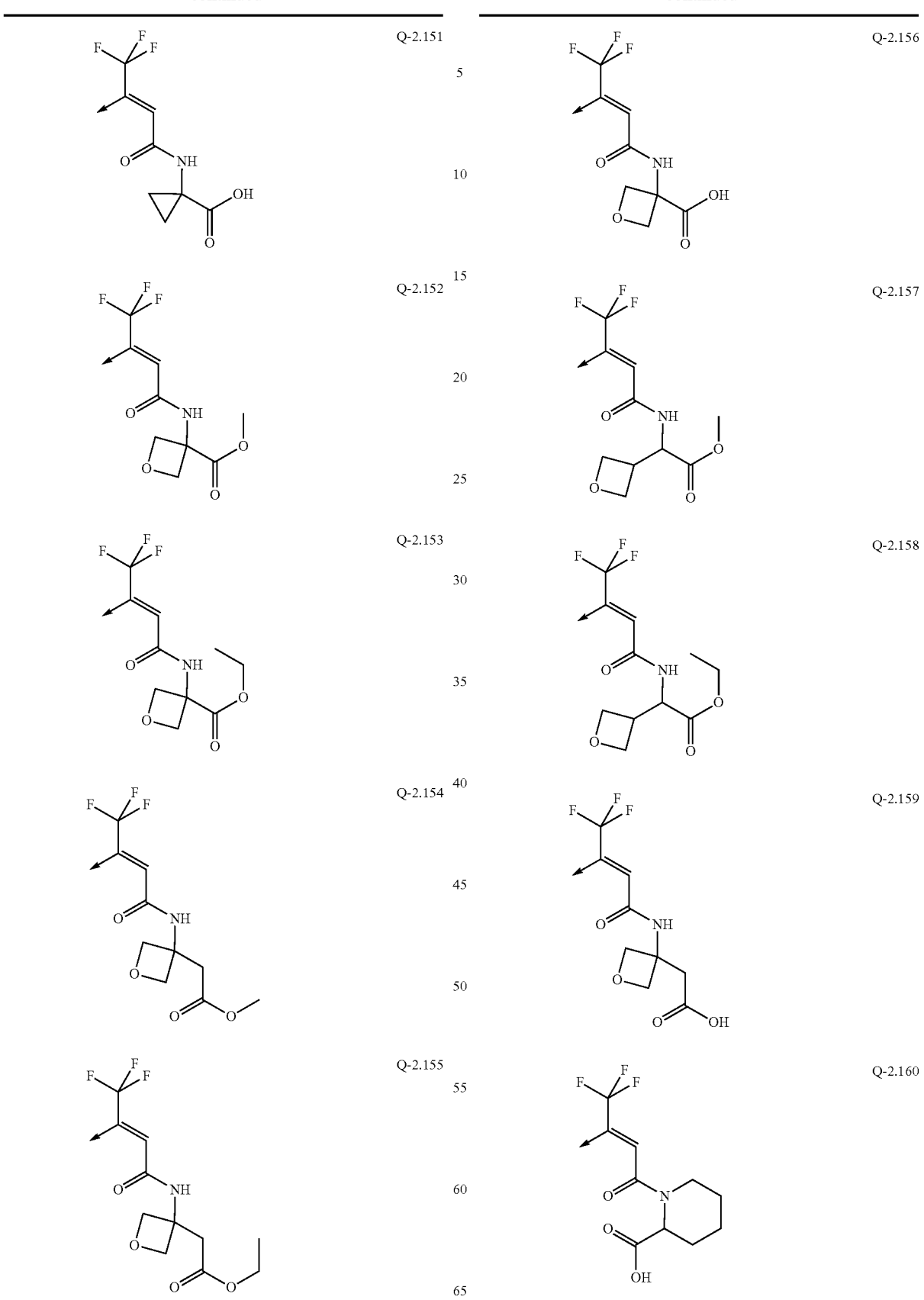

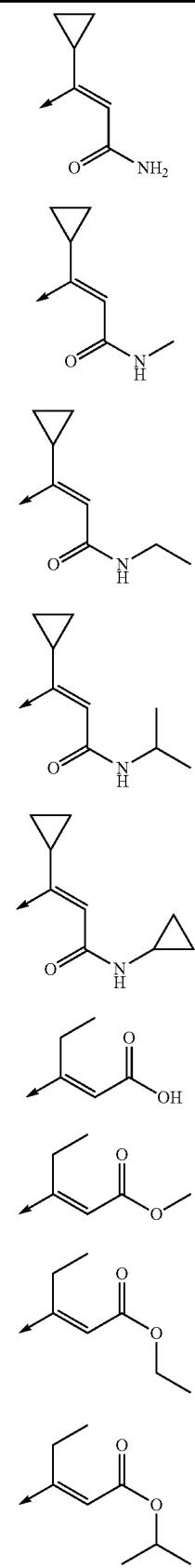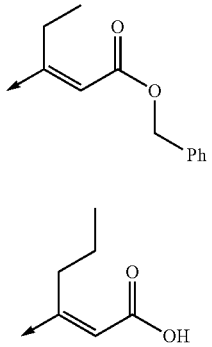

| 95 -continued | | 96 -continued | |
|---|---|---|---|
| 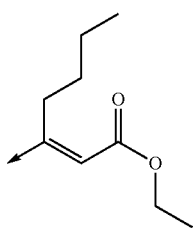 | Q-3.13 | 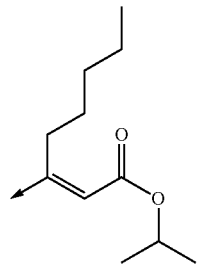 | Q-3.19 |
| 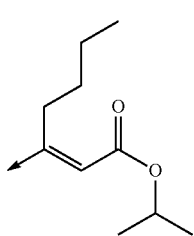 | Q-3.14 | 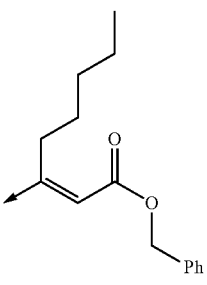 | Q-3.20 |
| 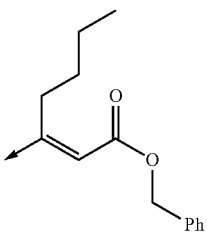 | Q-3.15 | 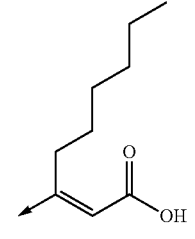 | Q-3.21 |
| 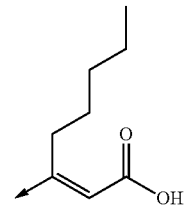 | Q-3.16 | 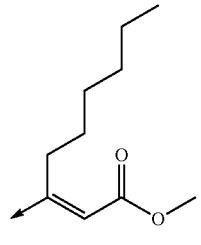 | Q-3.22 |
| 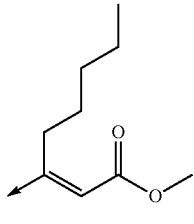 | Q-3.17 | 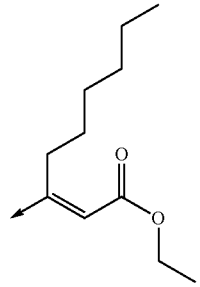 | Q-3.23 |
| 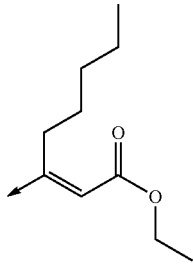 | Q-3.18 | 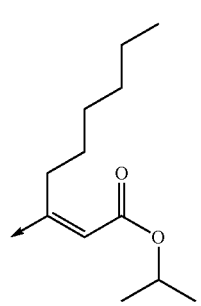 | Q-3.24 |

| 97 -continued | | 98 -continued | |
|---|---|---|---|
| 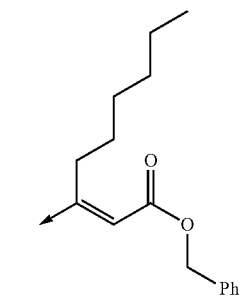 | Q-3.25 | 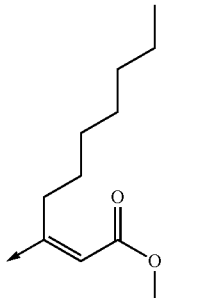 | Q-3.30 |
| 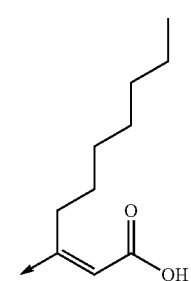 | Q-3.26 | 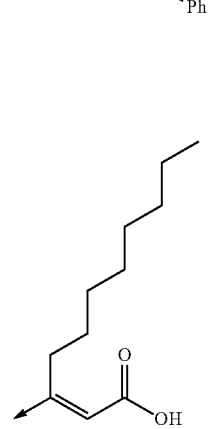 | Q-3.31 |
| 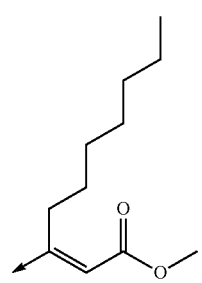 | Q-3.27 | | |
| 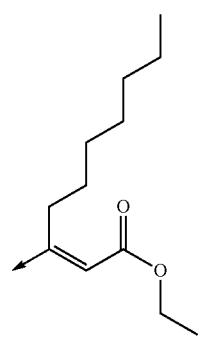 | Q-3.28 | 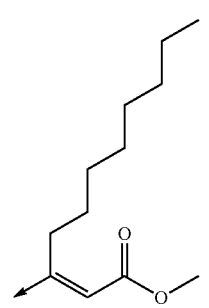 | Q-3.32 |
| 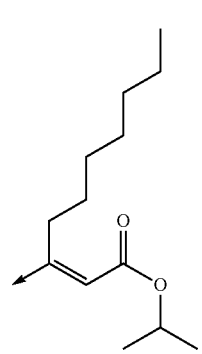 | Q-3.29 | 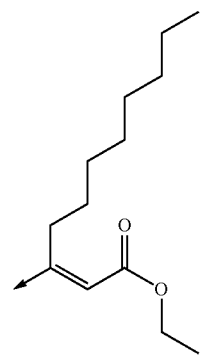 | Q-3.33 |

| | |
|---|---|
| 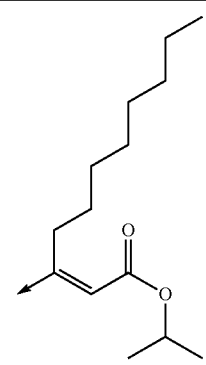 Q-3.34 | 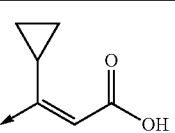 Q-3.41 |
| 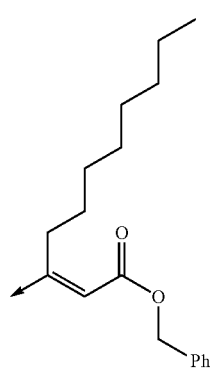 Q-3.35 | 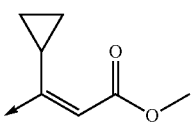 Q-3.42 |
| 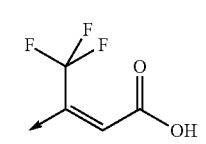 Q-3.36 | 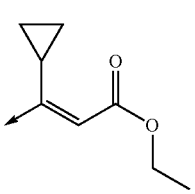 Q-3.43 |
| 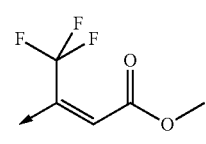 Q-3.37 | 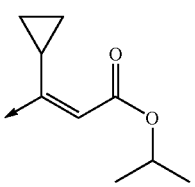 Q-3.44 |
| 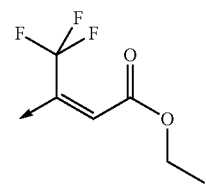 Q-3.38 | 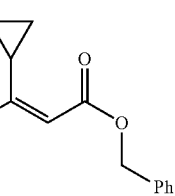 Q-3.45 |
| 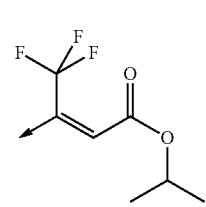 Q-3.39 | |
| 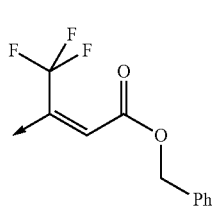 Q-3.40 | |
Specific preference is given to compounds of the formula (I) in which
[X—Y] represents the moieties
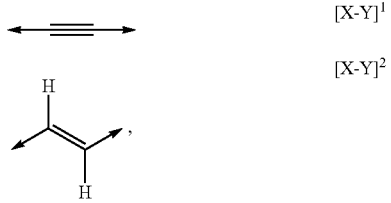
$[X\text{-}Y]^1$
$[X\text{-}Y]^2$
Q represents the moieties Q-1 to Q-3
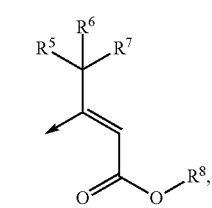 Q-1

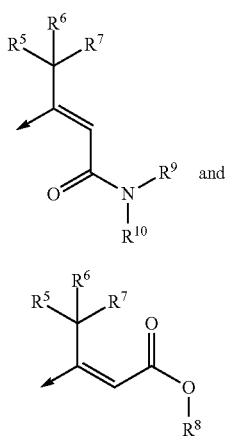

Q-2

Q-3 where $R^5$, $R^6$, $R^7$, $R^8$, $R^9$ and $R^{10}$ are each as defined below and where the arrow represents a bond to the respective [X—Y] grouping;

$R^1$ represents methyl, ethyl, n-propyl, n-butyl, isobutyl, isopropyl, n-pentyl, n-hexyl, isopentyl, cyclopropyl, cyclobutyl, cyclopentyl, 2,2,3,3,3-pentafluoropropyl, 3,3,2,2-tetrafluoropropyl, 4,4,4-trifluorobutyl, 1-fluoroethyl, 2-fluoroethyl, fluoromethyl, difluoromethyl, trifluoromethyl, pentafluoroethyl, heptafluoro-n-propyl, heptafluoroisopropyl, chlorodifluoromethyl, 2,2-difluoroethyl, 2,2,2-trifluoroethyl, 1,1,2,2-tetrafluoroethyl, 1,2,2,2-tetrafluoroethyl, 1,2,2,3,3,3-hexafluoropropyl, 1-methyl-2,2,2-trifluoroethyl, 1-chloro-2,2,2-trifluoroethyl, 1,2,2,3,3,4,4,4-octafluorobutyl, 1-fluoro-1-methylethyl, n-propoxydifluoromethyl, methoxydifluoromethyl, ethoxydifluoromethyl, $R^2$ represents hydrogen, tert-butyldimethylsilyl, trimethylsilyl, triethylsilyl, tri(isopropyl)silyl, tri-(n-propyl)silyl, tert-butyldiphenylsilyl, diethylisopropylsilyl, isopropyldimethylsilyl, tert-hexyldimethylsilyl, 2-(trimethylsilyl)ethoxymethyl, 2-(trimethylsilyl)ethyl, dimethyl(phenyl)silyl, $R^3$ and $R^4$ independently of one another represent methoxy, ethoxy, n-propoxy, n-butyloxy, methylthio, ethylthio, n-propylthio, n-butylthio or together with the atom to which they are attached form an oxo group, hydroxyimino group, methoxyimino, ethoxyimino, n-propoxyimino, isopropyloxyimino, n-butyloxyimino, isobutyloxyimino, cyclopropyloxyimino, cyclobutyloxyimino, cyclopropylmethoxyimino, benzyloxyimino, p-chlorophenylmethoxyimino, p-methylphenylmethoxyimino, p-methoxyphenylmethoxyimino, o-chlorophenylmethoxyimino, m-chlorophenylmethoxyimino or a 5- to 7-membered heterocyclic ring, for example a 1,3-dioxolanyl, 1,3-dioxanyl, 1,3-dithiolanyl, 1,3-dithianyl, 1,3-oxathianyl, 5-alkyl-1,3,5-dithiazinyl, 1,3-oxazolidinyl ring, which may optionally be substituted further by $(C_1-C_6)$-alkyl, $(C_1-C_6)$-alkoxycarbonyl, $(C_3-C_6)$-cycloalkyl, spiro-$(C_3-C_6)$-cycloalkyl, spiro-oxetanyl, $R^5$ and $R^6$ independently of one another represent hydrogen, fluorine, chlorine, bromine, iodine, methyl, ethyl, n-propyl, n-butyl, isobutyl, isopropyl, n-pentyl, n-hexyl, isopentyl, trifluoromethyl, pentafluoroethyl, heptafluoropropyl, nonafluorobutyl, chlorodifluoromethyl, 1-fluoroethyl, 2-fluoroethyl, fluoromethyl, difluoromethyl, 2,2-difluoroethyl, 2,2,2-trifluoroethyl, 2,2-dichloro-2-fluoroethyl, 2-chloro-2,2-difluoroethyl, difluoro-tert-butyl, $R^7$ represents fluorine, chlorine, bromine, iodine, $(C_1-C_8)$-alkyl, $(C_1-C_7)$-haloalkyl, $(C_1-C_7)$-haloalkoxy-$(C_1-C_7)$-alkyl, $(C_1-C_7)$-haloalkoxy-$(C_1-C_7)$-haloalkyl, $(C_1-C_6)$-alkoxy-$(C_1-C_6)$-haloalkyl, $(C_3-C_6)$-cycloalkyl, $(C_3-C_6)$-cyclohaloalkyl, $R^6$ and $R^7$ with the atoms to which they are bonded form a fully saturated 3- to 6-membered ring optionally interrupted by heteroatoms and optionally with further substitution, $R^8$ represents hydrogen, $(C_1-C_4)$-alkyl, $(C_1-C_4)$-alkoxy-$(C_1-C_4)$-alkyl, $(C_3-C_6)$-cycloalkyl, $(C_3-C_6)$-cycloalkyl-$(C_1-C_4)$-alkyl, optionally substituted phenyl, aryl-$(C_1-C_4)$-alkyl, heteroaryl-$(C_1-C_4)$-alkyl, $(C_2-C_6)$-alkenyl, $(C_2-C_4)$-alkynyl-$(C_1-C_4)$-alkyl, $(C_1-C_4)$-haloalkyl, $R^9$ represents hydrogen, $(C_1-C_4)$-alkyl, $(C_3-C_6)$-cycloalkyl, chlorine, $(C_2-C_6)$-alkenyl-$(C_1-C_4)$-alkyl, $(C_2-C_6)$-alkynyl-$(C_1-C_4)$-alkyl, $(C_1-C_4)$-haloalkyl, $(C_2-C_6)$-alkynyl, $(C_2-C_6)$-alkenyl, cyano-$(C_1-C_4)$-alkyl, $(C_3-C_6)$-cycloalkyl-$(C_1-C_4)$-alkyl, aryl-$(C_1-C_4)$-alkyl, heteroaryl-$(C_1-C_4)$-alkyl, $(C_1-C_4)$-alkylcarbonyl, $(C_1-C_4)$-alkoxycarbonyl, $(C_1-C_4)$-alkoxycarbonyl-$(C_1-C_4)$-alkyl, hydroxycarbonyl-$(C_1-C_4)$-alkyl, aryl-$(C_1-C_4)$-alkoxycarbonyl-$(C_1-C_4)$-alkyl, $(C_3-C_6)$-cycloalkyl-$(C_1-C_4)$-alkoxycarbonyl-$(C_1-C_4)$-alkyl, $(C_1-C_4)$-alkoxycarbonyl-$(C_3-C_6)$-cycloalkyl, hydroxycarbonyl-$(C_3-C_6)$-cycloalkyl, aryl-$(C_1-C_4)$-alkoxycarbonyl-$(C_3-C_6)$-cycloalkyl, $(C_2-C_6)$-alkenyloxycarbonyl-$(C_3-C_6)$-cycloalkyl, $(C_1-C_6)$-alkoxycarbonyl-$(C_4-C_6)$-cycloalkenyl, hydroxycarbonyl-$(C_4-C_6)$-cycloalkenyl, hydroxycarbonylheterocyclyl, $(C_1-C_4)$-alkoxycarbonylheterocyclyl, hydroxycarbonylheterocyclyl-$(C_1-C_4)$-alkyl, $(C_1-C_4)$-alkoxycarbonylheterocyclyl-$(C_1-C_4)$-alkyl, hydroxycarbonyl-$(C_3-C_6)$-cycloalkyl-$(C_1-C_4)$-alkyl, $(C_1-C_4)$-alkoxycarbonyl-$(C_3-C_6)$-cycloalkyl-$(C_1-C_6)$-alkyl, hydroxy, $(C_1-C_6)$-alkoxy, $R^{10}$ represents hydrogen, $(C_1-C_6)$-alkyl, $(C_3-C_6)$-cycloalkyl, $R^9$ and $R^{10}$ with the nitrogen to which they are attached form an optionally fluorine-, chlorine-, bromine-, iodine-, $(C_1-C_4)$-alkyl-, $(C_1-C_4)$-haloalkyl-, $(C_1-C_4)$-alkoxy-, $(C_1-C_4)$-alkoxycarbonyl-, $(C_3-C_6)$-cycloalkoxycarbonyl-, $(C_3-C_6)$-cycloalkyl-$(C_1-C_4)$-alkoxycarbonyl-, $(C_2-C_6)$-alkenyloxycarbonyl-, hydroxycarbonyl-, aminocarbonyl-, $(C_1-C_4)$-alkylaminocarbonyl-, $(C_3-C_6)$-cycloalkylaminocarbonyl-, aryl-$(C_1-C_4)$-alkylaminocarbonyl-substituted three- to seven-membered ring which is optionally interrupted by O, S or N or $R^9$ and $R^{10}$ together represent N-(di-n-butylsulfanylidene), N-(diisopropylsulfanylidene), N-(di-n-propylsulfanylidene), N-(di-n-pentylsulfanylidene), N-(diisobutylsulfanylidene), N-(cyclobutylisopropylsulfanylidene), N-(n-propylisopropylsulfanylidene), N-(cyclopropylisopropylsulfanylidene), N-(isobutylisopropylsulfanylidene), N,N-dimethylformylidene and Q additionally represents one of the Q-1.1 to Q-3.45 moieties described in the above-mentioned table.

The definitions of radicals stated above in general terms or in areas of preference apply both to the end products of the formula (I) and correspondingly to the starting materials or intermediates required in each case for preparation thereof. These radical definitions can be combined with one another as desired, i.e. including combinations between the given preferred ranges.

Likewise as yet unknown and thus forming a further part of the invention are compounds of the formula (II) or salts thereof

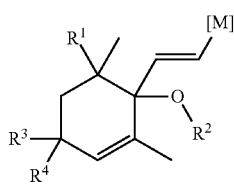

(II)

which serve as intermediates for preparation of the compounds of the formula (I) according to the invention,
where
$R^1$ represents $(C_1-C_8)$-alkyl, $(C_2-C_8)$-alkenyl, $(C_2-C_8)$-alkynyl, $(C_2-C_8)$-alkenyl-$(C_1-C_8)$-alkyl, $(C_2-C_8)$-alkynyl-$(C_1-C_8)$-alkyl, $(C_1-C_8)$-alkoxy-$(C_1-C_8)$-alkyl, hydroxy-$(C_1-C_8)$-alkyl, $(C_1-C_8)$-haloalkyl, $(C_2-C_8)$-haloalkenyl, $(C_2-C_8)$-haloalkynyl, $(C_1-C_8)$-haloalkoxy-$(C_1-C_8)$-alkyl, $(C_3-C_8)$-cycloalkyl, $(C_1-C_8)$-alkoxy-$(C_1-C_8)$-haloalkyl, $(C_1-C_8)$-haloalkoxy-$(C_1-C_8)$-haloalkyl, $(C_1-C_8)$-alkylthio-$(C_1-C_8)$-alkyl, $R^2$ represents hydrogen, $(C_1-C_8)$-alkyl, $(C_2-C_8)$-alkenyl, $(C_2-C_8)$-alkenyl-$(C_1-C_8)$-alkyl, $(C_1-C_8)$-alkoxy-$(C_1-C_8)$-alkyl, $(C_1-C_8)$-alkylcarbonyl, arylcarbonyl, heteroarylcarbonyl, $(C_3-C_8)$-cycloalkylcarbonyl, $(C_1-C_8)$-alkoxycarbonyl, $(C_2-C_8)$-alkenyloxycarbonyl, aryl-$(C_1-C_8)$-alkoxycarbonyl, aryl-$(C_1-C_8)$-alkoxy-$(C_1-C_8)$-alkyl, aryloxy-$(C_1-C_8)$-alkyl, aryl-$(C_1-C_8)$-alkyl, $(C_1-C_8)$-alkoxy-$(C_1-C_8)$-alkoxy-$(C_1-C_8)$-alkyl, $(C_1-C_8)$-alkylthio-$(C_1-C_8)$-alkyl, tri-$(C_1-C_8)$-alkylsilyl, $(C_1-C_8)$-alkyl-(bis-$(C_1-C_8)$-alkyl)silyl, $(C_1-C_8)$-alkyl(bisaryl)silyl, aryl(bis-$(C_1-C_8)$-alkyl)silyl, $(C_3-C_8)$-cycloalkyl(bis-$(C_1-C_6)$-alkyl)silyl, halo(bis-$(C_1-C_8)$-alkyl)silyl, tri-$(C_1-C_8)$-alkylsilyl-$(C_1-C_8)$-alkoxy-$(C_1-C_8)$-alkyl, tri-$(C_1-C_8)$-alkylsilyl-$(C_1-C_8)$-alkyl, $R^3$ and $R^4$ independently of one another represent $(C_1-C_8)$-alkoxy, $(C_1-C_8)$-alkoxy-$(C_1-C_8)$-alkoxy, $(C_3-C_8)$-cycloalkyl-$(C_1-C_8)$-alkoxy, $(C_1-C_8)$-haloalkoxy, $(C_1-C_8)$-alkylthio, $(C_1-C_8)$-haloalkylthio, aryl-$(C_1-C_8)$-alkoxy, aryl-$(C_1-C_8)$-alkylthio or together with the atom to which they are attached form an oxo group or a 5- to 7-membered heterocyclic ring, for example a 1,3-dioxolanyl, 1,3-dioxanyl, 1,3-dithiolanyl, 1,3-dithianyl, 1,3-oxathianyl, 5-alkyl-1,3,5-dithiazinyl, 1,3-oxazolidinyl ring, which may optionally be substituted further by $(C_1-C_6)$-alkyl, $(C_1-C_6)$-alkoxycarbonyl, $(C_3-C_6)$-cycloalkyl, spiro-$(C_3-C_6)$-cycloalkyl, spiro-oxetanyl and

[M] represents tris-[$(C_1-C_6)$-alkyl]stannyl, tris-[$(C_3-C_8)$-cycloalkyl]stannyl, tris-[$(C_1-C_8)$-alkyl]germanyl, tris-[$(C_3-C_8)$-cycloalkyl]germanyl, bis-(cyclopentadienyl)zirconyl, bis-(1,2,3,4,5-pentamethylcyclopentadienyl)zirconyl, bis-(cyclopentadienyl)hafnyl, bis-(1,2,3,4,5-pentamethylcyclopentadienyl)hafnyl, bis-(hydroxy)boryl, bis-[$(C_1-C_8)$-alkoxy]-boryl, $(C_1-C_6)$-alkyl-1,3,2-dioxaborolan-2-yl, bis-[$(C_1-C_6)$-alkyl]-1,3,2-dioxaborolan-2-yl, tetrakis-[$(C_1-C_6)$-alkyl]-1,3,2-dioxaborolan-2-yl, 1,3,2-dioxaborinan-2-yl, bis-[$(C_1-C_6)$-alkyl]-1,3,2-dioxaborinan-2-yl, $(C_1-C_6)$-alkyl-1,3,2-dioxaborinan-2-yl, tris-[$(C_1-C_6)$-alkyl]-1,3,2-dioxaborinan-2-yl, 2,6,7-trioxa-1-boranuidabicyclo[2.2.2]octanyl, $(C_1-C_6)$-alkyl-2,6,7-trioxa-1-boranuidabicyclo[2.2.2]octanyl, tris-[$(C_1-C_6)$-alkyl]plumbanyl, tris-[$(C_1-C_6)$-alkylcarbonyloxy]plumbanyl, tris-aryl-plumbanyl, bis-[$(C_1-C_6)$-alkylcarbonyloxy]arylplumbanyl, bis-[$(C_1-C_6)$-alkyl]-alanyl, bis-[$(C_1-C_6)$-cycloalkyl]-alanyl, dichloroalanyl, chloromagnesyl, bromomagnesyl, chlorozincyl, chlorohydrargyl, bromohydrargyl, $(C_1-C_6)$-alkylhydrargyl, $(C_3-C_6)$-cycloalkylhydrargyl, tris-[$(C_1-C_6)$-alkyl]silyl, $(C_1-C_6)$-alkyl-[bis-$(C_1-C_6)$-alkyl]silyl, $(C_1-C_6)$-alkyl-bis-(aryl)silyl, aryl-bis-[$(C_1-C_6)$-alkyl]silyl, $(C_3-C_7)$-cycloalkyl-bis-[$(C_1-C_6)$-alkyl]silyl.

Preference is given to compounds of the formula (II) where
$R^1$ represents $(C_1-C_6)$-alkyl, $(C_1-C_6)$-alkoxy-$(C_1-C_6)$-alkyl, $(C_1-C_6)$-haloalkyl, $(C_1-C_6)$-haloalkoxy-$(C_1-C_6)$-alkyl, $(C_3-C_6)$-cycloalkyl, $(C_1-C_6)$-alkoxy-$(C_1-C_6)$-haloalkyl, $(C_1-C_6)$-haloalkoxy-$(C_1-C_6)$-haloalkyl, $(C_1-C_6)$-alkylthio-$(C_1-C_6)$-alkyl, $R^2$ represents hydrogen, tri-$(C_1-C_6)$-alkylsilyl, $(C_1-C_6)$-alkyl-(bis-$(C_1-C_6)$-alkyl)silyl, $(C_1-C_6)$-alkyl(bis-aryl)silyl, aryl(bis-$(C_1-C_6)$-alkyl)silyl, $(C_3-C_6)$-cycloalkyl(bis-$(C_1-C_6)$-alkyl)silyl, halo(bis-$(C_1-C_6)$-alkyl)silyl, tri-$(C_1-C_6)$-alkylsilyl-$(C_1-C_6)$-alkoxy-$(C_1-C_6)$-alkyl, tri-$(C_1-C_6)$-alkylsilyl-$(C_1-C_6)$-alkyl, $R^3$ and $R^4$ independently of one another represent $(C_1-C_8)$-alkoxy, $(C_1-C_8)$-alkylthio, aryl-$(C_1-C_8)$-alkoxy, aryl-$(C_1-C_8)$-alkylthio or together with the atom to which they are attached form an oxo group or a 5- to 7-membered heterocyclic ring, for example a 1,3-dioxolanyl, 1,3-dioxanyl, 1,3-dithiolanyl, 1,3-dithianyl, 1,3-oxathianyl, 5-alkyl-1,3,5-dithiazinyl, 1,3-oxazolidinyl ring, which may optionally be substituted further by $(C_1-C_6)$-alkyl, $(C_1-C_6)$-alkoxycarbonyl, $(C_3-C_6)$-cycloalkyl, spiro-$(C_3-C_6)$-cycloalkyl, spiro-oxetanyl and

[M] represents tris-[$(C_1-C_6)$-alkyl]stannyl, tris-[$(C_3-C_6)$-cycloalkyl]stannyl, tris-[$(C_1-C_6)$-alkyl]germanyl, tris-[$(C_3-C_6)$-cycloalkyl]germanyl, bis-(cyclopentadienyl)zirconyl, bis-(1,2,3,4,5-pentamethylcyclopentadienyl)zirconyl, bis-(cyclopentadienyl)hafnyl, bis-(1,2,3,4,5-pentamethylcyclopentadienyl)hafnyl, bis-(hydroxy)boryl, bis-[$(C_1-C_6)$-alkoxy]-boryl, $(C_1-C_6)$-alkyl-1,3,2-dioxaborolan-2-yl, bis-[$(C_1-C_6)$-alkyl]-1,3,2-dioxaborolan-2-yl, tetrakis-[$(C_1-C_6)$-alkyl]-1,3,2-dioxaborolan-2-yl, 1,3,2-dioxaborinan-2-yl, bis-[$(C_1-C_6)$-alkyl]-1,3,2-dioxaborinan-2-yl, $(C_1-C_6)$-alkyl-1,3,2-dioxaborinan-2-yl, tris-[$(C_1-C_6)$-alkyl]-1,3,2-dioxaborinan-2-yl, 2,6,7-trioxa-1-boranuidabicyclo[2.2.2]octanyl, $(C_1-C_6)$-alkyl-2,6,7-trioxa-1-boranuidabicyclo[2.2.2]octanyl, tris-[$(C_1-C_6)$-alkyl]plumbanyl, tris-[$(C_1-C_6)$-alkylcarbonyloxy]plumbanyl, tris-aryl-plumbanyl, bis-[$(C_1-C_6)$-alkylcarbonyloxy]arylplumbanyl, bis-[$(C_1-C_6)$-alkyl]-alanyl, bis-[$(C_1-C_6)$-cycloalkyl]-alanyl, dichloroalanyl, chloromagnesyl, bromomagnesyl, chlorozincyl, chlorohydrargyl, bromohydrargyl, $(C_1-C_6)$-alkylhydrargyl, $(C_3-C_6)$-cycloalkylhydrargyl, tris-[$(C_1-C_6)$-alkyl]silyl, $(C_1-C_6)$-alkyl-[bis-$(C_1-C_6)$-alkyl]silyl, $(C_1-C_6)$-alkyl-bis-(aryl)silyl, aryl-bis-[$(C_1-C_6)$-alkyl]silyl, $(C_3-C_7)$-cycloalkyl-bis-[$(C_1-C_6)$-alkyl]silyl.

With regard to the compounds according to the invention, the terms used above and below will be explained. These are familiar to the person skilled in the art and especially have the definitions elucidated hereinafter:

According to the invention, "arylsulfonyl" represents optionally substituted phenylsulfonyl or optionally substituted polycyclic arylsulfonyl, here especially optionally substituted naphthylsulfonyl, for example substituted by fluorine, chlorine, bromine, iodine, cyano, nitro, alkyl, haloalkyl, haloalkoxy, amino, alkylamino, alkylcarbonylamino, dialkylamino or alkoxy groups.

According to the invention, "cycloalkylsulfonyl"—alone or as part of a chemical group—represents optionally substituted cycloalkylsulfonyl, preferably having 3 to 6 carbon atoms, for example cyclopropylsulfonyl, cyclobutylsulfonyl, cyclopentylsulfonyl or cyclohexylsulfonyl.

According to the invention, "alkylsulfonyl"—alone or as part of a chemical group—represents straight-chain or branched alkylsulfonyl, preferably having 1 to 8, or having 1 to 6 carbon atoms, for example methylsulfonyl, ethylsulfonyl, n-propylsulfonyl, isopropylsulfonyl, n-butylsulfonyl, isobutylsulfonyl, sec-butylsulfonyl and tert-butylsulfonyl.

According to the invention, "heteroarylsulfonyl" represents optionally substituted pyridylsulfonyl, pyrimidinylsulfonyl, pyrazinylsulfonyl or optionally substituted polycyclic heteroarylsulfonyl, here in particular optionally substituted quinolinylsulfonyl, for example substituted by fluorine, chlorine, bromine, iodine, cyano, nitro, alkyl, haloalkyl, haloalkoxy, amino, alkylamino, alkylcarbonylamino, dialkylamino or alkoxy groups.

According to the invention, "alkylthio"—alone or as a constituent of a chemical group—represents straight-chain or branched S-alkyl, preferably having 1 to 8 or having 1 to 6 carbon atoms, for example methylthio, ethylthio, n-propylthio, isopropylthio, n-butylthio, isobutylthio, sec-butylthio and tert-butylthio. Alkenylthio is an alkenyl radical bonded via a sulfur atom, alkynylthio is an alkynyl radical bonded via a sulfur atom, cycloalkylthio is a cycloalkyl radical bonded via a sulfur atom, and cycloalkenylthio is a cycloalkenyl radical bonded via a sulfur atom.

"Alkoxy" is an alkyl radical bonded via an oxygen atom, alkenyloxy is an alkenyl radical bonded via an oxygen atom, alkynyloxy is an alkynyl radical bonded via an oxygen atom, cycloalkyloxy is a cycloalkyl radical bonded via an oxygen atom, and cycloalkenyloxy is a cycloalkenyl radical bonded via an oxygen atom.

The term "aryl" means an optionally substituted mono-, bi- or polycyclic aromatic system having preferably 6 to 14, especially 6 to 10, ring carbon atoms, for example phenyl, naphthyl, anthryl, phenanthrenyl and the like, preferably phenyl.

The term "optionally substituted aryl" also includes polycyclic systems, such as tetrahydronaphthyl, indenyl, indanyl, fluorenyl, biphenylyl, where the bonding site is on the aromatic system. In systematic terms, "aryl" is generally also encompassed by the term "optionally substituted phenyl".

A heterocyclic radical (heterocyclyl) contains at least one heterocyclic ring (=carbocyclic ring in which at least one carbon atom has been replaced by a heteroatom, preferably by a heteroatom from the group of N, O, S, P) which is saturated, unsaturated, partly saturated or heteroaromatic and may be unsubstituted or substituted, where the bonding site is localized on a ring atom. If the heterocyclyl radical or the heterocyclic ring is optionally substituted, it can be fused to other carbocyclic or heterocyclic rings. In the case of optionally substituted heterocyclyl, polycyclic systems are also included, for example 8-azabicyclo[3.2.1]octanyl, 8-azabicyclo[2.2.2]octanyl or 1-azabicyclo[2.2.1]heptyl. In the case of optionally substituted heterocyclyl, spirocyclic systems are also included, for example 1-oxa-5-azaspiro[2.3]hexyl. Unless defined differently, the heterocyclic ring contains preferably 3 to 9 ring atoms and especially 3 to 6 ring atoms, and one or more, preferably 1 to 4 and especially 1, 2 or 3 heteroatoms in the heterocyclic ring, preferably from the group of N, O and S, although no two oxygen atoms should be directly adjacent, for example, with one heteroatom from the group of N, O and S, 1- or 2- or 3-pyrrolidinyl, 3,4-dihydro-2H-pyrrol-2- or 3-yl, 2,3-dihydro-1H-pyrrol-1- or 2- or 3- or 4- or 5-yl; 2,5-dihydro-1H-pyrrol-1- or 2- or 3-yl, 1- or 2- or 3- or 4-piperidinyl; 2,3,4,5-tetrahydropyridin-2- or 3- or 4- or 5-yl or 6-yl; 1,2,3,6-tetrahydropyridin-1- or 2- or 3- or 4- or 5- or 6-yl; 1,2,3,4-tetrahydropyridin-1- or 2- or 3- or 4- or 5- or 6-yl; 1,4-dihydropyridin-1- or 2- or 3- or 4-yl; 2,3-dihydro-pyridin-2- or 3- or 4- or 5- or 6-yl; 2,5-dihydropyridin-2- or 3- or 4- or 5- or 6-yl, 1- or 2- or 3- or 4-azepanyl; 2,3,4,5-tetrahydro-1H-azepin-1- or 2- or 3- or 4- or 5- or 6- or 7-yl; 2,3,4,7-tetrahydro-1H-azepin-1- or 2- or 3- or 4- or 5- or 6- or 7-yl; 2,3,6,7-tetrahydro-1H-azepin-1- or 2- or 3- or 4-yl; 3,4,5,6-tetrahydro-2H-azepin-2- or 3- or 4- or 5- or 6- or 7-yl; 4,5-dihydro-1H-azepin-1- or 2- or 3- or 4-yl; 2,5-dihydro-1H-azepin-1- or -2- or 3- or 4- or 5- or 6- or 7-yl; 2,7-dihydro-1H-azepin-1- or -2- or 3- or 4-yl; 2,3-dihydro-1H-azepin-1- or -2- or 3- or 4- or 5- or 6- or 7-yl; 3,4-dihydro-2H-azepin-2- or 3- or 4- or 5- or 6- or 7-yl; 3,6-dihydro-2H-azepin-2- or 3- or 4- or 5- or 6- or 7-yl; 5,6-dihydro-2H-azepin-2- or 3- or 4- or 5- or 6- or 7-yl; 4,5-dihydro-3H-azepin-2- or 3- or 4- or 5- or 6- or 7-yl; 1H-azepin-1- or -2- or 3- or 4- or 5- or 6- or 7-yl; 2H-azepin-2- or 3- or 4- or 5- or 6- or 7-yl; 3H-azepin-2- or 3- or 4- or 5- or 6- or 7-yl; 4H-azepin-2- or 3- or 4- or 5- or 6- or 7-yl, 2- or 3-oxolanyl (=2- or 3-tetrahydrofuranyl); 2,3-dihydrofuran-2- or 3- or 4- or 5-yl; 2,5-dihydrofuran-2- or 3-yl, 2- or 3- or 4-oxanyl (=2- or 3- or 4-tetrahydropyranyl); 3,4-dihydro-2H-pyran-2- or 3- or 4- or 5- or 6-yl; 3,6-dihydro-2H-pyran-2- or 3- or 4- or 5- or 6-yl; 2H-pyran-2- or 3- or 4- or 5- or 6-yl; 4H-pyran-2- or 3- or 4-yl, 2- or 3- or 4-oxepanyl; 2,3,4,5-tetrahydrooxepin-2- or 3- or 4- or 5- or 6- or 7-yl; 2,3,4,7-tetrahydrooxepin-2- or 3- or 4- or 5- or 6- or 7-yl; 2,3,6,7-tetrahydrooxepin-2- or 3- or 4-yl; 2,3-dihydrooxepin-2- or 3- or 4- or 5- or 6- or 7-yl; 4,5-dihydrooxepin-2- or 3- or 4-yl; 2,5-dihydrooxepin-2- or 3- or 4- or 5- or 6- or 7-yl; oxepin-2- or 3- or 4- or 5- or 6- or 7-yl; 2- or 3-tetrahydrothiophenyl; 2,3-dihydrothiophen-2- or 3- or 4- or 5-yl; 2,5-dihydrothiophen-2- or 3-yl; tetrahydro-2H-thiopyran-2- or 3- or 4-yl; 3,4-dihydro-2H-thiopyran-2- or 3- or 4- or 5- or 6-yl; 3,6-dihydro-2H-thiopyran-2- or 3- or 4- or 5- or 6-yl; 2H-thiopyran-2- or 3- or 4- or 5- or 6-yl; 4H-thiopyran-2- or 3- or 4-yl. Preferred 3-membered and 4-membered heterocycles are, for example, 1- or 2-aziridinyl, oxiranyl, thiiranyl, 1- or 2- or 3-azetidinyl, 2- or 3-oxetanyl, 2- or 3-thietanyl, 1,3-dioxetan-2-yl. Further examples of "heterocyclyl" are a partly or fully hydrogenated heterocyclic radical having two heteroatoms from the group of N, O and S, for example 1- or 2- or 3- or 4-pyrazolidinyl; 4,5-dihydro-3H-pyrazol-3- or 4- or 5-yl; 4,5-dihydro-1H-pyrazol-1- or 3- or 4- or 5-yl; 2,3-dihydro-1H-pyrazol-1- or 2- or 3- or 4- or 5-yl; 1- or 2- or 3- or 4-imidazolidinyl; 2,3-dihydro-1H-imidazol-1- or 2- or 3- or 4-yl; 2,5-dihydro-1H-imidazol-1- or 2- or 4- or 5-yl; 4,5-dihydro-1H-imidazol-1- or 2- or 4- or 5-yl; hexahydropyridazin-1- or 2- or 3- or 4-yl; 1,2,3,4-tetrahydropyridazin-1- or 2- or 3- or 4- or 5- or 6-yl; 1,2,3,6-tetrahydropyridazin-1- or 2- or 3- or 4- or 5- or 6-yl; 1,4,5,6-tetrahydropyridazin-1- or 3- or 4- or 5- or 6-yl; 3,4,5,6-tetrahydropyridazin-3- or 4- or 5-yl; 4,5-dihydropyridazin-3- or 4-yl; 3,4-dihydropyridazin-3- or 4- or 5- or 6-yl; 3,6-dihydropyridazin-3- or 4-yl; 1,6-dihydropyridazin-1- or 3- or 4- or 5- or 6-yl; hexahydropyrimidin-1- or 2- or 3- or 4-yl; 1,4,5,6-tetrahydropyrimidin-1- or 2- or 4- or 5- or 6-yl; 1,2,5,6-tetrahydropyrimidin-1- or 2- or 4- or 5- or 6-yl; 1,2,3,4-tetrahydropyrimidin-1- or 2- or 3- or 4- or 5- or 6-yl; 1,6-dihydropyrimidin-1- or 2- or 4- or 5- or 6-yl; 1,2-dihydropyrimidin-1- or 2- or 4- or 5- or 6-yl; 2,5-dihydropyrimidin-2- or 4- or 5-yl; 4,5-dihydropyrimidin-4- or 5- or 6-yl; 1,4-dihydropyrimidin-1- or 2- or 4- or 5- or 6-yl; 1- or 2- or 3-piperazinyl; 1,2,3,6-tetrahydropyrazin-1- or 2- or 3- or 5- or 6-yl; 1,2,3,4-tetrahydropyrazin-1- or 2- or 3- or 4- or 5- or 6-yl; 1,2-dihydropyrazin-1- or 2- or 3- or 5- or 6-yl; 1,4-dihydropyrazin-1- or 2- or 3-yl; 2,3-dihydropyrazin-2- or 3- or 5- or 6-yl; 2,5-dihydropyrazin-2- or 3-yl; 1,3-dioxolan-2- or 4- or 5-yl; 1,3-dioxol-2- or 4-yl; 1,3-dioxan-2- or 4- or 5-yl; 4H-1,3-dioxin-2- or 4- or 5- or 6-yl; 1,4-dioxan-2- or 3- or 5- or 6-yl; 2,3-dihydro-1,4-dioxin-2- or 3- or 5- or 6-yl; 1,4-dioxin-2- or 3-yl; 1,2-dithiolan-3- or 4-yl; 3H-1,2-dithiol-3- or 4- or 5-yl; 1,3-dithiolan-2- or 4-yl; 1,3-dithiol-2- or 4-yl; 1,2-dithian-3- or 4-yl; 3,4-dihydro-1,2-dithiin-3- or 4- or 5- or 6-yl; 3,6-dihydro-1,2-dithiin-3- or 4-yl; 1,2-dithiin-3- or 4-yl; 1,3-dithian-2- or 4- or 5-yl; 4H-1,3-dithiin-2- or 4- or 5- or 6-yl; isoxazolidin-2- or 3- or 4- or 5-yl; 2,3-dihydroisoxazol-2- or 3- or 4- or 5-yl; 2,5-dihydroisoxazol-2- or 3- or 4- or 5-yl; 4,5-dihydroisoxazol-3- or 4- or 5-yl; 1,3-oxazolidin-2- or 3- or 4- or 5-yl; 2,3-dihydro-1,3-oxazol-2- or 3- or 4- or 5-yl; 2,5-dihydro-1,3-oxazol-2- or 4- or 5-yl; 4,5-dihydro-1,3-oxazol-2- or 4- or 5-yl; 1,2-oxazinan-2- or 3- or 4- or 5- or 6-yl; 3,4-dihydro-2H-1,2-oxazin-2- or 3- or 4- or 5- or 6-yl; 3,6-dihydro-2H-1,2-oxazin-2- or 3- or 4- or 5- or 6-yl; 5,6-dihydro-2H-1,2-oxazin-2- or 3- or 4- or 5- or 6-yl; 5,6-dihydro-4H-1,2-oxazin-3- or 4- or 5- or 6-yl; 2H-1,2-oxazin-2- or 3- or 4- or 5- or 6-yl; 6H-1,2-oxazin-3- or 4- or 5- or 6-yl; 4H-1,2-oxazin-3- or 4- or 5- or 6-yl; 1,3-oxazinan-2- or 3- or 4- or 5- or 6-yl; 3,4-dihydro-2H-1,3-oxazin-2- or 3- or 4- or 5- or 6-yl; 3,6-dihydro-2H-1,3-oxazin-2- or 3- or 4- or 5- or 6-yl; 5,6-dihydro-2H-1,3-oxazin-2- or 4- or 5- or 6-yl; 5,6-dihydro-4H-1,3-oxazin-2- or 4- or 5- or 6-yl; 2H-1,3-oxazin-2- or 4- or 5- or 6-yl; 6H-1,3-oxazin-2- or 4- or 5- or 6-yl; 4H-1,3-oxazin-2- or 4- or 5- or 6-yl; morpholin-2- or 3- or 4-yl; 3,4-dihydro-2H-1,4-oxazin-2- or 3- or 4- or 5- or 6-yl; 3,6-dihydro-2H-1,4-oxazin-2- or 3- or 5- or 6-yl; 2H-1,4-oxazin-2- or 3- or 5- or 6-yl; 4H-1,4-oxazin-2- or 3-yl; 1,2-oxazepan-2- or 3- or 4- or 5- or 6- or 7-yl; 2,3,4,5-tetrahydro-1,2-oxazepin-2- or 3- or 4- or 5- or 6- or 7-yl; 2,3,4,7-tetrahydro-1,2-oxazepin-2- or 3- or 4- or 5- or 6- or 7-yl; 2,3,6,7-tetrahydro-1,2-oxazepin-2- or 3- or 4- or 5- or 6- or 7-yl; 2,5,6,7-tetrahydro-1,2-oxazepin-2- or 3- or 4- or 5- or 6- or 7-yl; 4,5,6,7-tetrahydro-1,2-oxazepin-3- or 4- or 5- or 6- or 7-yl; 2,3-dihydro-1,2-oxazepin-2- or 3- or 4- or 5- or 6- or 7-yl; 2,5-dihydro-1,2-oxazepin-2- or 3- or 4- or 5- or 6- or 7-yl; 2,7-dihydro-1,2-oxazepin-2- or 3- or 4- or 5- or 6- or 7-yl; 4,5-dihydro-1,2-oxazepin-3- or 4- or 5- or 6- or 7-yl; 4,7-dihydro-1,2-oxazepin-3- or 4- or 5- or 6- or 7-yl; 6,7-dihydro-1,2-oxazepin-3- or 4- or 5- or 6- or 7-yl; 1,2-oxazepin-3- or 4- or 5- or 6- or 7-yl; 1,3-oxazepan-2- or 3- or 4- or 5- or 6- or 7-yl; 2,3,4,5-tetrahydro-1,3-oxazepin-2- or 3- or 4- or 5- or 6- or 7-yl; 2,3,4,7-tetrahydro-1,3-oxazepin-2- or 3- or 4- or 5- or 6- or 7-yl; 2,3,6,7-tetrahydro-1,3-oxazepin-2- or 3- or 4- or 5- or 6- or 7-yl; 2,5,6,7-tetrahydro-1,3-oxazepin-2- or 4- or 5- or 6- or 7-yl; 4,5,6,7-tetrahydro-1,3-oxazepin-2- or 4- or 5- or 6- or 7-yl; 2,3-dihydro-1,3-oxazepin-2- or 3- or 4- or 5- or 6- or 7-yl; 2,5-dihydro-1,3-oxazepin-2- or 4- or 5- or 6- or 7-yl; 2,7-dihydro-1,3-oxazepin-2- or 4- or 5- or 6- or 7-yl; 4,5-dihydro-1,3-oxazepin-2- or 4- or 5- or 6- or 7-yl; 4,7-dihydro-1,3-oxazepin-2- or 4- or 5- or 6- or 7-yl; 6,7-dihydro-1,3-oxazepin-2- or 4- or 5- or 6- or 7-yl; 1,3-oxazepin-2- or 4- or 5- or 6- or 7-yl; 1,4-oxazepan-2- or 3- or 5- or 6- or 7-yl; 2,3,4,5-tetrahydro-1,4-oxazepin-2- or 3- or 4- or 5- or 6- or 7-yl; 2,3,4,7-tetrahydro-1,4-oxazepin-2- or 3- or 4- or 5- or 6- or 7-yl; 2,3,6,7-tetrahydro-1,4-oxazepin-2- or 3- or 5- or 6- or 7-yl; 2,5,6,7-tetrahydro-1,4-oxazepin-2- or 3- or 5- or 6- or 7-yl; 4,5,6,7-tetrahydro-1,4-oxazepin-2- or 3- or 4- or 5- or 6- or 7-yl; 2,3-dihydro-1,4-oxazepin-2- or 3- or 5- or 6- or 7-yl; 2,5-dihydro-1,4-oxazepin-2- or 3- or 5- or 6- or 7-yl; 2,7-dihydro-1,4-oxazepin-2- or 3- or 5- or 6- or 7-yl; 4,5-dihydro-1,4-oxazepin-2- or 3- or 4- or 5- or 6- or 7-yl; 4,7-dihydro-1,4-oxazepin-2- or 3- or 4- or 5- or 6- or 7-yl; 6,7-dihydro-1,4-oxazepin-2- or 3- or 5- or 6- or 7-yl; 1,4-oxazepin-2- or 3- or 5- or 6- or 7-yl; isothiazolidin-2- or 3- or 4- or 5-yl; 2,3-dihydroisothiazol-2- or 3- or 4- or 5-yl; 2,5-dihydroisothiazol-2- or 3- or 4- or 5-yl; 4,5-dihydroisothiazol-3- or 4- or 5-yl; 1,3-thiazolidin-2- or 3- or 4- or 5-yl; 2,3-dihydro-1,3-thiazol-2- or 3- or 4- or 5-yl; 2,5-dihydro-1,3-thiazol-2- or 4- or 5-yl; 4,5-dihydro-1,3-thiazol-2- or 4- or 5-yl; 1,3-thiazinan-2- or 3- or 4- or 5- or 6-yl; 3,4-dihydro-2H-1,3-thiazin-2- or 3- or 4- or 5- or 6-yl; 3,6-dihydro-2H-1,3-thiazin-2- or 3- or 4- or 5- or 6-yl; 5,6-dihydro-2H-1,3-thiazin-2- or 4- or 5- or 6-yl; 5,6-dihydro-4H-1,3-thiazin-2- or 4- or 5- or 6-yl; 2H-1,3-thiazin-2- or 4- or 5- or 6-yl; 6H-1,3-thiazin-2- or 4- or 5- or 6-yl; 4H-1,3-thiazin-2- or 4- or 5- or 6-yl. Further examples of "heterocyclyl" are a partly or fully hydrogenated heterocyclic radical having 3 heteroatoms from the group of N, O and S, for example 1,4,2-dioxazolidin-2- or 3- or 5-yl; 1,4,2-dioxazol-3- or 5-yl; 1,4,2-dioxazinan-2- or -3- or 5- or 6-yl; 5,6-dihydro-1,4,2-dioxazin-3- or 5- or 6-yl; 1,4,2-dioxazin-3- or 5- or 6-yl; 1,4,2-dioxazepan-2- or 3- or 5- or 6- or 7-yl; 6,7-dihydro-5H-1,4,2-dioxazepin-3- or 5- or 6- or 7-yl; 2,3-dihydro-7H-1,4,2-dioxazepin-2- or 3- or 5- or 6- or 7-yl; 2,3-dihydro-5H-1,4,2-dioxazepin-2- or 3- or 5- or 6- or 7-yl; 5H-1,4,2-dioxazepin-3- or 5- or 6- or 7-yl; 7H-1,4,2-dioxazepin-3- or 5- or 6- or 7-yl.

When a base structure is substituted "by one or more radicals" from a list of radicals (=group) or a generically defined group of radicals, this in each case includes simultaneous substitution by a plurality of identical and/or structurally different radicals.

In the case of a partly or fully saturated nitrogen heterocycle, this may be joined to the remainder of the molecule either via carbon or via the nitrogen.

Suitable substituents for a substituted heterocyclic radical are the substituents specified later on below, and additionally also oxo and thioxo. The oxo group as a substituent on a ring carbon atom is then, for example, a carbonyl group in the heterocyclic ring. As a result, lactones and lactams are preferably also included. The oxo group may also be present on the ring heteroatoms, which can exist in various oxidation states, for example on N and S, in which case they form, for example, the divalent groups N(O), S(O) (also SO for short) and S(O)2 (also SO2 for short) in the heterocyclic ring. In the case of —N(O)— and —S(O)— groups, in each case both enantiomers are included.

According to the invention, the expression "heteroaryl" represents heteroaromatic compounds, i.e. fully unsaturated aromatic heterocyclic compounds, preferably 5- to 7-membered rings having 1 to 4, preferably 1 or 2, identical or different heteroatoms, preferably O, S or N. Inventive heteroaryls are, for example, 1H-pyrrol-1-yl; 1H-pyrrol-2-yl; 1H-pyrrol-3-yl; furan-2-yl; furan-3-yl; thien-2-yl; thien-3-yl, 1H-imidazol-1-yl; 1H-imidazol-2-yl; 1H-imidazol-4-yl; 1H-imidazol-5-yl; 1H-pyrazol-1-yl; 1H-pyrazol-3-yl; 1H-pyrazol-4-yl; 1H-pyrazol-5-yl, 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-1-yl, 1H-1,2,4-triazol-3-yl, 4H-1,2,4-triazol-4-yl, 1,2,4-oxadiazol-3-yl, 1,2,4-oxadiazol-5-yl, 1,3,4-oxadiazol-2-yl, 1,2,3-oxadiazol-4-yl, 1,2,3-oxadiazol-5-yl, 1,2,5-oxadiazol-3-yl, azepinyl, pyridin-2-yl, pyridin-3-yl, pyridin-4-yl, pyrazin-2-yl, pyrazin-3-yl, pyrimidin-2-yl, pyrimidin-4-yl, pyrimidin-5-yl, pyridazin-3-yl, pyridazin-4-yl, 1,3,5-triazin-2-yl, 1,2,4-triazin-3-yl, 1,2,4-triazin-5-yl, 1,2,4-triazin-6-yl, 1,2,3-triazin-4-yl, 1,2,3-triazin-5-yl, 1,2,4-, 1,3,2-, 1,3,6- and 1,2,6-oxazinyl, isoxazol-3-yl, isoxazol-4-yl, isoxazol-5-yl, 1,3-oxazol-2-yl, 1,3-oxazol-4-yl, 1,3-oxazol-5-yl, isothiazol-3-yl, isothiazol-4-yl, isothiazol-5-yl, 1,3-thiazol-2-yl, 1,3-thiazol-4-yl, 1,3-thiazol-5-yl, oxepinyl, thiepinyl, 1,2,4-triazolonyl and 1,2,4-diazepinyl, 2H-1,2,3,4-tetrazol-5-yl, 1H-1,2,3,4-tetrazol-5-yl, 1,2,3,4-oxatriazol-5-yl, 1,2,3,4-thiatriazol-5-yl, 1,2,3,5-oxatriazol-4-yl, 1,2,3,5-thiatriazol-4-yl. The heteroaryl groups according to the invention may also be substituted by one or more identical or different radicals. When two adjacent carbon atoms are part of a further aromatic ring, the systems are fused heteroaromatic systems, such as benzofused or polyannulated heteroaromatics. Preferred examples are quinolines (e.g. quinolin-2-yl, quinolin-3-yl, quinolin-4-yl, quinolin-5-yl, quinolin-6-yl, quinolin-7-yl, quinolin-8-yl); isoquinolines (e.g. isoquinolin-1-yl, isoquinolin-3-yl, isoquinolin-4-yl, isoquinolin-5-yl, isoquinolin-6-yl, isoquinolin-7-yl, isoquinolin-8-yl); quinoxaline; quinazoline; cinnoline; 1,5-naphthyridine; 1,6-naphthyridine; 1,7-naphthyridine; 1,8-naphthyridine; 2,6-naphthyridine; 2,7-naphthyridine; phthalazine; pyridopyrazines; pyridopyrimidines; pyridopyridazines; pteridines; pyrimidopyrimidines. Examples of heteroaryl are also 5- or 6-membered benzof used rings from the group of 1H-indol-1-yl, 1H-indol-2-yl, 1H-indol-3-yl, 1H-indol-4-yl, 1H-indol-5-yl, 1H-indol-6-yl, 1H-indol-7-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1H-indazol-1-yl, 1H-indazol-3-yl, 1H-indazol-4-yl, 1H-indazol-5-yl, 1H-indazol-6-yl, 1H-indazol-7-yl, 2H-indazol-2-yl, 2H-indazol-3-yl, 2H-indazol-4-yl, 2H-indazol-5-yl, 2H-indazol-6-yl, 2H-indazol-7-yl, 2H-isoindol-2-yl, 2H-isoindol-1-yl, 2H-isoindol-3-yl, 2H-isoindol-4-yl, 2H-isoindol-5-yl, 2H-isoindol-6-yl; 2H-isoindol-7-yl, 1H-benzimidazol-1-yl, 1H-benzimidazol-2-yl, 1H-benzimidazol-4-yl, 1H-benzimidazol-5-yl, 1H-benzimidazol-6-yl, 1H-benzimidazol-7-yl, 1,3-benzoxazol-2-yl, 1,3-benzoxazol-4-yl, 1,3-benzoxazol-5-yl, 1,3-benzoxazol-6-yl, 1,3-benzoxazol-7-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1,2-benzisoxazol-3-yl, 1,2-benzisoxazol-4-yl, 1,2-benzisoxazol-5-yl, 1,2-benzisoxazol-6-yl, 1,2-benzisoxazol-7-yl, 1,2-benzisothiazol-3-yl, 1,2-benzisothiazol-4-yl, 1,2-benzisothiazol-5-yl, 1,2-benzisothiazol-6-yl, 1,2-benzisothiazol-7-yl.

The term "halogen" means, for example, fluorine, chlorine, bromine or iodine. If the term is used for a radical, "halogen" means, for example, a fluorine, chlorine, bromine or iodine atom.

According to the invention, "alkyl" means a straight-chain or branched open-chain, saturated hydrocarbyl radical which is optionally mono- or polysubstituted. Preferred substituents are halogen atoms, alkoxy, haloalkoxy, cyano, alkylthio, haloalkylthio, amino or nitro groups, particular preference being given to methoxy, methyl, fluoroalkyl, cyano, nitro, fluorine, chlorine, bromine or iodine.

"Haloalkyl", "-alkenyl" and "-alkynyl" mean, respectively, alkyl, alkenyl and alkynyl partly or fully substituted by identical or different halogen atoms, for example monohaloalkyl, for example $CH_2CH_2Cl$, $CH_2CH_2Br$, $CHClCH_3$, $CH_2Cl$, $CH_2F$; perhaloalkyl, for example $CCl_3$, $CClF_2$, $CFCl_2$, $CF_2CClF_2$, $CF_2CClFCF_3$; polyhaloalkyl, for example $CH_2CHFCl$, $CF_2CClFH$, $CF_2CBrFH$, $CH_2CF_3$; the term "perhaloalkyl" also encompasses the term "perfluoroalkyl".

"Partly fluorinated alkyl" means a straight-chain or branched, saturated hydrocarbon which is mono- or polysubstituted by fluorine, where the fluorine atoms in question may be present as substituents on one or more different carbon atoms of the straight-chain or branched hydrocarbyl chain, for example $CHFCH_3$, $CH_2CH_2F$, $CH_2CH_2CF_3$, $CHF_2$, $CH_2F$, $CHFCF_2CF_3$.

"Partly fluorinated haloalkyl" means a straight-chain or branched, saturated hydrocarbon which is substituted by different halogen atoms with at least one fluorine atom, where any other halogen atoms optionally present are selected from the group of fluorine, chlorine or bromine, iodine. The halogen atoms in question may be present as substituents on one or more different carbon atoms of the straight-chain or branched hydrocarbyl chain. Partly fluorinated haloalkyl also includes full substitution of the straight or branched chain by halogen including at least one fluorine atom.

Haloalkoxy is, for example, $OCF_3$, $OCHF_2$, $OCH_2F$, $OCF_2CF_3$, $OCH_2CF_3$ and $OCH_2CH_2Cl$; the situation is equivalent for haloalkenyl and other halogen-substituted radicals.

The expression "$(C_1-C_4)$-alkyl" mentioned here by way of example is a brief notation for straight-chain or branched alkyl having one to 4 carbon atoms according to the range stated for carbon atoms, i.e. encompasses the methyl, ethyl, 1-propyl, 2-propyl, 1-butyl, 2-butyl, 2-methylpropyl or tert-butyl radicals. General alkyl radicals with a larger specified range of carbon atoms, e.g. "$(C_1-C_6)$-alkyl", correspondingly also encompass straight-chain or branched alkyl radicals with a greater number of carbon atoms, i.e. according to the example also the alkyl radicals having 5 and 6 carbon atoms.

Unless stated specifically, preference is given to the lower carbon skeletons, for example having from 1 to 6 carbon atoms, or having from 2 to 6 carbon atoms in the case of unsaturated groups, in the case of the hydrocarbyl radicals such as alkyl, alkenyl and alkynyl radicals, including in combined radicals. Alkyl radicals, including in the composite radicals such as alkoxy, haloalkyl, etc., are, for example, methyl, ethyl, n-propyl or i-propyl, n-, i- or t- or 2-butyl, pentyls, hexyls such as n-hexyl, i-hexyl and 1,3-dimethylbutyl, heptyls such as n-heptyl, 1-methylhexyl and 1,4-dimethylpentyl; alkenyl and alkynyl radicals are defined as the possible unsaturated radicals corresponding to the alkyl radicals, where at least one double bond or triple bond is present. Preference is given to radicals having one double bond or triple bond.

The term "alkenyl" also includes, in particular, straight-chain or branched open-chain hydrocarbyl radicals having more than one double bond, such as 1,3-butadienyl and 1,4-pentadienyl, but also allenyl or cumulenyl radicals having one or more cumulated double bonds, for example allenyl (1,2-propadienyl), 1,2-butadienyl and 1,2,3-pentatrienyl. Alkenyl is, for example, vinyl which may optionally be substituted by further alkyl radicals, for example prop-1-en-1-yl, but-1-en-1-yl, allyl, 1-methylprop-2-en-1-yl, 2-methylprop-2-en-1-yl, but-2-en-1-yl, 1-methylbut-3-en-1-yl and 1-methylbut-2-en-1-yl, 2-methylprop-1-en-1-yl, 1-methylprop-1-en-1-yl, 1-methylprop-2-en-1-yl, 2-methylprop-2-en-1-yl, but-2-en-1-yl, but-3-en-1-yl, 1-methylbut-3-en-1-yl or 1-methylbut-2-en-1-yl, pentenyl, 2-methylpentenyl or hexenyl.

The term "alkynyl" also includes, in particular, straight-chain or branched open-chain hydrocarbyl radicals having more than one triple bond, or else having one or more triple bonds and one or more double bonds, for example 1,3-butatrienyl or 3-penten-1-yn-1-yl. $(C_2-C_6)$-Alkynyl is, for example, ethynyl, propargyl, 1-methylprop-2-yn-1-yl, 2-butynyl, 2-pentynyl or 2-hexynyl, preferably propargyl, but-2-yn-1-yl, but-3-yn-1-yl or 1-methylbut-3-yn-1-yl.

The term "cycloalkyl" means a carbocyclic saturated ring system having preferably 3-8 ring carbon atoms, for example cyclopropyl, cyclobutyl, cyclopentyl or cyclohexyl. In the case of optionally substituted cycloalkyl, cyclic systems with substituents are included, also including substituents with a double bond on the cycloalkyl radical, for example an alkylidene group such as methylidene. In the case of optionally substituted cycloalkyl, polycyclic aliphatic systems are also included, for example bicyclo[1.1.0]butan-1-yl, bicyclo

[1.1.0]butan-2-yl, bicyclo[2.1.0]pentan-1-yl, bicyclo[2.1.0] pentan-2-yl, bicyclo[2.1.0]pentan-5-yl, bicyclo[2.2.1]hept-2-yl (norbornyl), bicyclo[2.2.2]octan-2-yl, adamantan-1-yl and adamantan-2-yl. The expression "$(C_3\text{-}C_7)$-cycloalkyl" is a brief notation for cycloalkyl having three to 7 carbon atoms corresponding to the range specified for carbon atoms.

In the case of substituted cycloalkyl, spirocyclic aliphatic systems are also included, for example spiro[2.2]pent-1-yl, spiro[2.3]hex-1-yl, spiro[2.3]hex-4-yl, 3-spiro[2.3]hex-5-yl.

"Cycloalkenyl" means a carbocyclic, nonaromatic, partly unsaturated ring system having preferably 4-8 carbon atoms, e.g. 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3-cyclohexadienyl or 1,4-cyclohexadienyl, also including substituents with a double bond on the cycloalkenyl radical, for example an alkylidene group such as methylidene. In the case of optionally substituted cycloalkenyl, the elucidations for substituted cycloalkyl apply correspondingly.

The term "alkylidene", for example including in the form of $(C_1\text{-}C_{10})$-alkylidene, means the radical of a straight-chain or branched open-chain hydrocarbyl radical bonded via a double bond. Possible bonding sites for alkylidene are naturally only positions on the base structure where two hydrogen atoms can be replaced by the double bond; radicals are, for example, $=CH_2$, $=CH-CH_3$, $=C(CH_3)-CH_3$, $=C(CH_3)-C_2H_5$ or $=C(C_2H_5)-C_2H_5$. Cycloalkylidene is a carbocyclic radical bonded via a double bond.

The term "stannyl" represents a further-substituted radical containing a tin atom; "germanyl" analogously represents a further-substituted radical containing a germanium atom. "Zirconyl" represents a further-substituted radical containing a zirconium atom. "Hafnyl" represents a further-substituted radical containing a hafnium atom. "Boryl", "borolanyl" and "borinanyl" represent further-substituted and optionally cyclic groups each containing a boron atom. "Plumbanyl" represents a further-substituted radical containing a lead atom. "Hydrargyl" represents a further-substituted radical containing a mercury atom. "Alanyl" represents a further-substituted radical containing an aluminum atom. "Magnesyl" represents a further-substituted radical containing a magnesium atom. "Zincyl" represents a further-substituted radical containing a zinc atom.

According to the nature and the bonding of the substituents, the compounds of the formula (I) may be present as stereoisomers. The formula (I) embraces all possible stereoisomers defined by the specific three-dimensional form thereof, such as enantiomers, diastereomers, Z and E isomers. When, for example, one or more alkenyl groups are present, diastereomers (Z and E isomers) may occur. When, for example, one or more asymmetric carbon atoms are present, enantiomers and diastereomers may occur. Stereoisomers can be obtained from the mixtures obtained in the preparation by customary separation methods. The chromatographic separation can be effected either on the analytical scale to find the enantiomeric excess or the diastereomeric excess, or on the preparative scale to prepare test specimens for biological testing. It is equally possible to selectively prepare stereoisomers by using stereoselective reactions using optically active starting materials and/or auxiliaries. The invention thus also relates to all stereoisomers which are embraced by the formula (I) but are not shown in their specific stereomeric form, and to mixtures thereof.

Synthesis of substituted 5-(cyclohex-2-en-1-yl)penta-2,4-dienes and 5-(cyclohex-2-en-1-yl)pent-2-en-4-ynes and analogs thereof.

The substituted 5-(cyclohex-2-en-1-yl)penta-2,4-dienes and 5-(cyclohex-2-en-1-yl)pent-2-en-4-ynes of the formula (I) according to the invention can be prepared by known processes. The known and structurally related natural plant compound abscisic acid can be obtained by various synthesis routes (cf. Hanson et al. J. Chem. Res. (S), 2003, 426; Constantino et al. J. Org. Chem. 1986, 51, 253; Constantino et al. 1989, 54, 681; Marsh et al. Org. Biomol. Chem. 2006, 4, 4186; WO94/15467). Some of the processes described therein for the synthesis of the abscisic acid skeleton have been optimized and replaced by alternative synthesis steps. The synthesis routes used and examined proceed from commercially available or easily preparable cyclohexenones and alkynoic acid derivatives.

As a first key intermediate for the synthesis of the compounds of the formula (I) according to the invention a correspondingly substituted and optionally protected 8-ethynyl-1,4-dioxaspiro[4.5]dec-6-en-8-ol is prepared. For this purpose, a correspondingly further-substituted cyclohex-2-ene-1,4-dione is converted with an optionally substituted ethanediol, using catalytic amounts of p-toluenesulfonic acid or with p-toluenesulfonic acid in a mixture of dioxane and trimethoxyformic orthoester to the corresponding further-substituted 1,4-dioxaspiro[4.5]dec-6-en-8-one (cf. J. Org. Chem. 2009, 74, 2425; Org. Lett. 2001, 3, 1649; J. Label Compd. Radiopharm. 2003, 46, 273). The preparation of the appropriately substituted cyclohex-2-ene-1,4-dione building blocks is known from the literature (cf. U.S. Pat. No. 5,101,032, Can. J. Chem. 1987, 65, 69; Org. Lett. 2006, 8, 3149). It is also possible to utilize other alcohols and alkanediols. The further-substituted 1,4-dioxaspiro[4.5]dec-6-en-8-one can then be converted either directly with a lithium acetylide/ethylenediamine complex in a suitable polar-aprotic solvent (for example tetrahydrofuran) or in two steps by reaction with trimethylsilylacetylene and LDA (lithium diisopropylamide) within a temperature range from −78° C. to 0° C. in a suitable polar-aprotic solvent (for example tetrahydrofuran) and subsequent elimination of the trimethylsilyl group with the aid of a suitable trialkylammonium fluoride (for example tetrabutylammonium fluoride) in a polar-aprotic solvent or with a suitable carbonate base (for example potassium carbonate) in a polar-protic solvent (for example methanol) (cf. J. Chem. Res. (S) 2003, 426) to the correspondingly substituted 8-ethynyl-1,4-dioxaspiro[4.5]dec-6-en-8-ol (Scheme 1).

Scheme 1

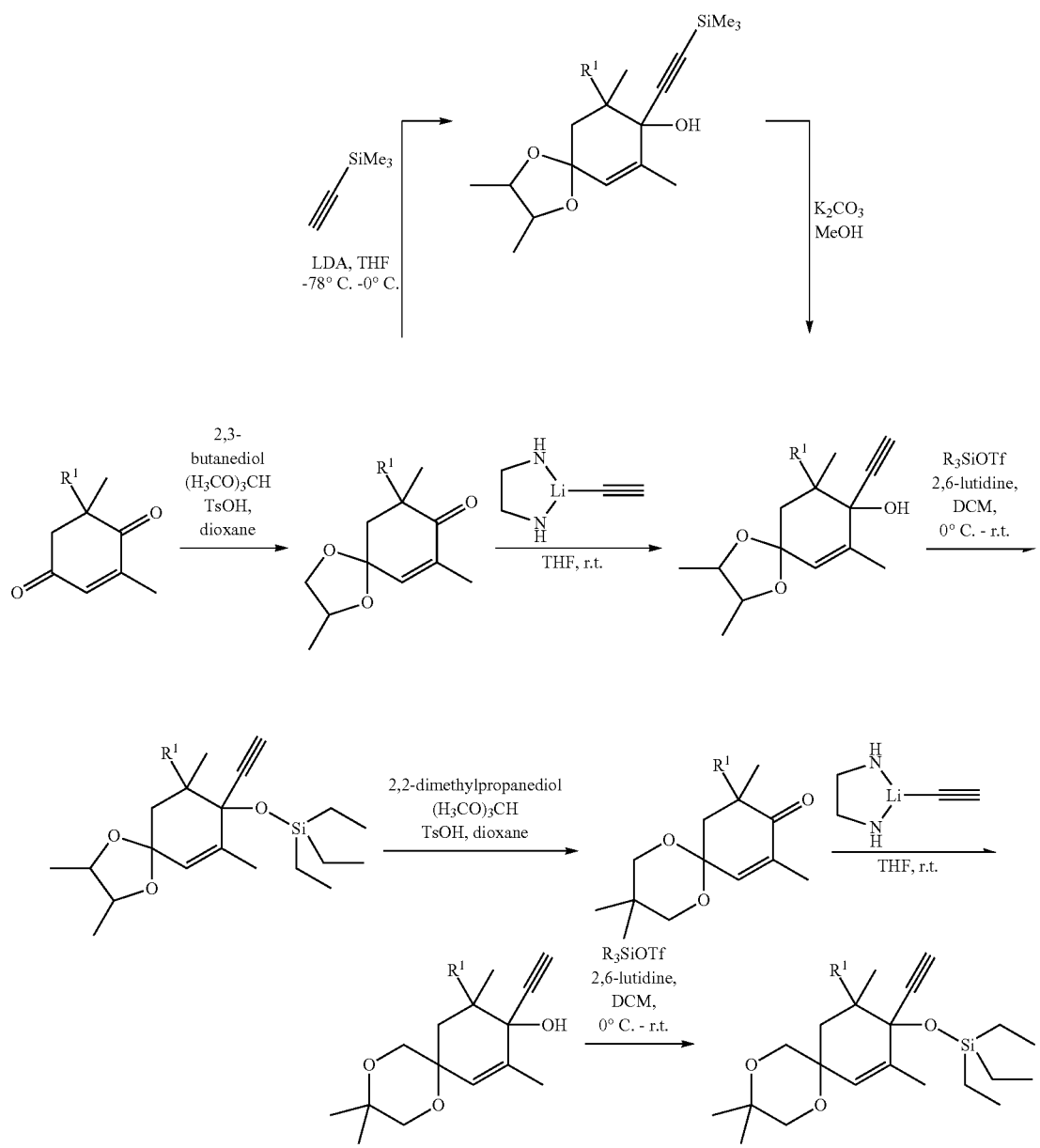

The substituted 8-ethynyl-1,4-dioxaspiro[4.5]dec-6-en-8-ol in question can be converted by reaction with a suitable silyl trifluoromethanesulfonate reagent, using a suitable base (e.g. 2,6-lutidine) in a suitable polar-aprotic solvent (e.g. dichloromethane), to a substituted (8-ethynyl-1,4-dioxaspiro[4.5]dec-6-en-8-yl)oxysilane. Through use of an optionally substituted propanediol in a first step, it is possible for the corresponding substituted 9-ethynyl-1,5-dioxaspiro[5.5]undec-7-en-9-ols to serve as key intermediates in analogous reactions for the reactions described hereinafter to give the compounds of the formula (I) according to the invention. Scheme 1 shows the above-described synthesis sequence, by way of example using 2,3-butanediol and 2,2-dimethylpropanediol, and also triethylsilyl trifluoromethanesulfonate.

Scheme 2

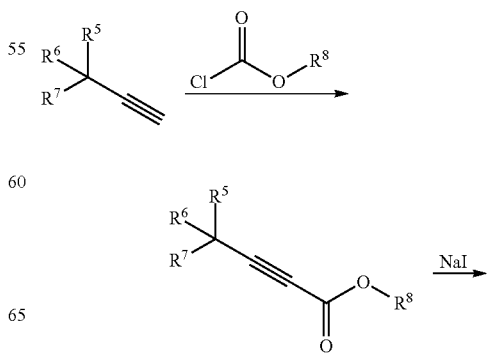

115
-continued

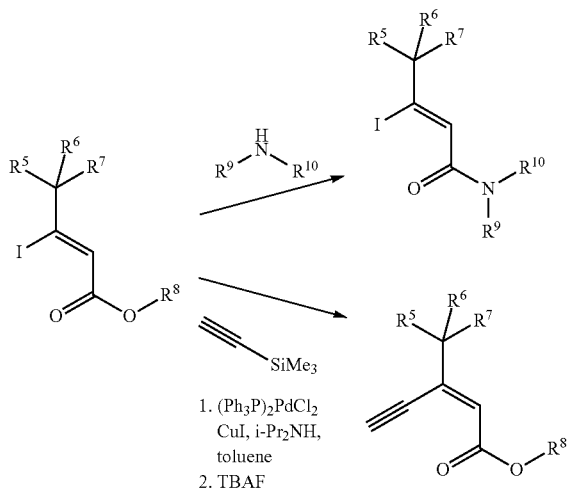

116

Starting with appropriately substituted 1-ethynyl-methyl-cyclohexen-1-ols, the (Z)-5-(cyclohex-2-en-1-yl)pent-2-en-4-ynoic acids I(a) according to the invention which are substituted further can be prepared by transition metal-catalyzed coupling with suitable substituted iodoalkenoic acid or alkynoic acid derivatives (cf. J. Chem. Res. (S), 2003, 426; J. Chem. Soc., Perkin Trans. 1 2001, 47; Adv. Synth. Catal. 2005, 347, 872) using a suitable transition metal catalyst system (for example bis-(triphenylphosphine)palladium dichloride, palladium(II) acetate together with triphenylphosphine or bis-(cycloacta-1,5-dienyl)iridium chloride in combination with a bidentate ligand, for example 2,2'-bis(diphenylphosphino)-1,1'-binaphthyl or 1,4-bis(diphenylphosphino)butane) and a suitable copper(I) halide (for example copper(I) iodide) in a suitable solvent mixture of an amine and a polar aprotic solvent (for example diisopropylamine and toluene or triethylamine and tetrahydrofuran) (Scheme 3).

Scheme 3

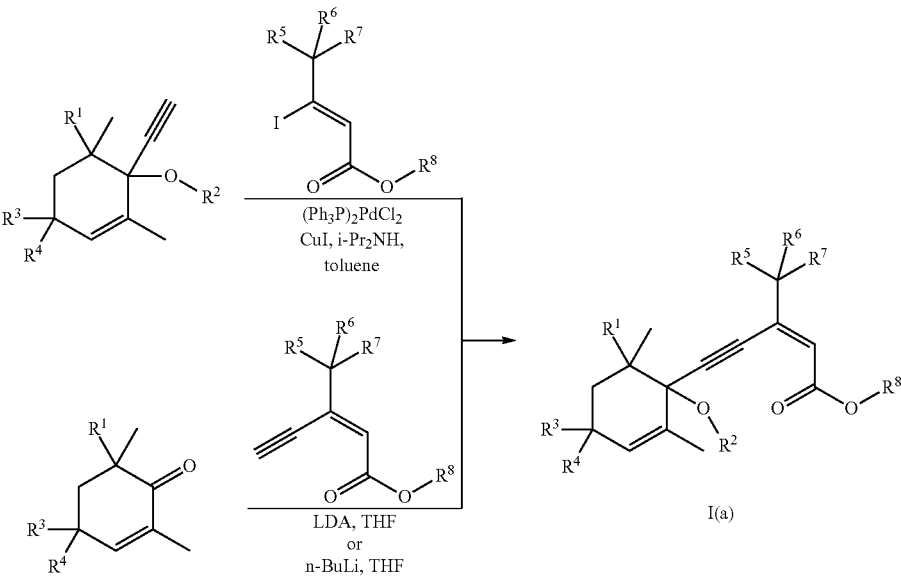

The corresponding (Z)-iodoalkenoic acid derivatives can be prepared, for example, by reacting a terminal alkyne with chloroformic esters using a suitable base (for example n-butyllithium) and subsequent reaction with sodium iodide (cf. J. Fluorine Chem. 1981, 17, 249; Org. Lett. 2000, 2, 3407; Tetrahedron Lett. 2008, 49, 794; Tetrahedron Lett. 1997, 38, 6729) (Scheme 2). Alternatively, the substituted (Z)-5-(cyclohex-2-en-1-yl)pent-2-en-4-ynoic acids I(a) according to the invention can also be prepared out by reacting a suitable substituted cyclohexenone with appropriate substituted (Z)-pent-2-en-4-ynoic acid derivatives using a suitable base (for example lithium diisopropylamide or n-butyllithium) in a suitable polar-aprotic solvent (for example tetrahydrofuran) (Scheme 3). The corresponding (Z)-pent-2-en-4-ynoic acid derivatives are accessible by transition metal-catalyzed coupling of a trialkylsilylalkyne with a (Z)-iodoalkenoic acid derivative (cf. J. Chem. Res. (S), 2003, 426; J. Chem. Soc., Perkin Trans. 1 2001, 47) using a suitable palladium catalyst (for example bis(triphenylphosphine)palladium dichloride) and a suitable copper(I) halide (for example copper(I) iodide) in a suitable solvent mixture of an amine and a polar aprotic solvent (for example diisopropylamine and toluene or triethylamine and tetrahydrofuran) and subsequent treatment with a suitable tetraalkylammonium fluoride (Scheme 2). Substituted (Z)-iodoalkenamides are accessible from the corresponding (Z)-iodoalkenoic acids by reaction with thionyl chloride and subsequent addition of the relevant amino component or by EDC and HOBt-mediated coupling with the amine component (Scheme 2). Here, EDC refers to 1-ethyl-3-(3-dimethylaminopropyl)carbodiimide and HOBt in this context refers to hydroxybenzotriazole.

yl)-pent-2-en-4-ynoic acids I(a) according to the invention by reaction with thionyl chloride and subsequent addition of the relevant amino component or by EDC- and HOBt-mediated coupling of the amine component or b) the transition metal-catalyzed coupling of an appropriately substituted 1-ethynyl-methylcyclohexen-1-ol and a (Z)-iodoalkenamide (cf. J. Chem. Res. (S), 2003, 426; J. Chem. Soc., Perkin Trans. 1 2001, 47) using a suitable palladium catalyst (for example bis(triphenylphosphine)palladium dichloride) and a suitable copper(I) halide (for example copper(I) iodide) in a suitable solvent mixture of an amine and a polar aprotic solvent (for example diisopropylamine and toluene or triethylamine and tetrahydrofuran).

The substituted (E,Z)-configured 5-(cyclohex-2-en-1-yl) penta-2,4-dienoic acid derivatives I(c) according to the invention can be prepared by a reduction of the alkyne group of the compounds I(a) according to the invention using suitable aluminum hydride reagents (for example sodium bis-(2-methoxyethoxy)aluminum hydride or lithium aluminum hydride) in a suitable polar-aprotic solvent (for example tetrahydrofuran) (cf. Org. Biomol. Chem. 2006, 4, 4186; Bioorg. Med. Chem. 2004, 12, 363-370; Tetrahedron 2003, 59, 9091-9100; Org. Biomol. Chem. 2006, 4, 1400-1412; Synthesis 1977, 561; Tetrahedron Letters 1992, 33, 3477 and Tetrahedron Letters 1974, 1593), using borohydride reagents (for example sodium borohydride) in a suitable polar-protic solvent (for example methanol) (cf. Org. Lett. 2004, 6, 1785), using lithium dissolved in a mixture of ethylamine and tert-butanol (for example Helvetica Chimica Acta 1986, 69, 368) or using a suitable trialkoxysilane in the presence of a suitable transition metal catalyst (for example tris-(acetonitrile)ruthe-

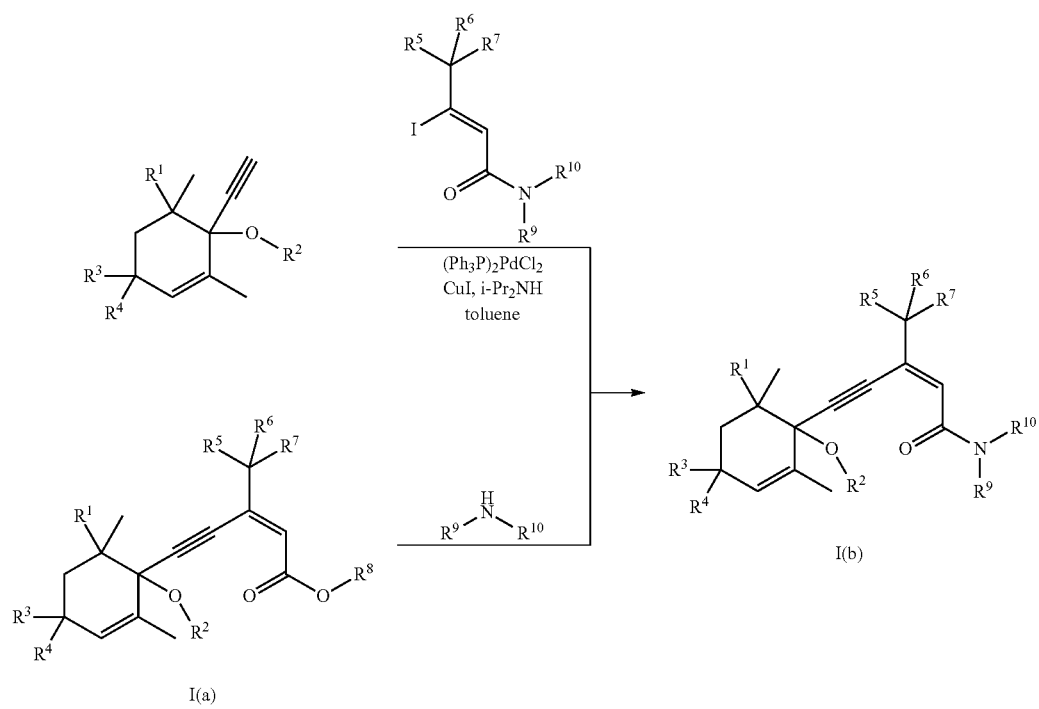

Scheme 4

Accordingly, the substituted (Z)-5-(cyclohex-2-en-1-yl)pent-2-en-4-ynoic acid amides I(b) according to the invention are accessible via two possible synthesis routes (Scheme 4), a) the conversion of the substituted (Z)-5-(cyclohex-2-en-1- nium-1,2,3,4,5-pentamethylcyclopentadienyl hexafluorophosphate or tris-(acetonitrile)rutheniumcyclopentadienyl hexafluorophosphate; cf. J. Am. Chem. Soc. 2002, 124, 7622; J. Am. Chem. Soc. 2005, 127, 17645) (Scheme 5). Depending on the reaction conditions, the hydrogenations of the triple bond can also afford, as further reaction products, the corresponding (E,E)-configured 5-(cyclohex-2-en-1-yl)penta-2,4-dienoic acid derivatives I(d) according to the invention.

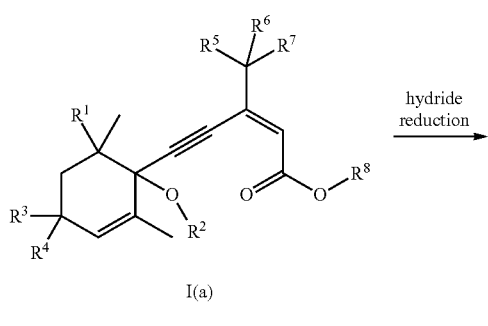

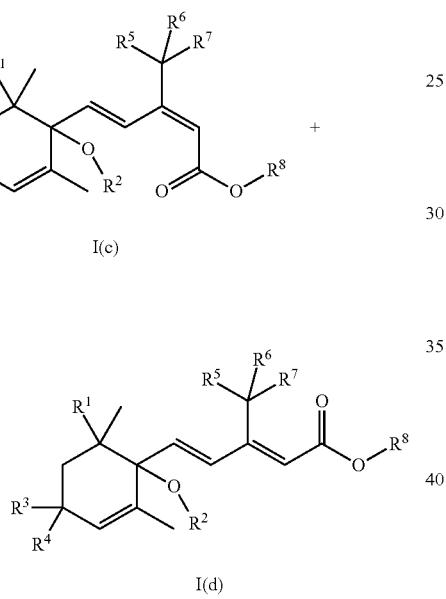

Alternative access to the substituted (E,Z)-configured 5-(cyclohex-2-en-1-yl)penta-2,4-dienoic acid derivatives I(c) according to the invention is offered by the metal hydride- or semimetal hydride-mediated conversion of the substituted 1-ethynylmethylcyclohexen-1-ols described above in a suitable polar-aprotic solvent (for example tetrahydrofuran or dichloromethane) into corresponding substituted (E)-[M]-1-vinylmethylcyclohexen-1-ols II (cf. Org. Lett. 2002, 4, 703; Angew. Int. Ed. 2006, 45, 2916), where [M] represents, for example, a further substituted metal or semimetal component from the group consisting of tin, germanium, lead, boron, aluminum and zirconium (for example [M]=tri-n-butylstannyl or biscyclopentadienylchlorozirconyl) (cf. also Org. Lett. 2010, 12, 1056; Org. Lett 2005, 7, 5191; J. Am. Chem. Soc. 2010, 132, 10961; Tetrahedron 1994, 50, 5189; Angew. Chem. Int. Ed. 2000, 39, 1930). The substituted (E)-[M]-1-vinylmethylcyclohexen-1-ols thus obtained can be converted by coupling with an appropriate substituted (Z)-haloalkenoic acid derivative in a suitable solvent (for example tetrahydrofuran or N,N-dimethylformamide) using suitable transition metal catalysts (for example bis(triphenylphosphine)palladium dicyanide, tetrakis(triphenylphosphine)palladium or bis(triphenylphosphine)palladium dichloride) to give the substituted (E,Z)-configured 5-(cyclohex-2-en-1-yl)penta-2,4-dienoic acid derivatives I(c) according to the invention (Scheme 6).

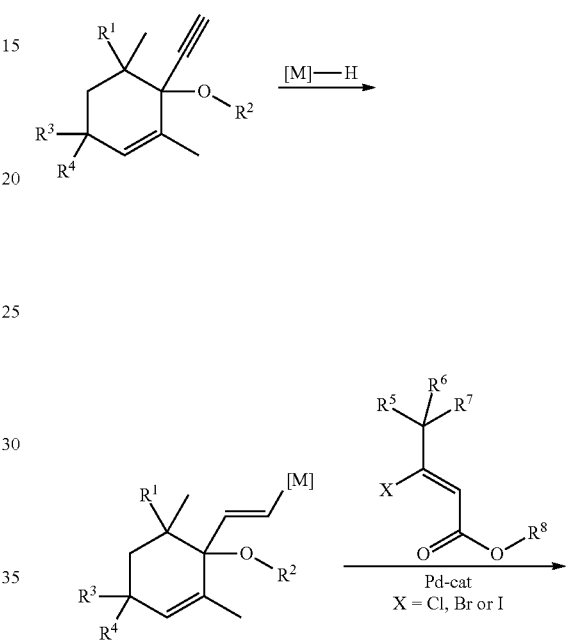

The corresponding substituted (E,Z)-configured 5-(cyclohex-2-en-1-yl)penta-2,4-dienamides I(e) according to the invention can be prepared by reacting compounds I(c) according to the invention with thionyl chloride and subsequent addition of the amino component in question or by EDC- and HOBt-mediated coupling of the amine component (Scheme 7).

Scheme 7

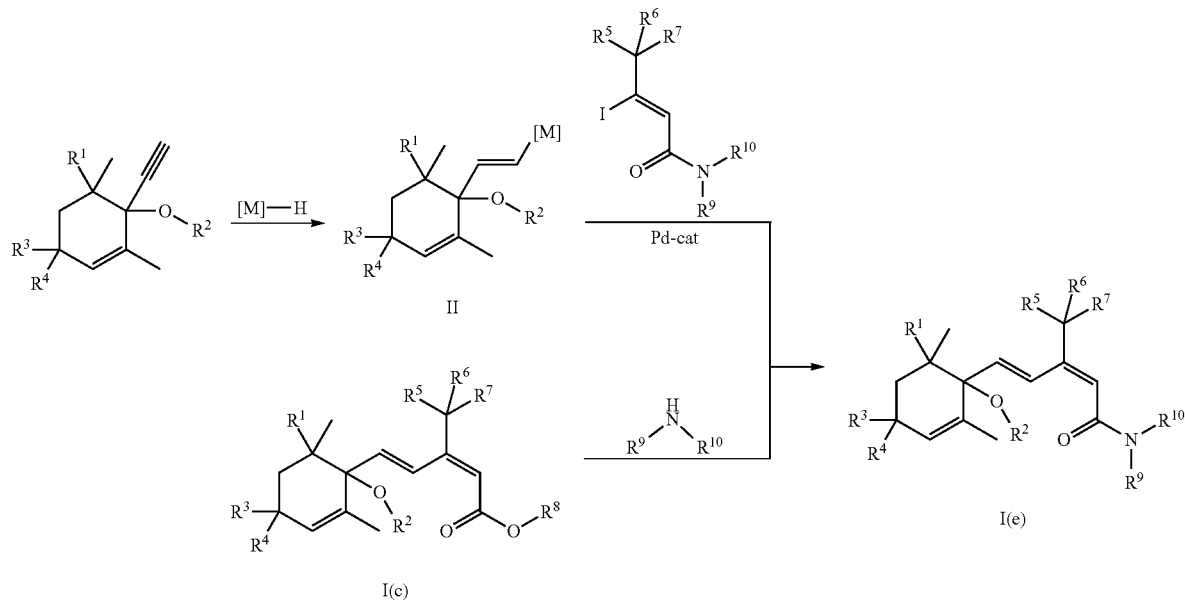

A further route providing access to the substituted (E,Z)-configured 5-(cyclohex-2-en-1-yl)penta-2,4-dienamides I(e) according to the invention is the coupling of substituted (E)-[M]-1-vinylmethylcyclohexen-1-ols with an appropriate substituted (Z)-haloalkenamide in a suitable solvent (for example tetrahydrofuran or N,N-dimethylformamide) using suitable transition metal catalysts (for example bis(triphenylphosphine)palladium dicyanide, tetrakis(triphenylphosphine)palladium or bis(triphenylphosphine)palladium dichloride) (Scheme 7).

Scheme 8

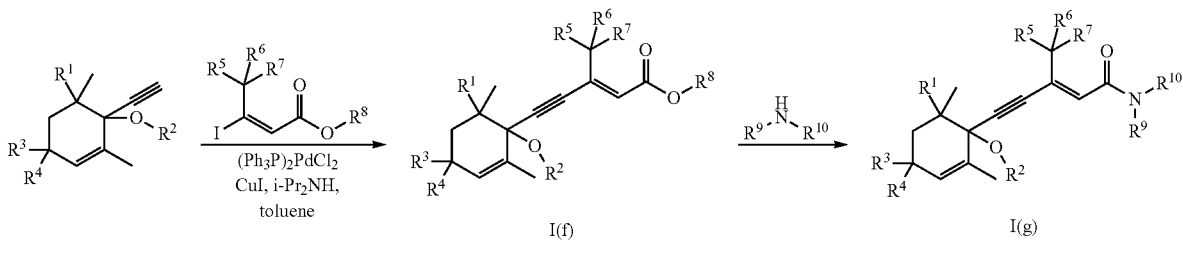

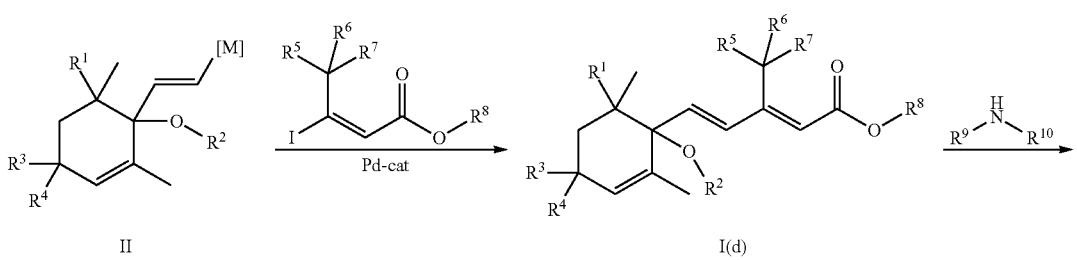

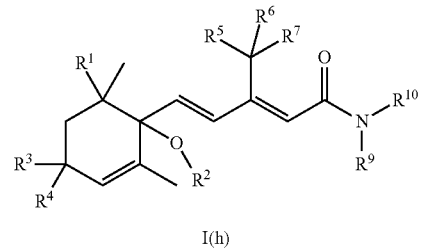

I(h)

The substituted (E)-5-(cyclohex-2-en-1-yl)pent-2-en-4-ynoic acid derivatives I(f) according to the invention, their corresponding amide analogs I(g) and the (E,E)-configured 5-(cyclohex-2-en-1-yl)penta-2,4-dienoic acid derivatives I(d) and the analogous amides I(h) can be prepared using the corresponding (E)-haloalkenoic acid derivatives and using the synthesis processes described above (Scheme 8).

Scheme 9

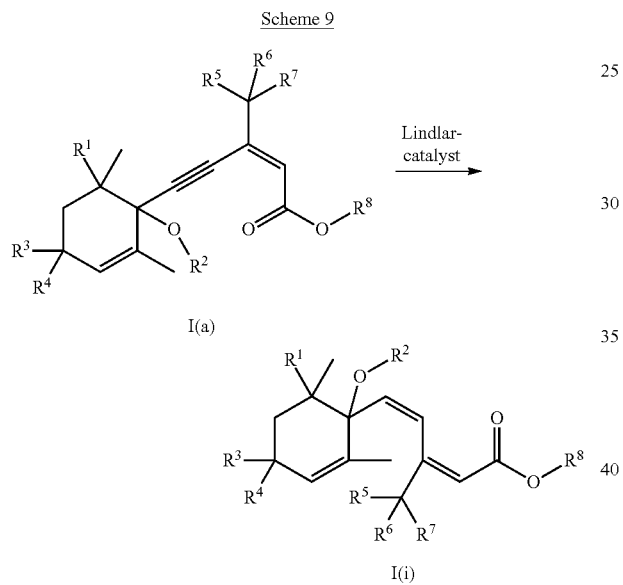

The reduction of substituted (Z)-5-(cyclohex-2-en-1-yl)pent-2-en-4-ynoic acid derivatives I(a) according to the invention to give the substituted (Z,Z)-configured 5-(cyclohex-2-en-1-yl)penta-2,4-dienoic acid derivatives I(i) according to the invention can be carried out in the presence of a transition metal catalyst such as, for example, Lindlar's catalyst with hydrogen in a suitable polar-aprotic solvent (such as, for example, n-butanol) (cf. Tetrahedron 1987, 43, 4107; Tetrahedron 1983, 39, 2315; J. Org. Synth. 1983, 48, 4436 and J. Am. Chem. Soc. 1984, 106, 2735) (Scheme 9).

Selected detailed synthesis examples for the compounds of the formula (I) according to the invention are given below. The example numbers mentioned correspond to the numberings in tables 1 to 5 below. The $^1$H NMR, $^{13}$C NMR and $^{19}$F NMR spectroscopy data which are reported for the chemical examples described in the paragraphs which follow (400 MHz for $^1$H NMR and 150 MHz for $^{13}$C NMR and 375 MHz for $^{19}$F NMR, solvent: CDCl$_3$, CD$_3$OD or d$_6$-DMSO, internal standard: tetramethylsilane δ=0.00 ppm), were obtained on a Bruker instrument, and the signals listed have the meanings given below: br=broad; s=singlet, d=doublet, t=triplet, dd=doublet of doublets, ddd=doublet of a doublet of doublets, m=multiplet, q=quartet, quint=quintet, sext=sextet, sept=septet, dq=doublet of quartets, dt=doublet of triplets. The abbreviations used for chemical groups are defined as follows: Me=CH$_3$, Et=CH$_2$CH$_3$, t-Hex =C(CH$_3$)$_2$CH(CH$_3$)$_2$, t-Bu=C(CH$_3$)$_3$, n-Bu=unbranched butyl, n-Pr=unbranched propyl, c-Hex=cyclohexyl. In the case of diastereomer mixtures, either the significant signals for each of the two diastereomers or the characteristic signal of the main diastereomer is/are reported.

SYNTHESIS EXAMPLES

No. I.1-1: Ethyl (2Z)-3-[(8-hydroxy-2,3,7,9,9-pentamethyl-1,4-dioxaspiro[4.5]dec-6-en-8-yl)ethynyl]hex-2-enoate

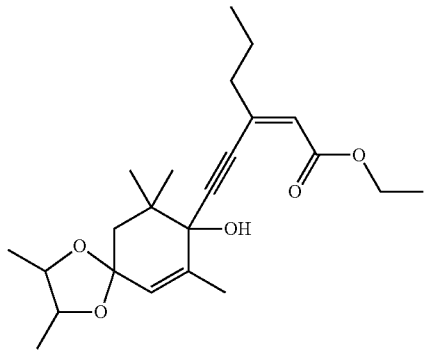 [SMILES: CCC/C(C#CC1(O)C(C)=CC2(CC1(C)C)OC(C)C(C)O2)=C/C(=O)OCC]

In a round-bottom flask under argon, 2,2,6-trimethyl-1,4-cyclohexanedione (15.40 g, 101.19 mmol) was dissolved in 2,3-butanediol (90 ml) and abs. toluene (90 ml), and trimethyl orthoformate (33.21 ml, 303.56 mmol) and p-toluenesulfonic acid (1.22 g, 7.08 mmol) were added. The resulting reaction mixture was stirred at 50° C. for 7 h. After cooling to room temperature, water and toluene were added and the aqueous phase was extracted repeatedly with toluene. The combined organic phases were dried over magnesium sulfate, filtered and concentrated under reduced pressure. By column chromatography purification of the resulting crude product (ethyl acetate/heptane gradient), 2,3,7,9,9-pentamethyl-1,4-dioxaspiro[4.5]dec-6-en-8-one (20.01 g, 88% of theory) was obtained. In a round-bottom flask under argon, 2,3,7,9,9-pentamethyl-1,4-dioxaspiro[4.5]dec-6-en-8-one (10.00 g, 44.58 mmol) was then dissolved in abs. tetrahydrofuran (50 ml) and added dropwise to a solution of a lithium acetylide/ethylenediamine complex (6.28 g, 57.96 mmol, 85% pure) in abs. tetrahydrofuran (70 ml). On completion of addition, the reaction mixture was stirred at room temperature for 4 h, then water was added and the mixture was concentrated under reduced pressure. The remaining residue was admixed with water and dichloromethane, and the aqueous phase was extracted repeatedly with dichloromethane. The combined organic phases were dried over magnesium sulfate, filtered and concentrated under reduced pressure. By column chromatography purification of the crude product obtained (ethyl acetate/heptane gradient), 8-ethynyl-2,3,7,9,9-pentamethyl-1,4-dioxaspiro[4.5]dec-6-en-8-ol (10.02 g, 85% of theory) was isolated as a colorless solid. Subsequently, copper(I) iodide (46 mg, 0.24 mmol) and bis(triphenylphosphine)palladium(II) chloride (126 mg, 0.18 mmol) were initially charged under argon in a baked-out round-bottom flask, and abs. toluene (8 ml) and ethyl (2Z)-3-iodohex-2-enoate (321 mg, 1.19 mmol) were added. Stirring at room temperature for 10 min was followed by the dropwise addition of a solution of 8-ethynyl-2,3,7,9,9-pentamethyl-1,4-dioxaspiro[4.5]dec-6-en-8-ol (300 mg, 1.19 mmol) in abs. toluene (2 ml) and of diisopropylamine (0.34 ml, 2.39 mmol). The resulting reaction mixture was stirred at room temperature for 3 h and then water was added. The aqueous phase was extracted repeatedly with dichloromethane. The combined organic phases were dried over magnesium sulfate, filtered and concentrated under reduced pressure. By final column chromatography purification of the crude product obtained (using an ethyl acetate/heptane gradient), ethyl (2Z)-3-[(8-hydroxy-2,3,7,9,9-pentamethyl-1,4-dioxaspiro[4.5]dec-6-en-8-yl)ethynyl]hex-2-enoate (440 mg, 94% of theory) was isolated in the form of a colorless oil. $^1$H-NMR (400 MHz, CDCl$_3$ δ, ppm) 5.97 (s, 1H), 5.49 (s, 1H), 4.18 (m, 3H), 3.59 (m, 1H), 2.22 (m, 2H), 2.02 (m, 1H), 1.92 (m, 4H), 1.58 (m, 3H), 1.24 (t, 3H), 1.20-1.12 (m, 12H), 0.91 (t, 3H).

No. I.1-2: Ethyl (2Z)-3-[(1-hydroxy-2,6,6-trimethyl-4-oxocyclohex-2-en-1-yl)ethynyl]hex-2-enoate

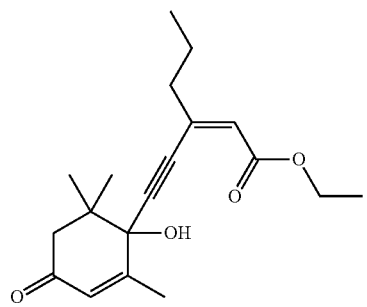 [SMILES: CCC/C(C#CC1(O)C(C)=CC(=O)CC1(C)C)=C/C(=O)OCC]

Ethyl (2Z)-3-[(8-hydroxy-2,3,7,9,9-pentamethyl-1,4-dioxaspiro[4.5]dec-6-en-8-yl)ethynyl]hex-2-enoate (100 mg, 0.26 mmol) was dissolved in acetone (5 ml) under argon in a round-bottom flask, and 5 drops of conc. hydrochloric acid were added.

The resulting reaction solution was stirred at room temperature for 3 h and then water was added. After removing acetone under reduced pressure, the aqueous phase was extracted repeatedly with dichloromethane. The combined organic phases were dried over magnesium sulfate, filtered and concentrated under reduced pressure. By column chromatography purification of the resulting crude product (ethyl acetate/heptane gradient), ethyl (2Z)-3-[(1-hydroxy-2,6,6-trimethyl-4-oxocyclohex-2-en-1-yl)ethynyl]hex-2-enoate (62 mg, 72% of theory) was isolated in the form of a colorless oil. $^1$H-NMR (400 MHz, CDCl$_3$ δ, ppm) 6.04 (s, 1H), 5.87 (s, 1H), 4.17 (q, 2H), 2.99 (br. s, 1H, OH), 2.59 (d, 1H), 2.42 (d, 1H), 2.23 (t, 2H), 2.15 (s, 3H), 1.59 (m, 2H), 1.29 (t, 3H), 1.25 (s, 3H), 1.13 (s, 3H), 0.93 (t, 3H).

No. I.1-3: Ethyl (2Z)-3-[(E)-2-(8-hydroxy-2,3,7,9,9-pentamethyl-1,4-dioxaspiro[4.5]dec-6-en-811)vinyl]hex-2-enoate

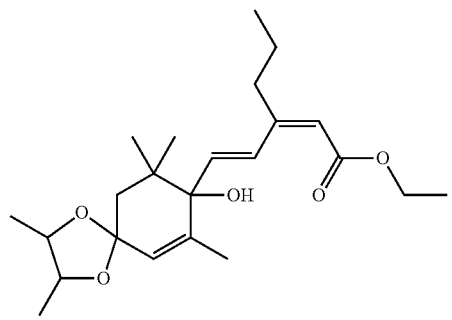 [SMILES: CCCC(=C/C(=O)OCC)/C=C/C1(O)C(C)=CC2(CC1(C)C)OC(C)C(C)O2]

Under argon, ethyl (2Z)-3-[(8-hydroxy-2,3,7,9,9-pentamethyl-1,4-dioxaspiro[4.5]dec-6-en-8-yl)ethynyl]-hex-2-enoate (340 mg, 0.87 mmol) was dissolved in a round-bottom flask in abs. dichloromethane (4 ml), and triethoxysilane (172 mg, 1.05 mmol) was added. The reaction solution was then cooled to 0° C., tris(acetonitrile)cyclopentadienylruthenium (II) hexafluorophosphate (18 mg, 0.04 mmol) was added and the mixture was stirred at room temperature for 2 h. Diethyl ether was then added, and the reaction mixture was concentrated under reduced pressure. The residue that remained was dissolved in abs. tetrahydrofuran (4 ml), copper(I) iodide (16 mg, 0.09 mmol) and tetra-n-butylammonium fluoride (289 mg, 1.11 mmol) were added, the mixture was stirred at room temperature for 4 h, and water was then added. The aqueous phase was repeatedly extracted thoroughly with dichloromethane. The combined organic phases were then dried over magnesium sulfate, filtered and concentrated under reduced pressure. Purification of the resulting crude product by column chromatography (ethyl acetate/heptane gradient) gave ethyl (2Z)-3-[(E)-2-(8-hydroxy-2,3,7,9,9-pentamethyl-1,4-dioxaspiro[4.5]-dec-6-en-8-yl)vinyl]hex-2-enoate (140 mg, 41% of theory) in the form of a colorless oil. $^1$H-NMR (400 MHz, CDCl$_3$ δ, ppm) 7.68 (d, 1H), 6.09 (d, 1H), 5.97 (s, 1H), 5.48 (s, 1H), 4.19 (m, 3H), 3.61 (m, 1H), 2.29 (m, 1H), 2.22 (m, 2H), 2.02 (m, 1H), 1.92 (m, 3H), 1.67 (m, 2H), 1.62 (m, 1H), 1.28 (m, 6H), 1.20-1.08 (m, 9H), 0.91 (t, 3H).

No. I.1-4: Ethyl (2Z)-3-[(E)-2-(1-hydroxy-2,6,6-trimethyl-4-oxocyclohex-2-en-1-yl)vinyl]hex-2-enoate

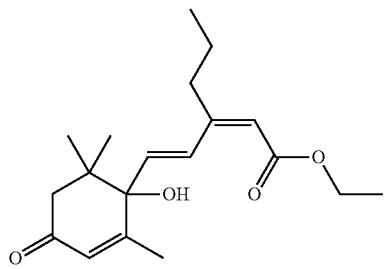 [SMILES: CCCC(=C/C(=O)OCC)/C=C/C1(O)C(C)=CC(=O)CC1(C)C]

Ethyl (2Z)-3-[(E)-2-(8-hydroxy-2,3,7,9,9-pentamethyl-1,4-dioxaspiro[4.5]-dec-6-en-8-yl)vinyl]hex-2-enoate (180 mg, 0.46 mmol) was dissolved in acetone (5 ml) under argon in a round-bottom flask, and 3 drops of conc. hydrochloric acid were added. The resulting reaction solution was stirred at room temperature for 30 minutes, and water was then added. After removing acetone under reduced pressure, the aqueous phase was extracted repeatedly with dichloromethane. The combined organic phases were dried over magnesium sulfate, filtered and concentrated under reduced pressure. By final column chromatography purification of the resulting crude product (ethyl acetate/heptane gradient), ethyl (2Z)-3-[(E)-2-(1-hydroxy-2,6,6-trimethyl-4-oxocyclohex-2-en-1-yl)vinyl]hex-2-enoate (114 mg, 74% of theory) was obtained in the form of a colorless oil. $^1$H-NMR (400 MHz, CDCl$_3$ δ, ppm) 7.77 (d, 1H), 6.15 (d, 1H), 6.05 (s, 1H), 5.93 (s, 1H), 4.19 (q, 2H), 2.96 (br. s, 1H, OH), 2.47 (d, 1H), 2.31 (d, 1H), 2.24 (t, 2H), 1.92 (s, 3H), 1.58 (m, 2H), 1.27 (t, 3H), 1.24 (s, 3H), 1.12 (s, 3H), 0.92 (t, 3H).

No. I.1-11: Ethyl (2Z,4E)-3-ethyl-5-{2,3,7,9,9-pentamethyl-8-[(triethylsilyl)oxy]-1,4-dioxaspiro[4.5]dec-6-en-8-yl}penta-2,4-dienoate

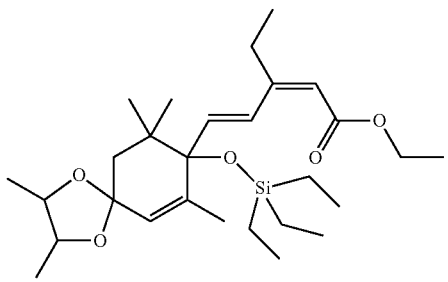 [SMILES: CCOC(=O)/C=C(\C=C\C1(O[Si](CC)(CC)CC)C(C)=CC2(CC1(C)C)OC(C)C(C)O2)CC]

A solution of biscyclopentadienyldimethyl[(E)-2-{2,3,7,9,9-pentamethyl-8-[(triethylsilyl)oxy]-1,4-dioxaspiro[4.5]dec-6-en-8-yl}vinyl]zirconium in abs. tetrahydrofuran was cooled to 0° C., and a solution of bis(triphenylphosphine)palladium(II) chloride (39 mg, 0.06 mmol), diisobutylaluminum hydride (16 mg, 0.11 mmol) and ethyl (2Z)-3-iodopent-2-enoate (260 mg, 1.15 mmol) in abs. tetrahydrofuran which had been stirred beforehand for 10 minutes was added dropwise. A solution of zink(II) chloride (149 mg, 1.09 mmol) in abs. tetrahydrofuran (3 ml) was then added directly. The resulting reaction mixture was stirred at room temperature for 7 h and then water was added. After removal of tetrahydrofuran under reduced pressure, the aqueous phase was extracted repeatedly with dichloromethane. The combined organic phases were then dried over magnesium sulfate, filtered and concentrated under reduced pressure. By final column chromatography purification of the crude product obtained (using an ethyl acetate/heptane gradient), ethyl (2Z,4E)-3-ethyl-5-{2,3,7,9,9-pentamethyl-8-[(triethylsilyl)oxy]-1,4-dioxaspiro[4.5]-dec-6-en-8-yl}penta-2,4-dienoate (21 mg, 3% of theory) was isolated in the form of a colorless oil. $^1$H-NMR (400 MHz, CDCl$_3$ δ, ppm) 7.52 (d, 1H), 6.38 (d, 1H), 6.04 (s, 1H), 5.39 (s, 1H), 4.28 (q, 1H), 4.23 (m, 1H), 3.59 (m, 1H), 2.29 (q, 2H), 2.20 (br. s, 1H, OH), 2.04 (d, 1H), 1.93 (s, 3H), 1.88 (d, 1H), 1.23 (m, 3H), 1.19-1.12 (m, 12H), 0.92 (t, 3H).

No. I.1-13: Ethyl (2E)-5-(8-hydroxy-2,3,7,9,9-pentamethyl-1,4-dioxaspiro[4.5]dec-6-en-8-yl)-3-(trifluoromethyl)pent-2-en-4-ynoate

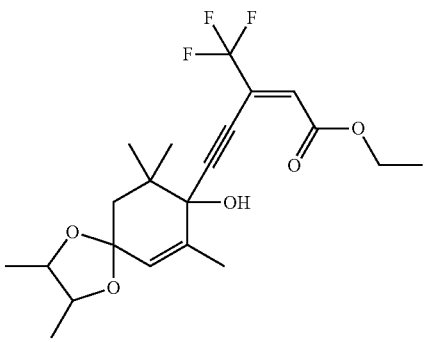 [SMILES: CCOC(=O)/C=C(\C#CC1(O)C(C)=CC2(CC1(C)C)OC(C)C(C)O2)C(F)(F)F]

Copper(I) iodide (46 mg, 0.24 mmol) and bis(triphenylphosphine)palladium(II)chlorid (126 mg, 0.18 mmol) were initially charged under argon in a round-bottom flask which had been dried by heating, and abs. toluene (9 ml) and ethyl (2Z)-4,4,4-trifluoro-3-iodobut-2-enoate (388 mg, 1.32 mmol) were added. Stirring at room temperature for 10 minutes was followed by the dropwise addition of a solution of 8-ethynyl-2,3,7,9,9-pentamethyl-1,4-dioxaspiro[4.5]dec-6-en-8-ol (300 mg, 1.19 mmol) in abs. toluene (3 ml) and of diisopropylamine (0.34 ml, 2.39 mmol). The resulting reaction mixture was stirred at room temperature for 3 h and then water was added. The aqueous phase was extracted repeatedly with dichloromethane. The combined organic phases were dried over magnesium sulfate, filtered and concentrated under reduced pressure. By final column chromatography purification of the crude product obtained (using an ethyl acetate/heptane gradient), ethyl (2E)-5-(8-hydroxy-2,3,7,9,9-pentamethyl-1,4-dioxaspiro[4.5]dec-6-en-8-yl)-3-(trifluoromethyl)pent-2-en-4-ynoate (300 mg, 57% of theory) was isolated in the form of a colorless oil. $^1$H-NMR (400 MHz, CDCl$_3$ δ, ppm) 6.61 (s, 1H), 5.56 (s, 1H), 4.22 (m, 3H), 3.58 (m, 1H), 2.21 (br. s, 1H, OH), 1.99 (m, 1H), 1.92 (m, 4H), 1.31 (t, 3H), 1.22-1.13 (m, 12H).

No. I.1-14: Ethyl (2E)-5-(1-hydroxy-2,6,6-trimethyl-4-oxocyclohex-2-en-1-yl)-3-(trifluoromethyl)pent-2-en-4-ynoate

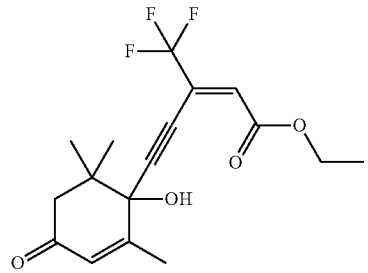 [SMILES: CCOC(=O)/C=C(\C#CC1(O)C(C)=CC(=O)CC1(C)C)C(F)(F)F]

Ethyl (2E)-5-(8-hydroxy-2,3,7,9,9-pentamethyl-1,4-dioxaspiro[4.5]dec-6-en-8-yl)-3-(trifluoromethyl)pent-2-en-4-ynoate (200 mg, 0.48 mmol) was dissolved in acetone (5 ml) under argon in a round-bottom flask, and 10% strength hydrochloric acid was added. The resulting reaction solution was stirred at room temperature for 45 minutes, and water was then added. After removing acetone under reduced pressure, the aqueous phase was extracted repeatedly with dichloromethane. The combined organic phases were dried over magnesium sulfate, filtered and concentrated under reduced pressure. By column chromatography purification of the resulting crude product (ethyl acetate/heptane gradient), ethyl (2E)-5-(1-hydroxy-2,6,6-trimethyl-4-oxocyclohex-2-en-1-yl)-3-(trifluoromethyl)pent-2-en-4-ynoate (130 mg, 79% of theory) was obtained in the form of a colorless oil.
$^1$H-NMR (400 MHz, CDCl$_3$ δ, ppm) 6.68 (s, 1H), 5.90 (s, 1H), 4.26 (q, 2H), 2.58 (m, 2H), 2.44 (d, 1H), 2.15 (s, 3H), 1.31 (t, 3H), 1.25 (s, 3H), 1.15 (s, 3H).

No. I.1-15: Ethyl (2E,4E)-5-(8-hydroxy-2,3,7,9,9-pentamethyl-1,4-dioxaspiro[4.5]dec-6-en-8-yl)-3-(trifluoromethyl)penta-2,4-dienoate

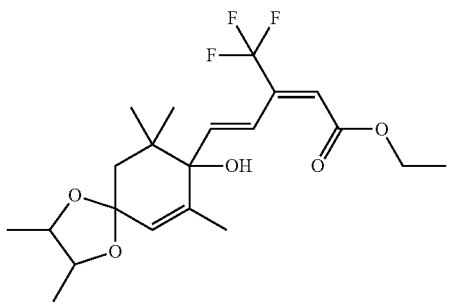 [SMILES: CCOC(=O)/C=C(\C=C\C1(O)C(C)=CC2(CC1(C)C)OC(C)C(C)O2)C(F)(F)F]

Under argon, 2,3,7,9,9-pentamethyl-8-[(E)-2-(tributylstannyl)vinyl]-1,4-dioxaspiro[4.5]dec-6-en-8-ol (300 mg, 0.55 mmol) and ethyl (2Z)-4,4,4-trifluoro-3-iodobut-2-enoate (163 mg, 0.55 mmol) in a round-bottom flask that had been dried by heating were dissolved in abs. N,N-dimethylformamide (4 ml), dichlorobis(acetonitrile)palladium(II) (7 mg, 0.03 mmol) was added and the mixture was stirred at room temperature for 3 h. After the addition of potassium fluoride solution, the reaction mixture was stirred further at room temperature overnight. The aqueous phase was then repeatedly extracted thoroughly with diethyl ether, and the combined organic phases were then dried over magnesium sulfate, filtered and concentrated under reduced pressure. By final column chromatography purification of the resulting crude product (ethyl acetate/heptane gradient), ethyl (2E,4E)-5-(8-hydroxy-2,3,7,9,9-pentamethyl-1,4-dioxaspiro[4.5]dec-6-en-8-yl)-3-(trifluoromethyl)penta-2,4-dienoate (150 mg, 61% of theory) was obtained in the form of a colorless oil.
$^1$H-NMR (400 MHz, CDCl$_3$ δ, ppm) 7.47 (d, 1H), 6.29 (d, 1H), 6.25 (s, 1H), 5.48 (s, 1H), 4.26 (q, 2H), 3.68 (m, 1H), 3.59 (m, 1H), 1.93 (d, 1H), 1.83 (br. m, 1H, OH), 1.77 (d, 1H), 1.69 (s, 3H), 1.32 (t, 3H), 1.25 (m, 3H), 1.18 (m, 3H), 1.10 (s, 3H), 0.91 (s, 3H).

No. I.1-16: Ethyl (2E,4E)-5-(1-hydroxy-2,6,6-trimethyl-4-oxocyclohex-2-en-1-yl)-3-(trifluoromethyl)penta-2,4-dienoate

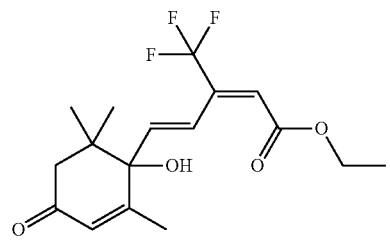 [SMILES: CCOC(=O)/C=C(\C=C\C1(O)C(C)=CC(=O)CC1(C)C)C(F)(F)F]

Ethyl (2E,4E)-5-(8-hydroxy-2,3,7,9,9-pentamethyl-1,4-dioxaspiro[4.5]dec-6-en-8-yl)-3-(trifluoromethyl)penta-2,4-dienoate (150 mg, 0.36 mmol) was dissolved in acetone (5 ml) under argon in a round-bottom flask, and 10% strength hydrochloric acid was added. The resulting reaction solution was stirred at room temperature for 40 minutes, and water was then added. After removing acetone under reduced pressure, the aqueous phase was extracted repeatedly with dichloromethane. The combined organic phases were dried over magnesium sulfate, filtered and concentrated under reduced pressure. By column chromatography purification of the resulting crude product (ethyl acetate/heptane gradient), ethyl (2E,4E)-5-(1-hydroxy-2,6,6-trimethyl-4-oxocyclohex-2-en-1-yl)-3-(trifluoromethyl)penta-2,4-dienoate (80 mg, 61% of theory) was obtained in the form of a colorless oil.
$^1$H-NMR (400 MHz, CDCl$_3$ δ, ppm) 7.55 (d, 1H), 6.37 (d, 1H), 6.33 (s, 1H), 5.97 (s, 1H), 4.25 (q, 2H), 2.47 (d, 1H), 2.34 (d, 1H), 1.92 (s, 3H), 1.90 (br. s, 1H, OH), 1.33 (t, 3H), 1.11 (s, 3H), 1.02 (s, 3H).

No. I.1-23: (2E)-5-(1-Hydroxy-2,6,6-trimethyl-4-oxocyclohex-2-en-1-yl)-3-(trifluoromethyl)pent-2-en-4-ynoic acid

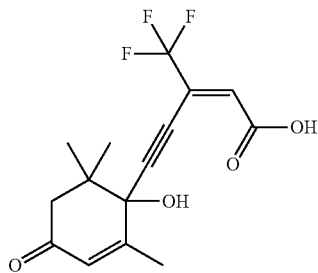 [SMILES: CC1=CC(=O)CC(C)(C)C1(O)C#C/C(=C\C(=O)O)C(F)(F)F]

In a round-bottom flask, ethyl (2E)-5-(1-hydroxy-2,6,6-trimethyl-4-oxocyclohex-2-en-1-yl)-3-(trifluoromethyl)pent-2-en-4-ynoate (130 mg, 0.38 mmol) was dissolved in a mixture of water and tetrahydrofuran, and sodium hydroxide (38 mg, 0.94 mmol) was then added. The resulting reaction mixture was stirred under reflux for 2 h and, after cooling to room temperature, acidified with aqueous hydrochloric acid. The aqueous phase was repeatedly extracted thoroughly with dichloromethane, and the combined organic phases were then dried over magnesium sulfate, filtered and concentrated under reduced pressure. By final column chromatography purification of the resulting crude product (ethyl acetate/heptane gradient), (2E)-5-(1-hydroxy-2,6,6-trimethyl-4-oxocyclohex-2-en-1-yl)-3-(trifluoromethyl)pent-2-en-4-ynoic acid (40 mg, 32% of theory) was obtained in the form of a colorless solid. $^1$H-NMR (400 MHz, CDCl$_3$ δ, ppm) 10.14 (br. s, 1H, OH), 6.70 (s, 1H), 5.92 (s, 1H), 2.61 (d, 1H), 2.43 (d, 1H), 2.30 (br. s, 1H, OH), 2.16 (s, 3H), 1.28 (s, 3H), 1.13 (s, 3H).

No. I.1-401: Ethyl (2E)-5-[1-hydroxy-4-(methoxyimino)-2,6,6-trimethylcyclohex-2-en-1-yl]-3-(trifluoromethyl)pent-2-en-4-ynoate

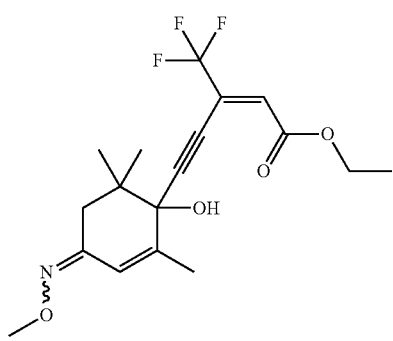 [SMILES: CCOC(=O)/C=C(\C#CC1(O)C(C)=CC(=NOC)CC1(C)C)C(F)(F)F]

Ethyl (2E)-5-(1-hydroxy-2,6,6-trimethyl-4-oxocyclohex-2-en-1-yl)-3-(trifluoromethyl)pent-2-en-4-ynoate (60 mg, 0.17 mmol), O-methylhydroxylamine hydrochloride (17 mg, 0.21 mmol) and sodium acetate (30 mg, 0.37 mmol) were dissolved in a 1:1 mixture of ethanol and water (4 ml) and then stirred at a temperature of 60° C. for 4 h. After cooling to room temperature, ethanol was removed under reduced pressure and the aqueous phase was extracted repeatedly with dichloromethane. The combined organic phases were dried over magnesium sulfate, filtered and concentrated under reduced pressure. By column chromatography purification of the resulting crude product (ethyl acetate/heptane gradient), ethyl (2E)-5-[1-hydroxy-4-(methoxyimino)-2,6,6-trimethylcyclohex-2-en-1-yl]-3-(trifluoromethyl)pent-2-en-4-ynoate (40 mg, 58% of theory) was obtained in the form of a colorless solid. $^1$H-NMR (400 MHz, CDCl$_3$ δ, ppm) 6.65/6.63 (s, 1H), 6.00/5.94 (s, 1H), 4.27 (q, 2H), 3.89/3.86 (s, 3H), 2.62/2.56 (br. s, 1H, OH), 2.46 (d, 1H), 2.39 (m, 1H), 2.08/2.05 (s, 3H), 1.31 (t, 3H), 1.18 (s, 3H), 1.11 (s, 3H).

No. I.1-521: Ethyl (2E)-5-[8-hydroxy-2,3,7,9-tetramethyl-9-(trifluoromethyl)-1,4-dioxa-spiro[4.5]dec-6-en-8-yl]-3-(trifluoromethyl)pent-2-en-4-ynoate

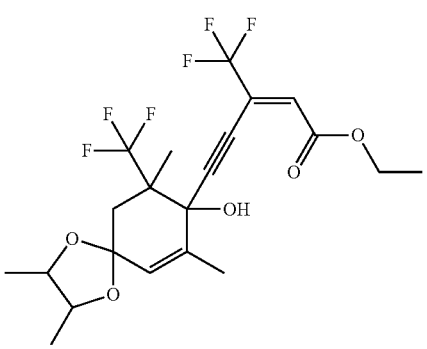 [SMILES: CCOC(=O)/C=C(\C#CC1(O)C(C)=CC2(CC1(C)C(F)(F)F)OC(C)C(C)O2)C(F)(F)F]

Acetylmethylenetriphenylphosphorane (12.91 g, 40.57 mmol) was dissolved in a mixture of diethyl ether (30 ml) and dichloromethane (10 ml) and stirred for 5 min, then 1,1,1-trifluoroacetone (5.00 g, 44.62 mmol) was added and the mixture was stirred at room temperature for 40 h. The precipitate formed was filtered off, the filter cake was washed with diethyl ether and the combined organic phases were concentrated cautiously under slightly reduced pressure. The crude solution of (3Z)-5,5,5-trifluoro-4-methylpent-3-en-2-one thus obtained was used without further purification in the next reaction step and taken up in toluene (25 ml). After the addition of ethyl acetoacetate (3.42 g, 26.29 mmol) and potassium tert-butoxide (0.88 g, 7.89 mmol), the resulting reaction mixture was stirred under reflux conditions for 5 h. After cooling to room temperature, water was added, the mixture was stirred vigorously for 5 minutes and then the aqueous phase was extracted repeatedly with dichloromethane. The combined organic phases were dried over magnesium sulfate, filtered and concentrated under reduced pressure. By final column chromatography purification of the resulting crude product (ethyl acetate/heptane gradient), it was possible to obtain 3,5-dimethyl-5-(trifluoromethyl)cyclohex-2-en-1-one (1.9 g, 38% of theory) in the form of a colorless oil. 3,5-Dimethyl-5-(trifluoromethyl)cyclohex-2-en-1-one (1.60 g, 8.33 mmol) was then dissolved in abs. toluene, and molybdatophosphoric acid hydrate (30 mg, 0.02 mmol), copper(II) sulfate pentahydrate (4 mg, 0.02 mmol) and molybdenum (VI) oxide (5 mg, 0.03 mmol) were added. The resulting reaction mixture was stirred with introduction of air under reflux conditions for 4 days. After cooling to room temperature, water was added, the mixture was stirred vigorously for 5 minutes and then the aqueous phase was extracted repeatedly with dichloromethane. The combined organic phases were dried over magnesium sulfate, filtered and concentrated under reduced pressure. By column chromatography purification of the resulting crude product (ethyl acetate/heptane gradient), it was possible to obtain 2,6-dimethyl-6-(trifluoromethyl)cyclohex-2-ene-1,4-dione (300 mg, 17% of theory) in the form of a colorless oil. 2,6-Dimethyl-6-(trifluoromethyl)cyclohex-2-ene-1,4-dione (520 mg, 2.52 mmol) was dissolved in 2,3-butanediol (4 ml) under argon, and trimethyl orthoformate (0.83 ml, 7.57 mmol) and p-toluenesulfonic acid (30 mg, 0.18 mmol) were added. The resulting reaction mixture was stirred at 50° C. for 6 h. After cooling to room temperature, water and toluene were added and the aqueous phase was extracted repeatedly with toluene. The combined organic phases were dried over magnesium sulfate, filtered and concentrated under reduced pressure. By column chromatography purification of the resulting crude product (ethyl acetate/heptane gradient), 2,3,7,9-tetramethyl-9-(trifluoromethyl)-1,4-dioxaspiro[4.5]dec-6-en-8-one (700 mg, 98% of theory) was obtained. In a round-bottom flask under argon, 2,3,7,9-tetramethyl-9-(trifluoromethyl)-1,4-dioxaspiro[4.5]dec-6-en-8-one (700 mg, 2.52 mmol) was then dissolved in abs. tetrahydrofuran (3 ml) and added dropwise to a solution of a lithium acetylide/ethylenediamine complex (376 mg, 3.27 mmol, 80% pure) in abs. tetrahydrofuran (5 ml). On completion of addition, the reaction mixture was stirred at room temperature for 4 h, then water was added and the mixture was concentrated under reduced pressure. The remaining residue was admixed with water and dichloromethane, and the aqueous phase was extracted repeatedly with dichloromethane. The combined organic phases were dried over magnesium sulfate, filtered and concentrated under reduced pressure. By column chromatography purification of the crude product obtained (ethyl acetate/heptane gradient), 8-ethynyl-2,3,7,9-tetramethyl-9-(trifluoromethyl)-1,4-dioxaspiro[4.5]dec-6-en-8-ol (550 mg, 68% of theory) was isolated as a colorless solid. Subsequently, copper(I) iodide (16 mg, 0.09 mmol) and bis(triphenylphosphine)palladium(II)chlorid (45 mg, 0.06 mmol) were initially charged under argon in a baked-out round-bottom flask, and abs. toluene (3 ml) and ethyl (2Z)-4,4,4-trifluoro-3-iodobut-2-enoate (126 mg, 0.43 mmol) were added. Stirring at room temperature for 10 min was followed by the dropwise addition of a solution of 8-ethynyl-2,3,7,9-tetramethyl-9-(trifluoromethyl)-1,4-dioxaspiro[4.5]dec-6-en-8-ol (130 mg, 0.43 mmol) in abs. toluene (1 ml) and of diisopropylamine (0.12 ml, 0.85 mmol). The resulting reaction mixture was stirred at room temperature for 3 h and then water was added. The aqueous phase was extracted repeatedly with dichloromethane. The combined organic phases were dried over magnesium sulfate, filtered and concentrated under reduced pressure. By final column chromatography purification of the crude product obtained (using an ethyl acetate/heptane gradient), ethyl (2E)-5-[8-hydroxy-2,3,7,9-tetramethyl-9-(trifluoromethyl)-1,4-dioxa-spiro[4.5]dec-6-en-8-yl]-3-(trifluoromethyl)pent-2-en-4-ynoate (110 mg, 52% of theory) was isolated in the form of a colorless oil. $^1$H-NMR (400 MHz, CDCl$_3$ δ, ppm) 6.65/6.63 (s, 1H), 5.54/5.51/5.29 (s, 1H), 4.28/3.96 (q, 2H), 4.27/3.60 (m, 2H), 2.62 (br. s, 1H, OH), 2.47/2.34 (d, 1H), 2.01/1.99 (s, 3H), 1.98/1.91 (d, 1H), 1.42 (s, 3H), 1.31 (t, 3H), 1.28 (m, 3H), 1.17 (m, 3H).

No. I.1-522: Ethyl (2E)-5-[1-hydroxy-2,6-dimethyl-4-oxo-6-(trifluoromethyl)cyclohex-2-en-1-yl]-3-(trifluoromethyl)pent-2-en-4-ynoate

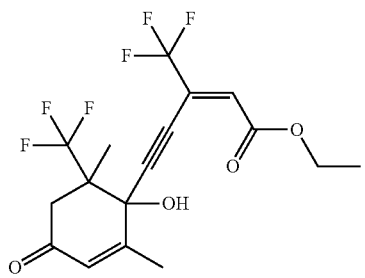 [SMILES: CCOC(=O)/C=C(\C#CC1(O)C(C)=CC(=O)CC1(C)C(F)(F)F)C(F)(F)F]

Ethyl (2E)-5-[8-hydroxy-2,3,7,9-tetramethyl-9-(trifluormethyl)-1,4-dioxaspiro[4.5]dec-6-en-8-yl]-3-(trifluoromethyl)pent-2-en-4-ynoate (110 mg, 0.23 mmol) was dissolved in acetone (5 ml) under argon in a round-bottom flask, and 5 drops of conc. hydrochloric acid were added. The resulting reaction solution was stirred at room temperature for 4 h and then water was added. After removing acetone under reduced pressure, the aqueous phase was extracted repeatedly with dichloromethane. The combined organic phases were dried over magnesium sulfate, filtered and concentrated under reduced pressure. By column chromatography purification of the resulting crude product (ethyl acetate/heptane gradient), ethyl (2E)-5-[1-hydroxy-2,6-dimethyl-4-oxo-6-(trifluoromethyl)cyclohex-2-en-1-yl]-3-(trifluoromethyl)pent-2-en-4-ynoate (70 mg, 71% of theory) was isolated in the form of a colorless viscous oil. $^1$H-NMR (400 MHz, CDCl$_3$ δ, ppm) 6.72/6.71 (s, 1H), 5.98/5.97 (s, 1H), 4.28/3.93 (q, 2H), 3.28 (br. s, 1H, OH), 3.00 (d, 1H), 2.66 (d, 1H), 2.21/2.18 (s, 3H), 1.49/1.37 (s, 3H), 1.32/1.09 (t, 3H).

No. I.1-531: Ethyl (2Z,4E)-3-cyclopropyl-5-[8-hydroxy-2,3,7,9-tetramethyl-9-(trifluoromethyl)-1,4-dioxaspiro[4.5]dec-6-en-8-yl]penta-2,4-dienoate

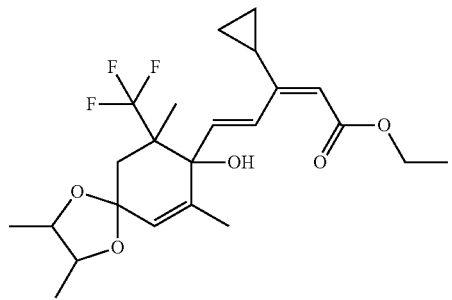 [SMILES: CCOC(=O)/C=C(\C=C\C1(O)C(C)=CC2(CC1(C)C(F)(F)F)OC(C)C(C)O2)C1CC1]

Under argon, 2,3,7,9-tetramethyl-8-[(E)-2-(tributylstannyl)vinyl]-9-(trifluoromethyl)-1,4-dioxaspiro[4.5]dec-6-en-8-ol (150 mg, 0.25 mmol) and ethyl (2Z)-3-cyclopropyl-3-iodoacrylate (67 mg, 0.25 mmol) in a round-bottom flask that had been dried by heating were dissolved in abs. tetrahydrofuran (4 ml), dichlorobis(acetonitrile)palladium(II) (3 mg, 0.01 mmol) was added and the mixture was stirred at room temperature for 3 h. After the addition of potassium fluoride solution, the reaction mixture was stirred further at room temperature overnight. The aqueous phase was then repeatedly extracted thoroughly with diethyl ether, and the combined organic phases were then dried over magnesium sulfate, filtered and concentrated under reduced pressure. By final column chromatography purification of the resulting crude product (ethyl acetate/heptane gradient), ethyl (2Z,4E)-3-cyclopropyl-5-[8-hydroxy-2,3,7,9-tetramethyl-9-(trifluoromethyl)-1,4-dioxaspiro[4.5]dec-6-en-8-yl]penta-2,4-dienoate (40 mg, 36% of theory) was obtained in the form of a colorless oil. $^1$H-NMR (400 MHz, CDCl$_3$ δ, ppm) 7.80/7.78 (d, 1H), 6.40/6.38 (d, 1H), 5.62/5.60 (s, 1H), 5.52/5.44 (s, 1H), 4.28/3.63 (m, 2H), 4.18 (q, 2H), 2.52/2.41 (d, 1H), 2.03/1.94 (d, 1H), 2.00 (br. s, 1H, OH), 1.72/1.69 (s, 3H), 1.62/1.55 (m, 1H), 1.40-1.34 (m, 3H), 1.29-1.17 (m, 6H), 0.92 (t, 3H), 0.83 (m, 2H), 0.58 (m, 2H).

No. I.1-532: Ethyl (2Z,4E)-3-cyclopropyl-5-[1-hydroxy-2,6-dimethyl-4-oxo-6-(trifluoromethyl)cyclohex-2-en-1-yl]penta-2,4-dienoate

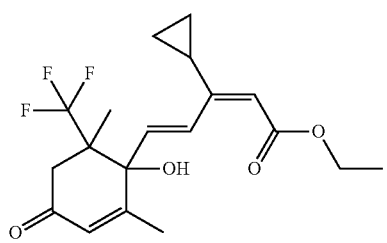 [SMILES: CCOC(=O)/C=C(\C=C\C1(O)C(C)=CC(=O)CC1(C)C(F)(F)F)C1CC1]

Ethyl (2Z,4E)-3-cyclopropyl-5-[8-hydroxy-2,3,7,9-tetramethyl-9-(trifluoromethyl)-1,4-dioxaspiro[4.5]dec-6-en-8-yl]penta-2,4-dienoate (40 mg, 0.09 mmol) was dissolved in acetone (4 ml) under argon in a round-bottom flask, and a few drops of conc. hydrochloric acid were added. The resulting reaction solution was stirred at room temperature for 4 h and then water was added. After removing acetone under reduced pressure, the aqueous phase was extracted repeatedly with dichloromethane. The combined organic phases were dried over magnesium sulfate, filtered and concentrated under reduced pressure. By column chromatography purification of the resulting crude product (ethyl acetate/heptane gradient), ethyl (2Z,4E)-3-cyclopropyl-5-[1-hydroxy-2,6-dimethyl-4-oxo-6-(trifluoromethyl)cyclohex-2-en-1-yl]penta-2,4-dienoate (15 mg, 45% of theory) was obtained in the form of a colorless oil. $^1$H-NMR (400 MHz, CDCl$_3$ δ, ppm) 7.88 (d, 1H), 6.37 (d, 1H), 6.01 (s, 1H), 5.64 (s, 1H), 4.17 (q, 2H), 2.92 (d, 1H), 2.52 (d, 1H), 2.39 (br. s, 1H, OH), 1.98 (s, 3H), 1.59 (m, 1H), 1.30 (t, 3H), 1.28 (s, 3H), 0.88 (m, 2H), 0.59 (m, 2H).

No. I.2-69: (2Z)-3-Ethyl-5-(8-hydroxy-2,3,7,9,9-pentamethyl-1,4-dioxaspiro[4.5]dec-6-en-8-yl)-N-propylpent-2-en-4-ynamide

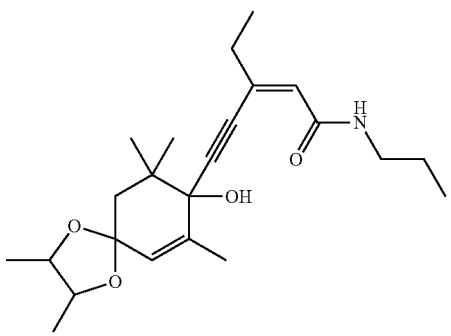 [SMILES: CCCNC(=O)/C=C(\C#CC1(O)C(C)=CC2(CC1(C)C)OC(C)C(C)O2)CC]

Pent-2-ynoic acid (1.50 g, 15.29 mmol) was dissolved in conc. acetic acid (15 ml), finely powdered sodium iodide (6.88 g, 45.87 mmol) was added and the mixture was stirred at a temperature of 110° C. for 3 h. After cooling to room temperature, methyl tert-butyl ether (MTBE) and saturated sodium thiosulfate solution were added. The aqueous phase was extracted repeatedly with MTBE, and the combined organic phases were dried over magnesium sulfate, filtered and concentrated under reduced pressure. By column chromatography purification of the resulting crude product (ethyl acetate/heptane gradient), it was possible to obtain (2Z)-3-iodopent-2-enoic acid (2.10 g, 61% of theory) in the form of a colorless solid. In a round-bottom flask under argon, (2Z)-3-iodopent-2-enoic acid (500 mg, 2.21 mmol) was then dissolved in abs. dichloromethane, and oxalyl chloride (0.16 ml, 1.88 mmol) was added dropwise. Following the addition of catalytic amounts of N,N-dimethylformamide, the reaction solution was stirred at a temperature of 60° C. for 3 h, and after cooling to room temperature, n-propylamine (78 mg, 1.33 mmol) and triethylamine (0.19 ml, 1.33 mmol) were added dropwise. After addition of water and dichloromethane, the aqueous phase was extracted repeatedly with dichloromethane and the combined organic phases were dried over magnesium sulfate, filtered and concentrated under reduced pressure. By column chromatography purification of the resulting crude product (ethyl acetate/heptane gradient), it was possible to obtain (2Z)-3-iodo-N-propylpent-2-enamide (230 mg, 74% of theory) in the form of a colorless solid. $^1$H-NMR (400 MHz, CDCl$_3$ δ, ppm) 6.27 (s, 1H), 5.73 (br. t, 1H, NH), 3.34 (m, 2H), 2.65 (q, 2H), 1.60 (m, 2H), 1.12 (t, 3H), 0.97 (t, 3H). Subsequently, copper(I) iodide (30 mg, 0.16 mmol) and bis(triphenylphosphine)palladium (II) chloride (84 mg, 0.12 mmol) were initially charged under argon in a baked-out round-bottom flask, and abs. toluene (4 ml) and (2Z)-3-iodo-N-propylpent-2-enamide (214 mg, 0.80 mmol) were added. Stirring at room temperature for 10 minutes was followed by the dropwise addition of a solution of 8-ethynyl-2,3,7,9,9-pentamethyl-1,4-dioxaspiro[4.5]dec-6-en-8-ol (200 mg, 0.80 mmol) in abs. toluene (1 ml) and of diisopropylamine (0.22 ml, 1.60 mmol). The resulting reaction mixture was stirred at room temperature for 4 h and then water was added. The aqueous phase was extracted repeatedly with dichloromethane. The combined organic phases were dried over magnesium sulfate, filtered and concentrated under reduced pressure. By final column chromatography purification of the crude product obtained (using an ethyl acetate/heptane gradient), (2Z)-3-ethyl-5-(8-hydroxy-2,3,7,9,9-pentamethyl-1,4-dioxaspiro[4.5]dec-6-en-8-yl)-N-propylpent-2-en-4-ynamide (280 mg, 85% of theory) was isolated in the form of a colorless, highly viscous oil. $^1$H-NMR (400 MHz, CDCl$_3$ δ, ppm) 6.83 (br. t, 1H, NH), 5.99 (s, 1H), 5.42 (s, 1H), 4.23 (m, 1H), 3.59 (m, 1H), 3.29 (m, 2H), 2.29 (q, 2H), 2.21 (br. s, 1H, OH), 2.02 (d, 1H), 1.92 (s, 3H), 1.85 (d, 1H), 1.57 (m, 2H), 1.23 (m, 3H), 1.19-1.12 (m, 12H), 0.92 (t, 3H).

No. I.2-70: (2Z)-3-Ethyl-5-(1-hydroxy-2,6,6-trimethyl-4-oxocyclohex-2-en-1-yl)-N-propylpent-2-en-4-ynamide

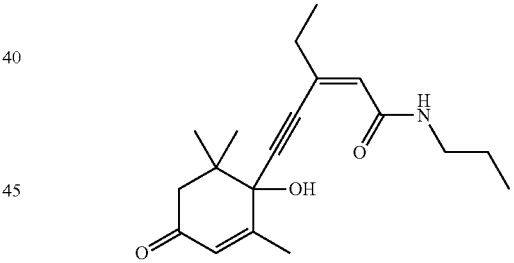

(2Z)-3-Ethyl-5-(8-hydroxy-2,3,7,9,9-pentamethyl-1,4-dioxaspiro[4.5]dec-6-en-8-yl)-N-propylpent-2-en-4-ynamide (280 mg, 0.72 mmol) was dissolved in acetone (4 ml) under argon in a round-bottom flask, and 10% strength hydrochloric acid was added. The resulting reaction solution was stirred at room temperature for 50 minutes, and water was then added. After removing acetone under reduced pressure, the aqueous phase was extracted repeatedly with dichloromethane. The combined organic phases were dried over magnesium sulfate, filtered and concentrated under reduced pressure. By final column chromatography purification of the resulting crude product (ethyl acetate/heptane gradient), it was possible to obtain (2Z)-3-ethyl-5-(1-hydroxy-2,6,6-trimethyl-4-oxocyclohex-2-en-1-yl)-N-propylpent-2-en-4-ynamide (200 mg, 88% of theory) in the form of a colorless solid. $^1$H-NMR (400 MHz, CDCl$_3$ δ, ppm) 6.08 (br. t, 1H, NH), 6.00 (s, 1H), 5.87 (s, 1H), 3.54 (br. s, 1H, OH), 3.27 (m, 2H), 2.53 (d, 1H), 2.42

(d, 1H), 2.27 (q, 2H), 2.17 (s, 3H), 1.56 (sext, 2H), 1.22 (s, 3H), 1.13 (s, 3H), 1.11 (t, 3H), 0.93 (t, 3H).

No. II.1: 2,3,7,9,9-Pentamethyl-8-[(E)-2-(tributyl-stannyl)vinyl]-1,4-dioxaspiro[4.5]dec-6-en-8-ol

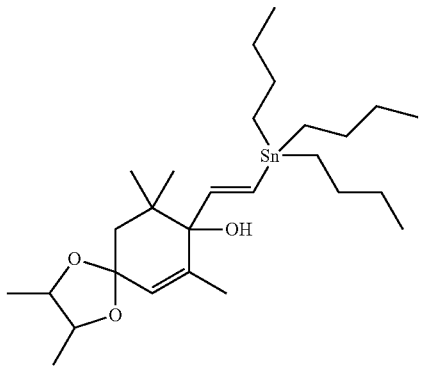 [SMILES: CCC[CH2][Sn](/[CH]=C/C1(O)C(C)=CC2(CC1(C)C)OC(C)C(C)O2)([CH2]CCC)[CH2]CCC]

Under argon, tetrakis(triphenylphosphine)palladium(0) (231 mg, 0.20 mmol) was initially charged in a round-bottom flask that had been dried by heating, and abs. tetrahydrofuran (25 ml) and 8-ethynyl-2,3,7,9,9-pentamethyl-1,4-dioxaspiro [4.5]dec-6-en-8-ol (1.0 g, 3.99 mmol) were added. Stirring at room temperature for 5 minutes was followed by the addition of tributyltin hydride (1.29 ml, 4.79 mmol). The resulting reaction mixture was stirred at room temperature for 1 h and then water was added. The aqueous phase was repeatedly extracted thoroughly with dichloromethane, and the combined organic phases were then dried over magnesium sulfate, filtered and concentrated under reduced pressure. By final column chromatography purification of the resulting crude product (ethyl acetate/heptane gradient), it was possible to obtain 2,3,7,9,9-pentamethyl-8-[(E)-2-(tributylstannyl)vinyl]-1,4-dioxaspiro[4.5]dec-6-en-8-ol (1.50 g, 66% of theory) in the form of a colorless oil. $^1$H-NMR (400 MHz, CDCl$_3$ δ, ppm) 6.13 (d, 1H), 5.93 (d, 1H), 5.42 (s, 1H), 4.22/3.63 (m, 2H), 1.61 (s, 3H), 1.59 (d, 1H), 1.52 (d, 1H), 1.49 (m, 6H), 1.32-1.24 (m, 12H), 1.09 (s, 3H), 0.89 (m, 18H).

No. II.25: Biscyclopentadienyldimethyl[(E)-2-{2,3,7,9,9-pentamethyl-8-[(triethylsilyl)oxy]-1,4-dioxas-piro[4.5]dec-6-en-8-yl}vinyl]zirconium

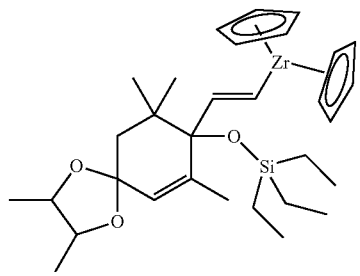

Under argon, 8-ethynyl-2,3,7,9,9-pentamethyl-1,4-dioxaspiro[4.5]dec-6-en-8-ol (500 mg, 1.99 mmol) was dissolved in a round-bottom flask in abs. dichloromethane (15 ml) and cooled to 0° C., and lutidine (0.58 ml, 4.99 mmol) and triethylsilyl trifluoromethanesulfonate (0.68 ml, 2.99 mmol) were added dropwise. The resulting reaction mixture was stirred at 0° C. for 1 h and at room temperature for a further hour, and water was added after the reaction had ended. The aqueous phase was repeatedly extracted thoroughly with dichloromethane, and the combined organic phases were then dried over magnesium sulfate, filtered and concentrated under reduced pressure. By final column chromatography purification of the resulting crude product (ethyl acetate/heptane gradient), [(8-ethynyl-2,3,7,9,9-pentamethyl-1,4-dioxaspiro [4.5]dec-6-en-8-yl)oxy](triethyl)silane (400 mg, 55% of theory) was obtained in the form of a colorless oil. $^1$H-NMR (400 MHz, CDCl$_3$ δ, ppm) 5.30 (s, 1H), 4.20 (m, 1H), 3.58 (m, 1H), 2.48 (s, 1H), 2.02 (d, 1H), 1.86 (s, 3H), 1.79 (d, 1H), 1.22 (m, 3H), 1.14-0.93 (m, 9H), 0.75 (m, 6H), 0.53 (t, 9H). A multi-necked round-bottom flask which had been dried thoroughly by heating was flushed with argon and evacuated repeatedly, and zirconocene chloride hydride (311 mg, 1.21 mmol) and degassed abs. tetrahydrofuran (3 ml) were then added under a constant stream of argon. The reaction solution was cooled to 0° C., and a solution of [(8-ethynyl-2,3,7,9,9-pentamethyl-1,4-dioxaspiro[4.5]dec-6-en-8-yl)oxy](triethyl)silane in abs. tetrahydrofuran (2 ml) was added dropwise. The resulting reaction solution was stirred at room temperature for 1 h and its analysis by NMR spectroscopy showed complete conversion into the desired biscyclopentadienyldimethyl[(E)-2-{2,3,7,9,9-pentamethyl-8-[(triethylsilyl)oxy]-1,4-dioxaspiro[4.5]dec-6-en-8-yl}vinyl]zirconium. $^1$H-NMR (400 MHz, CDCl$_3$ δ, ppm) 7.75 (m, 4H), 7.36 (m, 6H), 7.27 (d, 1H), 5.39 (d, 1H), 5.31 (s, 1H), 3.69 (m, 1H), 3.62 (m, 1H), 2.10-2.06 (m, 2H), 1.61 (s, 3H), 1.32-1.22 (m, 12H), 0.89 (m, 6H), 0.83 (t, 9H). The synthesis intermediate II.25 obtained in this manner was used in the subsequent reaction in question without further purification.

No. II.83: 2,3,7,9-Tetramethyl-8-[(E)-2-(tributylstan-nyl)vinyl]-9-(trifluoromethyl)-1,4-dioxaspiro[4.5]dec-6-en-8-ol

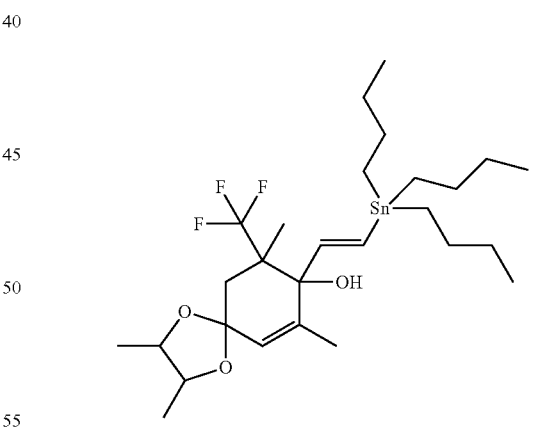

Under argon, tetrakis(triphenylphosphine)palladium(0) (19 mg, 0.02 mmol) was initially charged in a round-bottom flask that had been dried by heating, and abs. tetrahydrofuran (5 ml) and 8-ethynyl-2,3,7,9-tetramethyl-9-(trifluoromethyl)-1,4-dioxaspiro[4.5]dec-6-en-8-ol (100 mg, 0.33 mmol) were added. Stirring at room temperature for 5 minutes was followed by the addition of tributyltin hydride (0.11 ml, 0.39 mmol). The resulting reaction mixture was stirred at 55° C. for 1 h and, after cooling to room temperature, water was added. The aqueous phase was repeatedly extracted thoroughly with dichloromethane, and the combined organic phases were then dried over magnesium sulfate, filtered and concentrated under reduced pressure. By final column chromatography purification of the resulting crude product (ethyl acetate/heptane gradient), it was possible to obtain 2,3,7,9-tetramethyl-8-[(E)-2-(tributylstannyl)vinyl]-9-(trifluoromethyl)-1,4-dioxaspiro[4.5]dec-6-en-8-ol (160 mg, 82% of theory) in the form of a colorless oil. $^1$H-NMR (400 MHz, CDCl$_3$ δ, ppm) 6.33/6.31 (d, 1H), 5.97/5.92 (d, 1H), 5.51/5.42 (s, 1H), 4.24/3.64 (m, 2H), 2.46/2.35 (d, 1H), 1.92 (br. s, 1H, OH), 1.91/1.87 (d, 1H), 1.64/1.62 (s, 3H), 1.49 (m, 6H), 1.32-1.26 (m, 9H), 1.18 (m, 3H), 0.89 (m, 18H).

Analogously to the preparation examples given above and taking into account the general statements on the preparation of substituted 5-(cyclohex-2-en-1-yl)penta-2,4-dienes and 5-(cyclohex-2-en-1-yl)pent-2-en-4-ynes of the formula (I), the following compounds specifically mentioned in tables 1 to 4 are obtained:

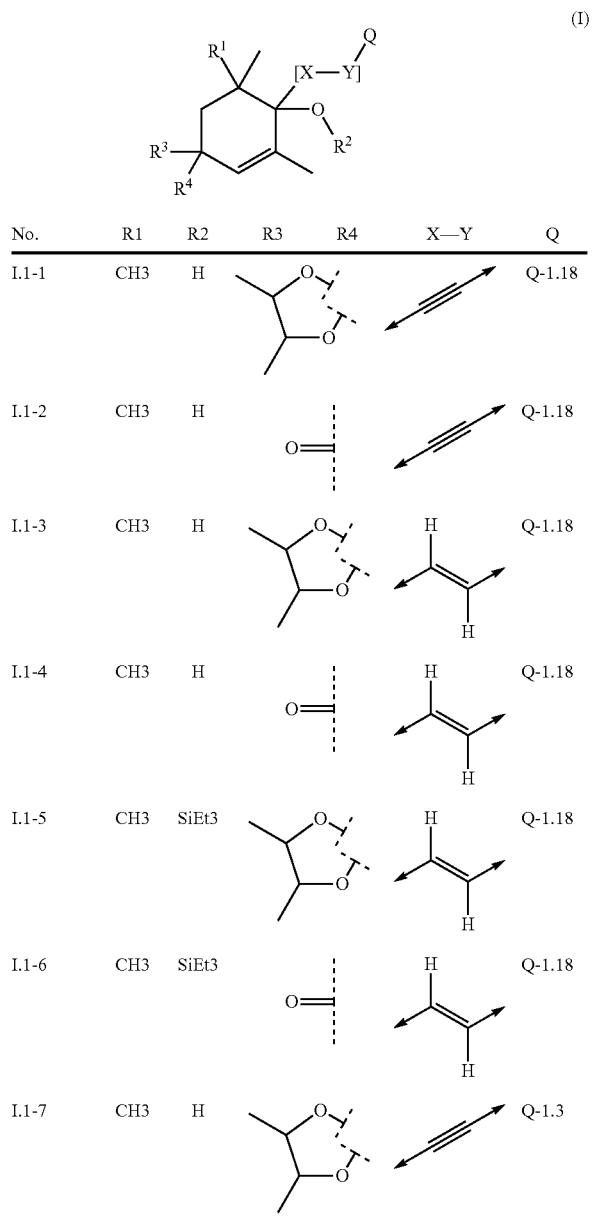

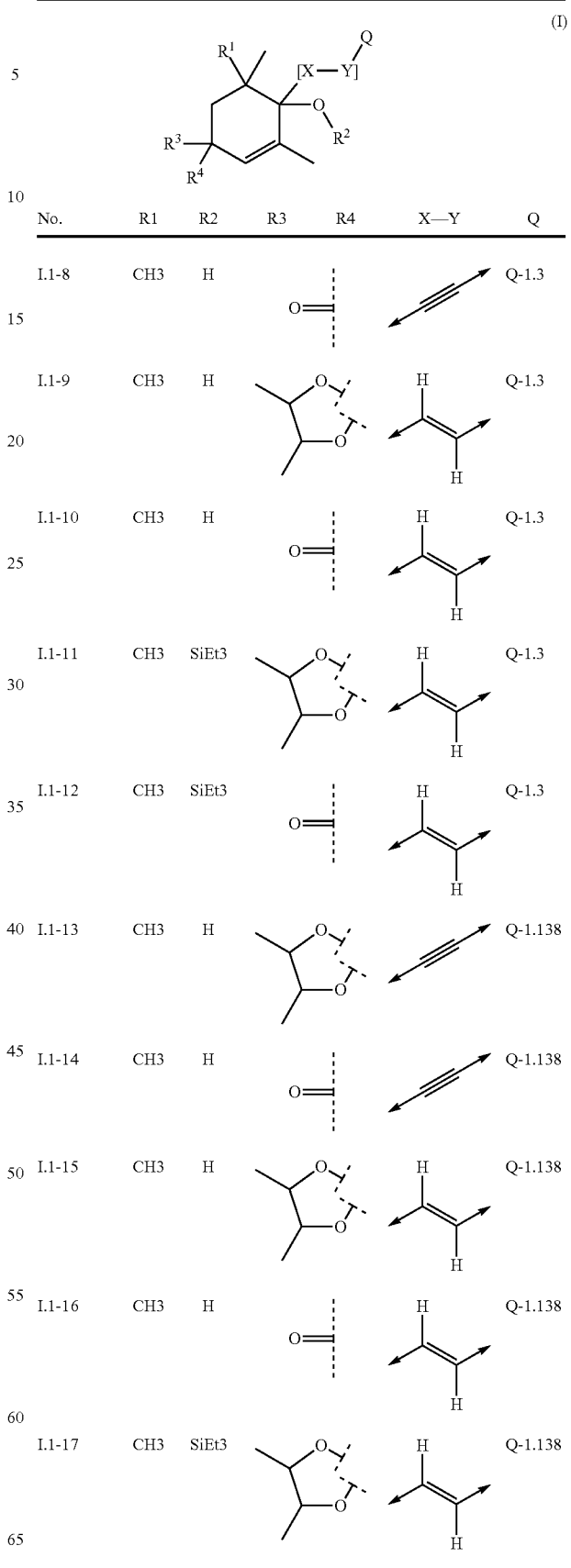

TABLE 1-continued
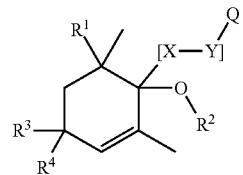
(I)
| No. | R1 | R2 | R3 | R4 | X—Y | Q |
|---|---|---|---|---|---|---|
| I.1-18 | CH3 | SiEt3 | =O | | CH=CH | Q-1.138 |
| I.1-19 | CH3 | H | =O | | C≡C | Q-1.1 |
| I.1-20 | CH3 | H | =O | | CH=CH | Q-1.1 |
| I.1-21 | CH3 | H | =O | | C≡C | Q-1.16 |
| I.1-22 | CH3 | H | =O | | CH=CH | Q-1.16 |
| I.1-23 | CH3 | H | =O | | C≡C | Q-1.136 |
| I.1-24 | CH3 | H | =O | | CH=CH | Q-1.136 |
| I.1-25 | CH3 | H | =O | | C≡C | Q-1.31 |
| I.1-26 | CH3 | H | =O | | CH=CH | Q-1.31 |
| I.1-27 | CH3 | H | =O | | C≡C | Q-1.46 |
| I.1-28 | CH3 | H | =O | | CH=CH | Q-1.46 |
TABLE 1-continued
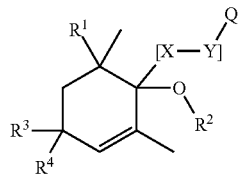
(I)
| No. | R1 | R2 | R3 | R4 | X—Y | Q |
|---|---|---|---|---|---|---|
| I.1-29 | CH3 | H | =O | | C≡C | Q-1.61 |
| I.1-30 | CH3 | H | =O | | CH=CH | Q-1.61 |
| I.1-31 | CH3 | H | =O | | C≡C | Q-1.76 |
| I.1-32 | CH3 | H | =O | | CH=CH | Q-1.76 |
| I.1-33 | CH3 | H | =O | | C≡C | Q-1.91 |
| I.1-34 | CH3 | H | =O | | CH=CH | Q-1.91 |
| I.1-35 | CH3 | H | =O | | C≡C | Q-1.106 |
| I.1-36 | CH3 | H | =O | | CH=CH | Q-1.106 |
| I.1-37 | CH3 | H | =O | | C≡C | Q-1.121 |
| I.1-38 | CH3 | H | =O | | CH=CH | Q-1.121 |
| I.1-39 | CH3 | H | =O | | C≡C | Q-1.151 |

TABLE 1-continued (I)

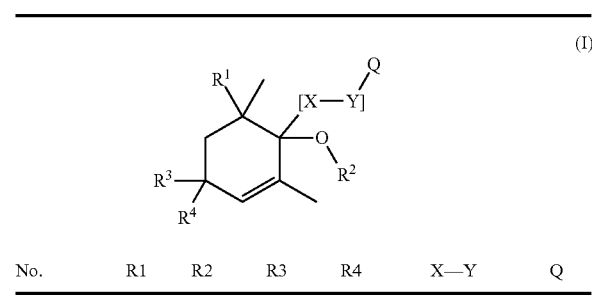

| No. | R1 | R2 | R3 | R4 | X—Y | Q |
|---|---|---|---|---|---|---|
| I.1-40 | CH3 | H | | | C=O | Q-1.151 (CH=CH2) |
| I.1-41 | CH3 | H | | | C=O | Q-1.156 (C≡C) |
| I.1-42 | CH3 | H | | | C=O | Q-1.156 (CH=CH2) |
| I.1-43 | CH3 | H | | | C=O | Q-1.161 (C≡C) |
| I.1-44 | CH3 | H | | | C=O | Q-1.161 (CH=CH2) |
| I.1-45 | CH3 | H | | | C=O | Q-1.166 (C≡C) |
| I.1-46 | CH3 | H | | | C=O | Q-1.166 (CH=CH2) |
| I.1-47 | CH3 | H | | | C=O | Q-1.171 (C≡C) |
| I.1-48 | CH3 | H | | | C=O | Q-1.171 (CH=CH2) |
| I.1-49 | CH3 | H | | | C=O | Q-1.176 (C≡C) |

TABLE 1-continued (I)

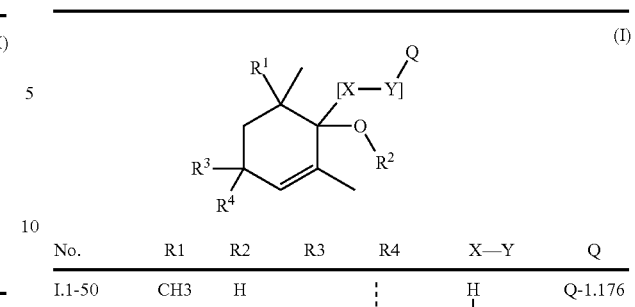

| No. | R1 | R2 | R3 | R4 | X—Y | Q |
|---|---|---|---|---|---|---|
| I.1-50 | CH3 | H | | | C=O | Q-1.176 (CH=CH2) |
| I.1-51 | CH3 | H | | | C=O | Q-1.181 (C≡C) |
| I.1-52 | CH3 | H | | | C=O | Q-1.181 (CH=CH2) |
| I.1-53 | CH3 | H | | | C=O | Q-1.186 (C≡C) |
| I.1-54 | CH3 | H | | | C=O | Q-1.186 (CH=CH2) |
| I.1-55 | CH3 | H | | | C=O | Q-1.191 (C≡C) |
| I.1-56 | CH3 | H | | | C=O | Q-1.191 (CH=CH2) |
| I.1-57 | CH3 | H | | | C=O | Q-1.196 (C≡C) |
| I.1-58 | CH3 | H | | | C=O | Q-1.196 (CH=CH2) |
| I.1-59 | CH3 | H | | | dioxolane | Q-1.33 (C≡C) |
| I.1-60 | CH3 | H | | | C=O | Q-1.33 (C≡C) |

TABLE 1-continued (I)

| No. | R1 | R2 | R3 | R4 | X—Y | Q |
|---|---|---|---|---|---|---|
| I.1-61 | CH3 | H | | | (dioxolane) | (vinyl H) | Q-1.33 |
| I.1-62 | CH3 | H | | | O= | (vinyl H) | Q-1.33 |
| I.1-63 | CH3 | SiEt3 | | | (dioxolane) | (vinyl H) | Q-1.33 |
| I.1-64 | CH3 | SiEt3 | | | O= | (vinyl H) | Q-1.33 |
| I.1-65 | CH3 | H | | | (dioxolane) | (alkynyl) | Q-1.48 |
| I.1-66 | CH3 | H | | | O= | (alkynyl) | Q-1.48 |
| I.1-67 | CH3 | H | | | (dioxolane) | (vinyl H) | Q-1.48 |
| I.1-68 | CH3 | H | | | O= | (vinyl H) | Q-1.48 |
| I.1-69 | CH3 | SiEt3 | | | (dioxolane) | (vinyl H) | Q-1.48 |
| I.1-70 | CH3 | SiEt3 | | | O= | (vinyl H) | Q-1.48 |
| I.1-71 | CH3 | H | | | (dioxolane) | (alkynyl) | Q-1.63 |
| I.1-72 | CH3 | H | | | O= | (alkynyl) | Q-1.63 |
| I.1-73 | CH3 | H | | | (dioxolane) | (vinyl H) | Q-1.63 |
| I.1-74 | CH3 | H | | | O= | (vinyl H) | Q-1.63 |
| I.1-75 | CH3 | SiEt3 | | | (dioxolane) | (vinyl H) | Q-1.63 |
| I.1-76 | CH3 | SiEt3 | | | O= | (vinyl H) | Q-1.63 |
| I.1-77 | CH3 | H | | | (dioxolane) | (alkynyl) | Q-1.78 |
| I.1-78 | CH3 | H | | | O= | (alkynyl) | Q-1.78 |
| I.1-79 | CH3 | H | | | (dioxolane) | (vinyl H) | Q-1.78 |
| I.1-80 | CH3 | H | | | O= | (vinyl H) | Q-1.78 |

TABLE 1-continued (I)

| No. | R1 | R2 | R3 | R4 | X—Y | Q |
|---|---|---|---|---|---|---|
| I.1-81 | CH3 | SiEt3 | (dioxolane) | | H / CH=CH2 | Q-1.78 |
| I.1-82 | CH3 | SiEt3 | =O | | H / CH=CH2 | Q-1.78 |
| I.1-83 | CH3 | H | (dioxolane) | | C≡C | Q-1.93 |
| I.1-84 | CH3 | H | =O | | C≡C | Q-1.93 |
| I.1-85 | CH3 | H | (dioxolane) | | H / CH=CH2 | Q-1.93 |
| I.1-86 | CH3 | H | =O | | H / CH=CH2 | Q-1.93 |
| I.1-87 | CH3 | SiEt3 | (dioxolane) | | H / CH=CH2 | Q-1.93 |
| I.1-88 | CH3 | SiEt3 | =O | | H / CH=CH2 | Q-1.93 |
| I.1-89 | CH3 | H | (dioxolane) | | C≡C | Q-1.108 |
| I.1-90 | CH3 | H | =O | | C≡C | Q-1.108 |
| I.1-91 | CH3 | H | (dioxolane) | | H / CH=CH2 | Q-1.108 |
| I.1-92 | CH3 | H | =O | | H / CH=CH2 | Q-1.108 |
| I.1-93 | CH3 | SiEt3 | (dioxolane) | | H / CH=CH2 | Q-1.108 |
| I.1-94 | CH3 | SiEt3 | =O | | H / CH=CH2 | Q-1.108 |
| I.1-95 | CH3 | H | (dioxolane) | | C≡C | Q-1.123 |
| I.1-96 | CH3 | H | =O | | C≡C | Q-1.123 |
| I.1-97 | CH3 | H | (dioxolane) | | H / CH=CH2 | Q-1.123 |
| I.1-98 | CH3 | H | =O | | H / CH=CH2 | Q-1.123 |
| I.1-99 | CH3 | SiEt3 | (dioxolane) | | H / CH=CH2 | Q-1.123 |
| I.1-100 | CH3 | SiEt3 | =O | | H / CH=CH2 | Q-1.123 |

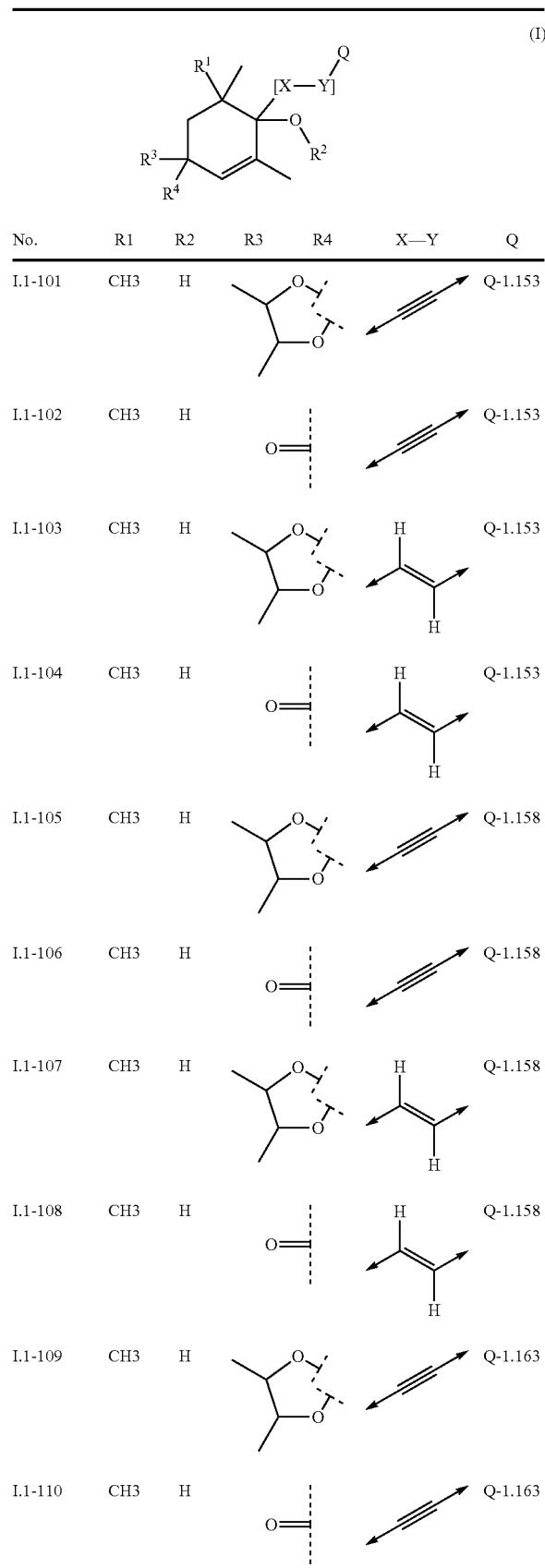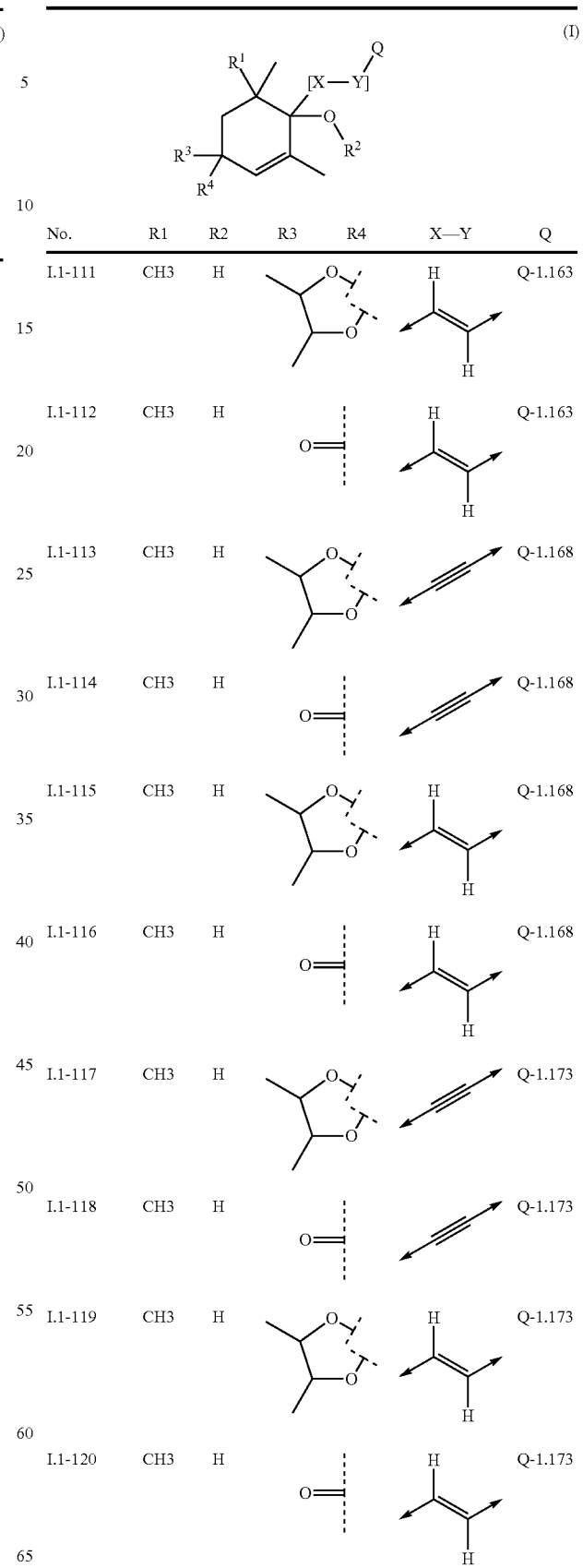

TABLE 1-continued
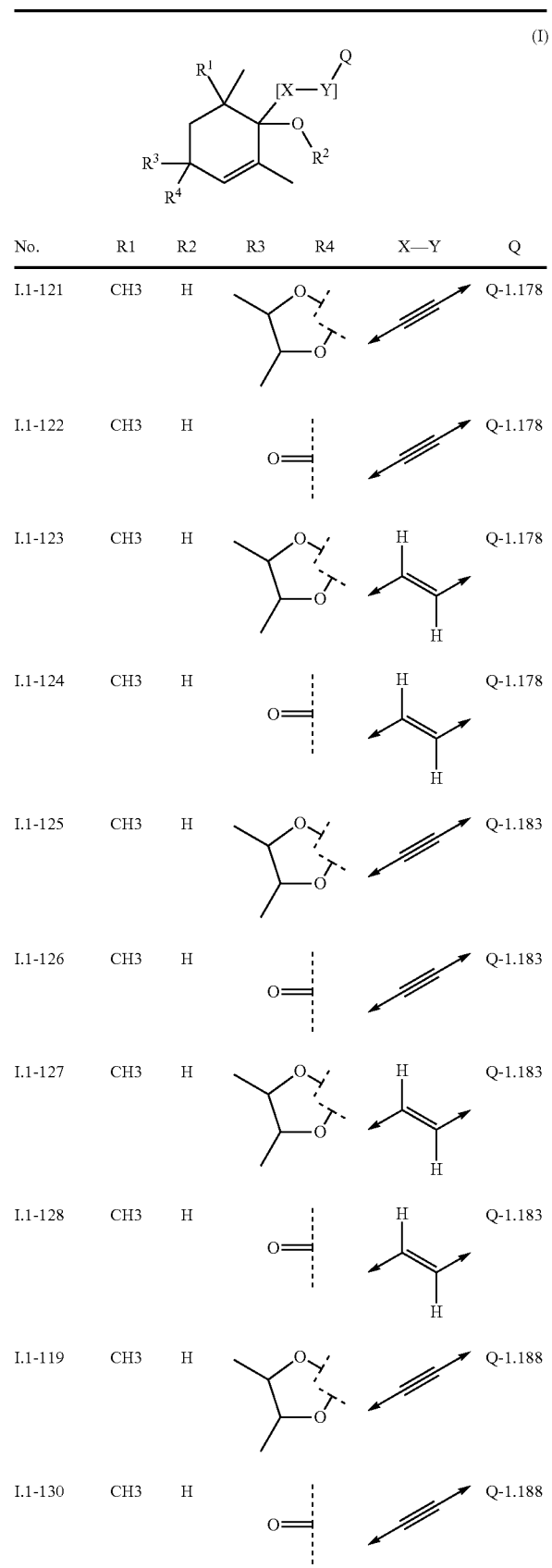
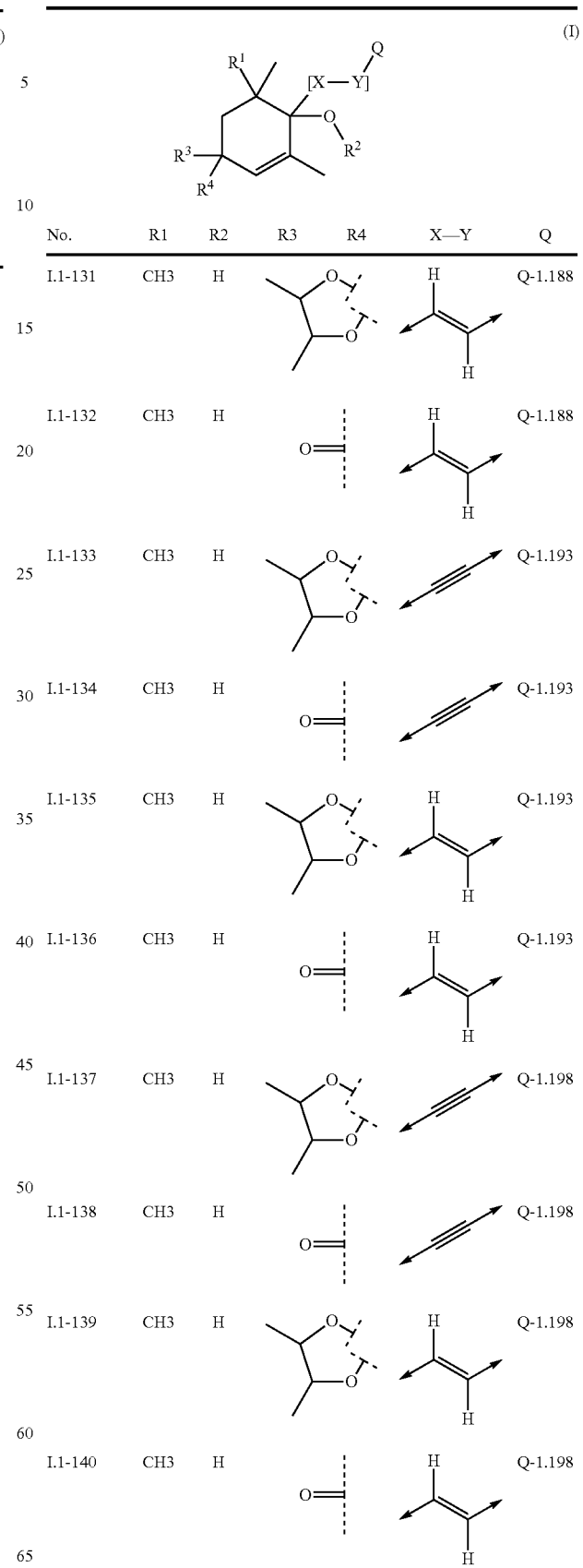

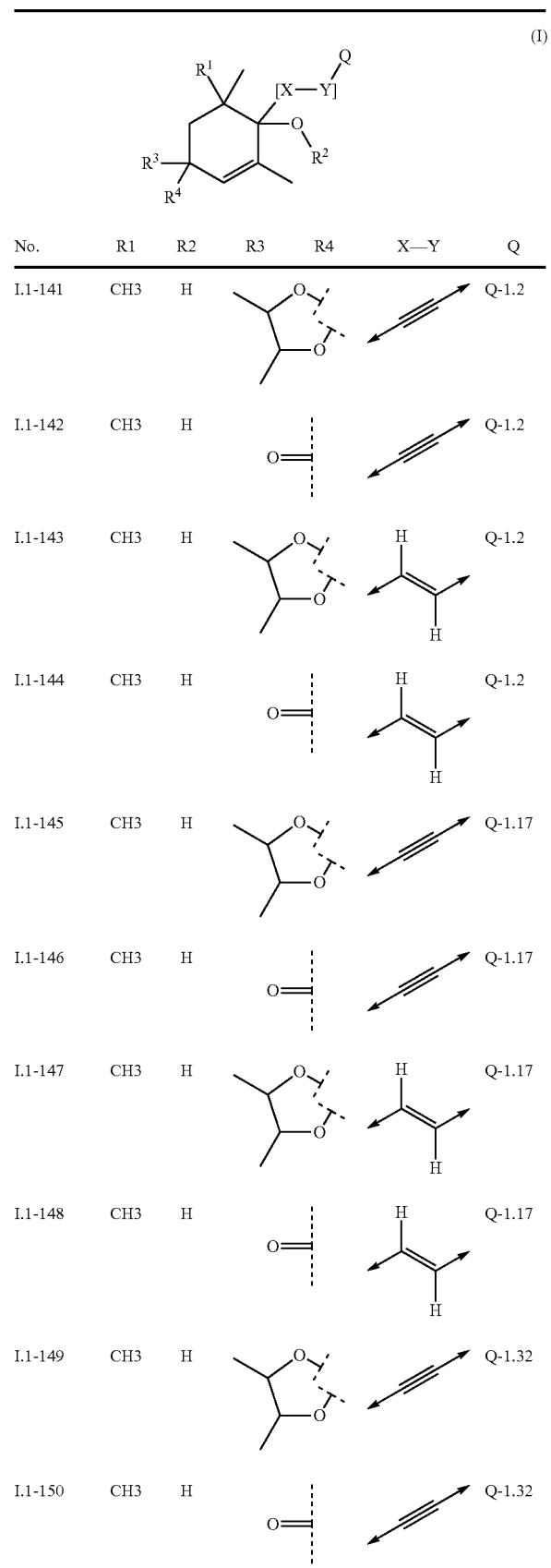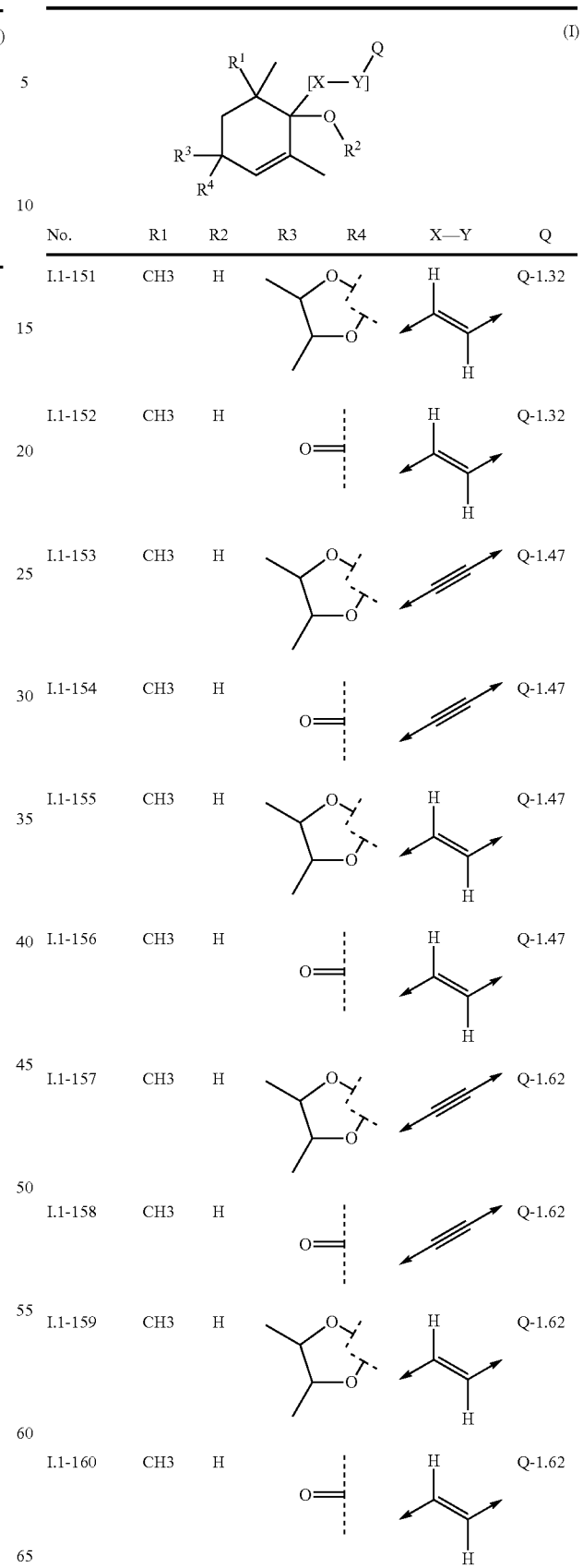

TABLE 1-continued (I)

| No. | R1 | R2 | R3 R4 | X—Y | Q |
|---|---|---|---|---|---|
| I.1-161 | CH3 | H | (dioxolane dimethyl) | alkyne | Q-1.77 |
| I.1-162 | CH3 | H | O= | alkyne | Q-1.77 |
| I.1-163 | CH3 | H | (dioxolane dimethyl) | vinyl | Q-1.77 |
| I.1-164 | CH3 | H | O= | vinyl | Q-1.77 |
| I.1-165 | CH3 | H | (dioxolane dimethyl) | alkyne | Q-1.92 |
| I.1-166 | CH3 | H | O= | alkyne | Q-1.92 |
| I.1-167 | CH3 | H | (dioxolane dimethyl) | vinyl | Q-1.92 |
| I.1-168 | CH3 | H | O= | vinyl | Q-1.92 |
| I.1-169 | CH3 | H | (dioxolane dimethyl) | alkyne | Q-1.107 |
| I.1-170 | CH3 | H | O= | alkyne | Q-1.107 |
| I.1-171 | CH3 | H | (dioxolane dimethyl) | vinyl | Q-1.107 |
| I.1-172 | CH3 | H | O= | vinyl | Q-1.107 |
| I.1-173 | CH3 | H | (dioxolane dimethyl) | alkyne | Q-1.122 |
| I.1-174 | CH3 | H | O= | alkyne | Q-1.122 |
| I.1-175 | CH3 | H | (dioxolane dimethyl) | vinyl | Q-1.122 |
| I.1-176 | CH3 | H | O= | vinyl | Q-1.122 |
| I.1-177 | CH3 | H | (dioxolane dimethyl) | alkyne | Q-1.152 |
| I.1-178 | CH3 | H | O= | alkyne | Q-1.152 |
| I.1-179 | CH3 | H | (dioxolane dimethyl) | vinyl | Q-1.152 |
| I.1-180 | CH3 | H | O= | vinyl | Q-1.152 |

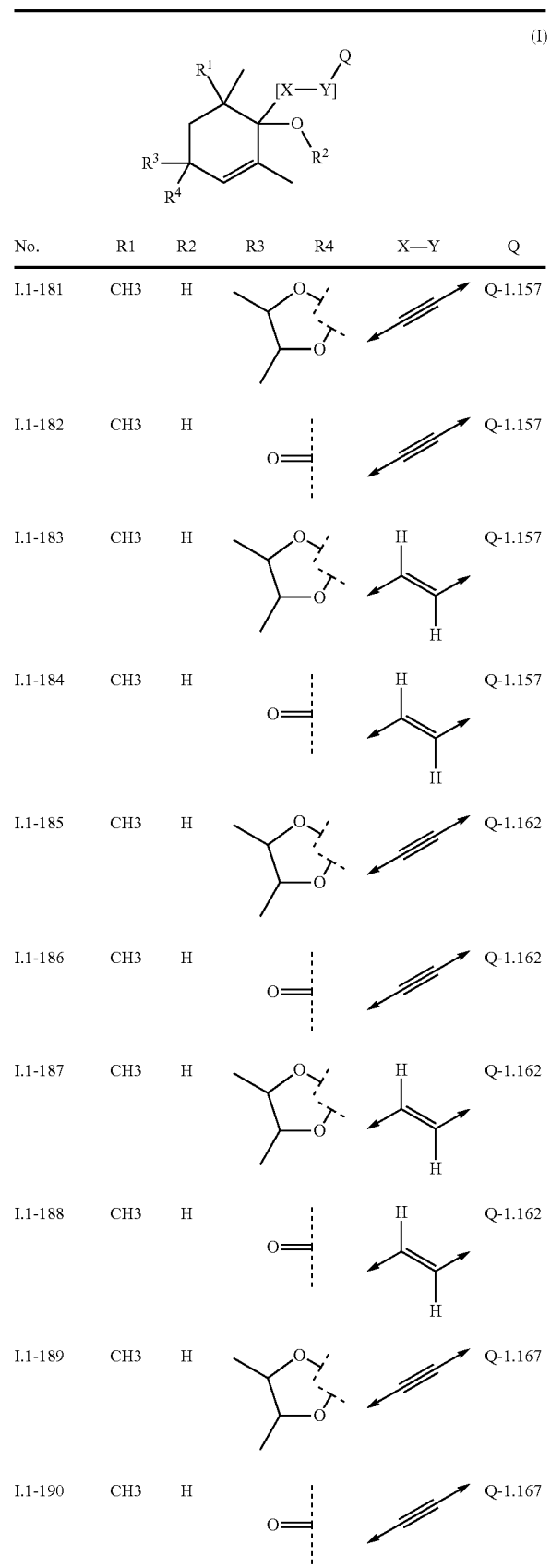
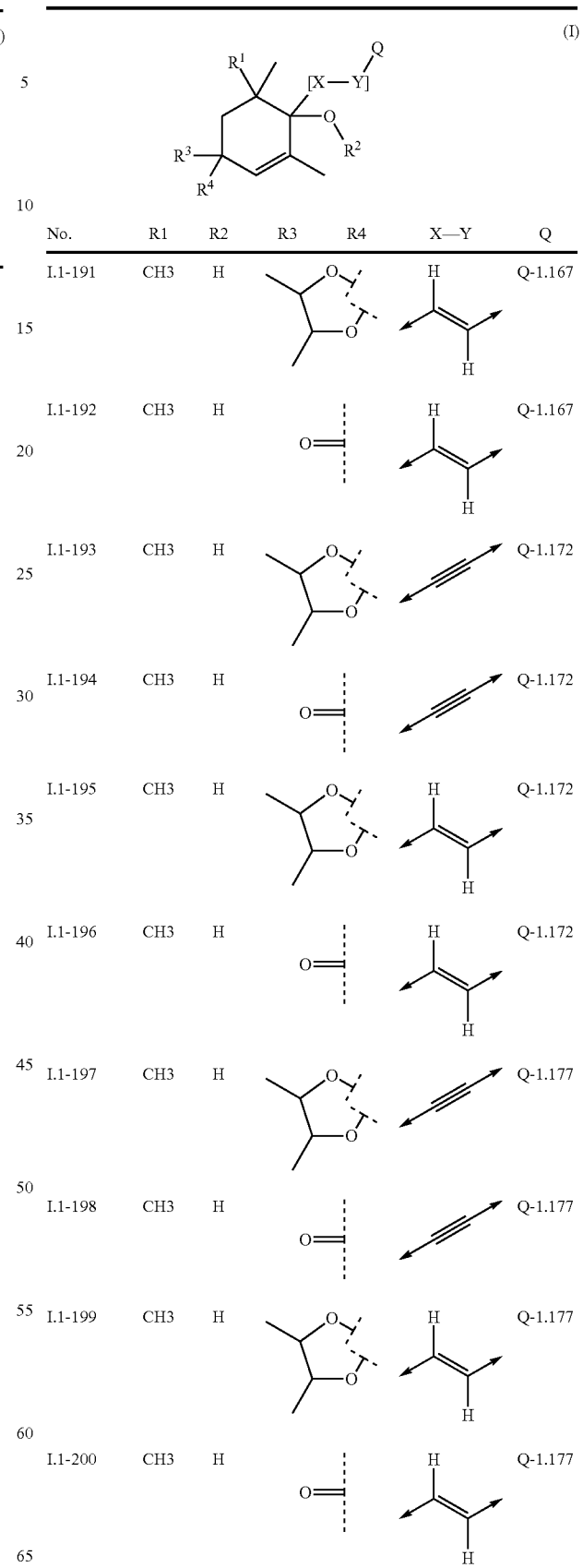

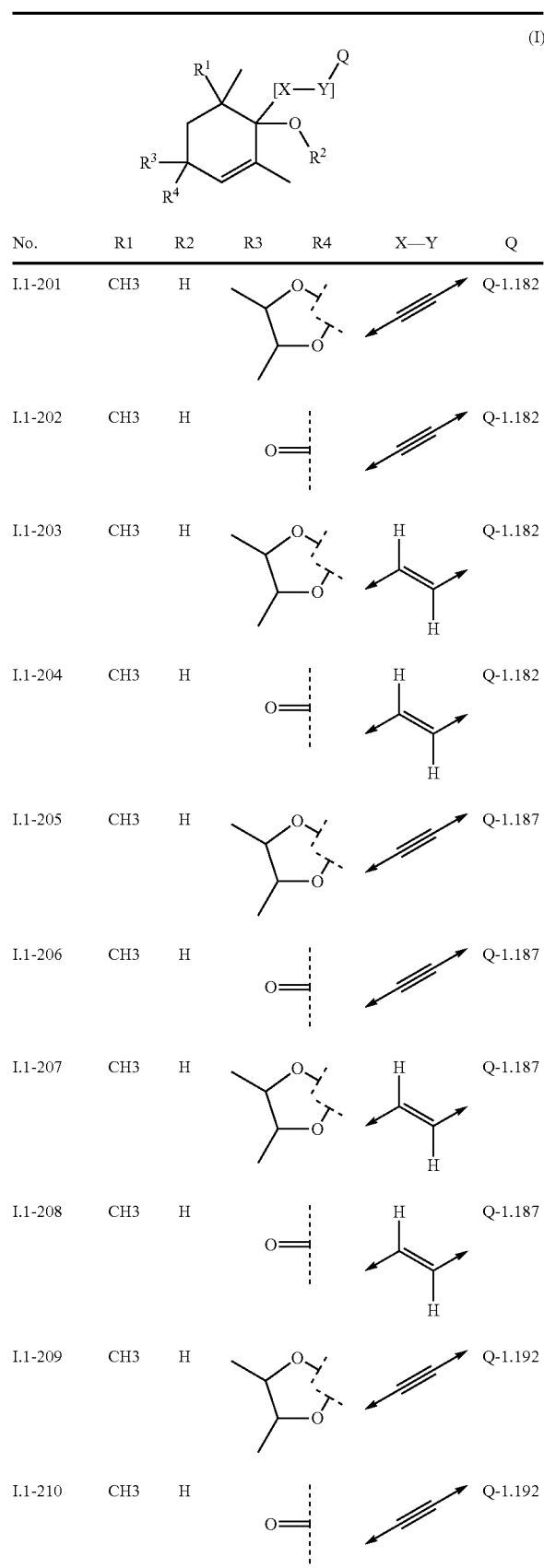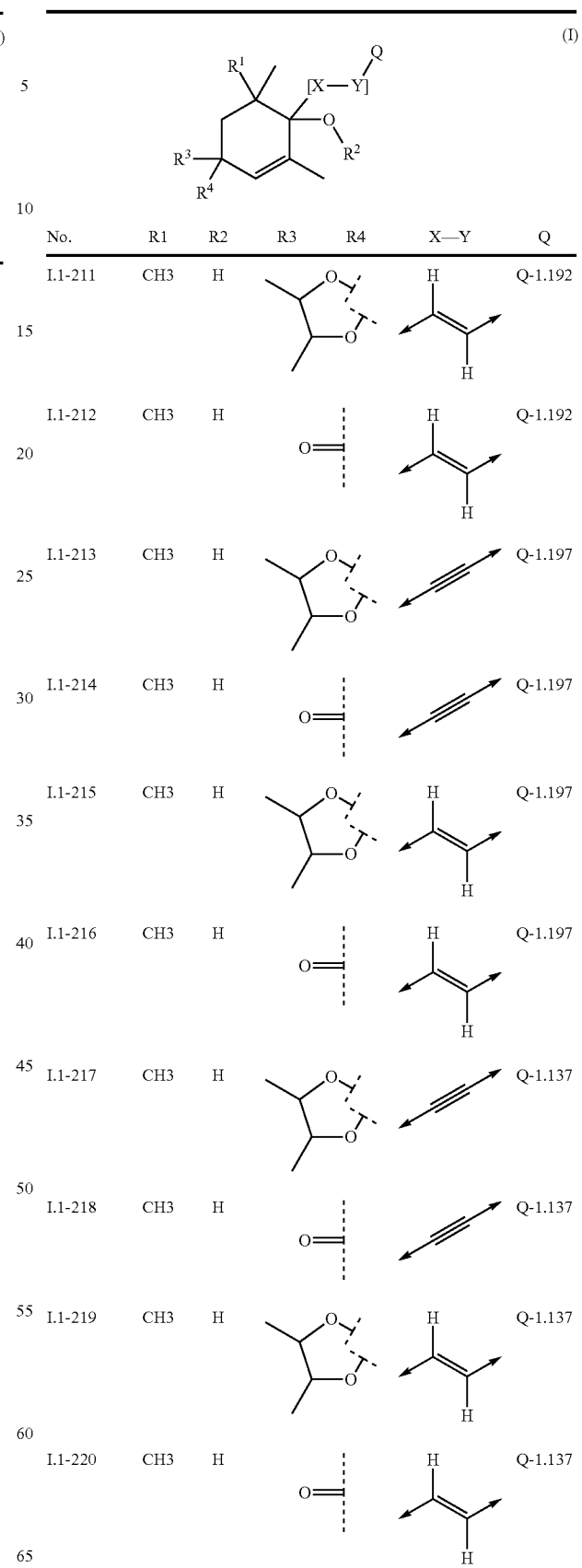

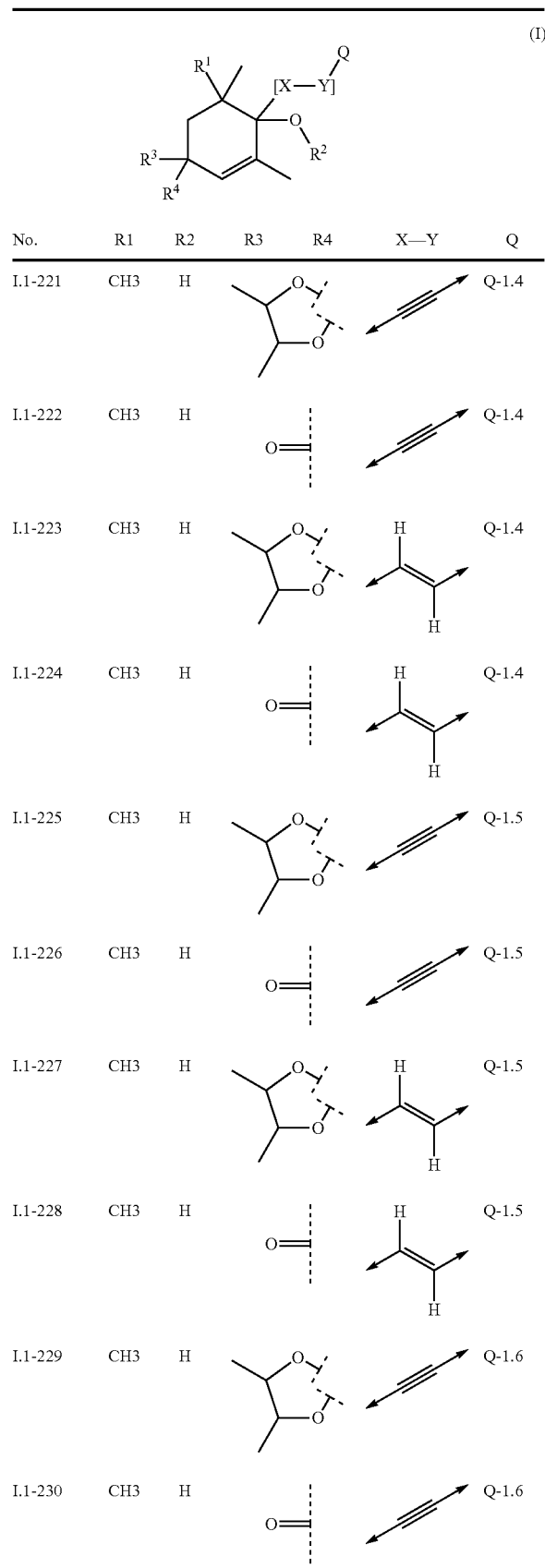
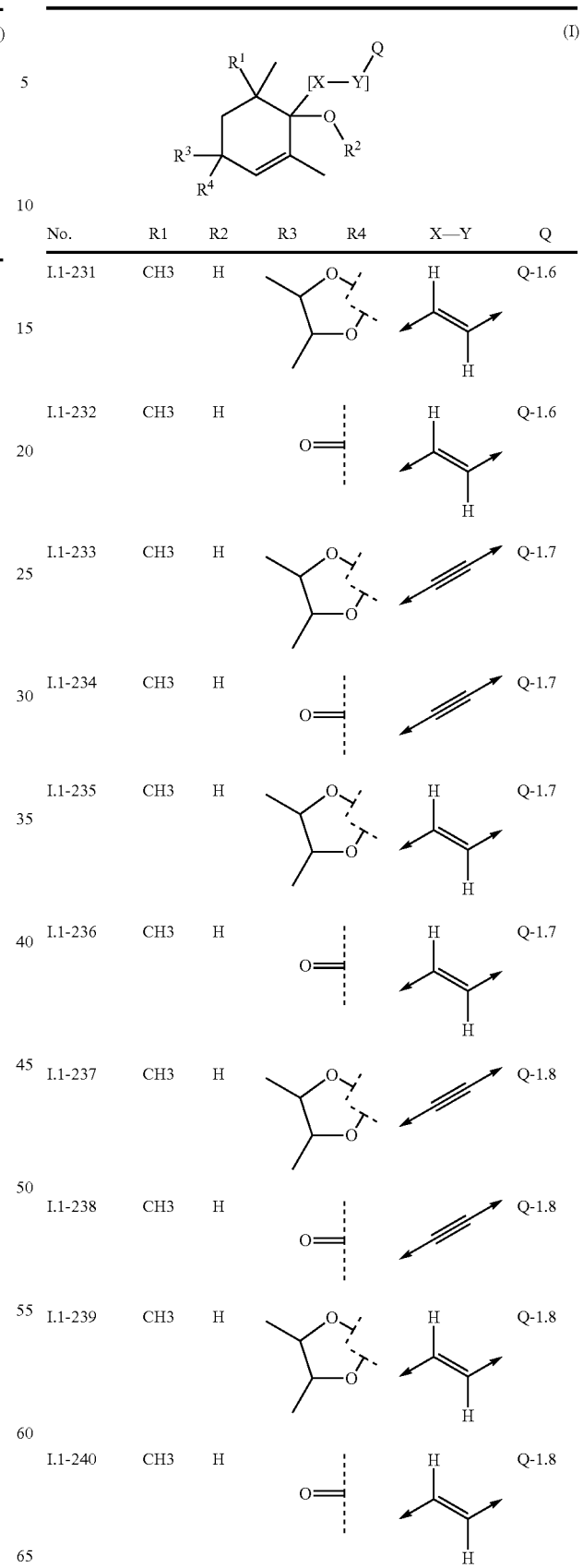

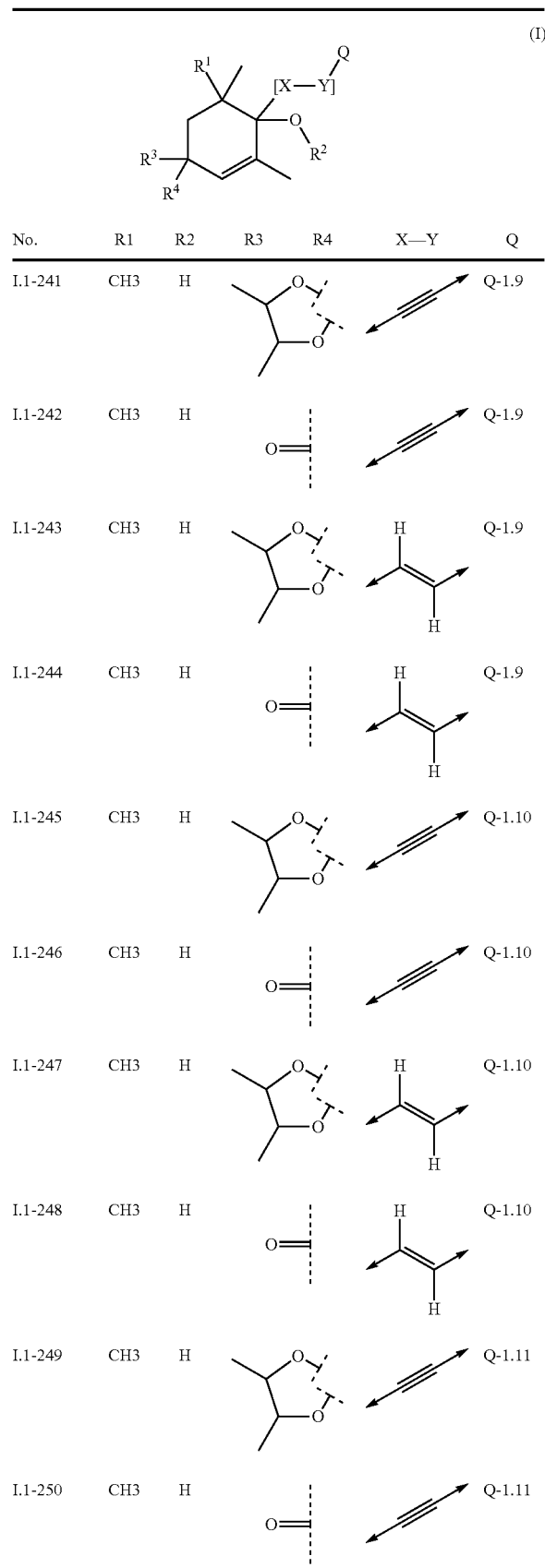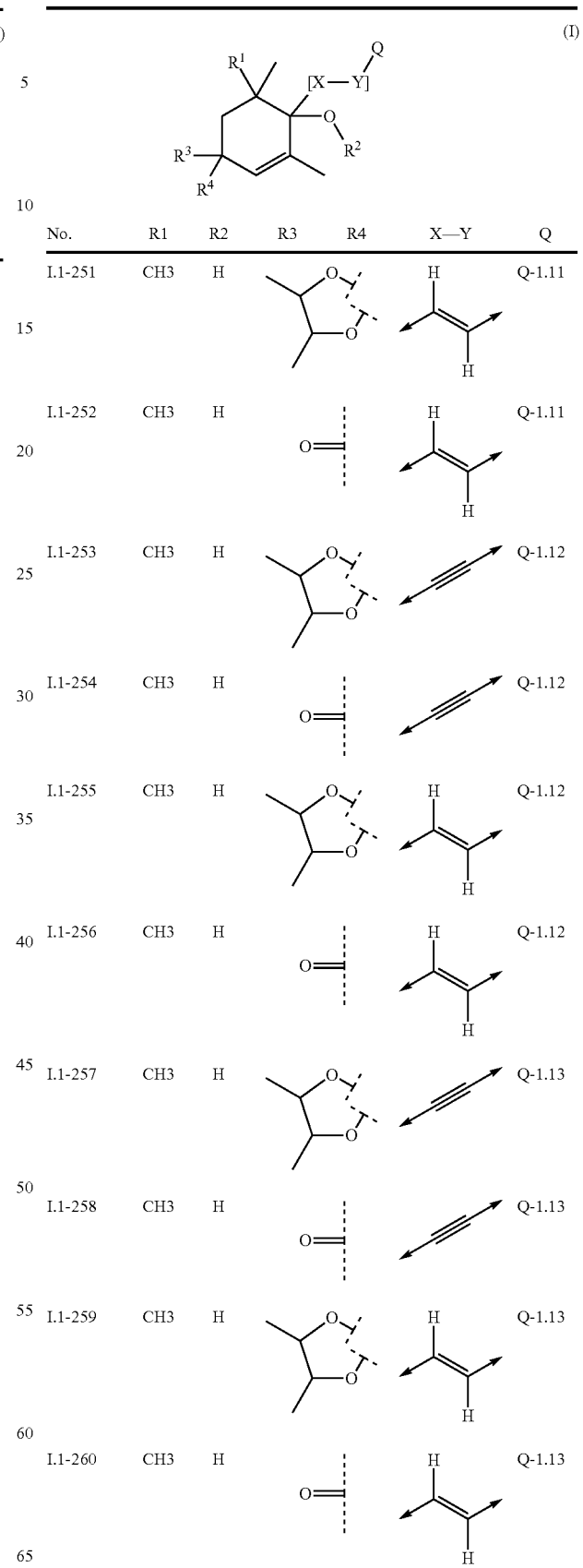

TABLE 1-continued
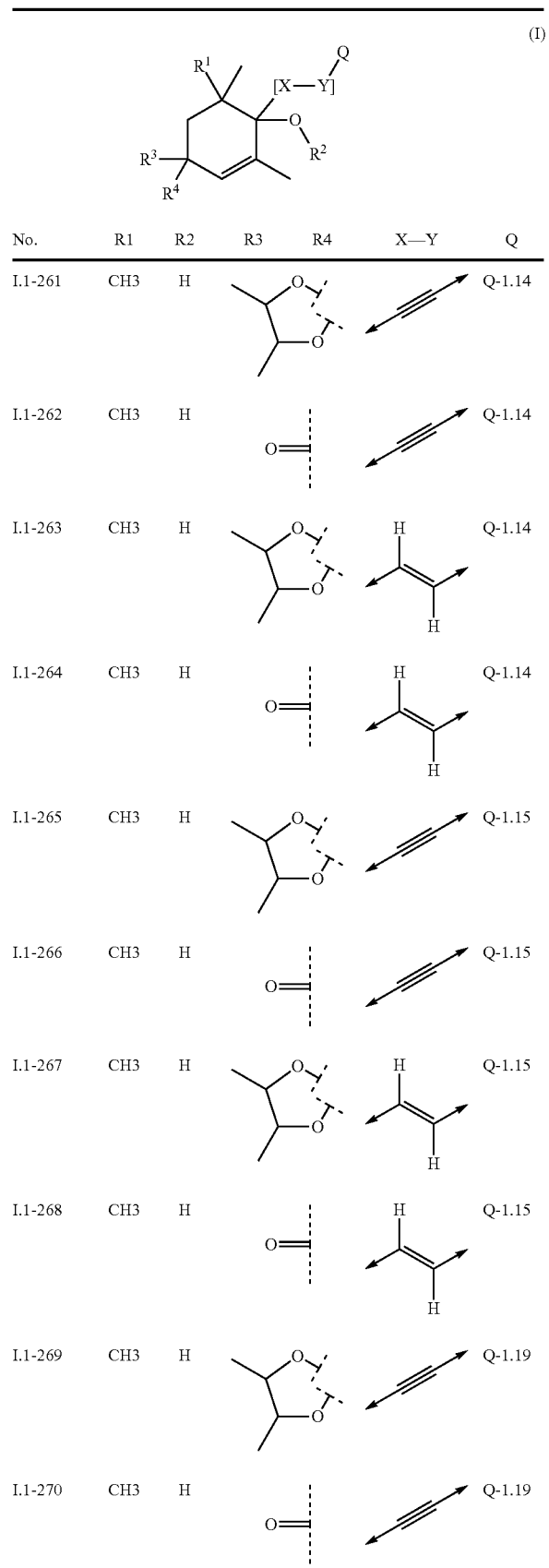
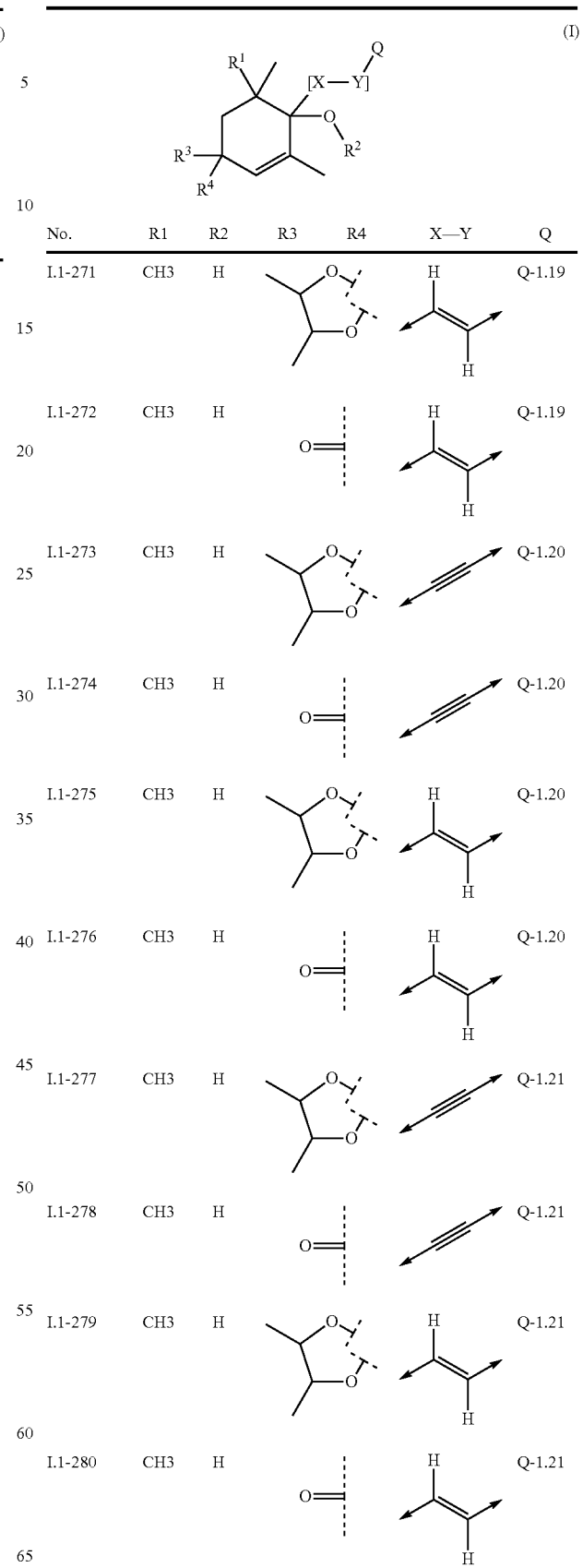

TABLE 1-continued (I)

| No. | R1 | R2 | R3 R4 | X—Y | Q |
|---|---|---|---|---|---|
| I.1-281 | CH3 | H | (dioxolane dimethyl) | alkyne | Q-1.22 |
| I.1-282 | CH3 | H | O= | alkyne | Q-1.22 |
| I.1-283 | CH3 | H | (dioxolane dimethyl) | alkene | Q-1.22 |
| I.1-284 | CH3 | H | O= | alkene | Q-1.22 |
| I.1-285 | CH3 | H | (dioxolane dimethyl) | alkyne | Q-1.23 |
| I.1-286 | CH3 | H | O= | alkyne | Q-1.23 |
| I.1-287 | CH3 | H | (dioxolane dimethyl) | alkene | Q-1.23 |
| I.1-288 | CH3 | H | O= | alkene | Q-1.23 |
| I.1-289 | CH3 | H | (dioxolane dimethyl) | alkyne | Q-1.24 |
| I.1-290 | CH3 | H | O= | alkyne | Q-1.24 |
| I.1-291 | CH3 | H | (dioxolane dimethyl) | alkene | Q-1.24 |
| I.1-292 | CH3 | H | O= | alkene | Q-1.24 |
| I.1-293 | CH3 | H | (dioxolane dimethyl) | alkyne | Q-1.25 |
| I.1-294 | CH3 | H | O= | alkyne | Q-1.25 |
| I.1-295 | CH3 | H | (dioxolane dimethyl) | alkene | Q-1.25 |
| I.1-296 | CH3 | H | O= | alkene | Q-1.25 |
| I.1-297 | CH3 | H | (dioxolane dimethyl) | alkyne | Q-1.26 |
| I.1-298 | CH3 | H | O= | alkyne | Q-1.26 |
| I.1-299 | CH3 | H | (dioxolane dimethyl) | alkene | Q-1.26 |
| I.1-300 | CH3 | H | O= | alkene | Q-1.26 |

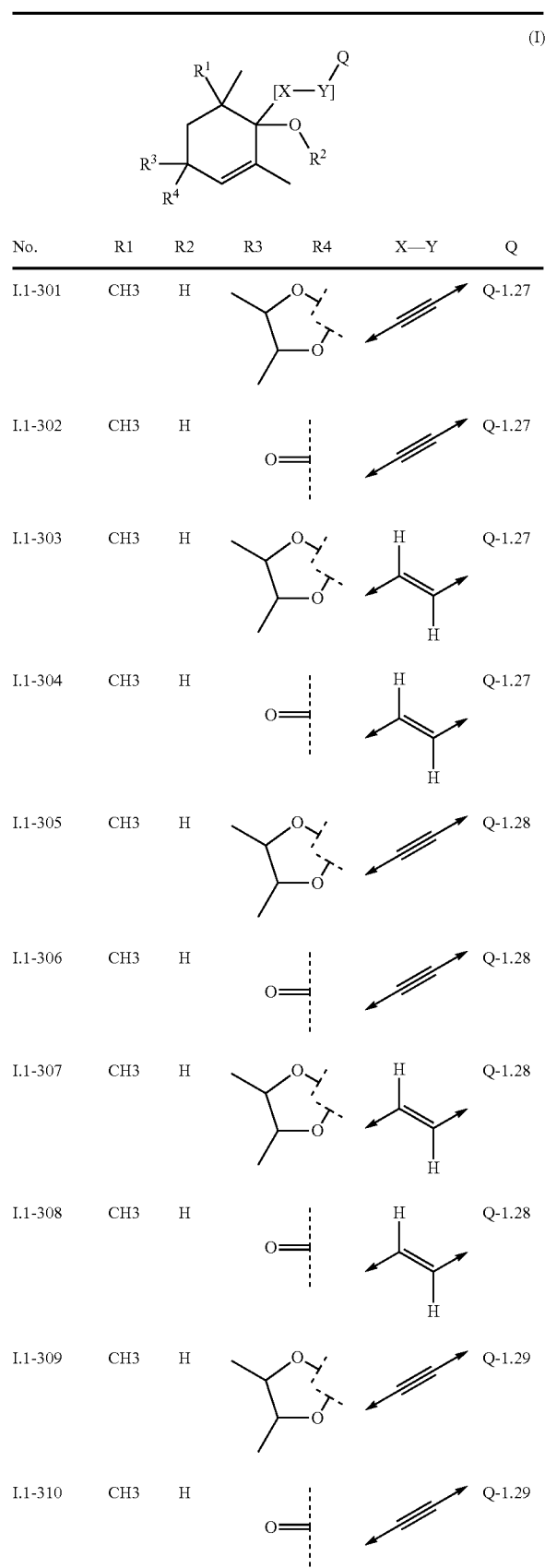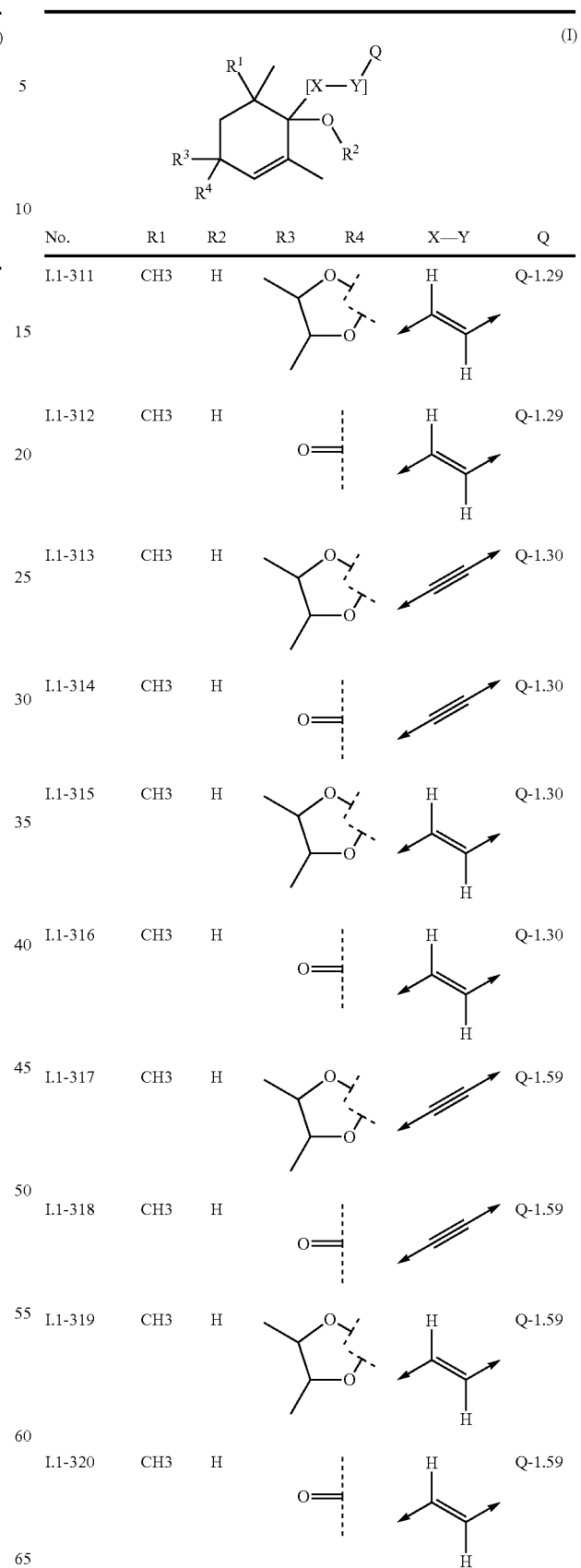

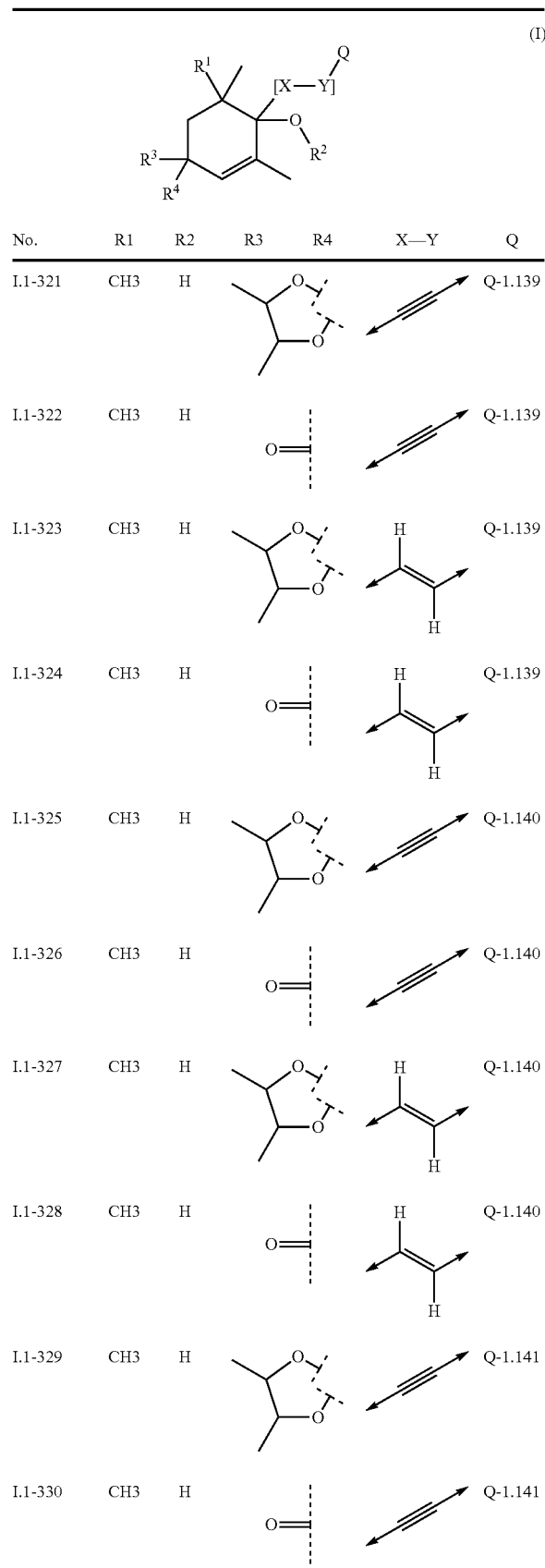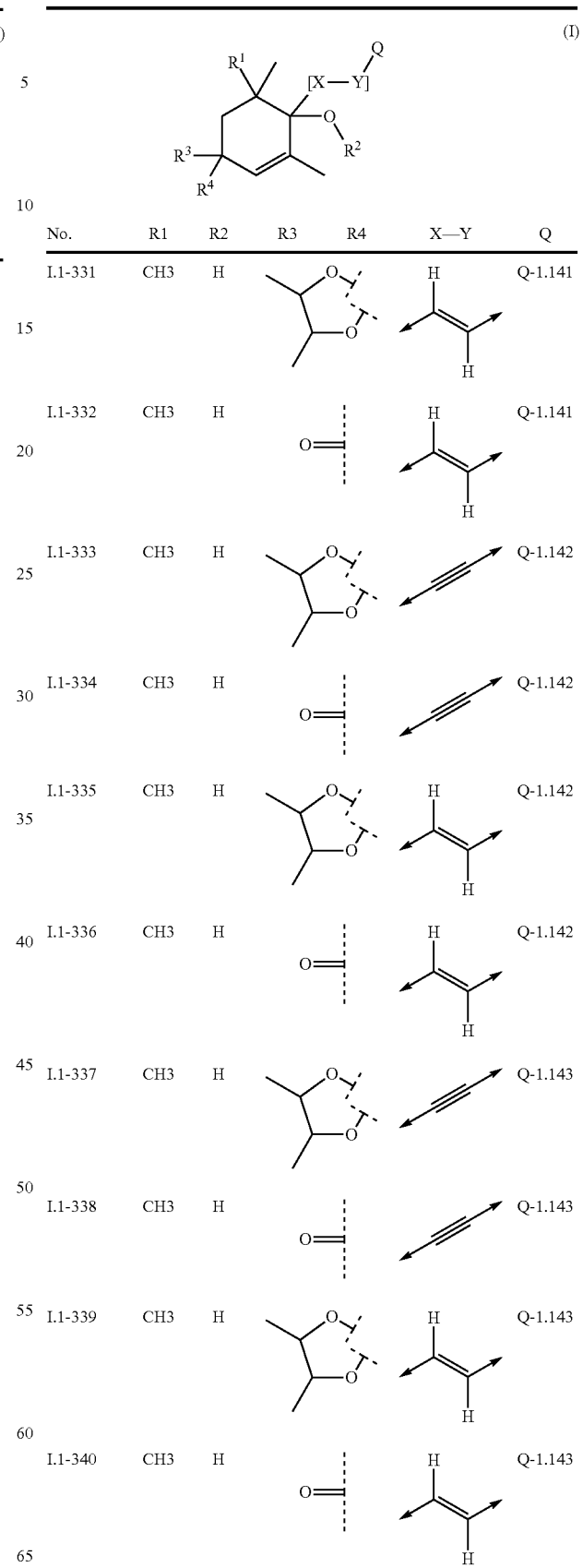

TABLE 1-continued (I)

| No. | R1 | R2 | R3 R4 | X—Y | Q |
|---|---|---|---|---|---|
| I.1-341 | CH3 | H | dioxolane (dimethyl) | alkyne | Q-1.144 |
| I.1-342 | CH3 | H | =O | alkyne | Q-1.144 |
| I.1-343 | CH3 | H | dioxolane (dimethyl) | CH=CH2 | Q-1.144 |
| I.1-344 | CH3 | H | =O | CH=CH2 | Q-1.144 |
| I.1-345 | CH3 | H | dioxolane (dimethyl) | alkyne | Q-1.145 |
| I.1-346 | CH3 | H | =O | alkyne | Q-1.145 |
| I.1-347 | CH3 | H | dioxolane (dimethyl) | CH=CH2 | Q-1.145 |
| I.1-348 | CH3 | H | =O | CH=CH2 | Q-1.145 |
| I.1-349 | CH3 | H | dioxolane (dimethyl) | alkyne | Q-1.146 |
| I.1-350 | CH3 | H | =O | alkyne | Q-1.146 |
| I.1-351 | CH3 | H | dioxolane (dimethyl) | CH=CH2 | Q-1.146 |
| I.1-352 | CH3 | H | =O | CH=CH2 | Q-1.146 |
| I.1-353 | CH3 | H | dioxolane (dimethyl) | alkyne | Q-1.147 |
| I.1-354 | CH3 | H | =O | alkyne | Q-1.147 |
| I.1-355 | CH3 | H | dioxolane (dimethyl) | CH=CH2 | Q-1.147 |
| I.1-356 | CH3 | H | =O | CH=CH2 | Q-1.147 |
| I.1-357 | CH3 | H | dioxolane (dimethyl) | alkyne | Q-1.148 |
| I.1-358 | CH3 | H | =O | alkyne | Q-1.148 |
| I.1-359 | CH3 | H | dioxolane (dimethyl) | CH=CH2 | Q-1.148 |
| I.1-360 | CH3 | H | =O | CH=CH2 | Q-1.148 |

TABLE 1-continued
(I)
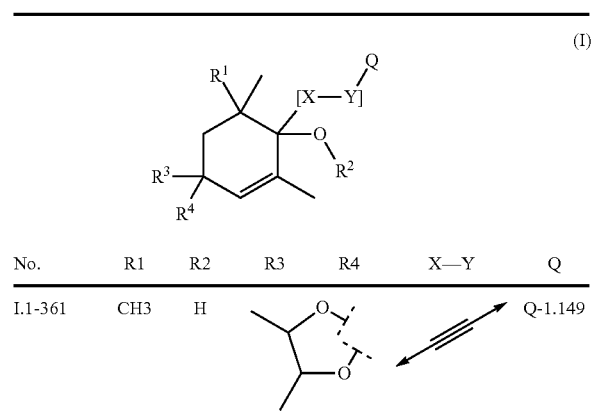
| No. | R1 | R2 | R3 | R4 | X—Y | Q |
|---|---|---|---|---|---|---|
| I.1-361 | CH3 | H | 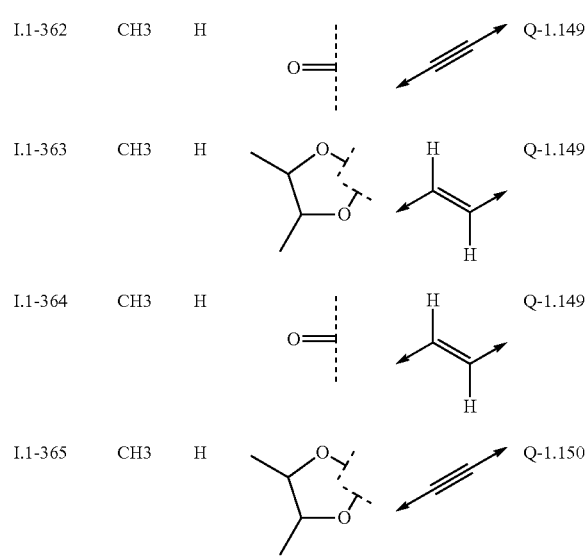 | | | Q-1.149 |
| I.1-362 | CH3 | H | | | | Q-1.149 |
| I.1-363 | CH3 | H | | | | Q-1.149 |
| I.1-364 | CH3 | H | | | | Q-1.149 |
| I.1-365 | CH3 | H | | | | Q-1.150 |
| I.1-366 | CH3 | H | | | | Q-1.150 |
| I.1-367 | CH3 | H | | | | Q-1.150 |
| I.1-368 | CH3 | H | | | | Q-1.150 |
| I.1-393 | CH3 | H | 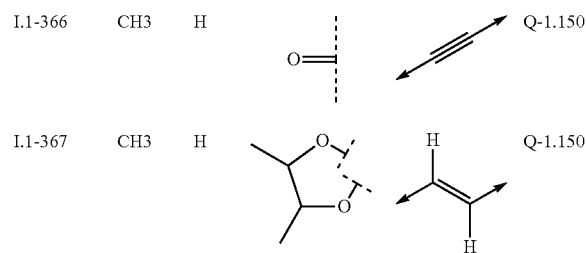 | | | Q-1.166 |
| I.1-394 | CH3 | H | 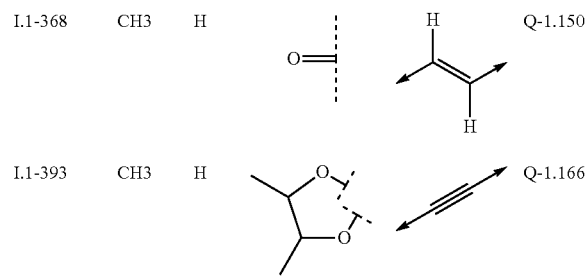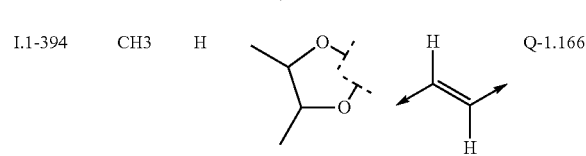 | | | Q-1.166 |
TABLE 1-continued
(I)
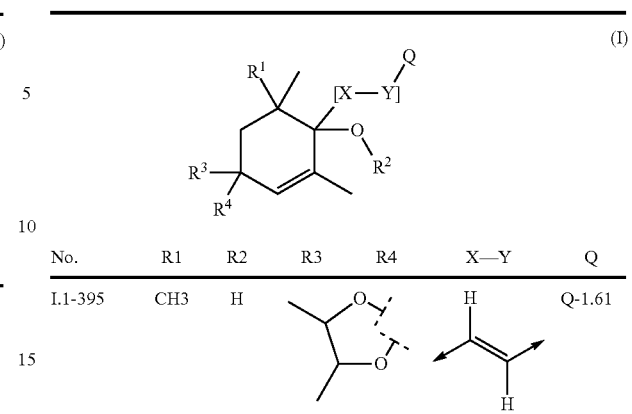
| No. | R1 | R2 | R3 | R4 | X—Y | Q |
|---|---|---|---|---|---|---|
| I.1-395 | CH3 | H | 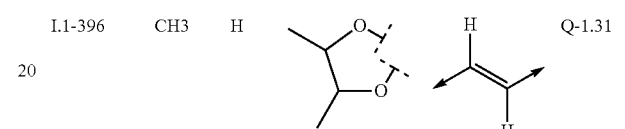 | | | Q-1.61 |
| I.1-396 | CH3 | H | 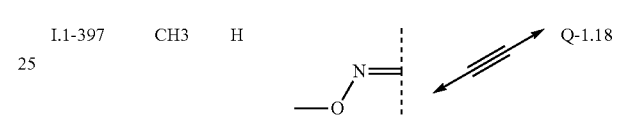 | | | Q-1.31 |
| I.1-397 | CH3 | H | 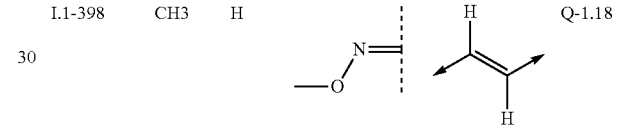 | | | Q-1.18 |
| I.1-398 | CH3 | H | 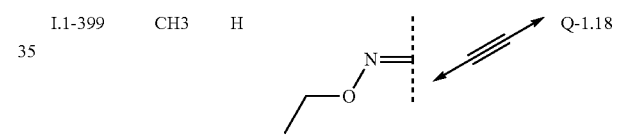 | | | Q-1.18 |
| I.1-399 | CH3 | H | 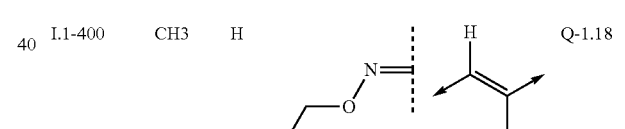 | | | Q-1.18 |
| I.1-400 | CH3 | H | 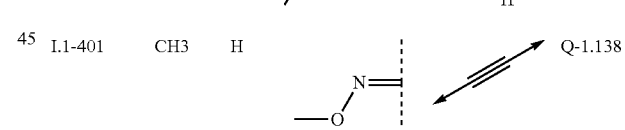 | | | Q-1.18 |
| I.1-401 | CH3 | H | 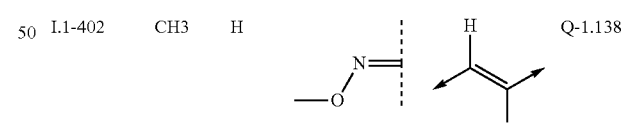 | | | Q-1.138 |
| I.1-402 | CH3 | H | 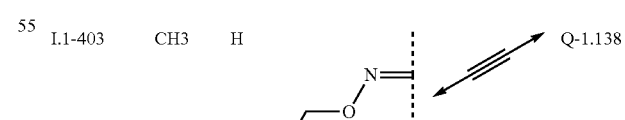 | | | Q-1.138 |
| I.1-403 | CH3 | H | 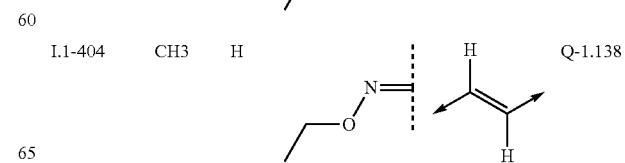 | | | Q-1.138 |
| I.1-404 | CH3 | H | | | | Q-1.138 |

TABLE 1-continued (I)

Structure shown with R¹, R², R³, R⁴ substituents on cyclohexene ring with [X—Y]—Q and O—R² groups.

| No. | R1 | R2 | R3 | R4 | X—Y | Q |
|---|---|---|---|---|---|---|
| I.1-405 | CH3 | H | | | —O—N= (methoxyimino) | Q-1.168 (alkyne) |
| I.1-406 | CH3 | H | | | —O—N= (methoxyimino) | Q-1.168 (CH=CH) |
| I.1-407 | CH3 | H | | | —O—N= (ethoxyimino) | Q-1.168 (alkyne) |
| I.1-408 | CH3 | H | | | —O—N= (ethoxyimino) | Q-1.168 (CH=CH) |
| I.1-409 | CH3 | H | | | —O—N= (methoxyimino) | Q-1.183 (alkyne) |
| I.1-410 | CH3 | H | | | —O—N= (methoxyimino) | Q-1.183 (CH=CH) |
| I.1-411 | CH3 | H | | | —O—N= (ethoxyimino) | Q-1.183 (alkyne) |
| I.1-412 | CH3 | H | | | —O—N= (ethoxyimino) | Q-1.183 (CH=CH) |
| I.1-413 | CH3 | H | | | —O—N= (methoxyimino) | Q-1.3 (alkyne) |
| I.1-414 | CH3 | H | | | —O—N= (methoxyimino) | Q-1.3 (CH=CH) |
| I.1-415 | CH3 | H | | | —O—N= (ethoxyimino) | Q-1.3 (alkyne) |
| I.1-416 | CH3 | H | | | —O—N= (ethoxyimino) | Q-1.3 (CH=CH) |
| I.1-417 | CH3 | H | | | —O—N= (methoxyimino) | Q-1.16 (alkyne) |
| I.1-418 | CH3 | H | | | —O—N= (methoxyimino) | Q-1.16 (CH=CH) |
| I.1-419 | CH3 | H | | | —O—N= (ethoxyimino) | Q-1.16 (alkyne) |
| I.1-420 | CH3 | H | | | —O—N= (ethoxyimino) | Q-1.16 (CH=CH) |
| I.1-421 | CH3 | H | | | —O—N= (methoxyimino) | Q-1.136 (alkyne) |
| I.1-422 | CH3 | H | | | —O—N= (methoxyimino) | Q-1.136 (CH=CH) |
| I.1-423 | CH3 | H | | | —O—N= (ethoxyimino) | Q-1.136 (alkyne) |
| I.1-424 | CH3 | H | | | —O—N= (ethoxyimino) | Q-1.136 (CH=CH) |

TABLE 1-continued (I)

| No. | R1 | R2 | R3 | R4 | X—Y | Q |
|---|---|---|---|---|---|---|
| I.1-425 | CH3 | H | | | —O—N= (methoxyimino) | alkyne, Q-1.166 |
| I.1-426 | CH3 | H | | | —O—N= (methoxyimino) | CH=CH2, Q-1.166 |
| I.1-427 | CH3 | H | | | ethoxyimino | alkyne, Q-1.166 |
| I.1-428 | CH3 | H | | | ethoxyimino | CH=CH2, Q-1.166 |
| I.1-429 | CH3 | H | | | methoxyimino | alkyne, Q-1.181 |
| I.1-430 | CH3 | H | | | methoxyimino | CH=CH2, Q-1.181 |
| I.1-431 | CH3 | H | | | ethoxyimino | alkyne, Q-1.181 |
| I.1-432 | CH3 | H | | | ethoxyimino | CH=CH2, Q-1.181 |
| I.1-433 | CH3 | H | | | methoxyimino | alkyne, Q-1.1 |
| I.1-434 | CH3 | H | | | methoxyimino | CH=CH2, Q-1.1 |
| I.1-435 | CH3 | H | | | ethoxyimino | alkyne, Q-1.1 |
| I.1-436 | CH3 | H | | | ethoxyimino | CH=CH2, Q-1.1 |
| I.1-437 | CH3 | H | | | dimethyldioxolane | alkyne, Q-1.201 |
| I.1-438 | CH3 | H | | | O= (oxo) | alkyne, Q-1.201 |
| I.1-439 | CH3 | H | | | dimethyldioxolane | CH=CH2, Q-1.201 |
| I.1-440 | CH3 | H | | | O= (oxo) | CH=CH2, Q-1.201 |
| I.1-441 | CH3 | H | | | dimethyldioxolane | alkyne, Q-1.202 |
| I.1-442 | CH3 | H | | | O= (oxo) | alkyne, Q-1.202 |
| I.1-443 | CH3 | H | | | dimethyldioxolane | CH=CH2, Q-1.202 |
| I.1-444 | CH3 | H | | | O= (oxo) | CH=CH2, Q-1.202 |

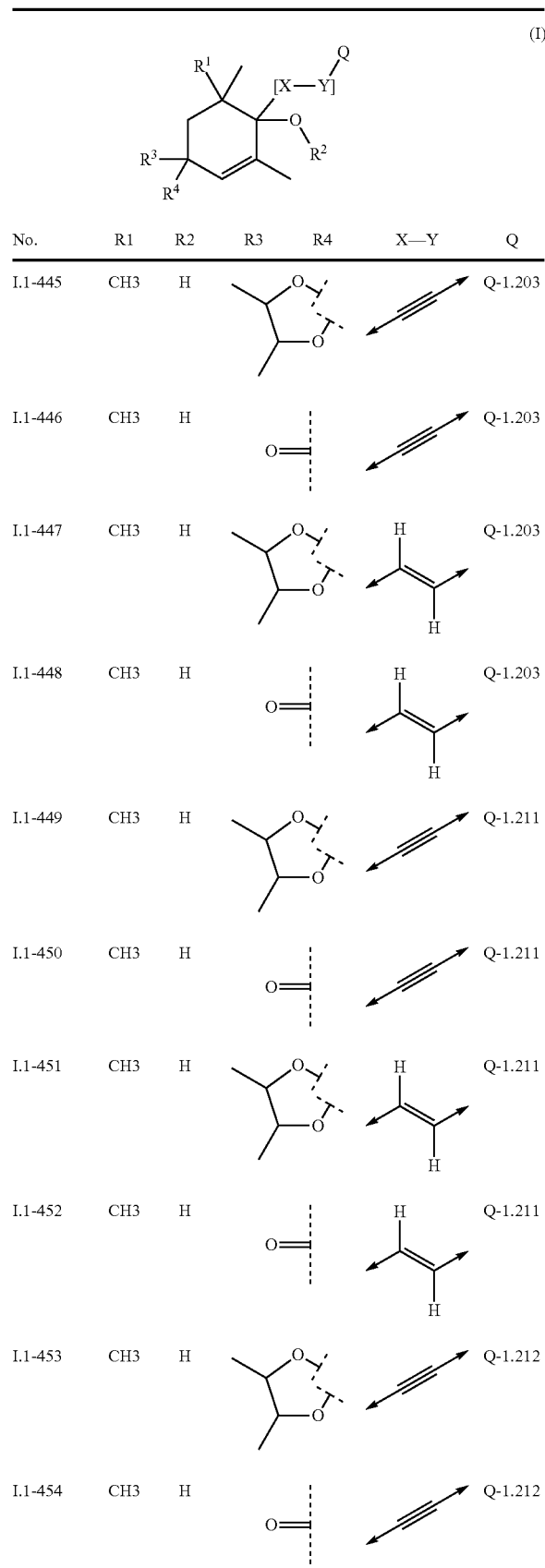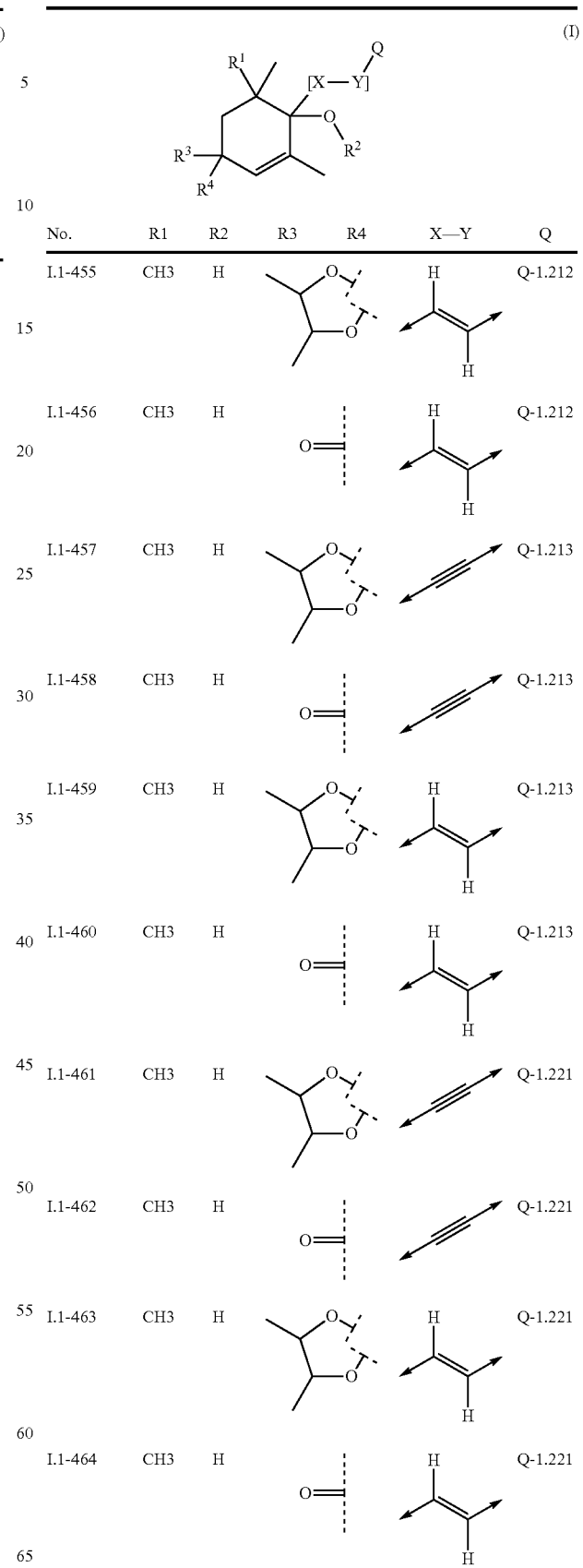

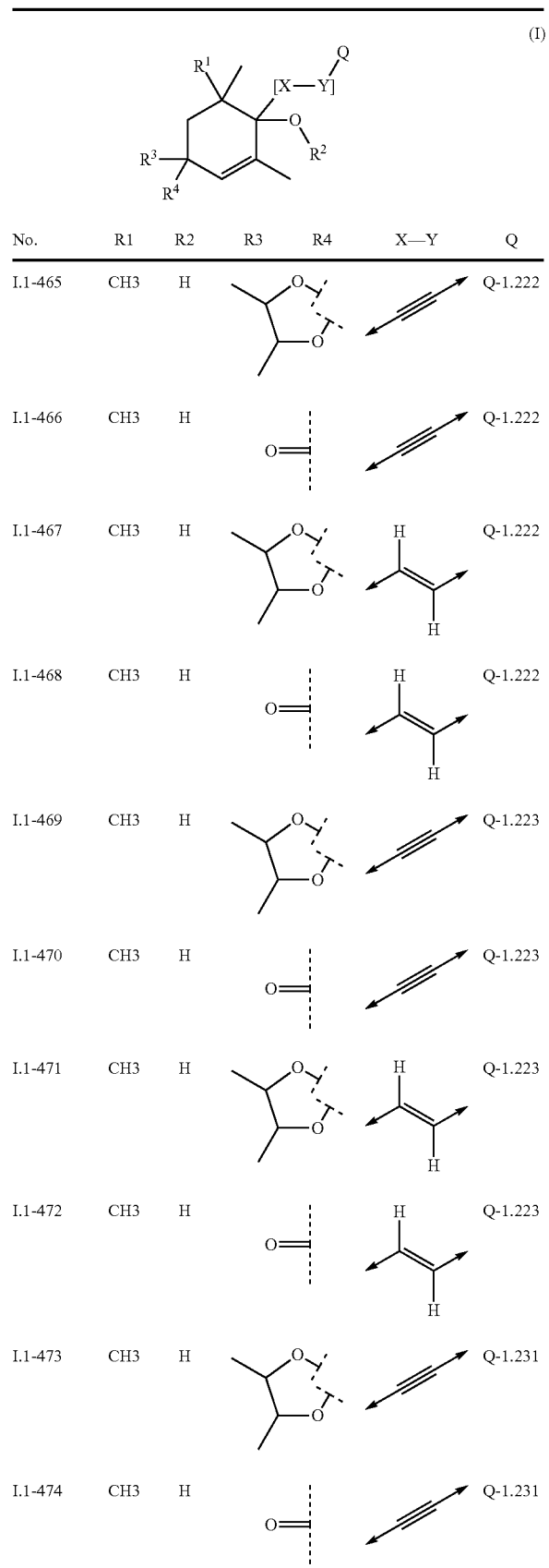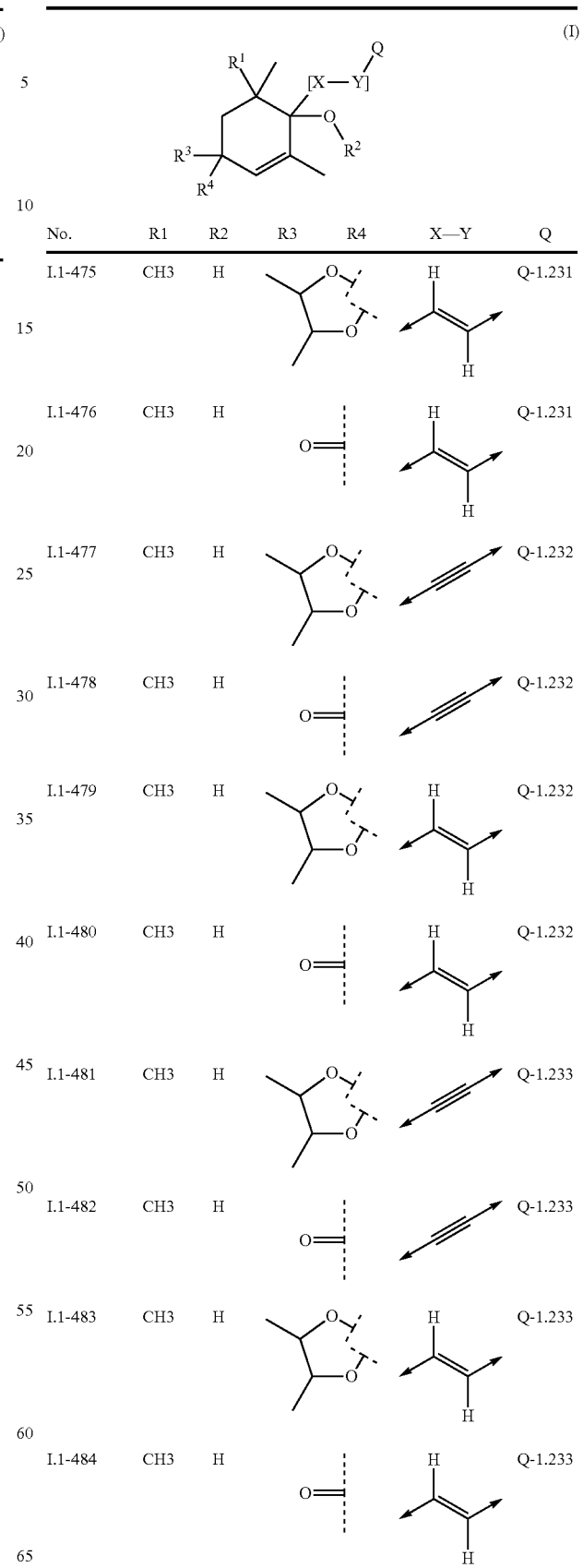

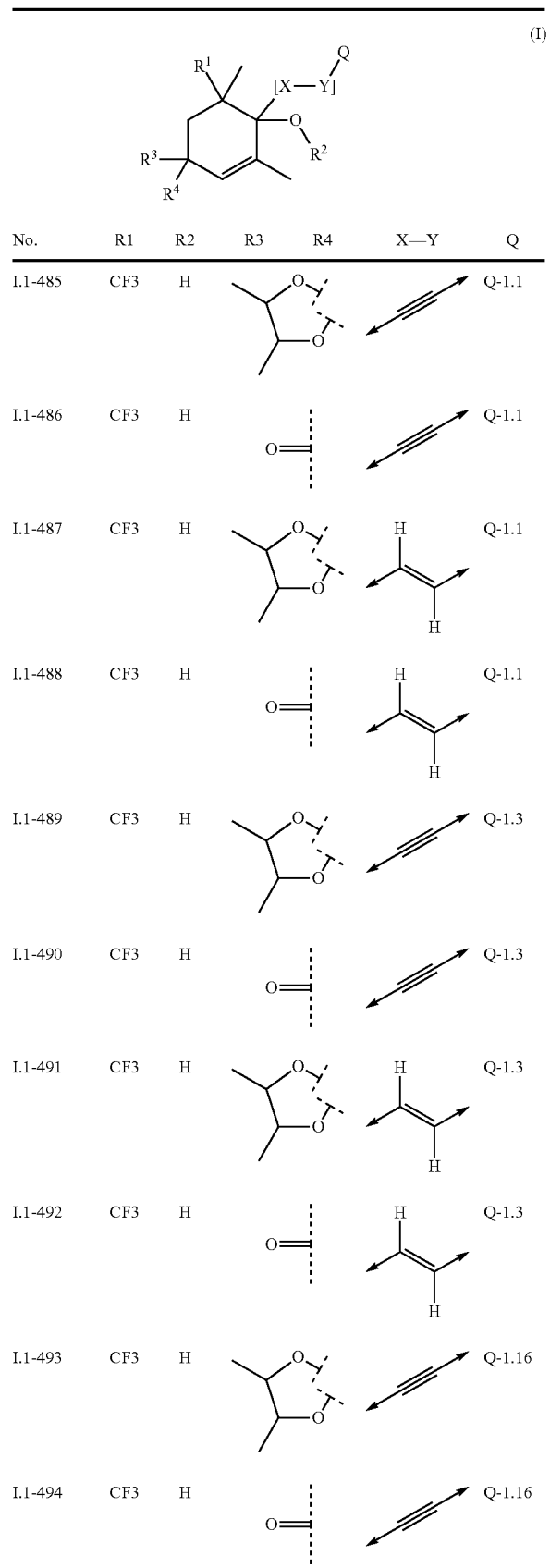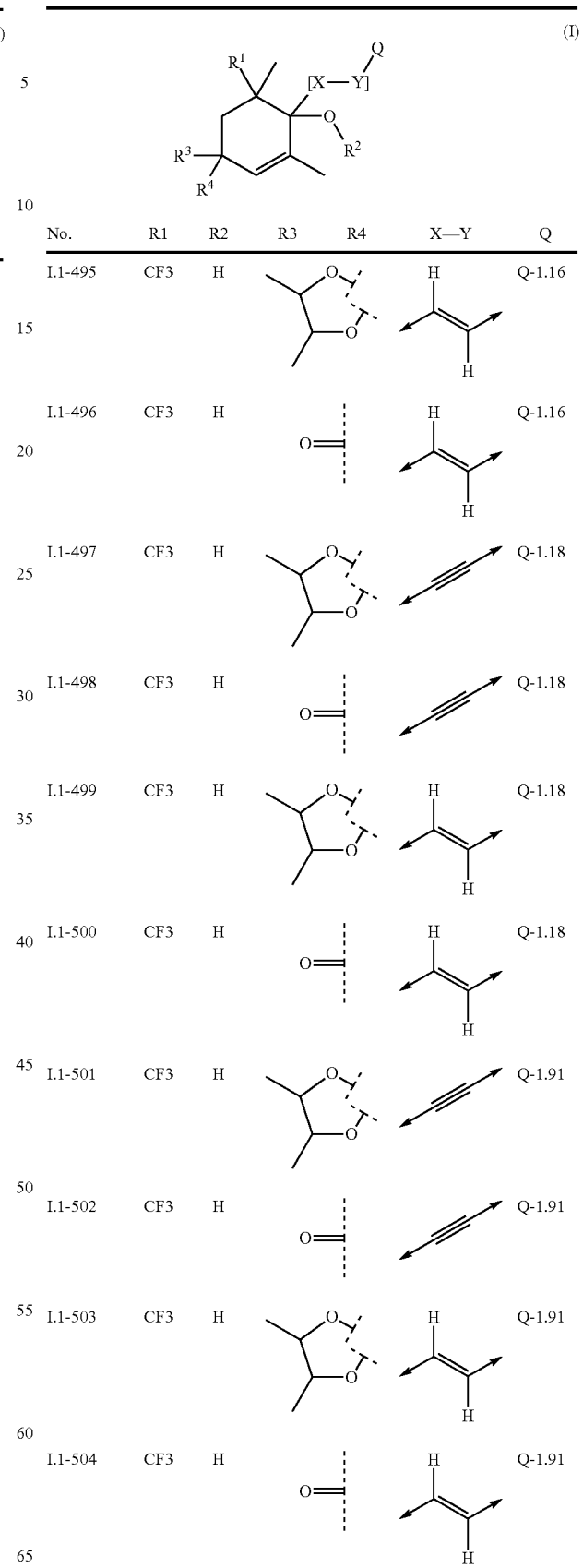

TABLE 1-continued
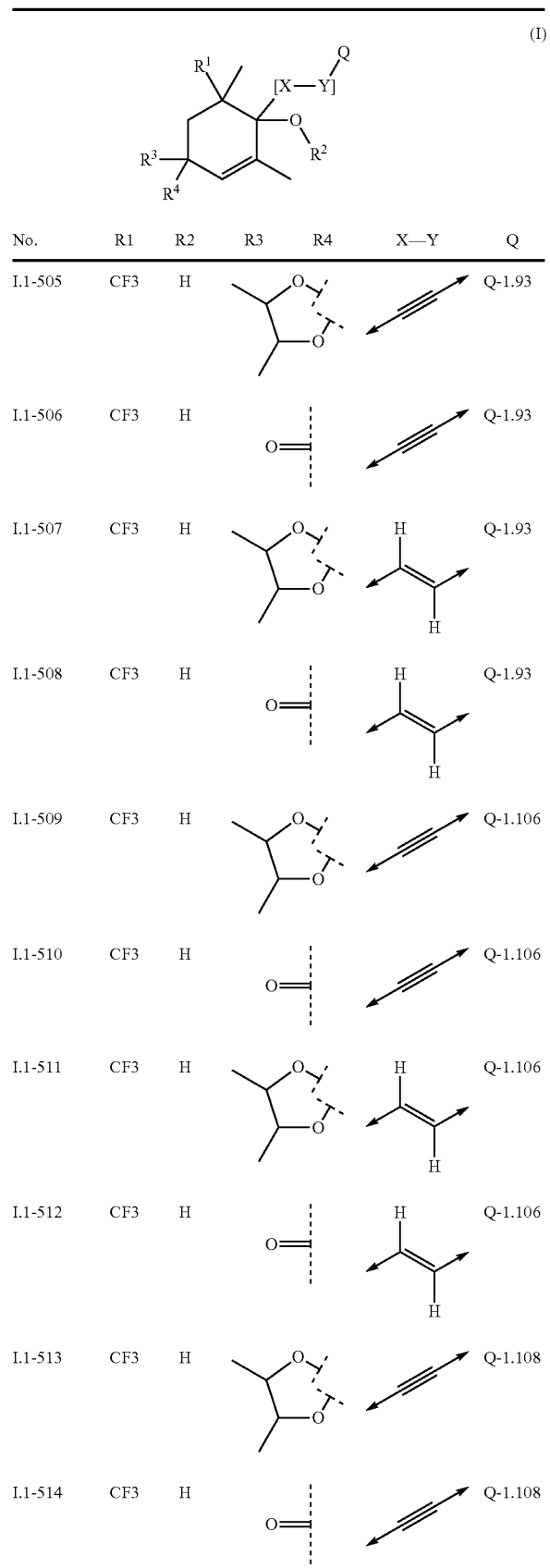
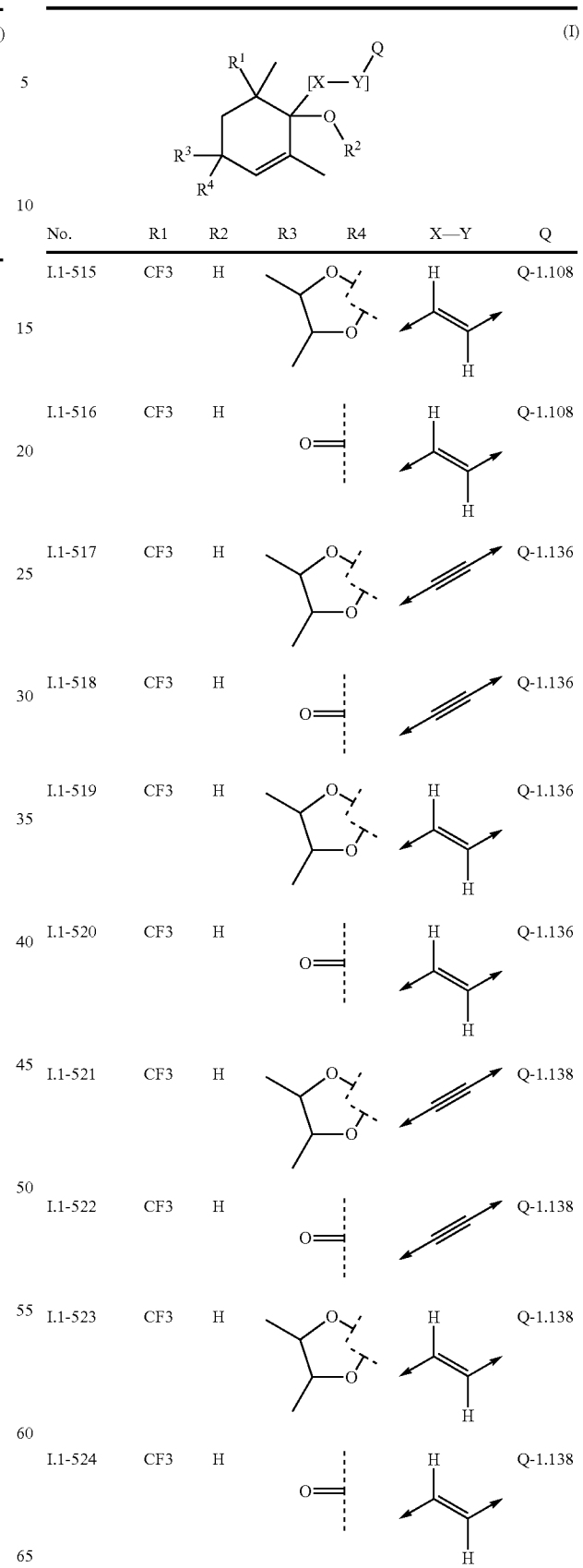

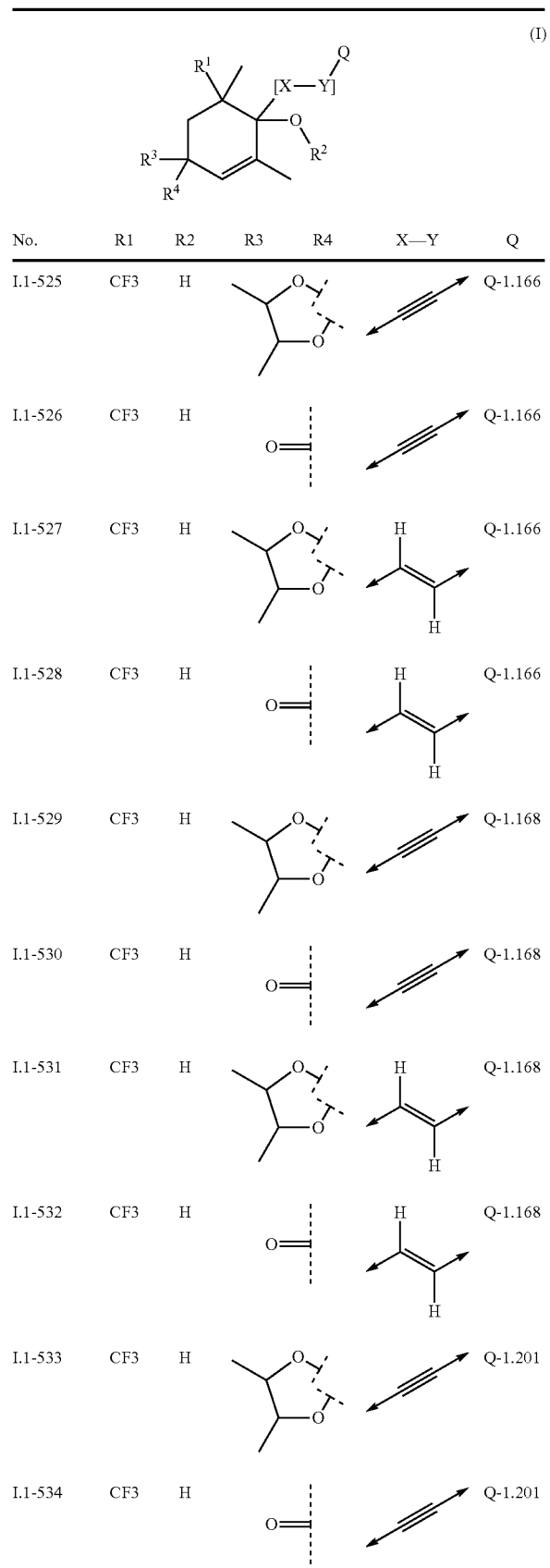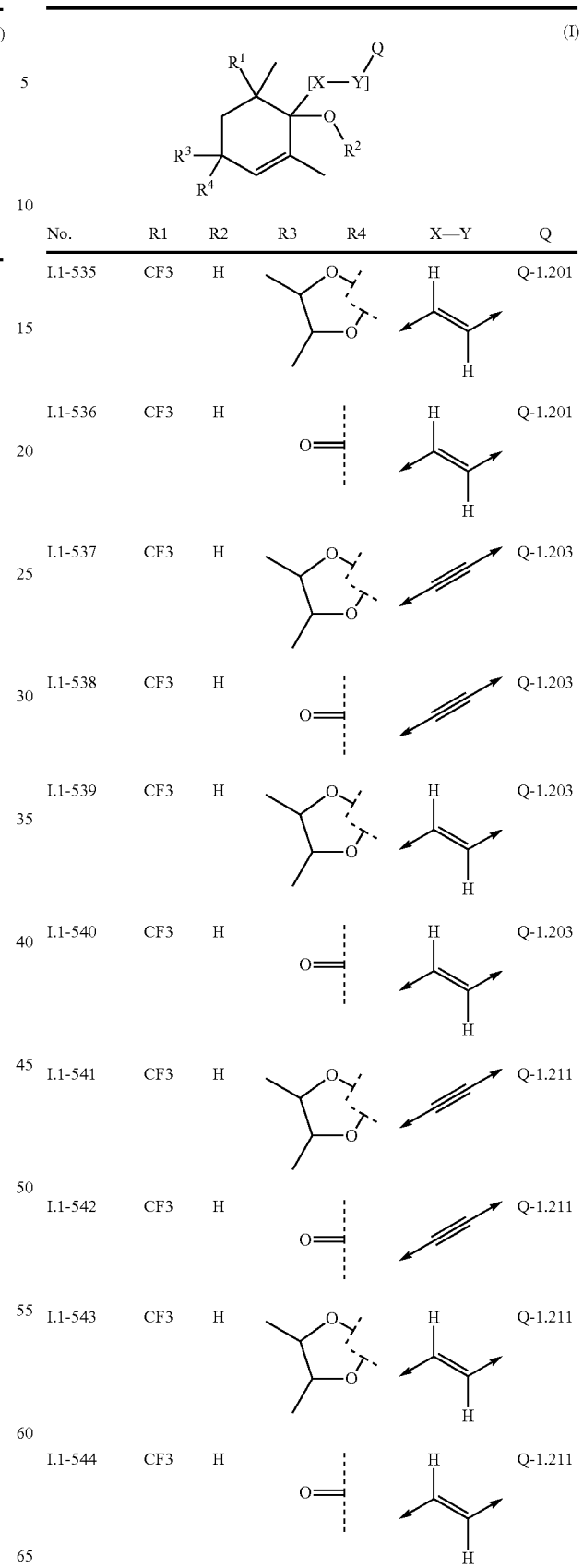

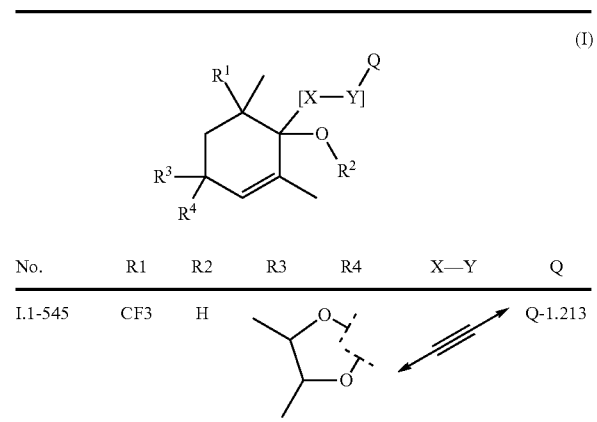
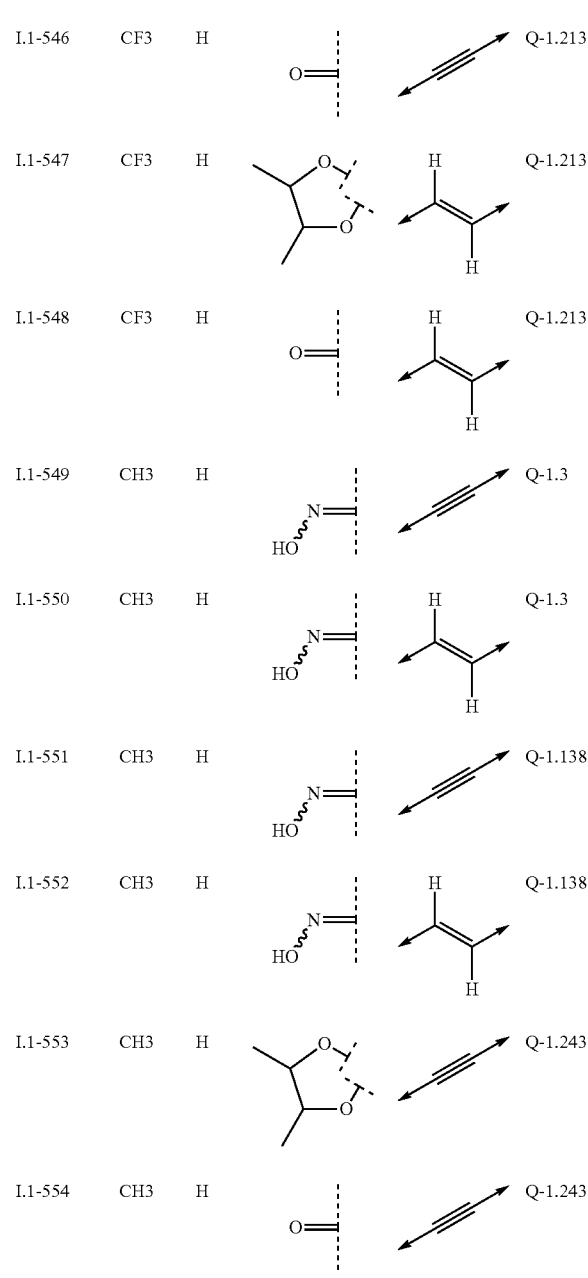
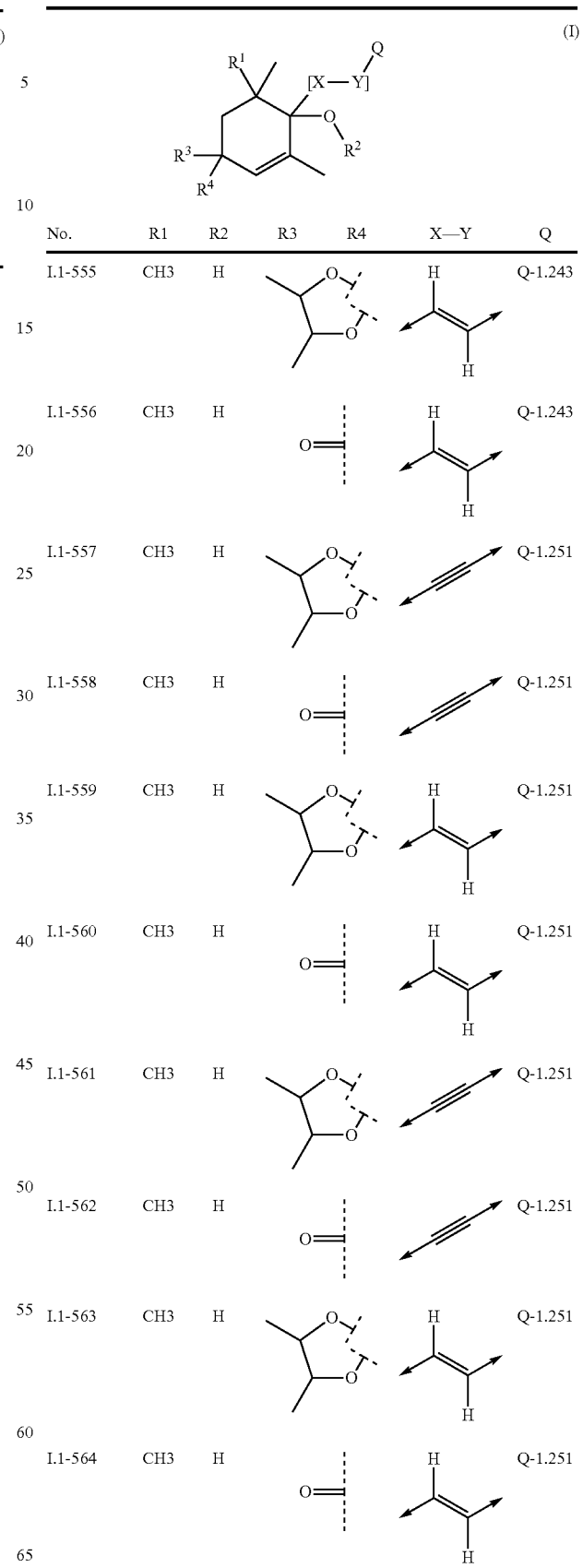

TABLE 1-continued (I) Structure with R¹, R², R³, R⁴, [X—Y], Q substituents on cyclohexene with O-R² group

| No. | R1 | R2 | R3 R4 | X—Y | Q |
|---|---|---|---|---|---|
| I.1-565 | CH3 | H | (dioxolane ring) | CH=CH₂ | Q-1.241 |
| I.1-566 | CH3 | H | O= | CH=CH₂ | Q-1.241 |

TABLE 2

(I) Structure with R¹, R², R³, R⁴, [X—Y], Q substituents on cyclohexene with O-R² group

| No. | R¹ | R² | R³ R⁴ | X-Y | Q |
|---|---|---|---|---|---|
| I.2-1 | CH₃ | H | (dioxolane ring) | C≡C | Q-2.1 |
| I.2-2 | CH₃ | H | O= | C≡C | Q-2.1 |
| I.2-3 | CH₃ | H | (dioxolane ring) | CH=CH₂ | Q-2.1 |
| I.2-4 | CH₃ | H | O= | CH=CH₂ | Q-2.1 |
| I.2-5 | CH₃ | H | (dioxolane ring) | C≡C | Q-2.2 |
| I.2-6 | CH₃ | H | O= | C≡C | Q-2.2 |

TABLE 2-continued (I) Structure with R¹, R², R³, R⁴, [X—Y], Q substituents on cyclohexene with O-R² group

| No. | R¹ | R² | R³ R⁴ | X-Y | Q |
|---|---|---|---|---|---|
| I.2-7 | CH₃ | H | (dioxolane ring) | CH=CH₂ | Q-2.2 |
| I.2-8 | CH₃ | H | O= | CH=CH₂ | Q-2.2 |
| I.2-9 | CH₃ | H | (dioxolane ring) | C≡C | Q-2.3 |
| I.2-10 | CH₃ | H | O= | C≡C | Q-2.3 |
| I.2-11 | CH₃ | H | (dioxolane ring) | CH=CH₂ | Q-2.3 |
| I.2-12 | CH₃ | H | O= | CH=CH₂ | Q-2.3 |
| I.2-13 | CH₃ | H | (dioxolane ring) | C≡C | Q-2.4 |
| I.2-14 | CH₃ | H | O= | C≡C | Q-2.4 |
| I.2-15 | CH₃ | H | (dioxolane ring) | CH=CH₂ | Q-2.4 |
| I.2-16 | CH₃ | H | O= | CH=CH₂ | Q-2.4 |

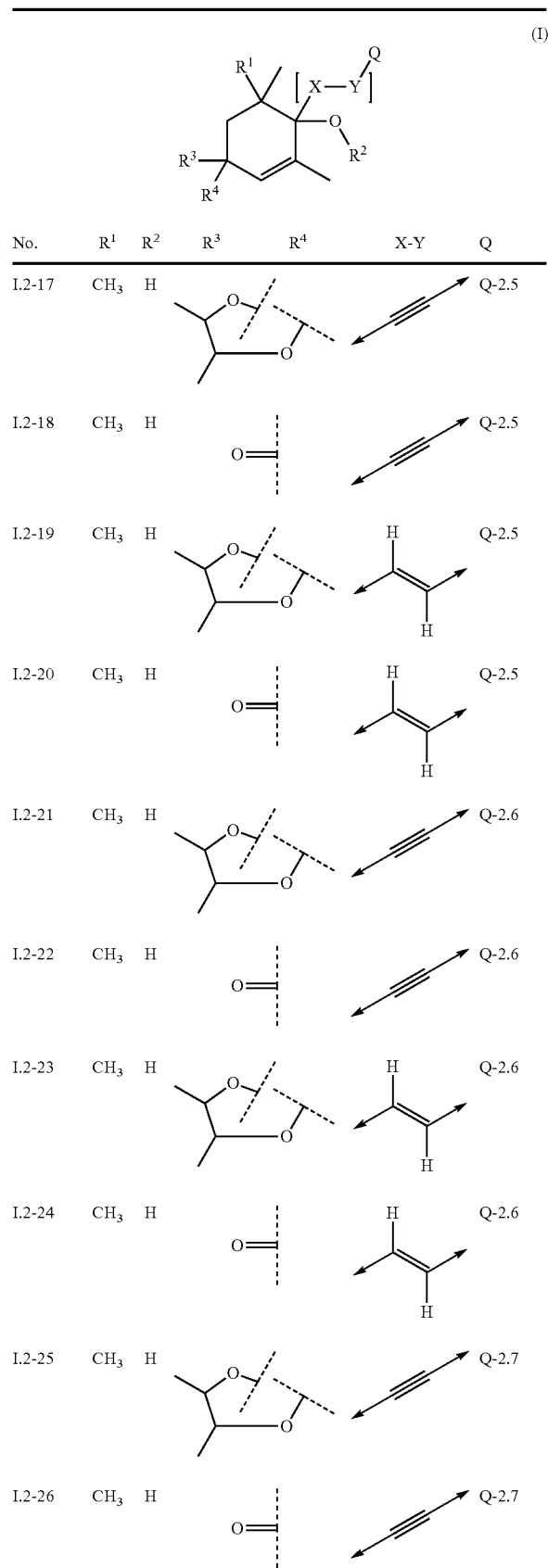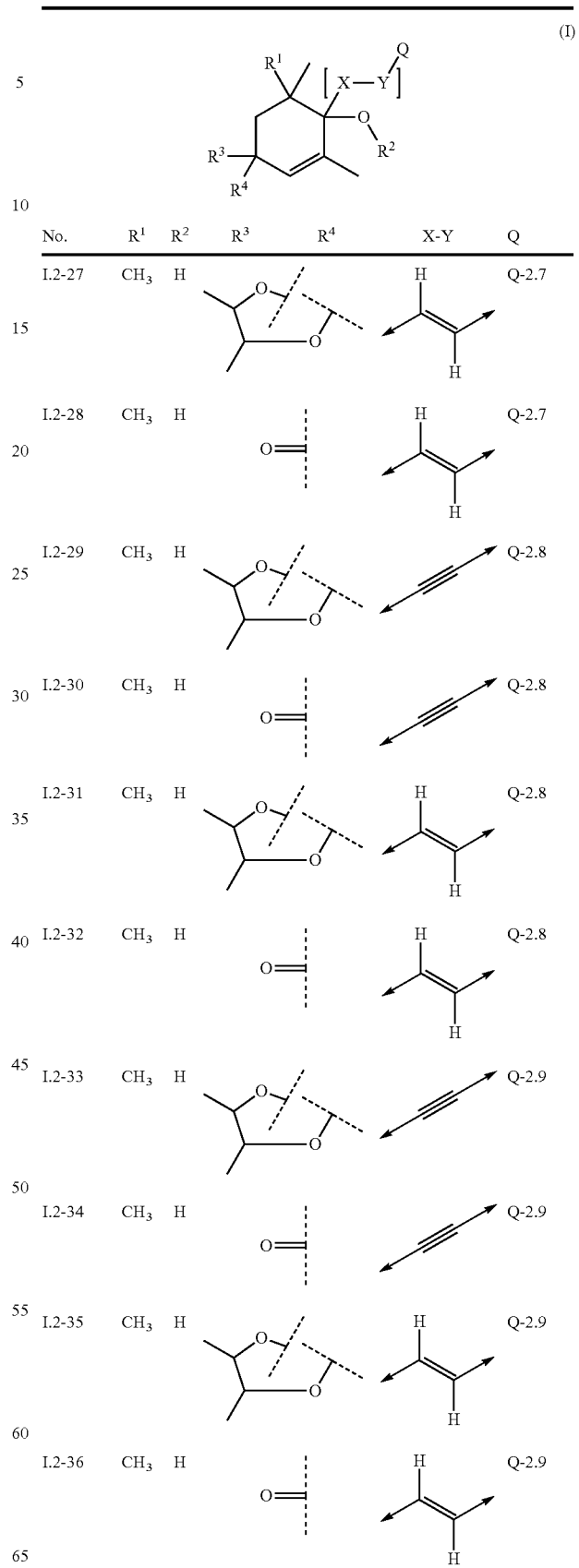

TABLE 2-continued
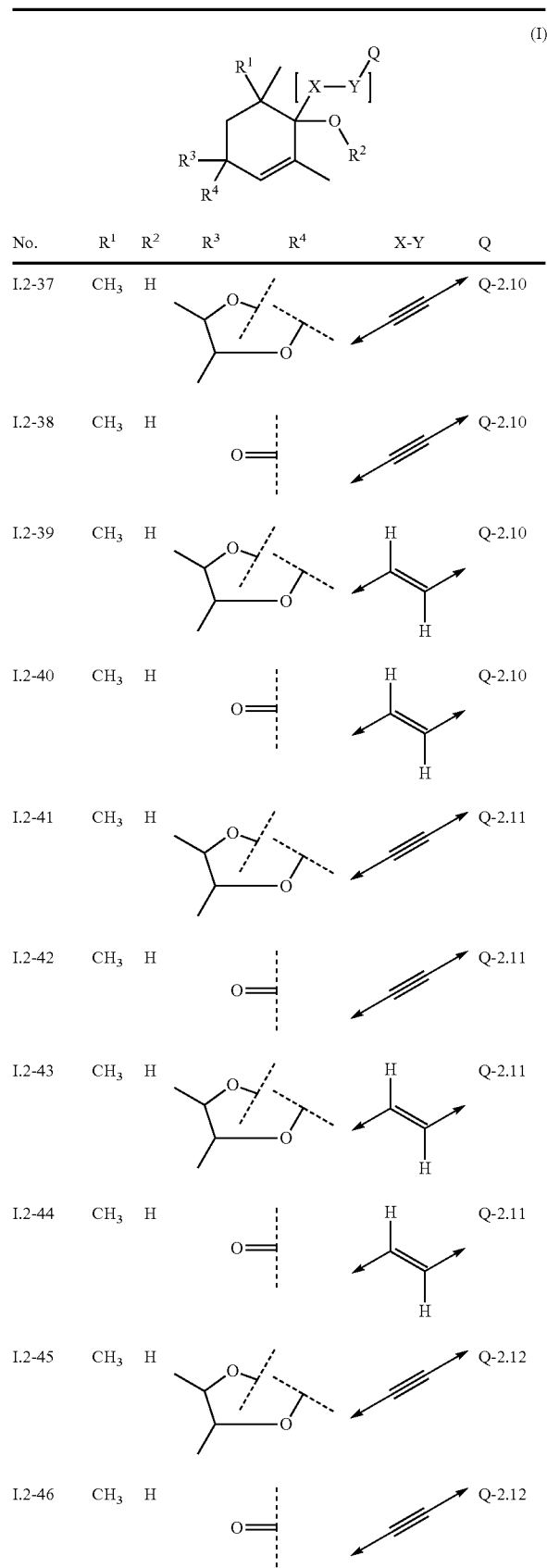
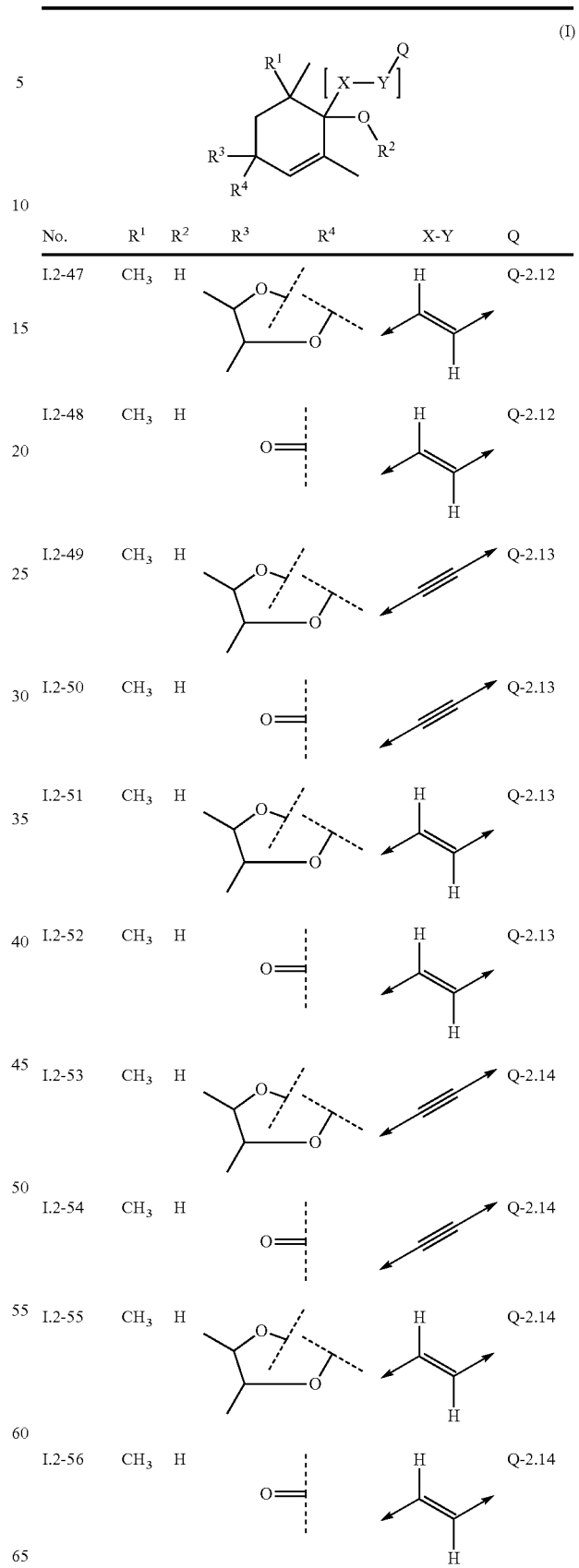

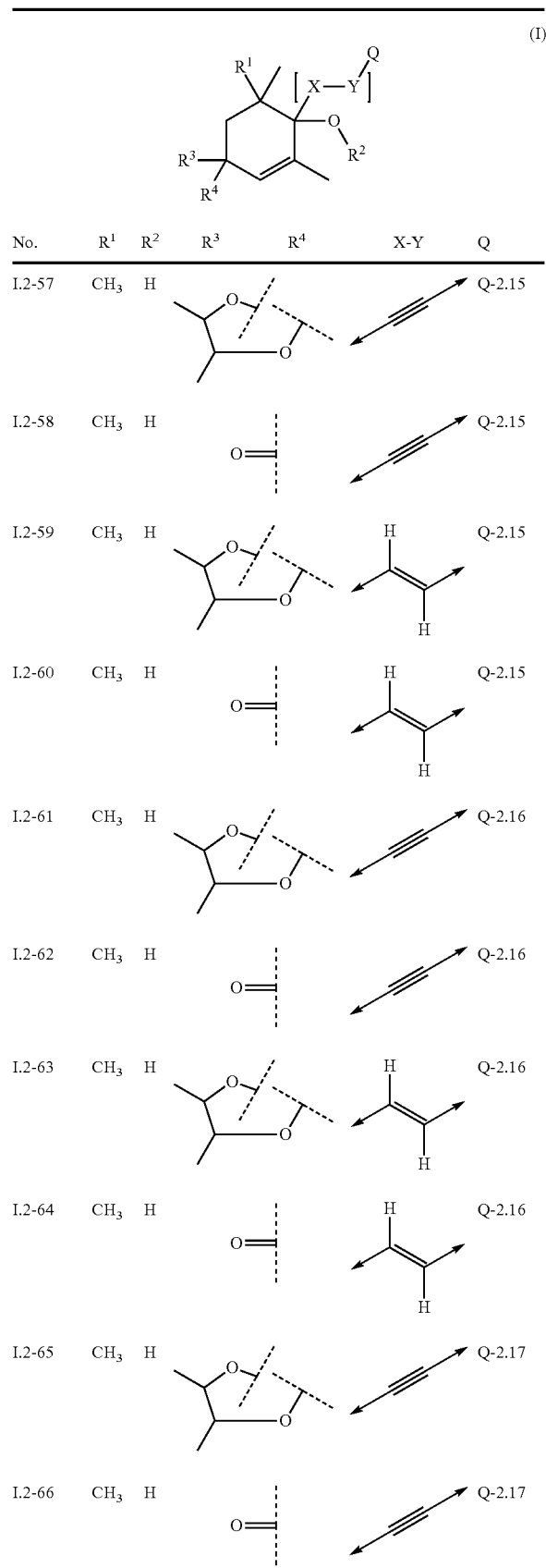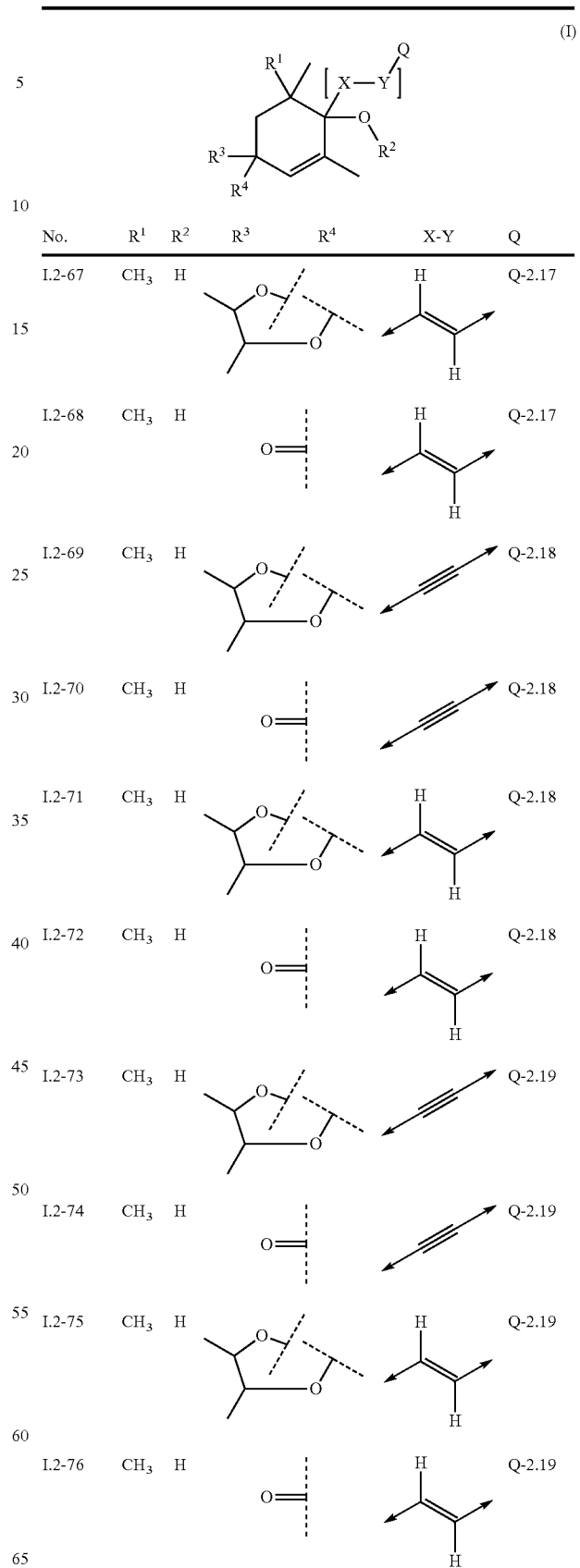

TABLE 2-continued

| No. | R¹ | R² | R³ | R⁴ | X-Y | Q |
|---|---|---|---|---|---|---|
| I.2-77 | CH₃ | H | (dioxolane) | | alkyne | Q-2.20 |
| I.2-78 | CH₃ | H | =O | | alkyne | Q-2.20 |
| I.2-79 | CH₃ | H | (dioxolane) | | alkene | Q-2.20 |
| I.2-80 | CH₃ | H | =O | | alkene | Q-2.20 |
| I.2-81 | CH₃ | H | (dioxolane) | | alkyne | Q-2.21 |
| I.2-82 | CH₃ | H | =O | | alkyne | Q-2.21 |
| I.2-83 | CH₃ | H | (dioxolane) | | alkene | Q-2.21 |
| I.2-84 | CH₃ | H | =O | | alkene | Q-2.21 |
| I.2-85 | CH₃ | H | (dioxolane) | | alkyne | Q-2.22 |
| I.2-86 | CH₃ | H | =O | | alkyne | Q-2.22 |
| I.2-87 | CH₃ | H | (dioxolane) | | alkene | Q-2.22 |
| I.2-88 | CH₃ | H | =O | | alkene | Q-2.22 |
| I.2-89 | CH₃ | H | (dioxolane) | | alkyne | Q-2.23 |
| I.2-90 | CH₃ | H | =O | | alkyne | Q-2.23 |
| I.2-91 | CH₃ | H | (dioxolane) | | alkene | Q-2.23 |
| I.2-92 | CH₃ | H | =O | | alkene | Q-2.23 |
| I.2-93 | CH₃ | H | (dioxolane) | | alkyne | Q-2.24 |
| I.2-94 | CH₃ | H | =O | | alkyne | Q-2.24 |
| I.2-95 | CH₃ | H | (dioxolane) | | alkene | Q-2.24 |
| I.2-96 | CH₃ | H | =O | | alkene | Q-2.24 |

TABLE 2-continued
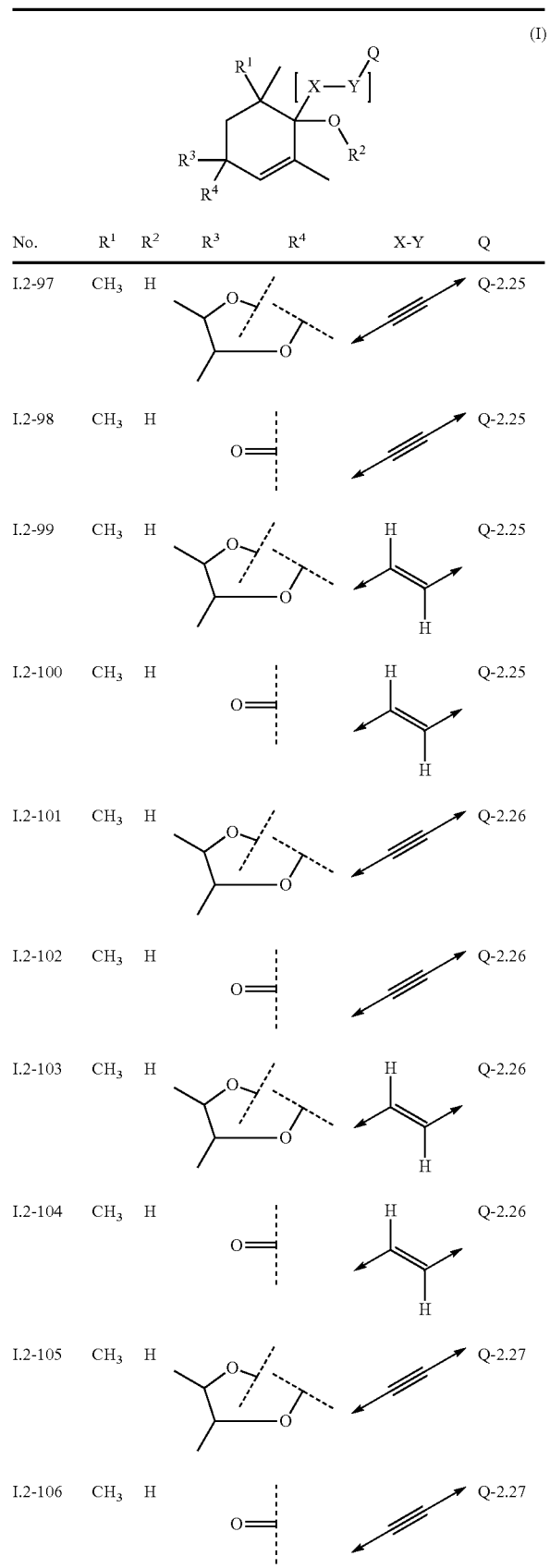
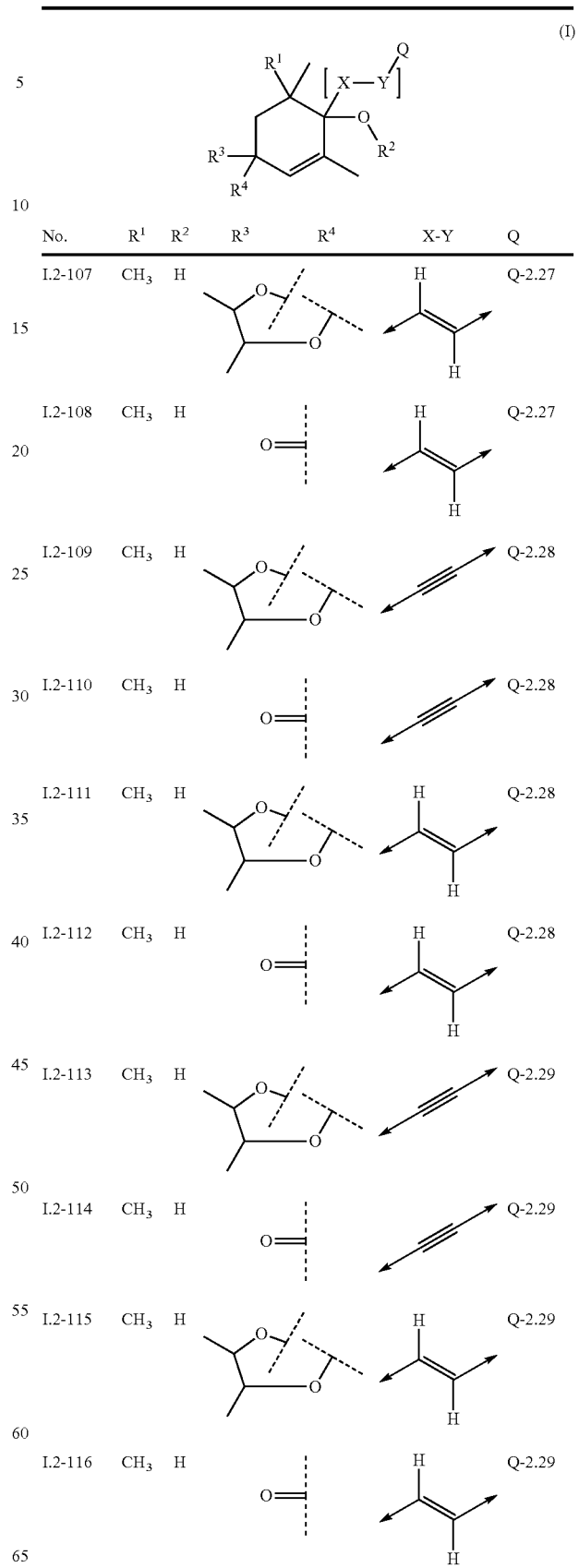

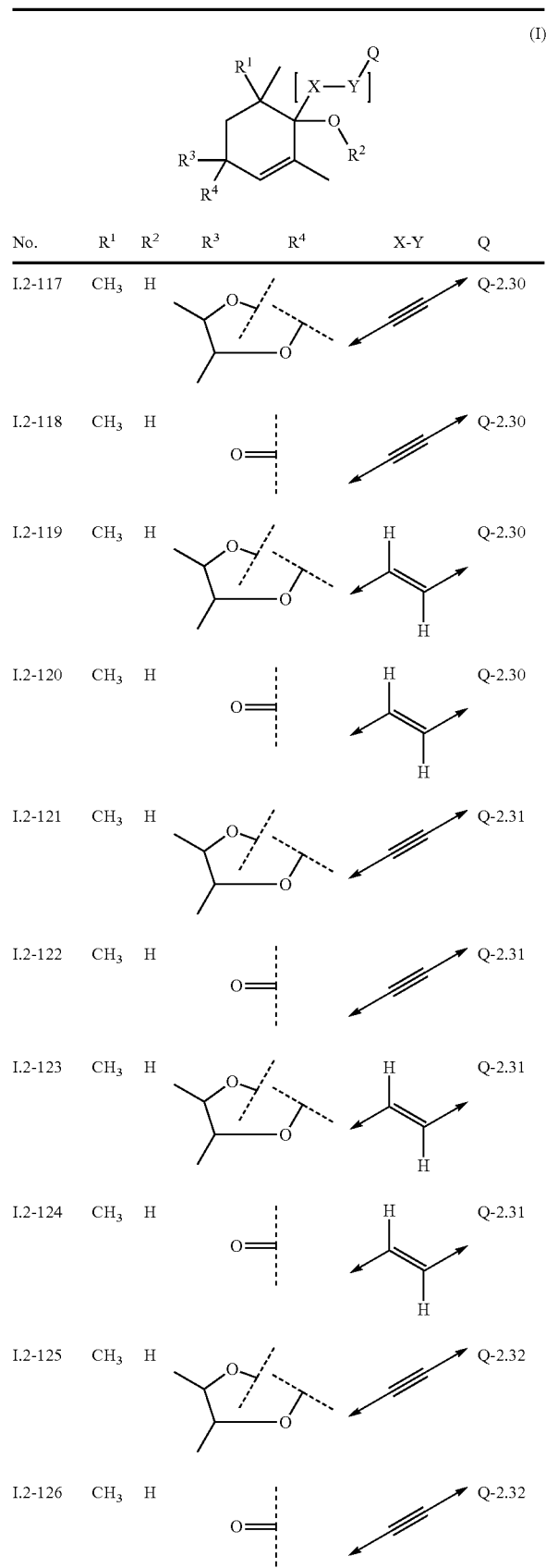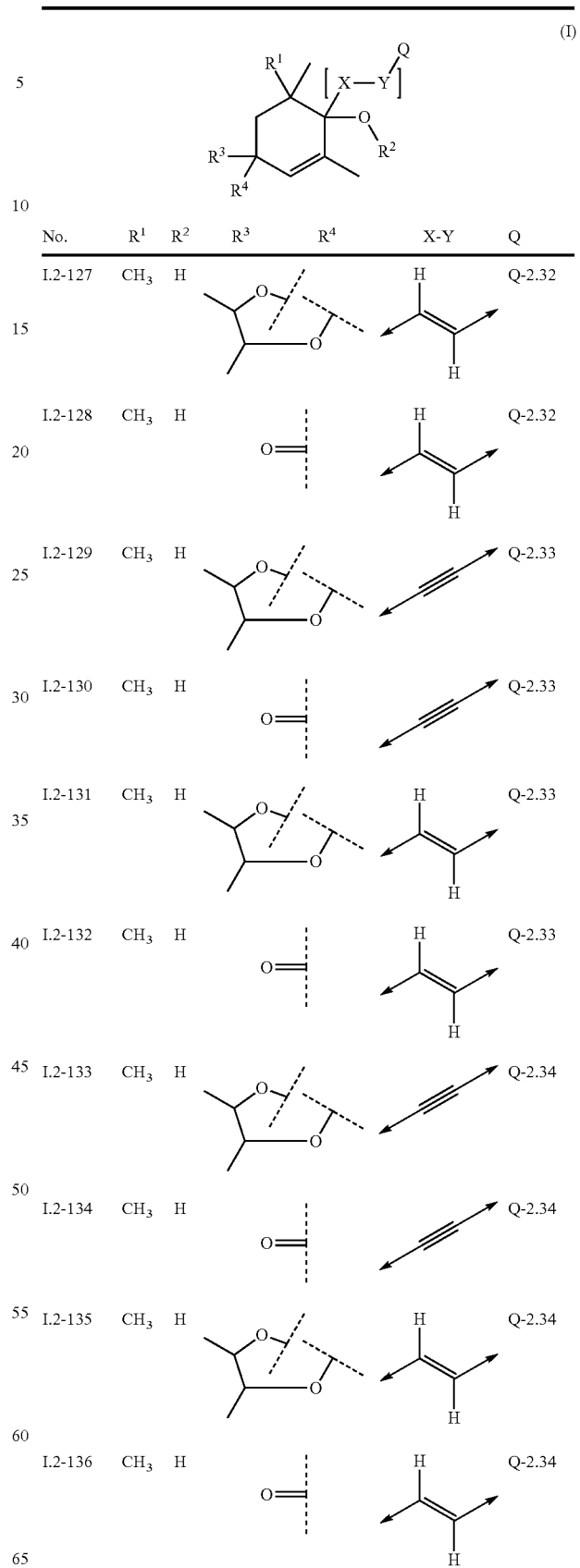

TABLE 2-continued
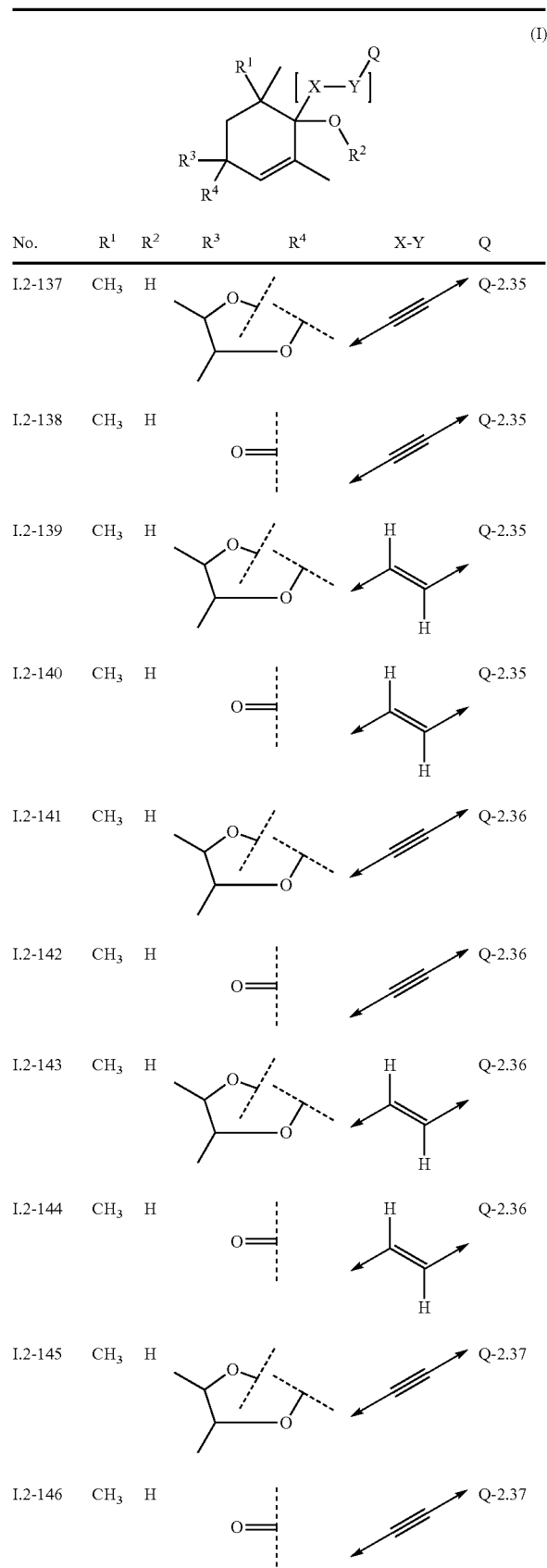
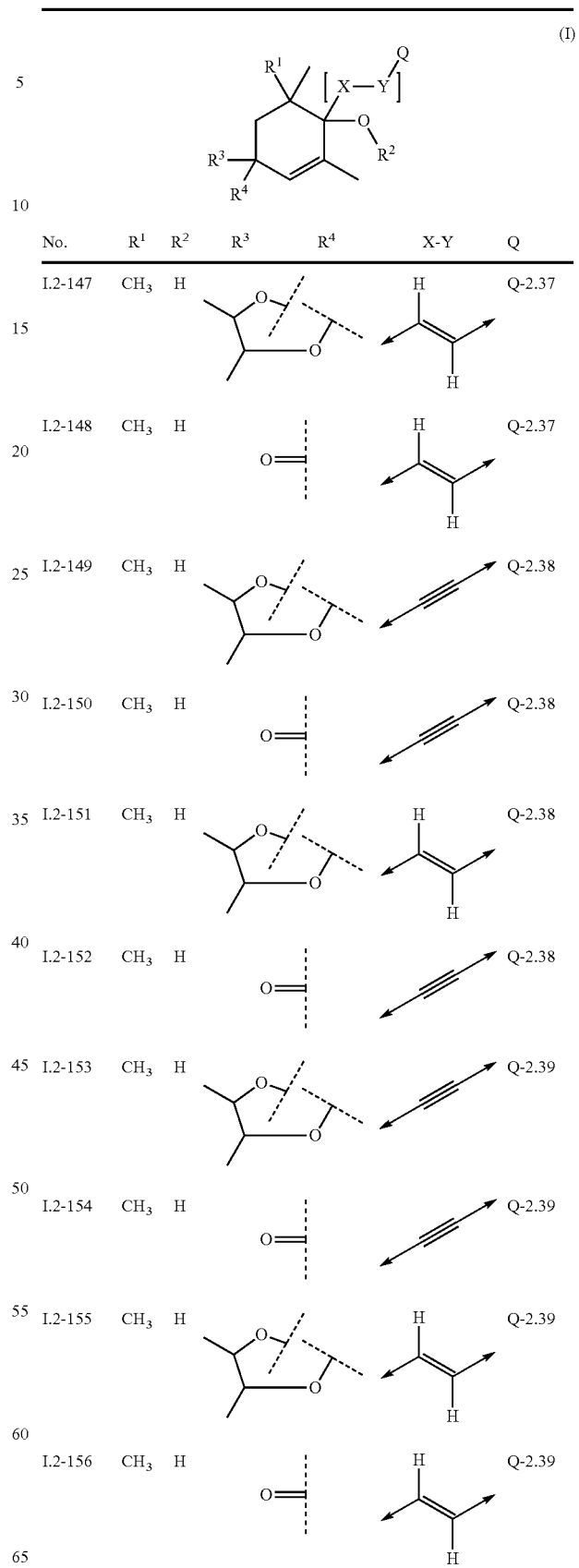

TABLE 2-continued

| No. | R¹ | R² | R³ | R⁴ | X-Y | Q |
|---|---|---|---|---|---|---|
| I.2-157 | $CH_3$ | H | (dioxolane ring) | | alkyne | Q-2.40 |
| I.2-158 | $CH_3$ | H | =O | | alkyne | Q-2.40 |
| I.2-159 | $CH_3$ | H | (dioxolane ring) | | alkene | Q-2.40 |
| I.2-160 | $CH_3$ | H | =O | | alkene | Q-2.40 |
| I.2-161 | $CH_3$ | H | (dioxolane ring) | | alkyne | Q-2.41 |
| I.2-162 | $CH_3$ | H | =O | | alkyne | Q-2.41 |
| I.2-163 | $CH_3$ | H | (dioxolane ring) | | alkene | Q-2.41 |
| I.2-164 | $CH_3$ | H | =O | | alkene | Q-2.41 |
| I.2-165 | $CH_3$ | H | (dioxolane ring) | | alkyne | Q-2.45 |
| I.2-166 | $CH_3$ | H | =O | | alkyne | Q-2.45 |
| I.2-167 | $CH_3$ | H | (dioxolane ring) | | alkene | Q-2.45 |
| I.2-168 | $CH_3$ | H | =O | | alkene | Q-2.45 |
| I.2-169 | $CH_3$ | H | (dioxolane ring) | | alkyne | Q-2.58 |
| I.2-170 | $CH_3$ | H | =O | | alkyne | Q-2.58 |
| I.2-171 | $CH_3$ | H | (dioxolane ring) | | alkene | Q-2.58 |
| I.2-172 | $CH_3$ | H | =O | | alkene | Q-2.58 |
| I.2-173 | $CH_3$ | H | (dioxolane ring) | | alkyne | Q-2.61 |
| I.2-174 | $CH_3$ | H | =O | | alkyne | Q-2.61 |
| I.2-175 | $CH_3$ | H | (dioxolane ring) | | alkene | Q-2.61 |
| I.2-176 | $CH_3$ | H | =O | | alkene | Q-2.61 |

TABLE 2-continued (I)

| No. | R¹ | R² | R³ | R⁴ | X-Y | Q |
|---|---|---|---|---|---|---|
| I.2-177 | CH₃ | H | (dioxolane) | | alkyne | Q-2.62 |
| I.2-178 | CH₃ | H | =O | | alkyne | Q-2.62 |
| I.2-179 | CH₃ | H | (dioxolane) | | alkene | Q-2.62 |
| I.2-180 | CH₃ | H | =O | | alkene | Q-2.62 |
| I.2-181 | CH₃ | H | (dioxolane) | | alkyne | Q-2.63 |
| I.2-182 | CH₃ | H | =O | | alkyne | Q-2.63 |
| I.2-183 | CH₃ | H | (dioxolane) | | alkene | Q-2.63 |
| I.2-184 | CH₃ | H | =O | | alkene | Q-2.63 |
| I.2-185 | CH₃ | H | (dioxolane) | | alkyne | Q-2.64 |
| I.2-186 | CH₃ | H | =O | | alkyne | Q-2.64 |
| I.2-187 | CH₃ | H | (dioxolane) | | alkene | Q-2.64 |
| I.2-188 | CH₃ | H | =O | | alkene | Q-2.64 |
| I.2-189 | CH₃ | H | (dioxolane) | | alkyne | Q-2.65 |
| I.2-190 | CH₃ | H | =O | | alkyne | Q-2.65 |
| I.2-191 | CH₃ | H | (dioxolane) | | alkene | Q-2.65 |
| I.2-192 | CH₃ | H | =O | | alkene | Q-2.65 |
| I.2-193 | CH₃ | H | (dioxolane) | | alkyne | Q-2.66 |
| I.2-194 | CH₃ | H | =O | | alkyne | Q-2.66 |
| I.2-195 | CH₃ | H | (dioxolane) | | alkene | Q-2.66 |
| I.2-196 | CH₃ | H | =O | | alkene | Q-2.66 |

TABLE 2-continued (I)

| No. | R¹ | R² | R³ | R⁴ | X-Y | Q |
|---|---|---|---|---|---|---|
| I.2-197 | CH₃ | H | (dioxolane) | | alkyne | Q-2.67 |
| I.2-198 | CH₃ | H | O= | | alkyne | Q-2.67 |
| I.2-199 | CH₃ | H | (dioxolane) | | alkene | Q-2.67 |
| I.2-200 | CH₃ | H | O= | | alkene | Q-2.67 |
| I.2-201 | CH₃ | H | (dioxolane) | | alkyne | Q-2.68 |
| I.2-202 | CH₃ | H | O= | | alkyne | Q-2.68 |
| I.2-203 | CH₃ | H | (dioxolane) | | alkene | Q-2.68 |
| I.2-204 | CH₃ | H | O= | | alkene | Q-2.68 |
| I.2-205 | CH₃ | H | (dioxolane) | | alkyne | Q-2.69 |
| I.2-206 | CH₃ | H | O= | | alkyne | Q-2.69 |
| I.2-207 | CH₃ | H | (dioxolane) | | alkene | Q-2.69 |
| I.2-208 | CH₃ | H | O= | | alkene | Q-2.69 |
| I.2-209 | CH₃ | H | (dioxolane) | | alkyne | Q-2.70 |
| I.2-210 | CH₃ | H | O= | | alkyne | Q-2.70 |
| I.2-211 | CH₃ | H | (dioxolane) | | alkene | Q-2.70 |
| I.2-212 | CH₃ | H | O= | | alkene | Q-2.70 |
| I.2-213 | CH₃ | H | (dioxolane) | | alkyne | Q-2.71 |
| I.2-214 | CH₃ | H | O= | | alkyne | Q-2.71 |
| I.2-215 | CH₃ | H | (dioxolane) | | alkene | Q-2.71 |
| I.2-216 | CH₃ | H | O= | | alkene | Q-2.71 |

TABLE 2-continued

| No. | R¹ | R² | R³ | R⁴ | X-Y | Q |
|---|---|---|---|---|---|---|
| I.2-217 | CH₃ | H | (dioxolane ring) | | alkyne | Q-2.72 |
| I.2-218 | CH₃ | H | | =O | alkyne | Q-2.72 |
| I.2-219 | CH₃ | H | (dioxolane ring) | | alkene | Q-2.72 |
| I.2-220 | CH₃ | H | | =O | alkene | Q-2.72 |
| I.2-221 | CH₃ | H | (dioxolane ring) | | alkyne | Q-2.73 |
| I.2-222 | CH₃ | H | | =O | alkyne | Q-2.73 |
| I.2-223 | CH₃ | H | (dioxolane ring) | | alkene | Q-2.73 |
| I.2-224 | CH₃ | H | | =O | alkene | Q-2.73 |
| I.2-225 | CH₃ | H | (dioxolane ring) | | alkyne | Q-2.74 |
| I.2-226 | CH₃ | H | | =O | alkyne | Q-2.74 |
| I.2-227 | CH₃ | H | (dioxolane ring) | | alkene | Q-2.74 |
| I.2-228 | CH₃ | H | | =O | alkene | Q-2.74 |
| I.2-229 | CH₃ | H | (dioxolane ring) | | alkyne | Q-2.75 |
| I.2-230 | CH₃ | H | | =O | alkyne | Q-2.75 |
| I.2-231 | CH₃ | H | (dioxolane ring) | | alkene | Q-2.75 |
| I.2-232 | CH₃ | H | | =O | alkene | Q-2.75 |
| I.2-233 | CH₃ | H | (dioxolane ring) | | alkyne | Q-2.76 |
| I.2-234 | CH₃ | H | | =O | alkyne | Q-2.76 |
| I.2-235 | CH₃ | H | (dioxolane ring) | | alkene | Q-2.76 |
| I.2-236 | CH₃ | H | | =O | alkyne | Q-2.76 |

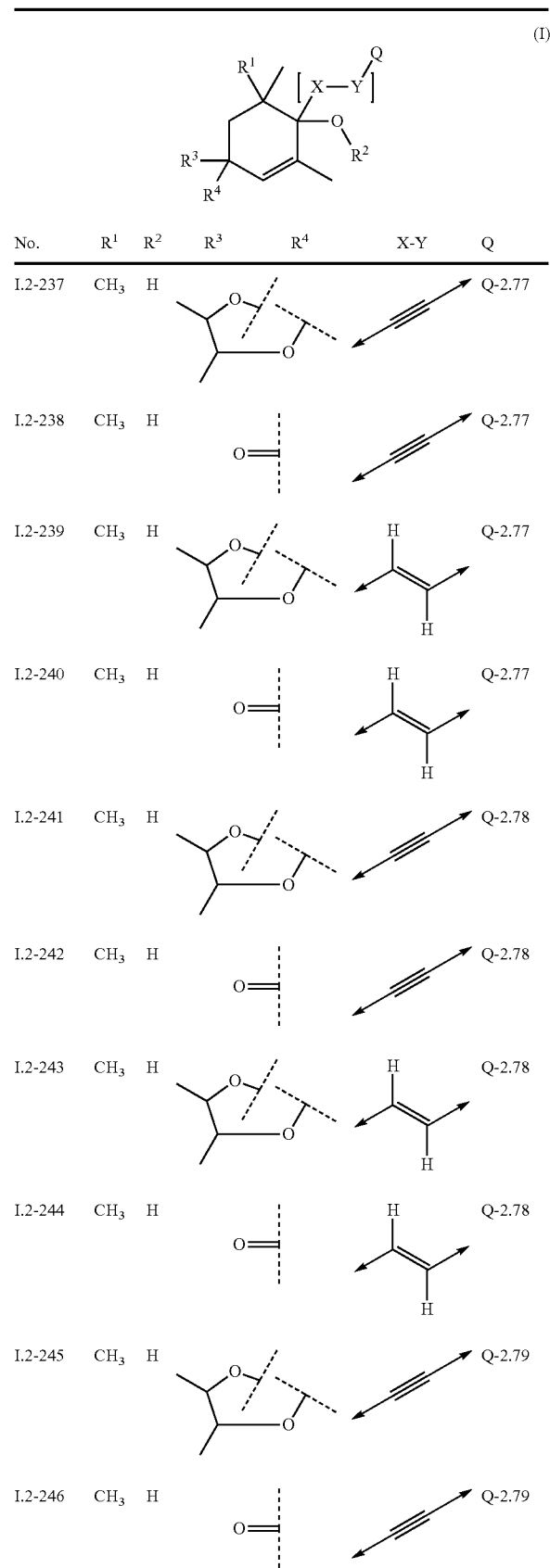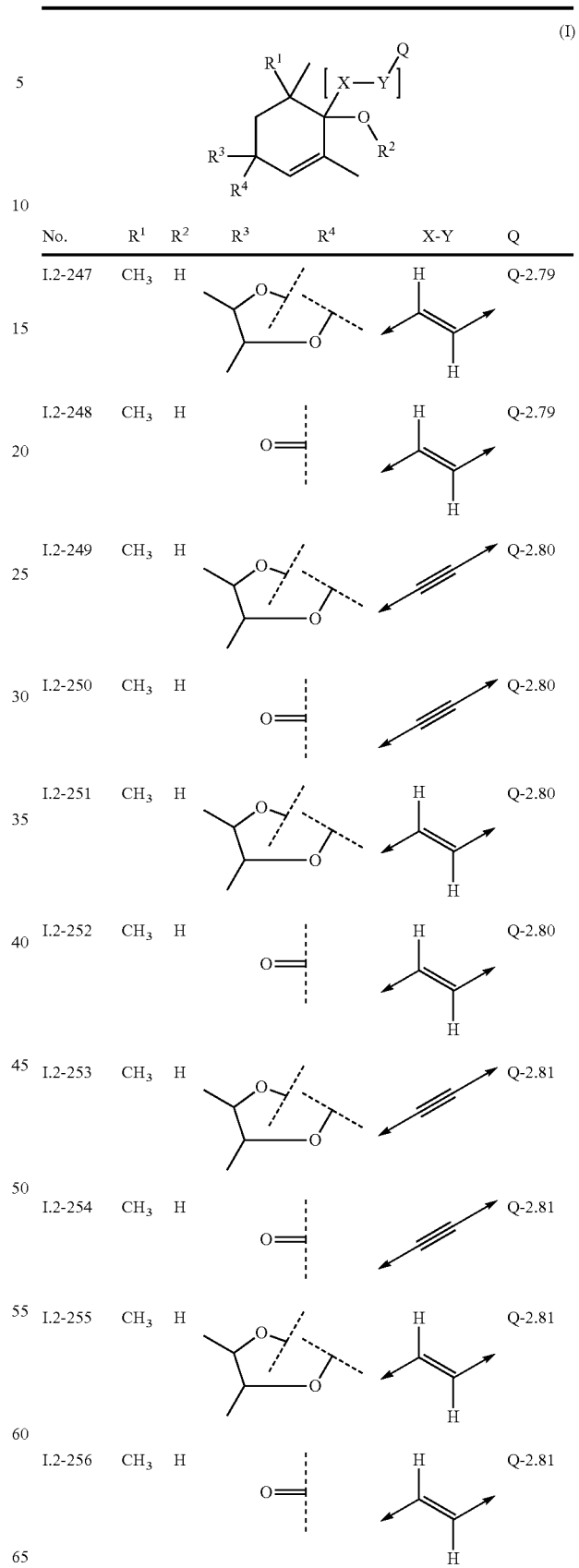

TABLE 2-continued
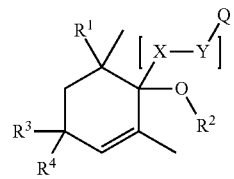
(I)
| No. | R¹ | R² | R³ | R⁴ | X-Y | Q |
|---|---|---|---|---|---|---|
| I.2-257 | CH₃ | H | | | | Q-2.83 |
| I.2-258 | CH₃ | H | | | | Q-2.83 |
| I.2-259 | CH₃ | H | | | | Q-2.83 |
| I.2-260 | CH₃ | H | | | | Q-2.83 |
| I.2-261 | CH₃ | H | | | | Q-2.86 |
| I.2-262 | CH₃ | H | | | | Q-2.86 |
| I.2-263 | CH₃ | H | | | | Q-2.86 |
| I.2-264 | CH₃ | H | | | | Q-2.86 |
| I.2-265 | CH₃ | H | | | | Q-2.88 |
| I.2-266 | CH₃ | H | | | | Q-2.88 |
TABLE 2-continued
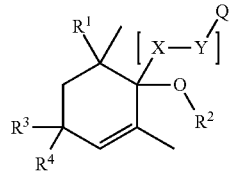
(I)
| No. | R¹ | R² | R³ | R⁴ | X-Y | Q |
|---|---|---|---|---|---|---|
| I.2-267 | CH₃ | H | | | | Q-2.88 |
| I.2-268 | CH₃ | H | | | | Q-2.88 |
| I.2-269 | CH₃ | H | | | | Q-2.96 |
| I.2-270 | CH₃ | H | | | | Q-2.96 |
| I.2-271 | CH₃ | H | | | | Q-2.96 |
| I.2-272 | CH₃ | H | | | | Q-2.96 |
| I.2-273 | CH₃ | H | | | | Q-2.98 |
| I.2-274 | CH₃ | H | | | | Q-2.98 |
| I.2-275 | CH₃ | H | | | | Q-2.98 |
| I.2-276 | CH₃ | H | | | | Q-2.98 |

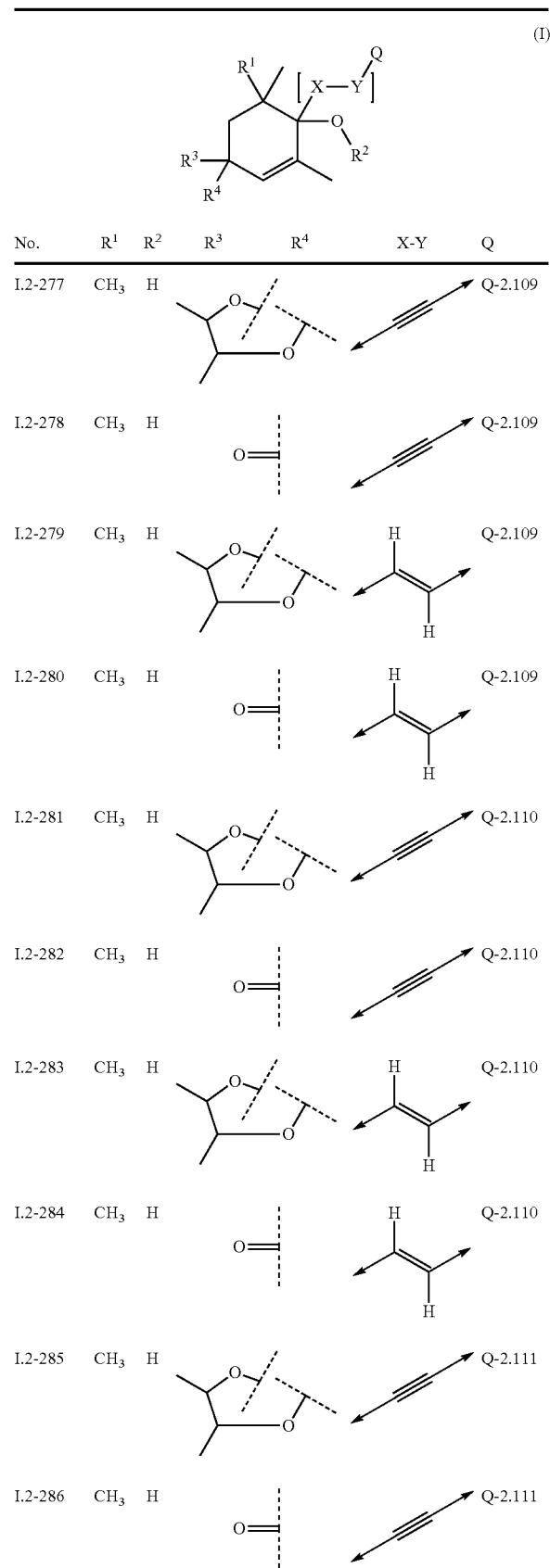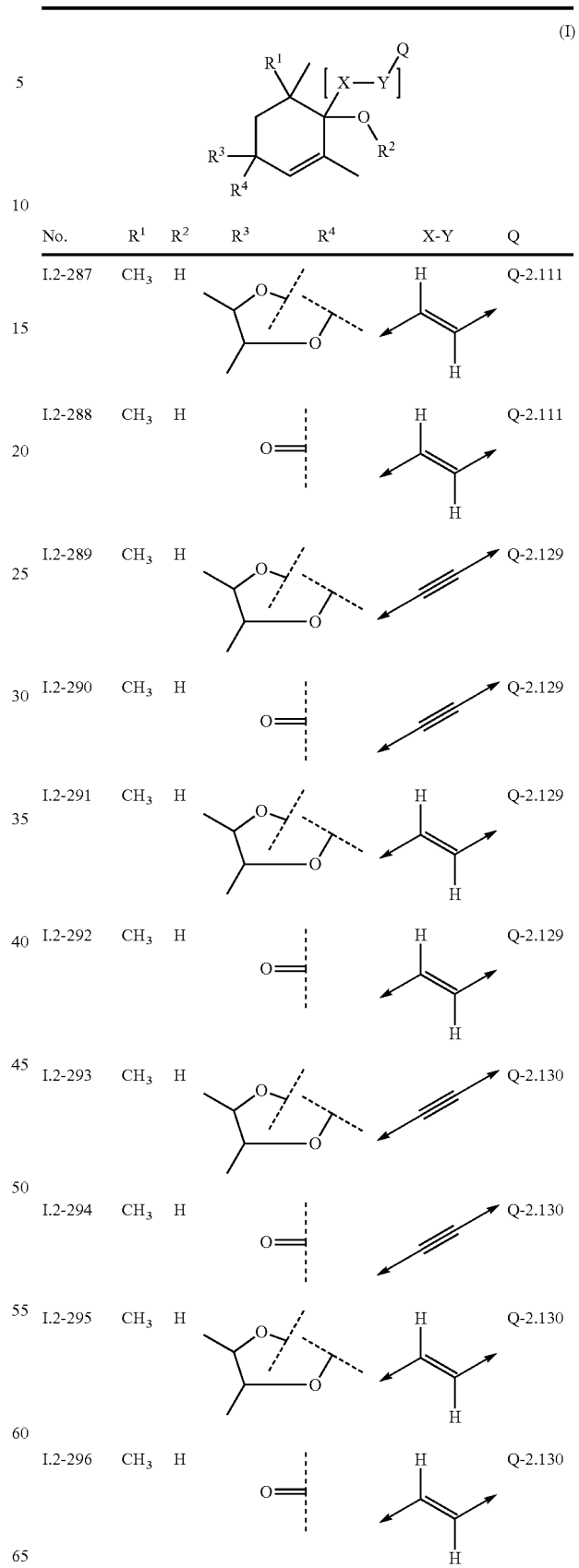

TABLE 2-continued

Structure (I): cyclohexene with R¹, R³, R⁴, [X—Y]—Q, O—R², and CH₃ substituents

| No. | R¹ | R² | R³ | R⁴ | X—Y | Q |
|---|---|---|---|---|---|---|
| I.2-297 | CH₃ | H | (dioxolane-type cyclic R³/R⁴) | | alkyne | Q-2.131 |
| I.2-298 | CH₃ | H | O= | | alkyne | Q-2.131 |
| I.2-299 | CH₃ | H | (dioxolane-type cyclic R³/R⁴) | | CH=CH (H,H) | Q-2.131 |
| I.2-300 | CH₃ | H | O= | | CH=CH (H,H) | Q-2.131 |

TABLE 3

Structure (I): cyclohexene with R¹, R³, R⁴, [X—Y]—Q, O—R², and CH₃ substituents

| No. | R¹ | R² | R³ | R⁴ | X—Y | Q |
|---|---|---|---|---|---|---|
| I.3-1 | CH₃ | H | O= | | alkyne | Q-3.1 |
| I.3-2 | CH₃ | H | O= | | alkyne | Q-3.2 |
| I.3-3 | CH₃ | H | O= | | alkyne | Q-3.3 |
| I.3-4 | CH₃ | H | O= | | alkyne | Q-3.4 |
| I.3-5 | CH₃ | H | O= | | alkyne | Q-3.5 |
| I.3-6 | CH₃ | H | O= | | alkyne | Q-3.6 |
| I.3-7 | CH₃ | H | O= | | CH=CH (H,H) | Q-3.1 |
| I.3-8 | CH₃ | H | O= | | CH=CH (H,H) | Q-3.2 |
| I.3-9 | CH₃ | H | O= | | CH=CH (H,H) | Q-3.3 |
| I.3-10 | CH₃ | H | O= | | CH=CH (H,H) | Q-3.4 |
| I.3-11 | CH₃ | H | O= | | CH=CH (H,H) | Q-3.5 |
| I.3-12 | CH₃ | H | O= | | CH=CH (H,H) | Q-3.6 |
| I.3-13 | CH₃ | H | O= | | alkyne | Q-3.7 |
| I.3-14 | CH₃ | H | O= | | alkyne | Q-3.8 |
| I.3-15 | CH₃ | H | O= | | alkyne | Q-3.11 |

TABLE 3-continued

Structure (I): cyclohexene with R¹ and CH₃ at one carbon, O-R² and [X-Y]-Q substituent, R³ and R⁴ substituents.

| No. | R¹ | R² | R³ | R⁴ | X—Y | Q |
|---|---|---|---|---|---|---|
| I.3-16 | CH₃ | H | | | O= , C≡C | Q-3.12 |
| I.3-17 | CH₃ | H | | | O= , C≡C | Q-3.13 |
| I.3-18 | CH₃ | H | | | O= , C≡C | Q-3.14 |
| I.3-19 | CH₃ | H | | | O= , CH=CH | Q-3.7 |
| I.3-20 | CH₃ | H | | | O= , CH=CH | Q-3.8 |
| I.3-21 | CH₃ | H | | | O= , CH=CH | Q-3.11 |
| I.3-22 | CH₃ | H | | | O= , CH=CH | Q-3.12 |
| I.3-23 | CH₃ | H | | | O= , CH=CH | Q-3.13 |
| I.3-24 | CH₃ | H | | | O= , CH=CH | Q-3.14 |
| I.3-25 | CH₃ | H | | | O= , C≡C | Q-3.16 |
| I.3-26 | CH₃ | H | | | O= , C≡C | Q-3.17 |
| I.3-27 | CH₃ | H | | | O= , C≡C | Q-3.18 |
| I.3-28 | CH₃ | H | | | O= , C≡C | Q-3.21 |
| I.3-29 | CH₃ | H | | | O= , C≡C | Q-3.22 |
| I.3-30 | CH₃ | H | | | O= , C≡C | Q-3.23 |
| I.3-31 | CH₃ | H | | | O= , CH=CH | Q-3.16 |
| I.3-32 | CH₃ | H | | | O= , CH=CH | Q-3.17 |
| I.3-33 | CH₃ | H | | | O= , CH=CH | Q-3.18 |
| I.3-34 | CH₃ | H | | | O= , CH=CH | Q-3.21 |
| I.3-35 | CH₃ | H | | | O= , CH=CH | Q-3.22 |
| I.3-36 | CH₃ | H | | | O= , CH=CH | Q-3.23 |

TABLE 3-continued (I structure with R¹, R², R³, R⁴, [X—Y], O, Q)

| No. | R¹ | R² | R³ | R⁴ | X—Y | Q |
|---|---|---|---|---|---|---|
| I.3-37 | CH₃ | H | | | O=, alkyne | Q-3.26 |
| I.3-38 | CH₃ | H | | | O=, alkyne | Q-3.27 |
| I.3-39 | CH₃ | H | | | O=, alkyne | Q-3.28 |
| I.3-40 | CH₃ | H | | | O=, alkyne | Q-3.31 |
| I.3-41 | CH₃ | H | | | O=, alkyne | Q-3.32 |
| I.3-42 | CH₃ | H | | | O=, alkyne | Q-3.33 |
| I.3-43 | CH₃ | H | | | O=, alkene | Q-3.26 |
| I.3-44 | CH₃ | H | | | O=, alkene | Q-3.27 |
| I.3-45 | CH₃ | H | | | O=, alkene | Q-3.28 |
| I.3-46 | CH₃ | H | | | O=, alkene | Q-3.31 |
| I.3-47 | CH₃ | H | | | O=, alkene | Q-3.32 |
| I.3-48 | CH₃ | H | | | O=, alkene | Q-3.33 |
| I.3-49 | CH₃ | H | | | O=, alkyne | Q-3.36 |
| I.3-50 | CH₃ | H | | | O=, alkyne | Q-3.37 |
| I.3-51 | CH₃ | H | | | O=, alkyne | Q-3.38 |
| I.3-52 | CH₃ | H | | | O=, alkyne | Q-3.41 |
| I.3-53 | CH₃ | H | | | O=, alkyne | Q-3.42 |
| I.3-54 | CH₃ | H | | | O=, alkyne | Q-3.43 |
| I.3-55 | CH₃ | H | | | O=, alkene | Q-3.36 |
| I.3-56 | CH₃ | H | | | O=, alkene | Q-3.37 |
| I.3-57 | CH₃ | H | | | O=, alkene | Q-3.38 |
| I.3-58 | CH₃ | H | | | O=, alkene | Q-3.41 |

TABLE 3-continued (I)
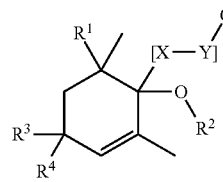

| No. | R¹ | R² | R³ | R⁴ | X—Y | Q |
|---|---|---|---|---|---|---|
| I.3-59 | CH₃ | H | | | O= with H / H (vinyl) | Q-3.42 |
| I.3-60 | CH₃ | H | | | O= with H / H (vinyl) | Q-3.43 |

TABLE 4

(II)
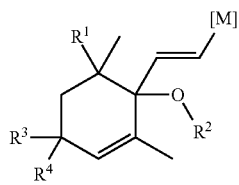

| No. | R¹ | R² | R³ | R⁴ | [M] |
|---|---|---|---|---|---|
| II.1 | CH₃ | H | \multicolumn{2}{c}{dioxolane ring} | Sn(n-Bu)₃ |
| II.2 | CH₃ | H | \multicolumn{2}{c}{=O} | Sn(n-Bu)₃ |
| II.3 | CH₃ | H | \multicolumn{2}{c}{dioxolane ring} | Sn(n-Pr)₃ |
| II.4 | CH₃ | H | \multicolumn{2}{c}{=O} | Sn(n-Pr)₃ |
| II.5 | CH₃ | H | \multicolumn{2}{c}{dioxolane ring} | Sn(c-Hex)₃ |
| II.6 | CH₃ | H | \multicolumn{2}{c}{=O} | Sn(c-Hex)₃ |

TABLE 4-continued (II)
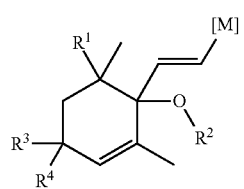

| No. | R¹ | R² | R³ | R⁴ | [M] |
|---|---|---|---|---|---|
| II.7 | CH₃ | SiEt₃ | \multicolumn{2}{c}{dioxolane} | Sn(n-Bu)₃ |
| II.8 | CH₃ | SiEt₃ | \multicolumn{2}{c}{=O} | Sn(n-Bu)₃ |
| II.9 | CH₃ | SiEt₃ | \multicolumn{2}{c}{dioxolane} | Sn(n-Pr)₃ |
| II.10 | CH₃ | SiEt₃ | \multicolumn{2}{c}{=O} | Sn(n-Pr)₃ |
| II.11 | CH₃ | SiEt₃ | \multicolumn{2}{c}{dioxolane} | Sn(c-Hex)₃ |
| II.12 | CH₃ | SiEt₃ | \multicolumn{2}{c}{=O} | Sn(c-Hex)₃ |
| II.13 | CH₃ | SiMe₂(t-Hex) | \multicolumn{2}{c}{dioxolane} | Sn(n-Bu)₃ |
| II.14 | CH₃ | SiMe₂(t-Hex) | \multicolumn{2}{c}{=O} | Sn(n-Bu)₃ |
| II.15 | CH₃ | SiMe₂Ph | \multicolumn{2}{c}{dioxolane} | Sn(n-Bu)₃ |
| II.16 | CH₃ | SiMe₂Ph | \multicolumn{2}{c}{=O} | Sn(n-Bu)₃ |

TABLE 4-continued
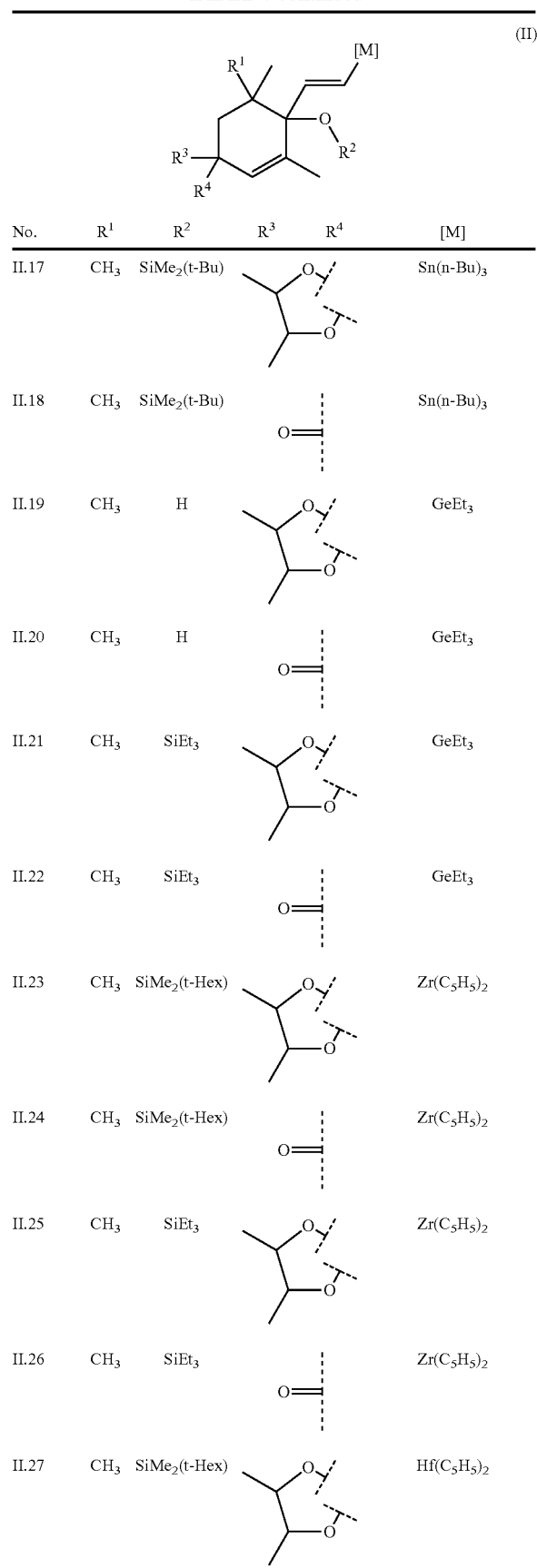
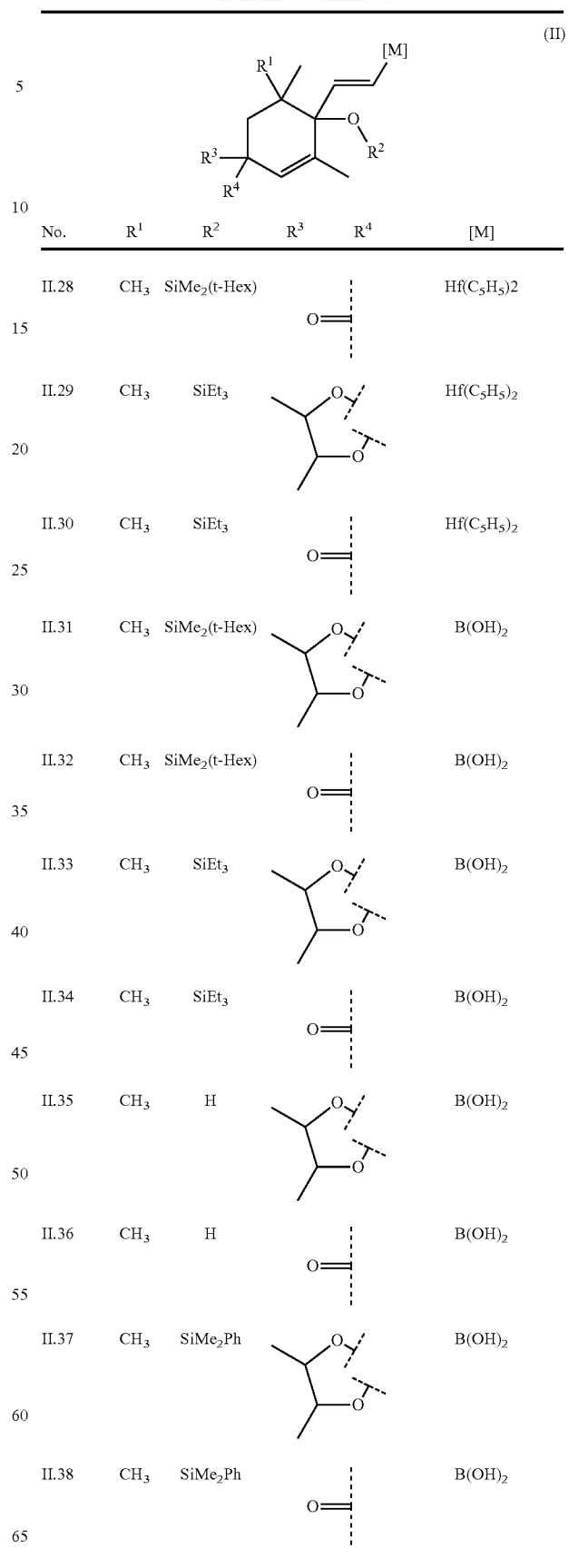

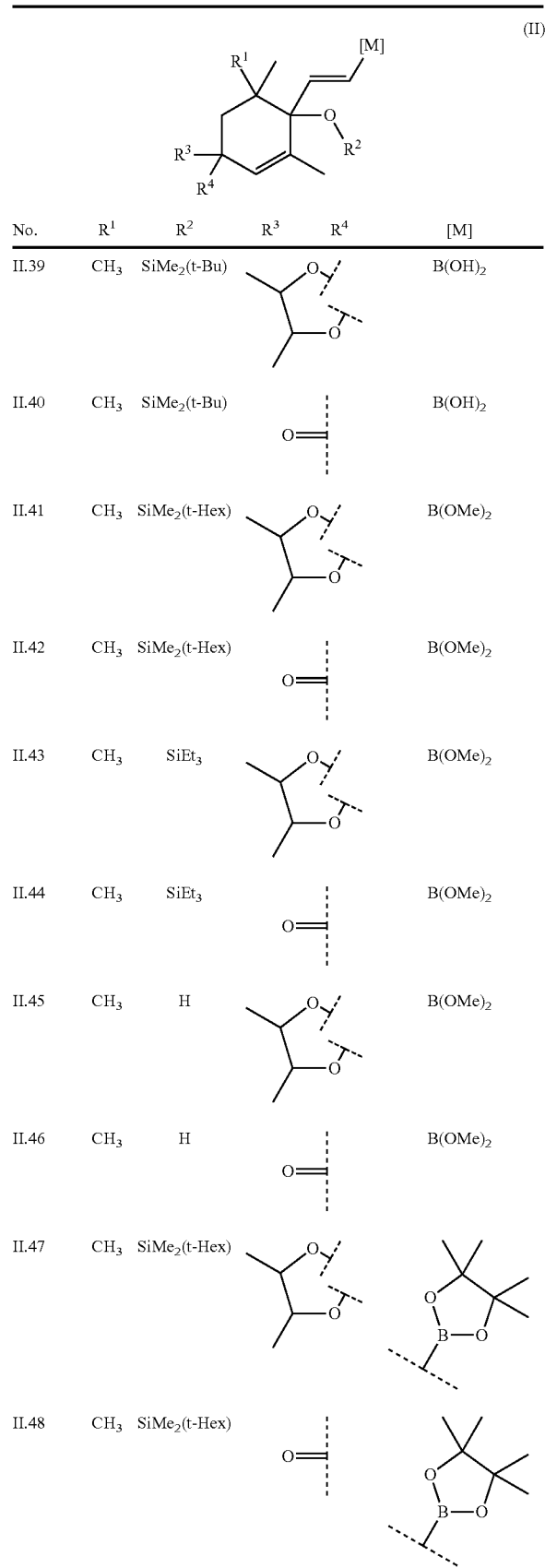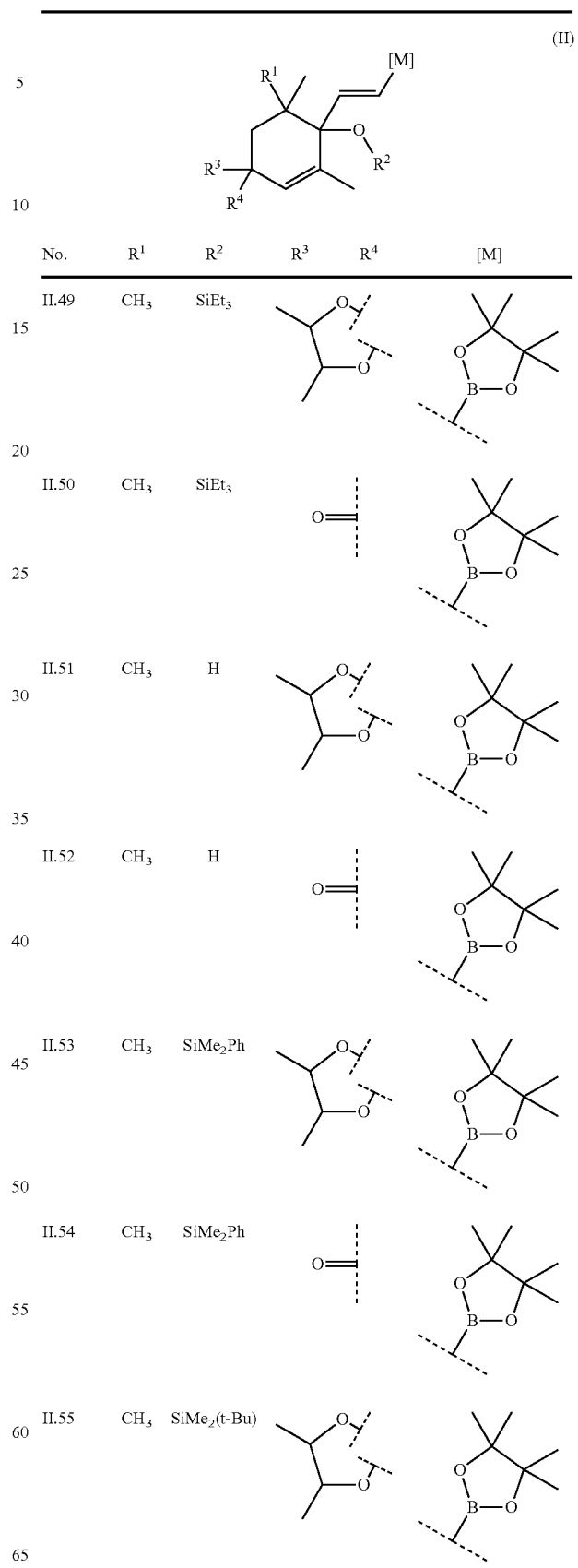

TABLE 4-continued

Structure (II): cyclohexene ring with R¹ and vinyl-[M] at one carbon, OR² at adjacent carbon, methyl on ring, R³ and R⁴ at another ring carbon.

| No. | R¹ | R² | R³ | R⁴ | [M] |
|---|---|---|---|---|---|
| II.56 | CH₃ | SiMe₂(t-Bu) | =O | | pinacol boronate (4,4,5,5-tetramethyl-1,3,2-dioxaborolane) |
| II.57 | CH₃ | SiMe₂(t-Hex) | 2,3-butanediol acetal | | 1,3,2-dioxaborinane |
| II.58 | CH₃ | SiMe₂(t-Hex) | =O | | 1,3,2-dioxaborinane |
| II.59 | CH₃ | SiEt₃ | 2,3-butanediol acetal | | 1,3,2-dioxaborinane |
| II.60 | CH₃ | SiEt₃ | =O | | 1,3,2-dioxaborinane |
| II.61 | CH₃ | H | 2,3-butanediol acetal | | 1,3,2-dioxaborinane |
| II.62 | CH₃ | H | =O | | 1,3,2-dioxaborinane |
| II.63 | CH₃ | SiMe₂Ph | 2,3-butanediol acetal | | 1,3,2-dioxaborinane |
| II.64 | CH₃ | SiMe₂Ph | =O | | 1,3,2-dioxaborinane |
| II.65 | CH₃ | SiMe₂(t-Bu) | 2,3-butanediol acetal | | 1,3,2-dioxaborinane |
| II.66 | CH₃ | SiMe₂(t-Bu) | =O | | 1,3,2-dioxaborinane |
| II.67 | CH₃ | SiMe₂(t-Hex) | 2,3-butanediol acetal | | 5,5-dimethyl-1,3,2-dioxaborinane |
| II.68 | CH₃ | SiMe₂(t-Hex) | =O | | 5,5-dimethyl-1,3,2-dioxaborinane |
| II.69 | CH₃ | SiEt₃ | 2,3-butanediol acetal | | 5,5-dimethyl-1,3,2-dioxaborinane |
| II.70 | CH₃ | SiEt₃ | =O | | 5,5-dimethyl-1,3,2-dioxaborinane |

TABLE 4-continued (II) [structure with R¹, R², R³, R⁴, and [M] substituents on cyclohexene ring]

| No. | R¹ | R² | R³ | R⁴ | [M] |
|---|---|---|---|---|---|
| II.71 | CH₃ | H | (4,5-dimethyl-1,3-dioxolane) | | (5,5-dimethyl-1,3,2-dioxaborinane) |
| II.72 | CH₃ | H | | =O | (5,5-dimethyl-1,3,2-dioxaborinane) |
| II.73 | CH₃ | SiMe₂Ph | (4,5-dimethyl-1,3-dioxolane) | | (5,5-dimethyl-1,3,2-dioxaborinane) |
| II.74 | CH₃ | SiMe₂Ph | | =O | (5,5-dimethyl-1,3,2-dioxaborinane) |
| II.75 | CH₃ | SiMe₂(t-Bu) | (4,5-dimethyl-1,3-dioxolane) | | (5,5-dimethyl-1,3,2-dioxaborinane) |
| II.76 | CH₃ | SiMe₂(t-Bu) | | =O | (5,5-dimethyl-1,3,2-dioxaborinane) |
| II.77 | CH₃ | H | (1,3-dioxolane) | | (pinacol boronate) |
| II.78 | CH₃ | SiEt₃ | (1,3-dioxolane) | | (pinacol boronate) |
| II.79 | CH₃ | SiMe₂(t-Bu) | (1,3-dioxolane) | | (pinacol boronate) |
| II.80 | CH₃ | H | (1,3-dioxolane) | | B(OH)₂ |
| II.81 | CH₃ | SiEt₃ | (1,3-dioxolane) | | B(OH)₂ |
| II.82 | CH₃ | SiMe₂(t-Bu) | (1,3-dioxolane) | | B(OH)₂ |
| II.83 | CF₃ | H | (4,5-dimethyl-1,3-dioxolane) | | Sn(n-Bu)₃ |
| II.84 | CF₃ | H | | =O | Sn(n-Bu)₃ |
| II.85 | CF₃ | H | (4,5-dimethyl-1,3-dioxolane) | | Sn(n-Pr)₃ |
| II.86 | CF₃ | H | | =O | Sn(n-Pr)₃ |
| II.87 | CF₃ | H | (4,5-dimethyl-1,3-dioxolane) | | Sn(c-Hex)₃ |

TABLE 4-continued (II)

| No. | R¹ | R² | R³ | R⁴ | [M] |
|---|---|---|---|---|---|
| II.88 | CF₃ | H | O= (ketone) | | Sn(c-Hex)₃ |
| II.89 | CF₃ | SiEt₃ | dioxolane | | Sn(n-Bu)₃ |
| II.90 | CF₃ | SiEt₃ | O= (ketone) | | Sn(n-Bu)₃ |
| II.91 | CF₃ | SiEt₃ | dioxolane | | Sn(n-Pr)₃ |
| II.92 | CF₃ | SiEt₃ | O= (ketone) | | Sn(n-Pr)₃ |
| II.93 | CF₃ | H | dioxolane | | GeEt₃ |
| II.94 | CF₃ | H | O= (ketone) | | GeEt₃ |
| II.95 | CF₃ | SiEt₃ | dioxolane | | GeEt₃ |
| II.96 | CF₃ | SiEt₃ | O= (ketone) | | GeEt₃ |
| II.97 | CF₃ | SiEt₃ | dioxolane | | B(OH)₂ |
| II.98 | CF₃ | SiEt₃ | O= (ketone) | | B(OH)₂ |
| II.99 | CF₃ | H | dioxolane | | B(OH)₂ |
| II.100 | CF₃ | H | O= (ketone) | | B(OH)₂ |

Spectroscopic data of selected table examples:

Example No. I.1-7

$^1$H-NMR (400 MHz, CDCl₃ δ, ppm) 5.98 (s, 1H), 5.51 (s, 1H), 4.21 (m, 1H), 4.17 (q, 2H), 3.60 (m, 1H), 2.48 (br. s, 1H, OH), 2.29 (q, 2H), 2.06 (d, 1H), 1.93 (s, 3H), 1.90 (d, 1H), 1.24 (m, 6H), 1.19-1.12 (m, 12H).

Example No. I.1-8

$^1$H-NMR (400 MHz, CDCl₃ δ, ppm) 6.05 (s, 1H), 5.87 (s, 1H), 4.19 (q, 2H), 3.10 (br. s, 1H, OH), 2.61 (d, 1H), 2.42 (d, 1H), 2.29 (t, 2H), 2.16 (s, 3H), 1.27 (t, 3H), 1.25 (s, 3H), 1.15 (t, 3H), 1.12 (s, 3H).

Example No. I.1-9

$^1$H-NMR (400 MHz, CDCl₃ δ, ppm) 7.70 (d, 1H), 6.10 (d, 1H), 5.68 (s, 1H), 5.51 (s, 1H), 4.22 (m, 1H), 4.18 (q, 2H), 3.58 (m, 1H), 2.29 (q, 2H), 2.05 (d, 1H), 1.93 (s, 3H), 1.84 (d, 1H), 1.31-1.22 (m, 6H), 1.17-1.09 (m, 12H).

Example No. I.1-10

$^1$H-NMR (400 MHz, CDCl₃ δ, ppm) 7.79 (d, 1H), 6.12 (d, 1H), 5.93 (s, 1H), 5.72 (s, 1H), 4.17 (q, 2H), 2.58 (d, 1H), 2.39 (d, 1H), 2.29 (q, 2H), 1.92 (s, 3H), 1.28 (t, 3H), 1.25 (s, 3H), 1.13 (t, 3H), 1.11 (s, 3H).

Example No. I.1-20

$^1$H-NMR (400 MHz, CDCl₃ δ, ppm) 7.71 (d, 1H), 6.17 (d, 1H), 5.96 (s, 1H), 5.77 (s, 1H), 2.48 (d, 1H), 2.41 (q, 2H), 2.29 (d, 1H), 1.91 (s, 3H), 1.12 (t, 3H), 1.10 (s, 3H), 1.04 (s, 3H).

Example No. I.1-22

$^1$H-NMR (400 MHz, CDCl₃ δ, ppm) 7.72 (d, 1H), 6.18 (d, 1H), 5.96 (s, 1H), 5.75 (s, 1H), 2.49 (d, 1H), 2.32 (q, 2H), 2.29 (d, 1H), 1.92 (s, 3H), 1.53 (sext, 2H), 1.12 (s, 3H), 1.04 (s, 3H), 0.92 (t, 3H).

Example No. I.1-26

$^1$H-NMR (400 MHz, CDCl₃ δ, ppm) 7.71 (d, 1H), 6.16 (d, 1H), 5.97 (s, 1H), 5.74 (s, 1H), 2.50 (d, 1H), 2.37 (m, 2H), 2.31 (d, 1H), 1.93 (s, 3H), 1.50 (quint, 2H), 1.34 (sext, 2H), 1.12 (s, 3H), 1.05 (s, 3H), 0.92 (t, 3H).

Example No. I.1-30

$^1$H-NMR (400 MHz, CDCl$_3$ δ, ppm) 7.69 (d, 1H), 6.17 (d, 1H), 5.96 (s, 1H), 5.75 (s, 1H), 2.50 (d, 1H), 2.35 (m, 2H), 2.32 (d, 1H), 1.92 (s, 3H), 1.58 (m, 2H), 1.49 (m, 2H), 1.30 (m, 4H), 1.13 (s, 3H), 1.03 (s, 3H), 0.89 (t, 3H).

Example No. I.1-46

$^1$H-NMR (400 MHz, CDCl$_3$ δ, ppm) 7.70 (d, 1H), 6.50 (d, 1H), 5.97 (s, 1H), 5.58 (s, 1H), 2.52 (d, 1H), 2.31 (d, 1H), 1.94 (s, 3H), 1.63 (m, 1H), 1.13 (s, 3H), 1.07 (s, 3H), 0.90 (m, 2H), 0.62 (m, 2H).

Example No. I.1-59

$^1$H-NMR (400 MHz, CDCl$_3$ δ, ppm) 5.96 (s, 1H), 5.89 (s, 1H), 4.20 (m, 1H), 4.18 (q, 2H), 3.58 (m, 1H), 2.52 (br. s, 1H, OH), 2.24 (m, 2H), 2.05 (d, 1H), 1.93 (s, 3H), 1.84 (d, 1H), 1.55 (quint, 2H), 1.31 (sext, 2H), 1.27 (t, 3H), 1.20 (s, 3H), 1.16 (d, 6H), 1.12 (s, 3H), 0.89 (t, 3H).

Example No. I.1-60

$^1$H-NMR (400 MHz, CDCl3 δ, ppm) 6.05 (s, 1H), 5.88 (s, 1H), 4.17 (q, 2H), 3.03 (br. s, 1H, OH), 2.59 (d, 1H), 2.41 (d, 1H), 2.27 (t, 2H), 2.15 (s, 3H), 1.54 (quint, 2H), 1.33 (sext, 2H), 1.28 (t, 3H), 1.25 (s, 3H), 1.13 (s, 3H), 0.91 (t, 3H).

Example No. I.1-61

$^1$H-NMR (400 MHz, CDCl$_3$ δ, ppm) 7.67 (d, 1H), 6.09 (d, 1H), 5.66 (s, 1H), 5.43 (s, 1H), 4.21 (m, 1H), 4.17 (q, 2H), 3.59 (m, 1H), 2.30 (m, 2H), 1.93 (d, 1H), 1.69 (s, 3H), 1.66 (d, 1H), 1.49 (m, 2H), 1.31-1.23 (m, 11H), 1.11 (s, 3H), 1.09 (s, 3H), 0.89 (t, 3H).

Example No. I.1-62

$^1$H-NMR (400 MHz, CDCl$_3$ δ, ppm) 7.78 (d, 1H), 6.16 (d, 1H), 5.94 (s, 1H), 5.72 (s, 1H), 4.18 (q, 2H), 2.47 (d, 1H), 2.32 (m, 2H), 2.28 (d, 1H), 1.93 (s, 3H), 1.46 (quint, 2H), 1.33 (sext, 2H), 1.29 (t, 3H), 1.11 (s, 3H), 1.02 (s, 3H), 0.90 (t, 3H).

Example No. I.1-65

$^1$H-NMR (400 MHz, CDCl$_3$ δ, ppm) 5.97 (s, 1H), 5.89 (s, 1H), 4.20 (m, 1H), 4.18 (q, 2H), 3.59 (m, 1H), 2.53 (br. s, 1H, OH), 2.22 (m, 2H), 2.04 (d, 1H), 1.92 (s, 3H), 1.83 (d, 1H), 1.57 (quint, 2H), 1.30-1.22 (m, 10H), 1.17 (d, 6H), 1.12 (s, 3H), 0.89 (t, 3H).

Example No. I.1-66

$^1$H-NMR (400 MHz, CDCl$_3$ δ, ppm) 6.04 (s, 1H), 5.87 (s, 1H), 4.19 (q, 2H), 3.01 (br. s, 1H, OH), 2.61 (d, 1H), 2.42 (d, 1H), 2.26 (t, 2H), 2.16 (s, 3H), 1.56 (quint, 2H), 1.29 (m, 7H), 1.24 (s, 3H), 1.13 (s, 3H), 0.89 (t, 3H).

Example No. I.1-67

$^1$H-NMR (400 MHz, CDCl$_3$ δ, ppm) 7.69 (d, 1H), 6.08 (d, 1H), 5.67 (s, 1H), 5.42 (s, 1H), 4.20 (m, 1H), 4.16 (q, 2H), 3.59 (m, 1H), 2.32 (m, 2H), 1.92 (d, 1H), 1.67 (s, 3H), 1.65 (d, 1H), 1.48 (m, 2H), 1.32-1.23 (m, 9H), 1.17 (m, 2H), 1.10 (s, 3H), 1.07 (s, 3H), 0.91 (m, 5H).

Example No. I.1-68

$^1$H-NMR (400 MHz, CDCl$_3$ δ, ppm) 7.75 (d, 1H), 6.12 (d, 1H), 5.93 (s, 1H), 5.73 (s, 1H), 4.17 (q, 2H), 2.45 (d, 1H), 2.31 (m, 2H), 2.29 (d, 1H), 1.92 (s, 3H), 1.49 (m, 2H), 1.30 (m, 7H), 1.11 (s, 3H), 1.01 (s, 3H), 0.87 (t, 3H).

Example No. I.1-71

$^1$H-NMR (400 MHz, CDCl$_3$ δ, ppm) 5.96 (s, 1H), 5.39 (s, 1H), 4.20 (m, 1H), 4.18 (q, 2H), 3.60 (m, 1H), 2.58 (br. s, 1H, OH), 2.24 (m, 2H), 2.04 (d, 1H), 1.92 (s, 3H), 1.83 (d, 1H), 1.57 (m, 2H), 1.30-1.22 (m, 16H), 1.18 (d, 6H), 1.11 (s, 3H), 0.87 (t, 3H).

Example No. I.1-72

$^1$H-NMR (400 MHz, CDCl$_3$ δ, ppm) 6.04 (s, 1H), 5.87 (s, 1H), 4.18 (q, 2H), 3.08 (br. s, 1H, OH), 2.59 (d, 1H), 2.41 (d, 1H), 2.27 (t, 2H), 2.15 (s, 3H), 1.53 (m, 2H), 1.29 (m, 12H), 1.13 (s, 3H), 0.88 (t, 3H).

Example No. I.1-73

$^1$H-NMR (400 MHz, CDCl$_3$ δ, ppm) 7.71 (d, 1H), 6.10 (d, 1H), 5.66 (s, 1H), 5.43 (s, 1H), 4.21 (m, 1H), 4.18 (q, 2H), 3.58 (m, 1H), 2.31 (m, 2H), 1.94 (d, 1H), 1.76 (d, 1H), 1.68 (s, 3H), 1.48 (m, 2H), 1.31-1.22 (m, 18H), 1.18 (m, 2H), 1.11 (s, 3H), 0.92 (t, 3H), 0.87 (t, 3H).

Example No. I.1-74

$^1$H-NMR (400 MHz, CDCl$_3$ δ, ppm) 7.76 (d, 1H), 6.13 (d, 1H), 5.94 (s, 1H), 5.72 (s, 1H), 4.18 (q, 2H), 2.47 (d, 1H), 2.33 (m, 2H), 2.31 (d, 1H), 1.92 (s, 3H), 1.48 (m, 2H), 1.34-1.25 (m, 9H), 1.11 (s, 3H), 1.02 (s, 3H), 0.88 (t, 3H).

Example No. I.1-77

$^1$H-NMR (400 MHz, CDCl$_3$ δ, ppm) 5.96 (s, 1H), 5.39 (s, 1H), 4.21 (m, 1H), 4.17 (q, 2H), 3.58 (m, 1H), 2.55 (br. s, 1H, OH), 2.23 (m, 2H), 2.03 (d, 1H), 1.93 (s, 3H), 1.86 (d, 1H), 1.55 (m, 2H), 1.30-1.22 (m, 14H), 1.15 (m, 6H), 1.12 (s, 3H), 0.88 (t, 3H).

Example No. I.1-78

$^1$H-NMR (400 MHz, CDCl$_3$ δ, ppm) 6.03 (s, 1H), 5.86 (s, 1H), 4.17 (q, 2H), 3.11 (br. s, 1H, OH), 2.61 (d, 1H), 2.43 (d, 1H), 2.26 (t, 2H), 2.15 (s, 3H), 1.55 (m, 2H), 1.29 (m, 16H), 1.13 (s, 3H), 0.87 (t, 3H).

Example No. I.1-79

$^1$H-NMR (400 MHz, CDCl$_3$ δ, ppm) 7.68 (d, 1H), 6.09 (d, 1H), 5.66 (s, 1H), 5.43 (s, 1H), 4.21 (m, 1H), 4.18 (q, 2H), 3.58 (m, 1H), 2.31 (m, 2H), 1.93 (d, 1H), 1.74 (d, 1H), 1.67 (s, 3H), 1.48 (m, 2H), 1.31-1.21 (m, 17H), 1.14 (m, 2H), 1.10 (s, 3H), 0.92 (t, 3H), 0.88 (t, 3H).

Example No. I.1-80

$^1$H-NMR (400 MHz, CDCl$_3$ δ, ppm) 7.77 (d, 1H), 6.12 (d, 1H), 5.94 (s, 1H), 5.71 (s, 1H), 4.18 (q, 2H), 2.45 (d, 1H), 2.31

(m, 2H), 2.29 (d, 1H), 1.93 (s, 3H), 1.48 (m, 2H), 1.33-1.23 (m, 13H), 1.11 (s, 3H), 1.03 (s, 3H), 0.87 (t, 3H).

Example No. I.1-83

$^1$H-NMR (400 MHz, CDCl$_3$ δ, ppm) 6.00 (s, 1H), 5.52/5.41 (s, 1H), 4.21/3.59 (m, 2H), 4.17 (q, 2H), 2.55/2.38 (br. s, 1H, OH), 2.50 (m, 1H), 2.05 (d, 1H), 1.95/1.92 (s, 3H), 1.88 (d, 1H), 1.30-1.22 (m, 9H), 1.19 (s, 3H), 1.14 (m, 9H).

Example No. I.1-84

$^1$H-NMR (400 MHz, CDCl$_3$ δ, ppm) 6.06 (s, 1H), 5.87 (s, 1H), 4.17 (q, 2H), 3.09 (br. s, 1H, OH), 2.60 (d, 1H), 2.52 (sept, 1H), 2.43 (d, 1H), 2.16 (s, 3H), 1.28 (t, 3H), 1.26 (s, 3H), 1.14 (s, 3H), 1.12 (d, 6H).

Example No. I.1-85

$^1$H-NMR (400 MHz, CDCl$_3$ δ, ppm) 7.66/7.65 (d, 1H), 6.10 (d, 1H), 5.66/5.65 (s, 1H), 5.55/5.43 (s, 1H), 4.23/3.59 (m, 2H), 4.18 (q, 2H), 2.82 (m, 1H), 2.09/1.98 (d, 1H), 1.82/1.73 (d, 1H), 1.69/1.68 (s, 3H), 1.28 (m, 6H), 1.19-1.10 (m, 12H), 0.93 (m, 3H).

Example No. I.1-86

$^1$H-NMR (400 MHz, CDCl$_3$ δ, ppm) 7.70 (d, 1H), 6.15 (d, 1H), 5.94 (s, 1H), 5.73 (s, 1H), 4.18 (q, 2H), 2.80 (sept, 1H), 2.50 (d, 1H), 2.30 (d, 1H), 1.99 (br. s, 1H, OH), 1.94 (s, 3H), 1.29 (t, 3H), 1.15-1.10 (m, 9H), 1.03 (s, 3H).

Example No. I.1-89

$^1$H-NMR (400 MHz, CDCl$_3$ δ, ppm) 6.03 (s, 1H), 5.58/5.40 (s, 1H), 4.19 (q, 2H), 4.05/3.59 (m, 2H), 2.72 (br. s, 1H, OH), 2.07/2.05 (d, 1H), 1.96/1.94 (s, 3H), 1.88/1.86 (d, 1H), 1.29-1.22 (m, 6H), 1.19-1.10 (m, 15H), 1.03 (s, 3H).

Example No. I.1-90

$^1$H-NMR (400 MHz, CDCl$_3$ δ, ppm) 6.09 (s, 1H), 5.87 (s, 1H), 4.19 (q, 2H), 3.22 (br. s, 1H, OH), 2.59 (d, 1H), 2.43 (d, 1H), 2.16 (s, 3H), 1.29 (t, 3H), 1.26 (s, 3H), 1.17 (s, 9H), 1.13 (s, 3H).

Example No. I.1-91

$^1$H-NMR (400 MHz, CDCl$_3$ δ, ppm) 6.42/6.38 (d, 1H), 5.72/5.67 (s, 1H), 5.62 (d, 1H), 5.53/5.41 (s, 1H), 4.22/3.58 (m, 2H), 4.11 (q, 2H), 2.08/1.99 (d, 1H), 1.92/1.84 (d, 1H), 1.74/1.72 (s, 3H), 1.24 (m, 6H), 1.19-1.10 (m, 15H), 0.94 (m, 3H).

Example No. I.1-92

$^1$H-NMR (400 MHz, CDCl$_3$ δ, ppm) 7.71 (d, 1H), 6.45 (d, 1H), 5.93 (s, 1H), 5.76 (s, 1H), 4.10 (q, 2H), 2.52 (d, 1H), 2.25 (d, 1H), 2.01 (br. s, 1H, OH), 2.00 (s, 3H), 1.26 (t, 3H), 1.11 (s, 9H), 1.10 (s, 3H), 1.06 (s, 3H).

Example No. I.1-113

$^1$H-NMR (400 MHz, CDCl$_3$ δ, ppm) 6.11 (s, 1H), 5.39 (s, 1H), 4.20 (m, 1H), 4.16 (q, 2H), 3.59 (m, 1H), 2.58 (br. s, 1H, OH), 2.01 (d, 1H), 1.91 (s, 3H), 1.86 (d, 1H), 1.62 (m, 1H), 1.24 (t, 3H), 1.21 (m, 3H), 1.13 (m, 6H), 1.11 (m, 3H), 0.88 (m, 2H), 0.81 (m, 2H).

Example No. I.1-114

$^1$H-NMR (400 MHz, CDCl$_3$ δ, ppm) 6.18 (s, 1H), 5.86 (s, 1H), 4.18 (q, 2H), 3.08 (br. s, 1H, OH), 2.54 (d, 1H), 2.42 (d, 1H), 2.14 (s, 3H), 1.67 (m, 1H), 1.28 (t, 3H), 1.24 (s, 3H), 1.11 (s, 3H), 0.83 (m, 4H).

Example No. I.1-115

$^1$H-NMR (400 MHz, CDCl$_3$ δ, ppm) 7.71 (d, 1H), 6.43 (d, 1H), 5.51 (s, 1H), 5.44 (s, 1H), 4.21 (m, 1H), 4.17 (q, 2H), 3.58 (m, 1H), 1.98 (d, 1H), 1.83 (d, 1H), 1.71 (s, 3H), 1.63 (m, 1H), 1.25-1.21 (m, 6H), 1.13 (m, 3H), 1.09 (m, 3H), 0.94 (m, 3H), 0.82 (m, 2H), 0.56 (m, 2H).

Example No. I.1-116

$^1$H-NMR (400 MHz, CDCl$_3$ δ, ppm) 7.81 (d, 1H), 6.52 (d, 1H), 5.95 (s, 1H), 5.59 (s, 1H), 4.17 (q, 2H), 2.51 (d, 1H), 2.32 (d, 1H), 1.94 (s, 3H), 1.61 (m, 1H), 1.28 (t, 3H), 1.12 (s, 3H), 1.03 (s, 3H), 0.85 (m, 2H), 0.58 (m, 2H).

Example No. I.1-121

$^1$H-NMR (400 MHz, CDCl$_3$ δ, ppm) 6.02 (s, 1H), 5.51/5.39 (s, 1H), 4.21/3.59 (m, 2H), 4.18 (q, 2H), 2.69/2.63 (m, 1H), 2.55/2.53 (br. s, 1H, OH), 2.04 (d, 1H), 1.94/1.92 (s, 3H), 1.89-1.77 (m, 3H), 1.71 (m, 2H), 1.62 (m, 4H), 1.28-1.22 (m, 9H), 1.18 (s, 3H), 1.14 (m, 3H).

Example No. I.1-122

$^1$H-NMR (400 MHz, CDCl$_3$ δ, ppm) 6.08 (s, 1H), 5.87 (s, 1H), 4.19 (q, 2H), 3.15 (br. s, 1H, OH), 2.66 (quint, 1H), 2.58 (d, 1H), 2.42 (d, 1H), 2.16 (s, 3H), 1.87 (m, 2H), 1.69 (m, 2H), 1.59 (m, 4H), 1.27 (t, 3H), 1.25 (s, 3H), 1.13 (s, 3H).

Example No. I.1-123

$^1$H-NMR (400 MHz, CDCl$_3$ δ, ppm) 7.71/7.70 (d, 1H), 6.10 (d, 1H), 5.69/5.68 (s, 1H), 5.55/5.43 (s, 1H), 4.22/3.59 (m, 2H), 4.18 (q, 2H), 2.91 (m, 1H), 2.08/1.96 (d, 1H), 1.91-1.82 (m, 3H), 1.69/1.68 (s, 3H), 1.68-1.60 (m, 4H), 1.51-1.43 (m, 2H), 1.28 (m, 6H), 1.19-1.09 (m, 6H), 0.92 (m, 3H).

Example No. I.1-124

$^1$H-NMR (400 MHz, CDCl$_3$ δ, ppm) 7.76 (d, 1H), 6.16 (d, 1H), 5.94 (s, 1H), 5.75 (s, 1H), 4.18 (q, 2H), 2.89 (pent, 1H), 2.49 (d, 1H), 2.30 (d, 1H), 2.00 (br. s, 1H, OH), 1.94 (s, 3H), 1.90 (m, 2H), 1.72 (m, 2H), 1.66 (m, 2H), 1.49 (m, 2H), 1.29 (t, 3H), 1.11 (s, 3H), 1.03 (s, 3H).

Example No. I.1-125

$^1$H-NMR (400 MHz, CDCl$_3$ δ, ppm) 5.97 (s, 1H), 5.39 (s, 1H), 4.21 (m, 1H), 4.19 (q, 2H), 3.60 (m, 1H), 2.56 (br, s, 1H, OH), 2.15 (m, 1H), 2.03 (d, 1H), 1.94 (s, 3H), 1.90 (d, 1H), 1.78 (m, 4H), 1.69 (m, 2H), 1.37 (m, 2H), 1.30-1.21 (m, 6H), 1.20-1.12 (m, 5H), 1.10 (m, 3H), 0.88 (m, 3H).

Example No. I.1-126

$^1$H-NMR (400 MHz, CDCl$_3$ δ, ppm) 6.04 (s, 1H), 5.87 (s, 1H), 4.18 (q, 2H), 3.07 (br. s, 1H, OH), 2.61 (d, 1H), 2.44 (d, 1H), 2.18 (m, 1H), 2.16 (s, 3H), 1.79 (m, 3H), 1.70 (m, 1H), 1.32-1.24 (m, 12H), 1.13 (s, 3H).

Example No. I.1-127

$^1$H-NMR (400 MHz, CDCl$_3$ δ, ppm) 7.58 (d, 1H), 6.06 (d, 1H), 5.63 (s, 1H), 5.45 (s, 1H), 4.21 (m, 1H), 4.18 (q, 2H), 3.59 (m, 1H), 2.41 (m, 1H), 1.94 (d, 1H), 1.81-1.73 (m, 5H), 1.70 (s, 3H), 1.64 (m, 2H), 1.32-1.21 (m, 8H), 1.20-1.12 (m, 5H), 1.10 (m, 3H), 0.92 (m, 3H).

Example No. I.1-128

$^1$H-NMR (400 MHz, CDCl$_3$ δ, ppm) 7.67 (d, 1H), 6.11 (d, 1H), 5.94 (s, 1H), 5.70 (s, 1H), 4.15 (q, 2H), 2.48 (d, 1H), 2.38 (m, 1H), 2.29 (d, 1H), 1.95 (s, 3H), 1.83-1.74 (m, 4H), 1.37-1.19 (m, 6H), 1.28 (t, 3H), 1.12 (s, 3H), 1.03 (s, 3H).

Example No. I.1-141

$^1$H-NMR (400 MHz, CDCl$_3$ δ, ppm) 5.98 (s, 1H), 5.43/5.40 (s, 1H), 4.16/3.59 (m, 2H), 3.72 (s, 3H), 2.50 (br. s, 1H, OH), 2.29 (q, 2H), 2.08 (d, 1H), 1.96/1.95 (s, 3H), 1.84 (d, 1H), 1.24 (m, 6H), 1.20 (s, 3H), 1.14 (m, 9H).

Example No. I.1-142

$^1$H-NMR (400 MHz, CDCl$_3$ δ, ppm) 6.06 (s, 1H), 5.87 (s, 1H), 3.72 (s, 3H), 2.99 (br. s, 1H, OH), 2.61 (d, 1H), 2.42 (d, 1H), 2.30 (q, 2H), 2.16 (s, 3H), 1.26 (s, 3H), 1.14 (t, 3H), 1.13 (s, 3H).

Example No. I.1-143

$^1$H-NMR (400 MHz, CDCl$_3$ δ, ppm) 7.70 (d, 1H), 6.11 (d, 1H), 5.68/5.67 (s, 1H), 5.56/5.43 (s, 1H), 4.23/3.59 (m, 2H), 3.71 (s, 3H), 2.38 (q, 2H), 2.08/1.97 (d, 1H), 1.83/1.73 (d, 1H), 1.69/1.68 (s, 3H), 1.26 (m, 3H), 1.17 (m, 3H), 1.11 (m, 6H), 0.91 (t, 3H).

Example No. I.1-144

$^1$H-NMR (400 MHz, CDCl$_3$ δ, ppm) 7.80 (d, 1H), 6.18 (d, 1H), 5.95 (s, 1H), 5.75 (s, 1H), 3.71 (s, 3H), 2.82 (br. s, 1H, OH), 2.49 (d, 1H), 2.38 (q, 2H), 2.31 (d, 1H), 1.93 (s, 3H), 1.13 (t, 3H), 1.11 (s, 3H), 1.02 (s, 3H).

Example No. I.1-147

$^1$H-NMR (400 MHz, CDCl$_3$ δ, ppm) 7.73/7.71 (d, 1H), 6.12 (d, 1H), 5.93/5.90 (s, 1H), 5.56/5.42 (s, 1H), 4.17/3.59 (m, 2H), 3.71 (s, 3H), 2.29 (m, 2H), 2.08/1.99 (d, 1H), 1.84 (d, 1H), 1.81/1.78 (s, 3H), 1.53 (m, 2H), 1.26 (m, 6H), 1.11 (m, 6H), 0.96 (m, 3H).

Example No. I.1-148

$^1$H-NMR (400 MHz, CDCl$_3$ δ, ppm) 7.78 (d, 1H), 6.16 (d, 1H), 5.95 (s, 1H), 5.72 (s, 1H), 3.71 (s, 3H), 2.48 (d, 1H), 2.30 (m, 3H), 1.97 (br. s, 1H, OH), 1.93 (s, 3H), 1.53 (m, 2H), 1.11 (s, 3H), 1.02 (s, 3H), 0.96 (t, 3H).

Example No. I.1-230

$^1$H-NMR (400 MHz, CDCl$_3$ δ, ppm) 6.07 (s, 1H), 5.87 (s, 1H), 4.08 (t, 2H), 3.02 (br. s, 1H, OH), 2.60 (d, 1H), 2.45 (q, 2H), 2.42 (d, 1H), 2.16 (s, 3H), 1.68 (sext, 2H), 1.25 (s, 3H), 1.15 (t, 3H), 1.10 (s, 3H), 0.95 (t, 3H).

Example No. I.1-231

$^1$H-NMR (400 MHz, CDCl$_3$ δ, ppm) 7.73/7.71 (d, 1H), 6.11 (d, 1H), 5.69/5.68 (s, 1H), 5.56/5.43 (s, 1H), 4.25/3.59 (m, 2H), 4.09 (t, 2H), 2.37 (q, 2H), 2.08/1.96 (d, 1H), 1.83/1.74 (d, 1H), 1.69 (m, 5H), 1.26 (m, 6H), 1.18-1.10 (m, 6H), 0.97 (m, 3H), 0.92 (m, 3H).

Example No. I.1-232

$^1$H-NMR (400 MHz, CDCl$_3$ δ, ppm) 7.81 (d, 1H), 6.17 (d, 1H), 5.94 (s, 1H), 5.75 (s, 1H), 4.08 (t, 2H), 2.49 (d, 1H), 2.39 (q, 2H), 2.32 (d, 1H), 1.95 (br. s, 1H, OH), 1.93 (s, 3H), 1.69 (sext, 2H), 1.13 (m, 6H), 1.02 (s, 3H), 0.97 (t, 3H).

Example No. I.1-279

$^1$H-NMR (400 MHz, CDCl$_3$ δ, ppm) 7.71/7.69 (d, 1H), 6.12 (d, 1H), 5.68/5.67 (s, 1H), 5.56/5.42 (s, 1H), 4.21/3.59 (m, 2H), 4.13 (t, 2H), 2.31 (m, 2H), 2.08/1.96 (d, 1H), 1.83/1.74 (d, 1H), 1.81-1.69 (m, 5H), 1.50 (m, 2H), 1.26 (m, 6H), 1.18-1.10 (m, 9H), 0.97 (m, 3H).

Example No. I.1-280

$^1$H-NMR (400 MHz, CDCl$_3$ δ, ppm) 7.80 (d, 1H), 6.15 (d, 1H), 5.94 (s, 1H), 5.73 (s, 1H), 4.11 (t, 2H), 2.49 (d, 1H), 2.30 (m, 3H), 1.98 (br. s, 1H, OH), 1.95 (s, 3H), 1.85 (m, 2H), 1.55 (m, 2H), 1.13 (s, 3H), 1.02 (m, 6H), 0.97 (t, 3H).

Example No. I.1-317

$^1$H-NMR (400 MHz, CDCl$_3$ δ, ppm) 5.97 (s, 1H), 5.40 (s, 1H), 4.21 (m, 1H), 4.14 (t, 2H), 3.58 (m, 1H), 2.57 (br. s, 1H, OH), 2.23 (t, 2H), 2.04 (d, 1H), 1.93 (s, 3H), 1.88 (d, 1H), 1.68 (m, 1H), 1.53 (quint, 2H), 1.29 (m, 4H), 1.23 (t, 3H), 1.19 (m, 6H), 1.14 (m, 5H), 0.90 (d, 6H), 0.78 (t, 3H).

Example No. I.1-318

$^1$H-NMR (400 MHz, CDCl$_3$ δ, ppm) 6.04 (s, 1H), 5.87 (s, 1H), 4.15 (t, 2H), 3.04 (br. s, 1H, OH), 2.59 (d, 1H), 2.41 (d, 1H), 2.26 (t, 2H), 2.15 (s, 3H), 1.69 (m, 1H), 1.56 (m, 2H), 1.54 (m, 2H), 1.29 (m, 4H), 1.24 (s, 3H), 1.12 (s, 3H), 0.93 (d, 6H), 0.88 (t, 3H).

Example No. I.1-319

$^1$H-NMR (400 MHz, CDCl$_3$ δ, ppm) 7.69 (d, 1H), 6.09 (d, 1H), 5.66 (s, 1H), 5.43 (s, 1H), 4.21 (m, 1H), 4.13 (t, 2H), 3.58 (m, 1H), 2.30 (m, 2H), 1.94 (d, 1H), 1.74 (d, 1H), 1.69 (s, 3H), 1.58 (s, 3H), 1.49 (quint, 2H), 1.29 (m, 4H), 1.26 (m, 4H), 1.18 (m, 3H), 1.09 (m, 4H), 0.91 (m, 9H), 0.88 (m, 3H).

Example No. I.1-320

$^1$H-NMR (400 MHz, CDCl$_3$ δ, ppm) 7.80 (d, 1H), 6.15 (d, 1H), 5.94 (s, 1H), 5.72 (s, 1H), 4.16 (t, 2H), 2.47 (d, 1H), 2.32 (d, 1H), 2.29 (m, 2H), 1.93 (s, 3H), 1.72 (m, 1H), 1.54 (m, 2H), 1.49 (m, 2H), 1.31 (m, 4H), 1.12 (s, 3H), 1.03 (s, 3H), 0.91 (d, 6H), 0.88 (t, 3H).

Example No. I.1-394

$^1$H-NMR (400 MHz, CDCl$_3$ δ, ppm) 7.68 (d, 1H), 6.46 (d, 1H), 5.52 (s, 1H), 5.44 (s, 1H), 4.22 (m, 1H), 3.58 (m, 1H), 2.45 (br. s, 1H, OH), 1.94 (d, 1H), 1.91 (m, 1H), 1.85 (d, 1H), 1.68 (s, 3H), 1.31 (m, 3H), 1.22 (m, 3H), 1.18 (m, 3H), 1.10 (m, 3H), 0.90 (m, 2H), 0.59 (m, 2H).

Example No. I.1-395

¹H-NMR (400 MHz, CDCl₃ δ, ppm) 7.63 (d, 1H), 6.14 (d, 1H), 5.68 (s, 1H), 5.44 (s, 1H), 4.22 (m, 1H), 3.58 (m, 1H), 2.34 (m, 2H), 1.93 (d, 1H), 1.76 (d, 1H), 1.68-1.63 (m, 5H), 1.49 (m, 2H), 1.34-1.22 (m, 11H), 1.18-1.13 (m, 2H), 1.10 (m, 3H), 0.90 (m, 6H).

Example No. I.1-396

¹H-NMR (400 MHz, CDCl₃ δ, ppm) 7.66 (d, 1H), 6.12 (d, 1H), 5.68 (s, 1H), 5.42 (s, 1H), 4.21 (m, 1H), 3.59 (m, 1H), 2.32 (m, 2H), 1.92 (d, 1H), 1.82 (d, 1H), 1.67 (s, 3H), 1.61 (m, 2H), 1.33 (m, 2H), 1.28 (m, 6H), 1.14 (m, 3H), 1.10 (m, 3H), 0.91 (t, 3H).

Example No. I.1-403

¹H-NMR (400 MHz, CDCl₃ δ, ppm) 6.67/6.64 (s, 1H), 6.63/6.01 (s, 1H), 4.28 (q, 2H), 4.11 (m, 2H), 2.62/2.56 (br. s, 1H, OH), 2.44-2.35 (m, 2H), 2.08/2.05 (s, 3H), 1.30 (t, 3H), 1.27 (t, 3H), 1.18 (s, 3H), 1.10 (s, 3H).

Example No. I.1-413

¹H-NMR (400 MHz, CDCl₃ δ, ppm) 6.59/6.58 (s, 1H), 6.02/5.95 (s, 1H), 4.19 (q, 2H), 3.89/3.86 (s, 3H), 2.74/2.66 (br. s, 1H, OH), 2.47 (d, 1H), 2.33 (m, 1H), 2.29 (q, 2H), 2.08/2.05 (s, 3H), 1.28 (t, 3H), 1.19 (s, 3H), 1.12 (t, 3H), 1.10 (s, 3H).

Example No. I.1-414

¹H-NMR (400 MHz, CDCl₃ δ, ppm) 7.71 (d, 1H), 6.64/5.99 (s, 1H), 6.11/6.09 (d, 1H), 5.71/5.70 (s, 1H), 4.18 (q, 2H), 3.90/3.87 (s, 3H), 2.77/2.73 (br. s, 1H, OH), 2.42 (d, 1H), 2.38 (m, 2H), 2.22 (m, 1H), 1.84/1.81 (s, 3H), 1.29 (t, 3H), 1.11 (m, 3H), 1.02 (s, 3H), 0.99 (s, 3H).

Example No. I.1-415

¹H-NMR (400 MHz, CDCl₃ δ, ppm) 6.62/6.02 (s, 1H), 6.01/5.97 (s, 1H), 4.18 (q, 2H), 4.11 (m, 2H), 2.71/2.62 (br. s, 1H, OH), 2.47 (d, 1H), 2.35 (m, 1H), 2.29 (q, 2H), 2.09/2.05 (s, 3H), 1.28 (m, 6H), 1.20 (s, 3H), 1.14 (t, 3H), 1.08 (s, 3H).

Example No. I.1-416

¹H-NMR (400 MHz, CDCl₃ δ, ppm) 7.71 (d, 1H), 6.67/5.98 (s, 1H), 6.12/6.08 (d, 1H), 5.71/5.69 (s, 1H), 4.18 (q, 2H), 4.12 (m, 2H), 2.80/2.76 (br. s, 1H, OH), 2.43 (d, 1H), 2.38 (q, 2H), 2.23 (m, 1H), 1.83/1.81 (s, 3H), 1.29 (m, 6H), 1.12 (m, 3H), 1.02 (s, 3H), 0.99 (s, 3H).

Example No. I.1-439

¹H-NMR (400 MHz, CDCl₃ δ, ppm) 7.61/7.58 (d, 1H), 6.11/6.10 (d, 1H), 5.68/5.65 (s, 1H), 5.56/5.43 (s, 1H), 4.22/3.58 (m, 2H), 2.59 (m, 1H), 2.08/1.93 (d, 1H), 1.92/1.91 (br. s, 1H, OH), 1.83/1.76 (d, 1H), 1.69/1.68 (s, 3H), 1.43 (m, 1H), 1.34 (m, 1H), 1.23 (m, 6H), 1.14-1.10 (m, 9H), 0.89 (m, 3H).

Example No. I.1-440

¹H-NMR (400 MHz, CDCl₃ δ, ppm) 7.62/7.61 (d, 1H), 6.15 (d, 1H), 5.97 (s, 1H), 5.72 (s, 1H), 2.58 (m, 1H), 2.49 (d, 1H), 2.31 (d, 1H), 1.98 (br. s, 1H, OH), 1.93 (s, 3H), 1.54 (m, 1H), 1.47 (m, 1H), 1.12 (m, 6H), 1.04 (m, 3H), 0.89 (m, 3H).

Example No. I.1-441

¹H-NMR (400 MHz, CDCl₃ δ, ppm) 5.98 (s, 1H), 5.51/5.40 (s, 1H), 4.21/3.59 (m, 2H), 3.72 (s, 3H), 2.53 (br. s, 1H, OH), 2.23/2.00 (m, 1H), 2.04 (m, 1H), 1.96/1.94 (s, 3H), 1.91-1.84 (m, 1H), 1.42 (m, 2H), 1.23 (m, 4H), 1.19 (s, 3H), 1.14-1.11 (m, 9H), 0.89/0.82 (t, 3H).

Example No. I.1-442

¹H-NMR (400 MHz, CDCl₃ δ, ppm) 6.05 (s, 1H), 5.87 (s, 1H), 3.72 (s, 3H), 3.06 (br. s, 1H, OH), 2.58 (d, 1H), 2.43 (d, 1H), 2.28 (m, 1H), 2.16 (s, 3H), 1.51 (m, 1H), 1.53 (m, 1H), 1.26 (s, 3H), 1.13 (s, 3H), 1.12/1.10 (d, 3H), 0.85 (t, 3H).

Example No. I.1-443

¹H-NMR (400 MHz, CDCl₃ δ, ppm) 7.62/7.60 (d, 1H), 6.10/6.07 (d, 1H), 5.64 (s, 1H), 5.56/5.43 (s, 1H), 4.23/3.58 (m, 2H), 3.71 (s, 3H), 2.59 (m, 1H), 2.08/1.93 (d, 1H), 1.92 (br. s, 1H, OH), 1.84/1.78 (d, 1H), 1.69/1.68 (s, 3H), 1.51 (m, 1H), 1.42 (m, 1H), 1.26 (m, 6H), 1.14-1.10 (m, 6H), 0.92-0.85 (m, 6H).

Example No. I.1-444

¹H-NMR (400 MHz, CDCl₃ δ, ppm) 7.71/7.66 (d, 1H), 6.14 (d, 1H), 5.95 (s, 1H), 5.70 (s, 1H), 3.71 (s, 3H), 2.56 (m, 1H), 2.49 (d, 1H), 2.31 (d, 1H), 1.94 (s, 3H), 1.54 (m, 1H), 1.43 (m, 1H), 1.11 (s, 3H), 1.09 (s, 3H), 1.03 (m, 3H), 0.88 (m, 3H).

Example No. I.1-457

¹H-NMR (400 MHz, CDCl₃ δ, ppm) 6.43/5.98 (s, 1H), 5.51/5.39 (s, 1H), 4.22/3.59 (m, 2H), 4.19 (q, 2H), 2.51 (br. s, 1H, OH), 2.33/2.16 (m, 1H), 2.02 (m, 1H), 1.94/1.91/1.89 (s, 3H), 1.88-1.78 (m, 1H), 1.53 (m, 2H), 1.29-1.21 (m, 12H), 1.20-1.17 (m, 3H), 1.15-1.08 (m, 5H), 0.89/0.82 (t, 3H).

Example No. I.1-458

¹H-NMR (400 MHz, CDCl₃ δ, ppm) 6.04 (s, 1H), 5.87 (s, 1H), 4.19 (q, 2H), 3.11 (br. s, 1H, OH), 2.58 (d, 1H), 2.43 (d, 1H), 2.38 (m, 1H), 2.16 (s, 3H), 1.49 (m, 1H), 1.35 (m, 1H), 1.31-1.23 (m, 8H), 1.13 (s, 3H), 1.11/1.09 (d, 3H), 0.88 (t, 3H).

Example No. I.1-459

¹H-NMR (400 MHz, CDCl₃ δ, ppm) 7.68/7.63 (d, 1H), 6.10/6.08 (d, 1H), 5.64/5.61 (s, 1H), 5.56/5.43 (s, 1H), 4.22/3.58 (m, 2H), 4.18 (q, 2H), 2.68 (m, 1H), 2.08/1.97 (d, 1H), 1.93/1.91 (br. s, 1H, OH), 1.84/1.77 (d, 1H), 1.69/1.68 (s, 3H), 1.49 (m, 1H), 1.37 (m, 1H), 1.28 (m, 9H), 1.18 (m, 2H), 1.12 (m, 6H), 0.93 (m, 3H), 0.89 (m, 3H).

Example No. I.1-460

¹H-NMR (400 MHz, CDCl₃ δ, ppm) 7.71/7.68 (d, 1H), 6.14/6.11 (d, 1H), 5.95/5.93 (s, 1H), 5.70 (s, 1H), 4.18 (q, 2H), 2.62 (m, 1H), 2.48 (d, 1H), 2.30 (d, 1H), 1.98 (br. s, 1H, OH), 1.95/1.90 (s, 3H), 1.49 (m, 1H), 1.38 (m, 1H), 1.30 (m, 5H), 1.11 (m, 6H), 1.02 (s, 3H), 0.88 (m, 3H).

Example No. I.1-489

$^1$H-NMR (400 MHz, CDCl$_3$ δ, ppm) 6.01 (s, 1H), 5.52/5.41 (s, 1H), 4.24/3.63 (m, 2H), 4.19 (q, 2H), 2.95 (br. s, 1H, OH), 2.58/2.48 (d, 1H), 2.38/1.92 (d, 1H), 2.29 (q, 2H), 2.02/2.00 (s, 3H), 1.43 (s, 3H), 1.28-1.24 (m, 6H), 1.18-1.04 (m, 6H).

Example No. I.1-490

$^1$H-NMR (400 MHz, CDCl$_3$ δ, ppm) 6.09 (s, 1H), 5.94 (s, 1H), 4.19 (q, 2H), 3.67 (br. s, 1H, OH), 2.97 (d, 1H), 2.70 (d, 1H), 2.32 (q, 2H), 2.21 (s, 3H), 1.50 (s, 3H), 1.29 (t, 3H), 1.15 (t, 3H).

Example No. I.1-497

$^1$H-NMR (400 MHz, CDCl$_3$ δ, ppm) 6.00 (s, 1H), 5.50/5.47/5.41 (s, 1H), 4.24/3.63 (m, 2H), 4.18 (q, 2H), 2.86/2.80 (br. s, 1H, OH), 2.48/2.37 (d, 1H), 2.23 (t, 2H), 2.01/1.92 (d, 1H), 2.00/1.99 (s, 3H), 1.60 (m, 2H), 1.42 (s, 3H), 1.28 (m, 6H), 1.18 (m, 3H), 0.92 (t, 3H).

Example No. I.1-498

$^1$H-NMR (400 MHz, CDCl$_3$ δ, ppm) 6.08 (s, 1H), 5.94 (s, 1H), 4.19 (q, 2H), 3.41 (br. s, 1H, OH), 2.96 (d, 1H), 2.70 (d, 1H), 2.25 (t, 2H), 2.20 (s, 3H), 1.58 (m, 2H), 1.50 (s, 3H), 1.28 (t, 3H), 0.94 (t, 3H).

Example No. I.1-505

$^1$H-NMR (400 MHz, CDCl$_3$ δ, ppm) 6.02 (s, 1H), 5.50/5.47/5.41 (s, 1H), 4.24/3.64 (m, 2H), 4.17 (q, 2H), 2.89/2.87 (br. s, 1H, OH), 2.52 (sept, 2H), 2.49/2.38 (d, 1H), 2.03/1.91 (d, 1H), 2.02/2.00 (s, 3H), 1.43 (s, 3H), 1.28 (m, 6H), 1.18 (m, 3H), 1.14 (m, 6H).

Example No. I.1-506

$^1$H-NMR (400 MHz, CDCl$_3$ δ, ppm) 6.10 (s, 1H), 5.94 (s, 1H), 4.18 (q, 2H), 3.41 (br. s, 1H, OH), 2.97 (d, 1H), 2.70 (d, 1H), 2.54 (sept, 2H), 2.21 (s, 3H), 1.51 (s, 3H), 1.28 (t, 3H), 1.15 (d, 6H).

Example No. I.1-529

$^1$H-NMR (400 MHz, CDCl$_3$ δ, ppm) 6.15 (s, 1H), 5.49/5.46/5.40 (s, 1H), 4.24/3.64 (m, 2H), 4.17 (q, 2H), 2.97/2.92 (br. s, 1H, OH), 2.47/2.36 (d, 1H), 2.02/1.91 (d, 1H), 1.99/1.97 (s, 3H), 1.67 (m, 1H), 1.40 (s, 3H), 1.27 (m, 6H), 1.18 (m, 3H), 0.84 (m, 4H).

Example No. I.1-530

$^1$H-NMR (400 MHz, CDCl$_3$ δ, ppm) 6.21 (s, 1H), 5.93 (s, 1H), 4.18 (q, 2H), 3.50 (br. s, 1H, OH), 2.96 (d, 1H), 2.66 (d, 1H), 2.18 (s, 3H), 1.69 (m, 1H), 1.48 (s, 3H), 1.28 (t, 3H), 0.90 (m, 2H), 0.82 (m, 2H).

Example No. I.1-549

$^1$H-NMR (400 MHz, CDCl$_3$ δ, ppm) 6.70/5.97 (s, 1H), 6.02/6.01 (s, 1H), 4.20 (q, 2H), 2.93/2.88 (br. s, 1H, OH), 2.59/2.49 (br. s, 1H, OH), 2.43 (d, 1H), 2.36 (m, 1H), 2.29 (q, 2H), 2.11/2.06 (s, 3H), 1.28 (t, 3H), 1.22 (s, 3H), 1.16 (t, 3H), 1.10 (s, 3H).

Example No. I.1-551

$^1$H-NMR (400 MHz, CDCl$_3$ δ, ppm) 6.74/6.01 (s, 1H), 6.65/5.64 (s, 1H), 4.28 (q, 2H), 2.70/2.60 (br. s, 1H, OH), 2.58/2.49 (br. s, 1H, OH), 2.42 (d, 1H), 2.39 (m, 1H), 2.11/2.06 (s, 3H), 1.31/1.26 (t, 3H), 1.19 (s, 3H), 1.13/1.10 (s, 3H).

Example No. I.1-553

$^1$H-NMR (400 MHz, CDCl$_3$ δ, ppm) 5.98 (s, 1H), 5.52/5.39 (s, 1H), 4.21/3.59 (m, 2H), 4.19 (q, 2H), 2.76 (br. s, 1H, OH), 2.02 (m, 1H), 1.93/1.89 (s, 3H), 1.79 (d, 1H), 1.29 (t, 3H), 1.27-1.21 (m, 6H), 1.20-1.08 (m, 14H), 0.77 (t, 3H).

Example No. I.1-554

$^1$H-NMR (400 MHz, CDCl$_3$ δ, ppm) 6.05 (s, 1H), 5.87 (s, 1H), 4.20 (q, 2H), 3.27 (br. s, 1H, OH), 2.57 (d, 1H), 2.42 (d, 1H), 2.16 (s, 3H), 1.52 (q, 2H), 1.29 (t, 1H), 1.23 (s, 6H), 1.12 (s, 3H), 1.11 (s, 3H), 0.77 (t, 3H).

Example No. I.1-555

$^1$H-NMR (400 MHz, CDCl$_3$ δ, ppm) 7.60/7.57 (d, 1H), 6.18/6.16 (d, 1H), 5.99/5.68 (s, 1H), 5.56/5.44 (s, 1H), 4.23/3.58 (m, 2H), 4.11 (q, 2H), 2.08/1.96 (d, 1H), 1.91/1.86 (d, 1H), 1.64/1.62 (s, 3H), 1.49 (m, 2H), 1.28 (m, 9H), 1.19-1.09 (m, 9H), 0.93-0.88 (m, 6H).

Example No. I.1-556

$^1$H-NMR (400 MHz, CDCl$_3$ δ, ppm) 7.71 (d, 1H), 6.00 (d, 1H), 5.93 (s, 1H), 5.38 (s, 1H), 4.10 (q, 2H), 2.48 (d, 1H), 2.27 (d, 1H), 1.99 (br. s, 1H, OH), 1.90 (s, 3H), 1.43 (q, 2H), 1.28 (t, 3H), 1.11 (s, 6H), 1.09 (s, 3H), 1.04 (s, 3H), 0.78 (t, 3H).

Example No. I.1-560

$^1$H-NMR (400 MHz, CDCl$_3$ δ, ppm) 7.80 (d, 1H), 6.18 (d, 1H), 5.94 (s, 1H), 5.74 (s, 1H), 4.15 (t, 2H), 3.59 (t, 2H), 2.49 (d, 1H), 2.39 (q, 2H), 2.32 (d, 1H), 2.01 (br. s, 1H, OH), 1.93 (s, 3H), 1.89 (m, 2H), 1.84 (m, 2H), 1.14 (t, 3H), 1.13 (s, 3H), 1.02 (s, 3H).

Example No. I.1-564

$^1$H-NMR (400 MHz, CDCl$_3$ δ, ppm) 7.79 (d, 1H), 6.17 (d, 1H), 5.94 (s, 1H), 5.72 (s, 1H), 4.15 (t, 2H), 3.60 (t, 2H), 2.48 (d, 1H), 2.31 (m, 1H), 1.98 (br. s, 1H, OH), 1.93 (s, 3H), 1.88 (m, 2H), 1.84 (m, 2H), 1.53 (m, 2H), 1.11 (s, 3H), 1.02 (s, 3H), 0.98 (t, 3H).

Example No. I.1-565

$^1$H-NMR (400 MHz, CDCl$_3$ δ, ppm) 7.60/7.57 (d, 1H), 5.73 (d, 1H), 5.69/5.68 (s, 1H), 5.66/5.43 (s, 1H), 4.19/3.58 (m, 2H), 2.59 (m, 1H), 1.98/1.95 (d, 1H), 1.91/1.88 (d, 1H), 1.72/1.71 (s, 3H), 1.44 (m, 2H), 1.26 (m, 6H), 1.12-1.09 (m, 9H), 0.96 (s, 3H), 0.88 (m, 3H).

Example No. I.1-566

$^1$H-NMR (400 MHz, CDCl$_3$ δ, ppm) 7.61 (d, 1H), 6.43 (d, 1H), 5.94 (s, 1H), 5.73 (s, 1H), 2.53 (d, 1H), 2.27 (d, 1H), 1.97 (s, 3H), 1.44 (q, 2H), 1.10 (s, 3H), 1.09 (s, 6H), 1.05 (s, 3H), 0.78 (t, 3H).

Example No. I.2-5

$^1$H-NMR (400 MHz, CDCl$_3$ δ, ppm) 6.83 (br. s, 1H, NH), 6.02 (s, 1H), 5.42 (s, 1H), 4.21 (m, 1H), 3.58 (m, 1H), 2.87 (d, 3H), 2.28 (q, 2H), 2.17 (br. s, 1H, OH), 2.00 (d, 1H), 1.91 (s, 3H), 1.83 (d, 1H), 1.24 (m, 6H), 1.19-1.12 (m, 9H).

Example No. I.2-6

$^1$H-NMR (400 MHz, CDCl$_3$ δ, ppm) 6.15 (br. s, 1H, NH), 6.01 (s, 1H), 5.88 (s, 1H), 3.44 (br. s, 1H, OH), 2.86 (d, 3H), 2.53 (d, 1H), 2.42 (d, 1H), 2.28 (q, 2H), 2.16 (s, 3H), 1.25 (s, 3H), 1.13 (s, 3H), 1.11 (t, 3H).

Example No. I.2-13

$^1$H-NMR (400 MHz, CDCl$_3$ δ, ppm) 6.68 (br. s, 1H, NH), 5.97 (s, 1H), 5.42 (s, 1H), 4.21 (m, 1H), 4.16 (m, 1H), 3.59 (m, 1H), 2.27 (q, 2H), 2.14 (br. s, 1H, OH), 1.99 (d, 1H), 1.93 (s, 3H), 1.88 (d, 1H), 1.23 (m, 3H), 1.18 (m, 6H), 1.15-1.12 (m, 12H).

Example No. I.2-14

$^1$H-NMR (400 MHz, CDCl$_3$ δ, ppm) 5.96 (s, 1H), 5.88 (s, 1H), 5.84 (br. s, 1H, NH), 4.15 (m, 1H), 3.29 (br. s, 1H, OH), 2.55 (d, 1H), 2.42 (d, 1H), 2.26 (q, 2H), 2.16 (s, 3H), 1.25 (s, 3H), 1.18 (d, 6H), 1.12 (s, 3H), 1.10 (t, 3H).

Example No. I.2-17

$^1$H-NMR (400 MHz, CDCl$_3$ δ, ppm) 6.97 (br. s, 1H, NH), 5.99 (s, 1H), 5.44 (s, 1H), 4.21 (m, 1H), 3.59 (m, 1H), 2.79 (m, 1H), 2.28 (q, 2H), 2.16 (br. s, 1H, OH), 2.01 (d, 1H), 1.92 (s, 3H), 1.86 (d, 1H), 1.23 (m, 3H), 1.18 (m, 3H), 1.14-1.10 (m, 9H), 0.78 (m, 2H), 0.59 (m, 2H).

Example No. I.2-18

$^1$H-NMR (400 MHz, CDCl$_3$ δ, ppm) 6.31 (br. s, 1H, NH), 5.97 (s, 1H), 5.88 (s, 1H), 3.24 (br. s, 1H, OH), 2.78 (m, 1H), 2.52 (d, 1H), 2.43 (d, 1H), 2.26 (q, 2H), 2.16 (s, 3H), 1.25 (s, 3H), 1.12 (s, 3H), 1.10 (t, 3H), 0.81 (m, 2H), 0.53 (m, 2H).

Example No. I.2-25

$^1$H-NMR (400 MHz, CDCl$_3$ δ, ppm) 6.74 (br. s, 1H, NH), 5.99 (s, 1H), 5.41 (s, 1H), 4.20 (m, 1H), 3.58 (m, 1H), 3.04 (d, 2H), 2.29 (q, 2H), 2.16 (s, 1H), 2.12 (br. s, 1H, OH), 1.94 (d, 1H), 1.90 (s, 3H), 1.87 (d, 1H), 1.23 (m, 3H), 1.12 (m, 6H), 1.09 (m, 6H).

Example No. I.2-41

$^1$H-NMR (400 MHz, CDCl$_3$ δ, ppm) 8.74 (d, 2H), 8.08 (br. t, 1H, NH), 7.22 (t, 1H), 6.09 (s, 1H), 5.42 (s, 1H), 4.88 (d, 2H), 4.21 (m, 1H), 3.59 (m, 1H), 2.32 (q, 2H), 2.01 (d, 1H), 1.89 (s, 3H), 1.87 (d, 1H), 1.22 (m, 6H), 1.17-1.12 (m, 9H).

Example No. I.3-1

$^1$H-NMR (400 MHz, CDCl$_3$ δ, ppm) 6.38 (d, 1H), 6.21 (d, 1H), 5.92 (s, 1H), 5.84 (s, 1H), 2.45 (d, 1H), 2.28 (d, 1H), 1.95 (q, 2H), 1.90 (s, 3H), 1.10 (s, 3H), 1.08 (t, 3H), 1.03 (s, 3H).

Example No. II.19

$^1$H-NMR (400 MHz, CDCl$_3$ δ, ppm) 5.42 (d, 1H), 5.31 (d, 1H), 5.30 (s, 1H), 3.60 (m, 2H), 2.08 (d, 1H), 1.90 (s, 3H), 1.82 (d, 1H), 1.24 (t, 9H), 1.19 (q, 6H), 1.14 (d, 6H), 1.11 (s, 3H), 1.09 (s, 3H).

The present invention further provides for the use of at least one compound selected from the group consisting of substituted 5-(cyclohex-2-en-1-yl)penta-2,4-dienes and 5-(cyclohex-2-en-1-yl)pent-2-en-4-ynes of the formula (I), and of any desired mixtures of these substituted 5-(cyclohex-2-en-1-yl)penta-2,4-dienes and 5-(cyclohex-2-en-1-yl)pent-2-en-4-ynes of the formula (I) according to the invention, with active agrochemical compounds in accordance with the definition below, for enhancement of the resistance of plants to abiotic stress factors, preferably drought stress, and for invigoration of plant growth and/or for increasing plant yield.

The present invention further provides a spray solution for treatment of plants, comprising an amount, effective for enhancement of the resistance of plants to abiotic stress factors, of at least one compound selected from the group consisting of substituted 5-(cyclohex-2-en-1-yl)penta-2,4-dienes and 5-(cyclohex-2-en-1-yl)pent-2-en-4-ynes of the formula (I). The abiotic stress conditions which can be relativized may include, for example, heat, drought, cold and aridity stress (stress caused by aridity and/or lack of water), osmotic stress, waterlogging, elevated soil salinity, elevated exposure to minerals, ozone conditions, strong light conditions, limited availability of nitrogen nutrients, limited availability of phosphorus nutrients.

In one embodiment, it is possible to provide, for example, that the compounds envisaged in accordance with the invention, i.e. the appropriate substituted 5-(cyclohex-2-en-1-yl)penta-2,4-dienes and 5-(cyclohex-2-en-1-yl)pent-2-en-4-ynes of the formula (I), are applied by spray application to appropriate plants or plant parts to be treated. The compounds of the formula (I) or salts thereof are used as envisaged in accordance with the invention preferably with a dosage between 0.00005 and 3 kg/ha, more preferably between 0.0001 and 2 kg/ha, especially preferably between 0.0005 and 1 kg/ha, specifically preferably between 0.001 and 0.25 kg/ha.

The term "resistance to abiotic stress" is understood in the context of the present invention to mean various kinds of advantages for plants. Such advantageous properties are manifested, for example, in the following improved plant characteristics: improved root growth with regard to surface area and depth, increased stolon or tiller formation, stronger and more productive stolons and tillers, improvement in shoot growth, increased lodging resistance, increased shoot base diameter, increased leaf area, higher yields of nutrients and constituents, for example carbohydrates, fats, oils, proteins, vitamins, minerals, essential oils, dyes, fibers, better fiber quality, earlier flowering, increased number of flowers, reduced content of toxic products such as mycotoxins, reduced content of residues or disadvantageous constituents of any kind, or better digestibility, improved storage stability of the harvested material, improved tolerance to disadvantageous temperatures, improved tolerance to drought and aridity, and also oxygen deficiency as a result of waterlogging, improved tolerance to elevated salt contents in soils and water, enhanced tolerance to ozone stress, improved compatibility with respect to herbicides and other plant treatment compositions, improved water absorption and photosynthesis performance, advantageous plant properties, for example acceleration of ripening, more homogeneous ripening, greater attractiveness to beneficial animals, improved pollination, or other advantages well known to a person skilled in the art.

More particularly, the use according to the invention of one or more compounds of the formula (I) exhibits the advantages described in spray application to plants and plant parts. Combinations of the appropriate substituted 5-(cyclohex-2-en-1-yl)penta-2,4-dienes and 5-(cyclohex-2-en-1-yl)pent-2-en-4-ynes of the formula (I) with substances including insecticides, attractants, acaricides, fungicides, nematicides, herbicides, growth regulators, safeners, substances which influence plant maturity, and bactericides can likewise be employed in the control of plant disorders in the context of the present invention. In addition, the combined use of appropriate substituted 5-(cyclohex-2-en-1-yl)penta-2,4-dienes and 5-(cyclohex-2-en-1-yl)pent-2-en-4-ynes of the formula (I) with genetically modified cultivars with a view to increased tolerance to abiotic stress is likewise possible.

As is known, the various advantages for plants, which have been mentioned further above, can be combined in part, and generally applicable terms can be used to describe them. Such terms are, for example, the following names: phytotonic effect, resistance to stress factors, less plant stress, plant health, healthy plants, plant fitness, plant wellness, plant concept, vigor effect, stress shield, protective shield, crop health, crop health properties, crop health products, crop health management, crop health therapy, plant health, plant health properties, plant health products, plant health management, plant health therapy, greening effect or regreening effect, freshness, or other terms with which a person skilled in the art is quite familiar.

In the context of the present invention, a good effect on resistance to abiotic stress is understood to mean, without limitation,

- at least an emergence improved by generally 3%, especially more than 5%, more preferably more than 10%,
- at least a yield enhanced by generally 3%, especially more than 5%, more preferably more than 10%,
- at least a root development improved by generally 3%, especially more than 5%, more preferably more than 10%,
- at least a shoot size rising by generally 3%, especially more than 5%, more preferably more than 10%,
- at least a leaf area increased by generally 3%, especially more than 5%, more preferably more than 10%,
- at least a photosynthesis performance improved by generally 3%, especially more than 5%, more preferably more than 10%, and/or
- at least a flower formation improved by generally 3%, especially more than 5%, more preferably more than 10%, and the effects may occur individually or else in any combination of two or more effects.

The present invention further provides a spray solution for treatment of plants, comprising an amount, effective for enhancement of the resistance of plants to abiotic stress factors, of at least one compound of the formula (I). The spray solution may comprise other customary constituents, such as solvents, formulation aids, especially water. Further constituents may include active agrochemical compounds which are described further below.

The present invention further provides for the use of corresponding spray solutions for increasing the resistance of plants to abiotic stress factors. The remarks which follow apply both to the use according to the invention of the compounds of the formula (I) per se and to the corresponding spray solutions.

In accordance with the invention, it has additionally been found that the application, to plants or in their environment, of the compounds of the formula (I) in combination with at least one fertilizer as defined further below is possible.

Fertilizers which can be used in accordance with the invention together with the compounds of the formula (I) elucidated in detail above are generally organic and inorganic nitrogen-containing compounds, for example ureas, urea/formaldehyde condensation products, amino acids, ammonium salts and ammonium nitrates, potassium salts (preferably chlorides, sulfates, nitrates), salts of phosphoric acid and/or salts of phosphorous acid (preferably potassium salts and ammonium salts). In this context, particular mention should be made of the NPK fertilizers, i.e. fertilizers which contain nitrogen, phosphorus and potassium, calcium ammonium nitrate, i.e. fertilizers which additionally contain calcium, or ammonia nitrate sulfate (formula $(NH_4)_2SO_4NH_4NO_3$), ammonium phosphate and ammonium sulfate. These fertilizers are common knowledge to those skilled in the art; see also, for example, Ullmann's Encyclopedia of Industrial Chemistry, 5th edition, Vol. A 10, pages 323 to 431, Verlagsgesellschaft, Weinheim, 1987.

The fertilizers may also contain salts of micronutrients (preferably calcium, sulfur, boron, manganese, magnesium, iron, boron, copper, zinc, molybdenum and cobalt) and phytohormones (for example vitamin B1 and indole-3-acetic acid) or mixtures thereof. Fertilizers used in accordance with the invention may also contain other salts such as monoammonium phosphate (MAP), diammonium phosphate (DAP), potassium sulfate, potassium chloride, magnesium sulfate. Suitable amounts for the secondary nutrients, or trace elements, are amounts of 0.5 to 5% by weight, based on the overall fertilizer. Further possible ingredients are crop protection compositions, insecticides or fungicides, growth regulators or mixtures thereof. This will be explained in more detail further below.

The fertilizers can be used, for example, in the form of powders, granules, prills or compactates. However, the fertilizers can also be used in liquid form, dissolved in an aqueous medium. In this case, dilute aqueous ammonia can also be used as a nitrogen fertilizer. Further possible ingredients for fertilizers are described, for example, in Ullmann's Encyclopedia of Industrial Chemistry, 5th edition, 1987, volume A 10, pages 363 to 401, DE-A 41 28 828, DE-A 19 05 834 and DE-A 196 31 764. The general composition of the fertilizers which, within the context of the present invention, may take the form of straight and/or compound fertilizers, for example composed of nitrogen, potassium or phosphorus, may vary within a wide range. In general, a content of 1 to 30% by weight of nitrogen (preferably 5 to 20% by weight), 1 to 20% by weight of potassium (preferably 3 to 15% by weight) and a content of 1 to 20% by weight of phosphorus (preferably 3 to 10% by weight) is advantageous. The microelement content is usually in the ppm range, preferably in the range from 1 to 1000 ppm.

In the context of the present invention, the fertilizer and the compounds of the formula (I) may be administered simultaneously. However, it is also possible first to apply the fertilizer and then a compound of the formula (I), or first to apply a compound of the formula (I) and then the fertilizer. In the case of nonsynchronous application of a compound of the formula (I) and the fertilizer, the application in the context of the present invention is, however, effected in a functional relationship, especially within a period of generally 24 hours, preferably 18 hours, more preferably 12 hours, specifically 6 hours, more specifically 4 hours, even more specifically within 2 hours. In very particular embodiments of the present invention, the compound of the formula (I) according to the invention and the fertilizer are applied within a time frame of less than 1 hour, preferably less than 30 minutes, more preferably less than 15 minutes.

Preference is given to the use of compounds of the formula (I) on plants from the group of the useful plants, ornamentals, turfgrass types, commonly used trees which are used as ornamentals in the public and domestic sectors, and forestry trees. Forestry trees include trees for the production of timber, cellulose, paper and products made from parts of the trees. The term "useful plants" as used here refers to crop plants which are employed as plants for obtaining foods, animal feeds, fuels or for industrial purposes.

The useful plants include, for example, the following types of plants: triticale, durum (hard wheat), turf, vines, cereals, for example wheat, barley, rye, oats, rice, corn and millet/sorghum; beet, for example sugar beet and fodder beet; fruits, for example pome fruit, stone fruit and soft fruit, for example apples, pears, plums, peaches, almonds, cherries and berries, for example strawberries, raspberries, blackberries; legumes, for example beans, lentils, peas and soybeans; oil crops, for example oilseed rape, mustard, poppies, olives, sunflowers, coconuts, castor oil plants, cacao beans and peanuts; cucurbits, for example pumpkin/squash, cucumbers and melons; fiber plants, for example cotton, flax, hemp and jute; citrus fruit, for example, oranges, lemons, grapefruit and tangerines; vegetables, for example spinach, lettuce, asparagus, cabbage species, carrots, onions, tomatoes, potatoes and bell peppers; Lauraceae, for example avocado, *Cinnamomum*, camphor, or also plants such as tobacco, nuts, coffee, eggplant, sugar cane, tea, pepper, grapevines, hops, bananas, latex plants and ornamentals, for example flowers, shrubs, deciduous trees and coniferous trees. This enumeration does not constitute a restriction.

The following plants are considered to be particularly suitable target crops for the application of the method according to the invention: oats, rye, triticale, durum, cotton, eggplant, turf, pome fruit, stone fruit, soft fruit, corn, wheat, barley, cucumber, tobacco, vines, rice, cereals, pear, peppers, beans, soybeans, oilseed rape, tomato, bell pepper, melons, cabbage, potatoes and apple.

Examples of trees which can be improved by the method according to the invention include: *Abies* sp., *Eucalyptus* sp., *Picea* sp., *Pinus* sp., *Aesculus* sp., *Platanus* sp., *Tilia* sp., *Acer* sp., *Tsuga* sp., *Fraxinus* sp., *Sorbus* sp., *Betula* sp., *Crataegus* sp., *Ulmus* sp., *Quercus* sp., *Fagus* sp., *Salix* sp., *Populus* sp.

Preferred trees which can be improved by the method according to the invention include: from the tree species *Aesculus: A. hippocastanum, A. pariflora, A. carnea*; from the tree species *Platanus: P. aceriflora, P. occidentalis, P. racemosa*; from the tree species *Picea: P. abies*; from the tree species *Pinus: P. radiate, P. ponderosa, P. contorta, P. sylvestre, P. elliottii, P. montecola, P. albicaulis, P. resinosa, P. palustris, P. taeda, P. flexilis, P. jeffregi, P. baksiana, P. strobes*; from the tree species *Eucalyptus: E. grandis, E. globulus, E. camadentis, E. nitens, E. obliqua, E. regnans, E. pilularus*.

Particularly preferred trees which can be improved by the method according to the invention include: from the tree species *Pinus: P. radiate, P. ponderosa, P. contorta, P. sylvestre, P. strobes*; from the tree species *Eucalyptus: E. grandis, E. globulus* and *E. camadentis*.

Particularly preferred trees which can be improved by the method according to the invention include: horse chestnut, Platanaceae, linden tree, maple tree.

The present invention can also be applied to any turfgrass types, including cool-season turfgrasses and warm-season turfgrasses. Examples of cool-season turfgrasses are bluegrasses (*Poa* spp.), such as Kentucky bluegrass (*Poa pratensis* L.), rough bluegrass (*Poa trivialis* L.), Canada bluegrass (*Poa compressa* L.), annual bluegrass (*Poa annua* L.), upland bluegrass (*Poa glaucantha* Gaudin), wood bluegrass (*Poa nemoralis* L.) and bulbous bluegrass (*Poa bulbosa* L.); bentgrasses (*Agrostis* spp.) such as creeping bentgrass (*Agrostis palustris* Huds.), colonial bentgrass (*Agrostis tenuis* Sibth.), velvet bentgrass (*Agrostis canina* L.), South German Mixed Bentgrass (*Agrostis* spp. including *Agrostis tenius* Sibth., *Agrostis canina* L., and *Agrostis palustris* Huds.), and redtop (*Agrostis alba* L.);

fescues (*Festuca* spp.), such as red fescue (*Festuca rubra* L. spp. rubra), creeping fescue (*Festuca rubra* L.), chewings fescue (*Festuca rubra* commutata Gaud.), sheep fescue (*Festuca ovina* L.), hard fescue (*Festuca longifolia* Thuill.), hair fescue (*Festucu capillata* Lam.), tall fescue (*Festuca arundinacea* Schreb.) and meadow fescue (*Festuca elanor* L.);

ryegrasses (*Lolium* spp.), such as annual ryegrass (*Lolium multiflorum* Lam.), perennial ryegrass (*Lolium perenne* L.) and italian ryegrass (*Lolium multiflorum* Lam.);

and wheatgrasses (*Agropyron* spp.), such as fairway wheatgrass (*Agropyron cristatum* (L.) Gaertn.), crested wheatgrass (*Agropyron desertorum* (Fisch.) Schult.) and western wheatgrass (*Agropyron smithii* Rydb.).

Examples of further cool-season turfgrasses are beachgrass (*Ammophila breviligulata* Fern.), smooth bromegrass (*Bromus inermis* Leyss.), cattails such as Timothy (*Phleum pratense* L.), sand cattail (*Phleum subulatum* L.), orchard grass (*Dactylis glomerata* L.), weeping alkaligrass (*Puccinellia distans* (L.) Parl.) and crested dog's-tail (*Cynosurus cristatus* L.).

Examples of warm-season turfgrasses are Bermuda grass (*Cynodon* spp. L. C. Rich), *zoysia* grass (*Zoysia* spp. Willd.), St. Augustine grass (*Stenotaphrum secundatum* Walt Kuntze), centipede grass (*Eremochloa ophiuroides* Munro Hack.), carpet grass (*Axonopus affinis* Chase), Bahia grass (*Paspalum notatum* Flugge), Kikuyu grass (*Pennisetum clandestinum* Hochst. ex Chiov.), buffalo grass (*Buchloe dactyloids* (Nutt.) Engelm.), Blue gramma (*Bouteloua gracilis* (H.B.K.) Lag. ex Griffiths), seashore *paspalum* (*Paspalum vaginatum* Swartz) and sideoats grama (*Bouteloua curtipendula* (Michx. Torr.). Cool-season turfgrasses are generally preferred for the use in accordance with the invention. Especially preferred are bluegrass, bentgrass and redtop, fescues and ryegrasses. Bentgrass is especially preferred.

Particular preference is given to using the compounds of the formula (I) according to the invention to treat plants of the respective commercially available or commonly used plant cultivars. Plant cultivars are to be understood as meaning plants having new properties ("traits") and which have been obtained by conventional breeding, by mutagenesis or with the aid of recombinant DNA techniques. Crop plants may accordingly be plants which can be obtained by conventional breeding and optimization methods or by biotechnological and genetic engineering methods or combinations of these methods, including the transgenic plants and including the plant cultivars which are protectable and non-protectable by plant breeders' rights.

The treatment method according to the invention can thus also be used for the treatment of genetically modified organisms (GMOs), for example plants or seeds. Genetically modified plants (or transgenic plants) are plants in which a heterologous gene has been stably integrated into the genome. The expression "heterologous gene" essentially means a gene which is provided or assembled outside the plant and when introduced into the nuclear, chloroplastic or mitochondrial genome gives the transformed plant new or improved agronomic or other properties by expressing a protein or polypeptide of interest or by downregulating or silencing (an)other gene(s) which is/are present in the plant (using for example antisense technology, cosuppression technology or RNAi technology [RNA interference]). A heterologous gene that is located in the genome is also called a transgene. A transgene that is defined by its particular location in the plant genome is called a transformation or transgenic event.

Plants and plant varieties which are preferably treated with the compounds of the formula (I) according to the invention include all plants which have genetic material which imparts particularly advantageous, useful traits to these plants (whether obtained by breeding and/or biotechnological means).

Plants and plant varieties which can likewise be treated with the compounds of the formula (I) according to the invention are those plants which are resistant to one or more abiotic stress factors. Abiotic stress conditions may include, for example, heat, drought, cold and drought stress, osmotic stress, waterlogging, increased soil salinity, increased exposure to minerals, ozone conditions, strong light conditions, limited availability of nitrogen nutrients, limited availability of phosphorus nutrients or shade avoidance.

Plants and plant cultivars which can likewise be treated with the compounds of the formula (I) according to the invention are those plants which are characterized by enhanced yield characteristics. Enhanced yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can also be affected by improved plant architecture (under stress and non-stress conditions), including early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may also be treated with the compounds of the formula (I) according to the invention are hybrid plants that already express the characteristics of heterosis, or hybrid effect, which results in generally higher yield, higher vigor, better health and better resistance towards biotic and abiotic stress factors. Such plants are typically made by crossing an inbred male-sterile parent line (the female parent) with another inbred male-fertile parent line (the male parent). Hybrid seed is typically harvested from the male-sterile plants and sold to growers. Male-sterile plants can sometimes (for example in corn) be produced by detasseling (i.e. mechanical removal of the male reproductive organs or male flowers); however, it is more typical for male sterility to be the result of genetic determinants in the plant genome. In that case, and especially when seed is the desired product to be harvested from the hybrid plants, it is typically beneficial to ensure that male fertility in hybrid plants, which contain the genetic determinants responsible for male sterility, is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described for Brassica species (WO 92/005251, WO 95/009910, WO 98/27806, WO 05/002324, WO 06/021972 and U.S. Pat. No. 6,229,072). However, genetic determinants for male sterility can also be located in the nuclear genome. Male-sterile plants can also be obtained by plant biotechnology methods such as genetic engineering. A particularly useful means of obtaining male-sterile plants is described in WO 89/10396 in which, for example, a ribonuclease such as a barnase is selectively expressed in the tapetum cells in the stamens. Fertility can then be restored by expression in the tapetum cells of a ribonuclease inhibitor such as barstar (e.g. WO 91/002069).

Plants or plant varieties (obtained by plant biotechnology methods such as genetic engineering) which may also be treated with the compounds of the formula (I) according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., Science (1983), 221, 370-371), the CP4 gene of the bacterium *Agrobacterium* sp. (Barry et al., Curr. Topics Plant Physiol. (1992), 7, 139-145), the genes encoding a petunia EPSPS (Shah et al., Science (1986), 233, 478-481), a tomato EPSPS (Gasser et al., J. Biol. Chem. (1988), 263, 4280-4289) or an *Eleusine* EPSPS (WO 01/66704). It can also be a mutated EPSPS, as described, for example, in EP-A 0837944, WO 00/066746, WO 00/066747 or WO 02/026995.

Glyphosate-tolerant plants can also be obtained by expressing a gene that encodes a glyphosate oxidoreductase enzyme as described in U.S. Pat. No. 5,776,760 and U.S. Pat. No. 5,463,175. Glyphosate-tolerant plants can also be obtained by expressing a gene that encodes a glyphosate acetyl transferase enzyme as described, for example, in WO 02/036782, WO 03/092360, WO 05/012515 and WO 07/024, 782. Glyphosate-tolerant plants can also be obtained by selecting plants containing naturally occurring mutations of the above-mentioned genes as described, for example, in WO 01/024615 or WO 03/013226.

Other herbicide-resistant plants are for example plants which have been made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is, for example, an enzyme encoding a phosphinothricin acetyltransferase (such as the bar or pat protein from *Streptomyces* species for example).

Plants expressing an exogenous phosphinothricin acetyltransferase are described, for example, in U.S. Pat. No. 5,561,236; U.S. Pat. No. 5,648,477; U.S. Pat. No. 5,646,024; U.S. Pat. No. 5,273,894; U.S. Pat. No. 5,637,489; U.S. Pat. No. 5,276,268; U.S. Pat. No. 5,739,082; U.S. Pat. No. 5,908,810 and U.S. Pat. No. 7,112,665.

Further herbicide-tolerant plants are also plants that have been made tolerant to the herbicides inhibiting the enzyme hydroxyphenylpyruvate dioxygenase (HPPD). Hydroxyphenylpyruvate dioxygenases are enzymes that catalyze the reaction in which para-hydroxyphenylpyruvate (HPP) is converted to homogentisate. Plants tolerant to HPPD inhibitors can be transformed with a gene encoding a naturally-occurring resistant HPPD enzyme, or a gene encoding a mutated HPPD enzyme according to WO 96/038567, WO 99/024585 and WO 99/024586. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 99/034008 and WO 2002/36787. Tolerance of plants to HPPD inhibitors can also be improved by transforming plants with a gene encoding a prephenate dehydrogenase enzyme in addition to a gene encoding an HPPD-tolerant enzyme, as described in WO 2004/024928.

Further herbicide-resistant plants are plants that have been made tolerant to acetolactate synthase (ALS) inhibitors. Known ALS inhibitors include, for example, sulfonylurea, imidazolinone, triazolopyrimidines, pyrimidinyl oxy(thio)benzoates, and/or sulfonylaminocarbonyltriazolinone herbicides. Different mutations in the ALS enzyme (also known as acetohydroxy acid synthase, AHAS) are known to confer tolerance to different herbicides and groups of herbicides, as described, for example, in Tranel and Wright, Weed Science (2002), 50, 700-712, and also in U.S. Pat. No. 5,605,011, U.S. Pat. No. 5,378,824, U.S. Pat. No. 5,141,870 and U.S. Pat. No. 5,013,659. The production of sulfonylurea-tolerant plants and imidazolinone-tolerant plants has been described in U.S. Pat. No. 5,605,011; U.S. Pat. No. 5,013,659; U.S. Pat. No. 5,141,870; U.S. Pat. No. 5,767,361; U.S. Pat. No. 5,731,180; U.S. Pat. No. 5,304,732; U.S. Pat. No. 4,761,373; U.S. Pat. No. 5,331,107; U.S. Pat. No. 5,928,937; and U.S. Pat. No. 5,378,824; and also in the international publication WO 96/033270. Further imidazolinone-tolerant plants have also been described, for example in WO 2004/040012, WO 2004/106529, WO 2005/020673, WO 2005/093093, WO 2006/007373, WO 2006/015376, WO 2006/024351 and WO 2006/060634. Further sulfonylurea- and imidazolinone-tolerant plants have also been described, for example in WO 2007/024782.

Further plants tolerant to ALS-inhibitors, in particular to imidazolinones, sulfonylureas and/or sulfamoylcarbonyltriazolinones can be obtained by induced mutagenesis, by selection in cell cultures in the presence of the herbicide or by mutation breeding, as described, for example, for soybeans in U.S. Pat. No. 5,084,082, for rice in WO 97/41218, for sugarbeet in U.S. Pat. No. 5,773,702 and WO 99/057965, for lettuce in U.S. Pat. No. 5,198,599 or for sunflower in WO 2001/065922.

Plants or plant cultivars (obtained by plant biotechnology methods such as genetic engineering) which may also be treated with the compounds of the formula (I) according to the invention are insect-resistant transgenic plants, i.e. plants made resistant to attack by certain target insects. Such plants can be obtained by genetic transformation, or by selection of plants containing a mutation imparting such insect resistance.

In the present context, the term "insect-resistant transgenic plant" includes any plant containing at least one transgene comprising a coding sequence encoding:

1) an insecticidal crystal protein from *Bacillus thuringiensis* or an insecticidal portion thereof, such as the insecticidal crystal proteins compiled by Crickmore et al., Microbiology and Molecular Biology Reviews (1998), 62, 807-813, updated by Crickmore et al. (2005) in the *Bacillus thuringiensis* toxin nomenclature, (online at: http://www.lifesci.sussex.ac.uk/Home/Neil_Crickmore/Bt/), or insecticidal portions thereof, for example proteins of the Cry protein classes Cry1Ab, Cry1Ac, Cry1F, Cry2Ab, Cry3Ae or Cry3Bb or insecticidal portions thereof; or 2) a crystal protein from *Bacillus thuringiensis* or a portion thereof which is insecticidal in the presence of a second, other crystal protein from *Bacillus thuringiensis* or a portion thereof, such as the binary toxin made up of the Cy34 and Cy35 crystal proteins (Moellenbeck et al., Nat. Biotechnol. (2001), 19, 668-72; Schnepf et al., Applied Environm. Microb. (2006), 71, 1765-1774); or 3) a hybrid insecticidal protein comprising parts of two different insecticidal crystal proteins from *Bacillus thuringiensis*, such as a hybrid of the proteins of 1) above or a hybrid of the proteins of 2) above, for example the Cry1A. 105 protein produced by corn event MON98034 (WO 2007/027777); or 4) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation, such as the Cry3Bb1 protein in corn events MON863 or MON88017, or the Cry3A protein in corn event MIR 604; or 5) an insecticidal secreted protein from *Bacillus thuringiensis* or *Bacillus cereus*, or an insecticidal portion thereof, such as the vegetative insecticidal proteins (VIPs) listed under the following link, for example proteins from the VIP3Aa protein class: http://www.lifesci.sussex.ac.uk/Home/Neil_Crickmore/Bt/vip.html; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or 7) a hybrid insecticidal protein comprising portions from different secreted proteins from *Bacillus thuringiensis* or *Bacillus cereus*, such as a hybrid of the proteins in 1) above or a hybrid of the proteins in 2) above; or 8) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation (while still encoding an insecticidal protein), such as the VIP3Aa protein in cotton event COT 102.

Of course, insect-resistant transgenic plants, as used herein, also include any plant comprising a combination of genes encoding the proteins of any one of the above classes 1 to 8. In one embodiment, an insect-resistant plant contains more than one transgene encoding a protein of any one of the above classes 1 to 8, to expand the range of the target insect species affected or to delay insect resistance development to the plants, by using different proteins insecticidal to the same target insect species but having a different mode of action, such as binding to different receptor binding sites in the insect.

Plants or plant cultivars (obtained by plant biotechnology methods such as genetic engineering) which may also be treated with the compounds of the formula (I) according to the invention are tolerant to abiotic stress factors. Such plants can be obtained by genetic transformation, or by selection of plants containing a mutation imparting such stress resistance. Particularly useful stress tolerance plants include:

a. plants which contain a transgene capable of reducing the expression and/or the activity of the poly(ADP-ribose)polymerase (PARP) gene in the plant cells or plants, as described in WO 2000/004173 or EP 04077984.5 or EP 06009836.5;

b. plants which contain a stress tolerance-enhancing transgene capable of reducing the expression and/or the activity of the PARG-encoding genes of the plants or plant cells, as described, for example, in WO 2004/090140;

c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyl transferase, nicotinamide adenine dinucleotide synthetase or nicotinamide phosphoribosyltransferase, as described, for example, in EP 04077624.7 or WO 2006/133827 or PCT/EP07/002, 433.

Plants or plant varieties (obtained by plant biotechnology methods such as genetic engineering) which may also be treated with the compounds of the formula (I) according to the invention show altered quantity, quality and/or storage stability of the harvested product and/or altered properties of specific ingredients of the harvested product such as, for example:

1) Transgenic plants which synthesize a modified starch which is altered with respect to its chemophysical traits, in particular the amylose content or the amylose/amylopectin ratio, the degree of branching, the average chain length, the distribution of the side chains, the viscosity behavior, the gel resistance, the grain size and/or grain morphology of the starch in comparison to the synthesized starch in wild-type plant cells or plants, such that this modified starch is better suited for certain applications. These transgenic plants synthesizing a modified starch are described, for example, in EP 0571427, WO 95/004826, EP 0719338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO 99/58688, WO 99/58690, WO 99/58654, WO 2000/008184, WO 2000/008185, WO 2000/28052, WO 2000/77229, WO 2001/12782, WO 2001/12826, WO 2002/101059, WO 2003/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 2000/22140, WO 2006/063862, WO 2006/072603, WO 2002/034923, EP 06090134.5, EP 06090228.5, EP 06090227.7, EP 07090007.1, EP 07090009.7, WO 2001/14569, WO 2002/79410, WO 2003/33540, WO 2004/078983, WO 2001/19975, WO 95/26407, WO 96/34968, WO 98/20145, WO 99/12950, WO 99/66050, WO 99/53072, U.S. Pat. No. 6,734, 341, WO 2000/11192, WO 98/22604, WO 98/32326, WO 2001/98509, WO 2001/98509, WO 2005/002359, U.S. Pat. No. 5,824,790, U.S. Pat. No. 6,013,861, WO 94/004693, WO 94/009144, WO 94/11520, WO 95/35026 and WO 97/20936.

2) Transgenic plants which synthesize non starch carbohydrate polymers or which synthesize non starch carbohydrate polymers with altered properties in comparison to wild type plants without genetic modification. Examples are plants producing polyfructose, especially of the inulin and levan type, as described in EP 0663956, WO 96/001904, WO 96/021023, WO 98/039460 and WO 99/024593, plants producing alpha-1,4-glucans, as described in WO 95/031553, US 2002/031826, U.S. Pat. No. 6,284,479, U.S. Pat. No. 5,712,107, WO 97/047806, WO 97/047807, WO 97/047808 and WO 2000/14249, plants producing alpha-1,6-branched alpha-1,4-glucans, as described in WO 2000/73422, and plants producing alternan, as described in WO 2000/047727, EP 06077301.7, U.S. Pat. No. 5,908,975 and EP 0728213.

3) Transgenic plants which produce hyaluronan, as for example described in WO 06/032538, WO 2007/039314, WO 2007/039315, WO 2007/039316, JP 2006/304779 and WO 2005/012529.

Plants or plant cultivars (obtained by plant biotechnology methods such as genetic engineering) which may also be treated with the compounds of the formula (I) according to the invention are plants, such as cotton plants, with altered fiber characteristics. Such plants can be obtained by genetic transformation, or by selection of plants containing a mutation imparting such altered fiber characteristics and include:

a) plants, such as cotton plants, which contain an altered form of cellulose synthase genes, as described in WO 98/000549;

b) plants, such as cotton plants, which contain an altered form of rsw2 or rsw3 homologous nucleic acids, as described in WO 2004/053219;

c) plants, such as cotton plants, with an increased expression of sucrose phosphate synthase, as described in WO 2001/017333;

d) plants, such as cotton plants, with an increased expression of sucrose synthase, as described in WO 02/45485;

e) plants, such as cotton plants, wherein the timing of the plasmodesmatal gating at the basis of the fiber cell is altered, for example through downregulation of fiber-selective $\beta$-1,3-glucanase as described in WO 2005/017157;

f) plants, such as cotton plants, which have fibers with altered reactivity, for example through expression of the N-acetylglucosamine transferase gene including nodC and chitin synthase genes, as described in WO 2006/136351.

Plants or plant cultivars (obtained by plant biotechnology methods such as genetic engineering) which may also be treated with the compounds of the formula (I) according to the invention are plants, such as oilseed rape or related *Brassica* plants, with altered oil profile characteristics. Such plants can be obtained by genetic transformation, or by selection of plants containing a mutation imparting such altered oil characteristics and include:

a) plants, such as oilseed rape plants, which produce oil having a high oleic acid content, as described, for example, in U.S. Pat. No. 5,969,169, U.S. Pat. No. 5,840,946 or U.S. Pat. No. 6,323,392 or U.S. Pat. No. 6,063,947;

b) plants, such as oilseed rape plants, which produce oil having a low linolenic acid content, as described in U.S. Pat. No. 6,270,828, U.S. Pat. No. 6,169,190 or U.S. Pat. No. 5,965,755;

c) plants, such as oilseed rape plants, which produce oil having a low level of saturated fatty acids, as described, for example, in U.S. Pat. No. 5,434,283.

Particularly useful transgenic plants which may be treated with the compounds of the formula (I) according to the invention are plants containing transformation events, or a combination of transformation events, and that are listed for example in the databases of various national or regional regulatory agencies.

Particularly useful transgenic plants which may be treated with the compounds of the formula (I) according to the invention are, for example, plants which comprise one or more genes which encode one or more toxins and are the transgenic plants available under the following trade names: YIELD GARD® (for example corn, cotton, soybeans), KnockOut® (for example corn), BiteGard® (for example corn), BT-Xtra® (for example corn), StarLink® (for example corn), Bollgard® (cotton), Nucotn® (cotton), Nucotn 33B® (cotton), NatureGard® (for example corn), Protecta® and NewLeaf® (potato). Examples of herbicide-tolerant plants which may be mentioned are maize varieties, cotton varieties and soy bean varieties which are available under the following trade names: Roundup Ready® (tolerance to glyphosate, for example corn, cotton, soybeans), Liberty Link® (tolerance to phosphinothricin, for example oilseed rape), IMI® (tolerance to imidazolinone) and SOS® (tolerance to sulfonylurea), for example corn. Herbicide-resistant plants (plants bred in a conventional manner for herbicide tolerance) which should be mentioned include the varieties sold under the Clearfield® name (for example corn).

The compounds of the formula (I) to be used in accordance with the invention can be converted to customary formulations, such as solutions, emulsions, wettable powders, water- and oil-based suspensions, powders, dusts, pastes, soluble powders, soluble granules, granules for broadcasting, suspoemulsion concentrates, natural substances impregnated with active ingredient, synthetic substances impregnated with active ingredient, fertilizers, and also microencapsulations in polymeric substances. In the context of the present invention, it is especially preferred when the compounds of the formula (I) are used in the form of a spray formulation.

The present invention therefore additionally also relates to a spray formulation for enhancing the resistance of plants to abiotic stress. A spray formulation is described in detail hereinafter:

The formulations for spray application are produced in a known manner, for example by mixing the compounds of the formula (I) for use in accordance with the invention with extenders, i.e. liquid solvents and/or solid carriers, optionally with use of surfactants, i.e. emulsifiers and/or dispersants and/or foam formers. Further customary additives, for example customary extenders and solvents or diluents, dyes, wetting agents, dispersants, emulsifiers, antifoams, preservatives, secondary thickeners, stickers, gibberellins and also water, can optionally also be used. The formulations are produced either in suitable facilities or else before or during application.

The auxiliaries used may be those substances which are suitable for imparting, to the composition itself and/or to preparations derived therefrom (for example spray liquors), particular properties such as particular technical properties and/or else special biological properties. Typical auxiliaries include: extenders, solvents and carriers.

Suitable extenders are, for example, water, polar and nonpolar organic chemical liquids, for example from the classes of the aromatic and nonaromatic hydrocarbons (such as paraffins, alkylbenzenes, alkylnaphthalenes, chlorobenzenes), the alcohols and polyols (which may optionally also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulfones and sulfoxides (such as dimethyl sulfoxide).

If the extender used is water, it is also possible to use, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulfoxide, and also water.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

Suitable wetting agents which may be present in the formulations which can be used in accordance with the invention are all substances which promote wetting and which are conventionally used for the formulation of agrochemical active compounds. Preference is given to using alkylnaphthalenesulfonates, such as diisopropyl or diisobutylnaphthalenesulfonates.

Suitable dispersants and/or emulsifiers which may be present in the formulations which can be used in accordance with the invention are all nonionic, anionic and cationic dispersants conventionally used for the formulation of agrochemical active compounds. Preference is given to using nonionic or anionic dispersants or mixtures of nonionic or anionic dispersants. Suitable nonionic dispersants are especially ethylene oxide/propylene oxide block polymers, alkylphenol polyglycol ethers and tristryrylphenol polyglycol ethers, and the phosphated or sulfated derivatives thereof. Suitable anionic dispersants are, in particular, lignosulfonates, polyacrylic acid salts and arylsulfonate/formaldehyde condensates.

Suitable antifoams which may be present in the formulations which can be used in accordance with the invention are all foam-inhibiting substances conventionally used for the formulation of agrochemically active compounds. Silicone antifoams and magnesium stearate can preferably be used.

Suitable preservatives which may be present in the formulations which can be used in accordance with the invention are all substances usable for such purposes in agrochemical compositions. Dichlorophene and benzyl alcohol hemiformal may be mentioned by way of example.

Suitable secondary thickeners which may be present in the formulations which can be used in accordance with the invention are all substances usable for such purposes in agrochemical compositions. Cellulose derivatives, acrylic acid derivatives, xanthan, modified clays and finely divided silica are preferred.

Suitable stickers which may be present in the formulations which can be used in accordance with the invention include all customary binders usable in seed-dressing products. Polyvinylpyrrolidone, polyvinyl acetate, polyvinyl alcohol and tylose may be mentioned as being preferred. Suitable gibberellins which can be present in the formulations which can be used in accordance with the invention are preferably the gibberellins A1, A3 (=gibberellic acid), A4 and A7; gibberellic acid is especially preferably used. The gibberellins are known (cf. R. Wegler "Chemie der Pflanzenschutz- and Schädlingsbekämpfungsmittel" [Chemistry of the Crop Protection Compositions and Pesticides], vol. 2, Springer Verlag, 1970, pp. 401-412).

Other possible additives are perfumes, mineral or vegetable oils which are optionally modified, waxes and nutrients (including trace nutrients), such as salts of iron, manganese, boron, copper, cobalt, molybdenum and zinc. Additionally present may be stabilizers, such as cold stabilizers, antioxidants, light stabilizers or other agents which improve chemical and/or physical stability.

The formulations contain generally between 0.01 and 98% by weight, preferably between 0.5 and 90%, of the compound of the formula (I).

The compounds of the formula (I) according to the invention may be present in commercially available formulations, and also in the use forms, prepared from these formulations, as a mixture with other active compounds, such as insecticides, attractants, sterilizing agents, bactericides, acaricides, nematicides, fungicides, growth-regulating substances, herbicides, safeners, fertilizers or semiochemicals.

In addition, the described positive effect of the compounds of the formula (I) on the plants' own defenses can be supported by an additional treatment with insecticidally, fungicidally or bactericidally active compounds.

Preferred times for the application of compounds of the formula (I) for enhancing resistance to abiotic stress are treatments of the soil, stems and/or leaves with the approved application rates.

The active compounds of the formula (I) may generally additionally be present in their commercial formulations and in the use forms prepared from these formulations in mixtures with other active compounds, such as insecticides, attractants, sterilants, acaricides, nematicides, fungicides, bactericides, growth-regulating substances, substances which influence plant maturity, safeners or herbicides. Particularly favorable mixing partners are, for example, the active compounds of the different classes, specified below in groups, without any preference resulting from the sequence thereof:

Fungicides:

F1) nucleic acid synthesis inhibitors, for example benalaxyl, benalaxyl-M, bupirimate, chiralaxyl, clozylacon, dimethirimol, ethirimol, furalaxyl, hymexazole, metalaxyl, metalaxyl-M, ofurace, oxadixyl, oxolinic acid;

F2) mitosis and cell division inhibitors, for example benomyl, carbendazim, diethofencarb, fuberidazole, fluopicolid, pencycuron, thiabendazole, thiophanate-methyl, zoxamide and chloro-7-(4-methylpiperidin-1-yl)-6-(2,4,6-trifluorophenyl)[1,2,4]triazolo[1,5-a]pyrimidine;

F3) respiratory chain complex I/II inhibitors, for example diflumetorim, bixafen, boscalid, carboxin, diflumethorim, fenfuram, fluopyram, flutolanil, furametpyr, mepronil, oxycarboxin, penflufen, penthiopyrad, thifluzamid, N-[2-(1,3-dimethylbutyl)phenyl]-5-fluoro-1,3-dimethyl-1H-pyrazole-4-carboxamide, isopyrazam, sedaxan, 3-(difluoromethyl)-1-methyl-N-(3',4',5'-trifluorobiphenyl-2-yl)-1H-pyrazole-4-carboxamide, 3-(difluoromethyl)-1-methyl-N-[2-(1,1,2,2-tetrafluoroethoxy)phenyl]-1H-pyrazole-4-carboxamide, 3-(difluoromethyl)-N-[4-fluoro-2-(1,1,2,3,3,3-hexafluoropropoxy)phenyl]-1-methyl-1H-pyrazole-4-carboxamide, N-[1-(2,4-dichlorophenyl)-1-methoxypropan-2-yl]-3-(difluoromethyl)-1-methyl-1H-pyrazole-4-carboxamide and corresponding salts;

F4) respiratory chain complex III inhibitors, for example amisulbrom, azoxystrobin, cyazofamid, dimoxystrobin, enestrobin, famoxadon, fenamidon, fluoxastrobin, kresoxim-methyl, metominostrobin, orysastrobin, pyraclostrobin, pyribencarb, picoxystrobin, trifloxystrobin, (2E)-2-(2-{[(6-(3-chloro-2-methylphenoxy)-5-fluoropyrimidin-4-yl]oxy}phenyl)-2-(methoxyimino)-N-methylethanamide, (2E)-2-(ethoxyimino)-N-methyl-2-(2-{[({(1E)-1-[3-(trifluoromethyl)phenyl]ethylidene}amino)oxy]methyl}phenyl)ethanamide and corresponding salts, (2E)-2-(methoxyimino)-N-methyl-2-{2-[(E)-({1-[3-(trifluoromethyl)phenyl]ethoxy}imino)methyl]phenyl}ethanamide, (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide, (2E)-2-{2-[({[(2E,3E)-4-(2,6-dichlorophenyl)but-3-en-2-ylidene]amino}oxy)methyl]phenyl}-2-(methoxyimino)-N-methylethanamide, 2-chloro-N-(1,1,3-trimethyl-2,3-dihydro-1H-inden-4-yl)pyridine-3-carboxamide, 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, 2-methyl (2-[({cyclopropyl[(4-methoxyphenyl)imino]methyl}sulfanyl)methyl]phenyl}-3-methoxyacrylate, N-(3-ethyl-3,5,5-trimethylcyclohexyl)-3-(formylamino)-2-hydroxybenzamide and corresponding salts;

F5) decouplers, for example dinocap, fluazinam;

F6) ATP production inhibitors, for example fentin acetate, fentin chloride, fentin hydroxide, silthiofam F7) amino acid and protein biosynthesis inhibitors, for example andoprim, blasticidin-S, cyprodinil, kasugamycin, kasugamycin hydrochloride hydrate, mepanipyrim, pyrimethanil F8) signal transduction inhibitors, for example fenpiclonil, fludioxonil, quinoxyfen F9) lipid and membrane synthesis inhibitors, for example chlozolinate, iprodione, procymidone, vinclozolin, ampropylfos, potassium-ampropylfos, edifenphos, iprobenfos (IBP), isoprothiolane, pyrazophos, tolclofos-methyl, biphenyl, iodocarb, propamocarb, propamocarb hydrochloride F10) ergosterol biosynthesis inhibitors, for example fenhexamid, azaconazole, bitertanol, bromuconazole, diclobutrazole, difenoconazole, diniconazole, diniconazole-M, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, spiroxamine, tebuconazole, triadimefon, triadimenol, triticonazole, uniconazole, voriconazole, imazalil, imazalil sulfate, oxpoconazole, fenarimol, flurprimidol, nuarimol, pyrifenox, triforin, pefurazoate, prochloraz, triflumizole, viniconazole, aldimorph, dodemorph, dodemorph acetate, fenpropimorph, tridemorph, fenpropidin, naftifin, pyributicarb, terbinafin, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N'-{5-(difluoromethyl)-2-methyl-4-[3-(trimethylsilyl)propoxy]phenyl}-N-ethyl-N-methylimidoformamide, N-ethyl-N-methyl-N'-{2-methyl-5-(trifluoromethyl)-4-[3-(trimethylsilyl)propoxy]phenyl}imidoformamide and O-{1-[(4-methoxyphenoxy)methyl]-2,2-dimethylpropyl}-1H-imidazole-1-carbothioate;

F11) cell wall synthesis inhibitors, for example benthiavalicarb, bialaphos, dimethomorph, flumorph, iprovalicarb, polyoxins, polyoxorim, validamycin A F12) melanine biosynthesis inhibitors, for example capropamide, diclocymet, fenoxanil, phthalide, pyroquilon, tricyclazole F13) resistance induction, for example acibenzolar-5-methyl, probenazole, tiadinil F14) multisite, for example captafol, captan, chlorothalonil, copper salts such as: copper hydroxide, copper naphthenate, copper oxychloride, copper sulfate, copper oxide, oxine-copper and Bordeaux mixture, dichlofluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulfur and sulfur preparations containing calcium polysulfide, thiram, tolylfluanid, zineb, ziram F15) unknown mechanism, for example amibromdol, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methyl sulfate, diphenylamine, ethaboxam, ferimzone, flumetover, flusulfamide, fluopicolide, fluoroimide, fosatyl-Al, hexachlorobenzene, 8-hydroxyquinoline sulfate, iprodione, irumamycin, isotianil, methasulfocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrolnitrin, quintozene, tecloftalam, tecnazene, triazoxide, trichlamide, zarilamid and 2,3,5,6-tetrachloro-4-(methylsulfonyl)pyridine, N-(4-chloro-2-nitrophenyl)-N-ethyl-4-methylbenzenesulfonamide, 2-amino-4-methyl-N-phenyl-5-thiazolecarboxamide, 2-chloro-N-(2,3-dihydro-1,1,3-trimethyl-1H-inden-4-yl)-3-pyridinecarboxamide, 3-[5-(4-chlorophenyl)-2,3-dimethylisoxazolidin-3-yl]pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl)phenyl]ethylidene]amino]oxy]methyl]phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxyphenyhimino]methyl]thio]methyl]-.alpha.-(methoxymethylene)benzacetate, 4-chloro-alpha-propynyloxy-N-[2-[3-methoxy-4-(2-propynyloxy)phenyl]ethyl]benzacetamide, (2S)—N-[2-[4-[[3-(4-chlorophenyl)-2-propynyl]oxy]-3-methoxyphenyl]ethyl]-3-methyl-2-[(methylsulfonyl)amino]butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidine-7-amine, 5-chloro-N-[(1R)-1,2-dimethylpropyl]-6-(2,4,6-trifluorophenyl)[1,2,4]triazolo[1,5-a]pyrimidine-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N-{(Z)-[(cyclopropylmethoxy)imino][6-(difluoromethoxy)-2,3-difluorophenyl]methyl}-2-benzacetamide, N-(3-ethyl-3,5,5-trimethylcyclohexyl)-3-formylamino-2-hydroxybenzamide, 2-[[[[1-[3-(1-fluoro-2-phenylethyl)oxy]phenyl]ethylidene]amino]oxy]methyl]-alpha-(methoxyimino)-N-methyl-alphaE-benzacetamide, N-{2-[3-chloro-5-(trifluoromethyl)pyridin-2-yl]ethyl}-2-(trifluoromethyl)benzamide, N-(3',4'-dichloro-5-fluorobiphenyl-2-yl)-3-(difluoromethyl)-1-methyl-1H-pyrazole-4-carboxamide, N-(6-methoxy-3-pyridinyl)cyclopropanecarboxamide, 1-[(4-methoxyphenoxy)methyl]-2,2-dimethylpropyl-1H-imidazole-1-carboxylic acid, O-[1-[(4-methoxyphenoxy)methyl]-2,2-dimethylpropyl]-1H-imidazole-1-carbothioic acid, 2-(2-{([6-(3-chloro-2-methylphenoxy)-5-fluoropyrimidin-4-yl]oxy}phenyl)-2-(methoxyimino)-N-methylacetamide.

Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulfate and other copper preparations.

Insecticides/Acaricides/Nematicides:

I1) acetylcholinesterase (AChE) inhibitors, for example carbamates, e.g. alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, e.g. acephate, azamethiphos, azinphos (-methyl, -ethyl), cadusafos, chlorethoxyfos, chlorfenvinphos, chlormephos, chlorpyrifos (-methyl), coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, isofenphos, isopropyl O-(methoxyaminothiophosphoryl) salicylate, isoxathion, malathion, mecarbam, methamidophos, methidathion, mevinphos, monocrotophos, nalad, omethoate, oxydemeton-methyl, parathion (-methyl), phenthoate, phorate, phosalone, phosmet, phosphamidon, phoxim, pirimiphos (-methyl), profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

I2) GABA-gated chloride channel antagonists, for example organochlorines, e.g. chlordane and endosulfan (alpha-); or fiproles (phenylpyrazoles), e.g. ethiprole, fipronil, pyrafluprole and pyriprole.

I3) Sodium channel modulators/voltage-gated sodium channel blockers, for example pyrethroids, e.g. acrinathrin, allethrin (d-cis-trans, d-trans), bifenthrin, bioallethrin, bioallethrin-5-cyclopentenyl, bioresmethrin, cycloprothrin, cyfluthrin (beta-), cyhalothrin (gamma-, lambda-), cypermethrin (alpha-, beta-, theta-, zeta-), cyphenothrin [(1R)-trans-isomers], deltamethrin, dimefluthrin, empenthrin [(EZ)-(1R)-isomers], esfenvalerate, etofenprox, fenpropathrin, fenvalerate, flucythrinate, flumethrin, fluvalinate (tau-), halfenprox, imiprothrin, metofluthrin, permethrin, phenothrin [(1R)-trans-isomer], prallethrin, profluthrin, pyrethrins (pyrethrum), resmethrin, RU 15525, silafluofen, tefluthrin, tetramethrin [(1R)-isomers], tralomethrin, transfluthrin and ZXI 8901; or _DDT; or methoxychlor.

I4) Nicotinergic acetylcholine receptor agonists, for example neonicotinoids, e.g. acetamiprid, clothianidin, dinotefuran, imidacloprid, nitenpyram, thiacloprid, thiamethoxam; or nicotine.

I5) Allosteric acetylcholine receptor modulators (agonists) for example spinosyns, e.g. spinetoram and spinosad.

I6) Chloride channel activators, for example avermectins/milbemycins, e.g. abamectin, emamectin, emamectin benzoate, lepimectin and milbemectin.

I7) Juvenile hormone analogs, e.g. hydroprene, kinoprene, methoprene; or fenoxycarb; pyriproxyfen.

I8) Active ingredients with unknown or non-specific mechanisms of action, for example fumigants, for example methyl bromide and other alkyl halides; or chloropicrin; sulfuryl fluoride; borax; tartar emetic.

I9) Selective antifeedants, e.g. pymetrozine; or flonicamid.

I10) Mite growth inhibitors, e.g. clofentezine, diflovidazin, hexythiazox, etoxazole.

I11) Microbial disruptors of the insect gut membrane, for example *Bacillus thuringiensis* subspecies *israelensis, Bacillus sphaericus, Bacillus thuringiensis* subspecies *aizawai, Bacillus thuringiensis* subspecies *kurstaki, Bacillus thuringiensis* subspecies *tenebrionis*, and BT plant proteins, for example Cry1Ab, Cry1Ac, Cry1Fa, Cry2Ab, mCry3A, Cry3Ab, Cry3Bb, Cry34/35Ab1.

I12) Oxidative phosphorylation inhibitors, ATP disruptors, for example diafenthiuron; or organotin compounds, e.g. azocyclotin, cyhexatin, fenbutatin oxide; or propargite; tetradifon.

I13) Oxidative phosphorylation decouplers through interruption of the H proton gradient, for example chlorfenapyr and DNOC.

I14) Nicotinergic acetylcholine receptor antagonists, for example bensultap, cartap (-hydrochloride), thiocyclam, and thiosultap (-sodium).

I15) Chitin biosynthesis inhibitors, type 0, for example benzoylureas, e.g. bistrifluoron, chlorfluazuron, diflubenzuron, flucycloxuron, flufenoxuron, hexaflumuron, lufenuron, novaluron, noviflumuron, teflubenzuron and triflumuron.

I16) Chitin biosynthesis inhibitors, type 1, for example buprofezin.

I17) Molting disruptors, for example cyromazine.

I18) Ecdysone agonists/disruptors, for example diacylhydrazines, for example chromafenozide, halofenozide, methoxyfenozide and tebufenozide.

I19) Octopaminergic agonists, for example amitraz.

I20) Complex III electron transport inhibitors, for example hydramethylnone; acequinocyl; fluacrypyrim.

I21) Complex I electron transport inhibitors, for example from the group of the METI acaricides, e.g. fenazaquin, fenpyroximate, pyrimidifen, pyridaben, tebufenpyrad, tolfenpyrad; or rotenone (Derris).

I22) Voltage-gated sodium channel blockers, e.g. indoxacarb; metaflumizone.

I23) Inhibitors of acetyl-CoA carboxylase, for example tetronic acid derivatives, e.g. spirodiclofen and spiromesifen; or tetramic acid derivatives, e.g. spirotetramat.

I24) Complex IV electron transport inhibitors, for example phosphines, e.g. aluminum phosphide, calcium phosphide, phosphine, zinc phosphide; or cyanide.

I25) Complex II electron transport inhibitors, for example cyenopyrafen.

I26) Ryanodine receptor effectors, for example diamides, e.g. flubendiamide, chlorantraniliprole (Rynaxypyr), cyantraniliprole (Cyazypyr) and 3-bromo-N-{2-bromo-4-chloro-6-[(1-cyclopropylethyl)carbamoyl]phenyl}-1-(3-chloropyridin-2-yl)-1H-pyrazole-5-carboxamide (known from WO2005/077934) or methyl 2-[3,5-dibromo-2-{([3-bromo-1-(3-chloropyridin-2-yl)-1H-pyrazol-5-yl]carbonyl}amino)benzoyl]-1,2-dimethyl hydrazinecarboxylate (known from WO2007/043677).

Further active compounds having an unknown mechanism of action, such as, for example, azadirachtin, amidoflumet, benzoximate, bifenazate, chinomethionat, cryolite, cyflumetofen, dicofol, 5-chloro-2-[(3,4,4-trifluorobut-3-en-1-yl) sulfonyl]-1,3-thiazole, flufenerim, pyridalyl and pyrifluquinazon; furthermore preparations based on *Bacillus firmus* (I-1582, BioNeem, Votivo) and the following known active compounds 4-{[(6-bromopyrid-3-yl)methyl](2-fluoroethyl) amino}furan-2(5H)-one (known from WO 2007/115644), 4-{[(6-fluoropyrid-3-yl)methyl](2,2-difluoroethyl) amino}furan-2(5H)-one (known from WO 2007/115644), 4-{[(2-chloro-1,3-thiazol-5-yl)methyl](2-fluoroethyl) amino}furan-2(5H)-one (known from WO 2007/115644), 4-{[(6-chloropyrid-3-yl)methyl](2-fluoroethyl) amino}furan-2(5H)-one (known from WO 2007/115644), 4-{[(6-chloropyrid-3-yl)methyl](2,2-difluoroethyl) amino}furan-2(5H)-one (known from WO 2007/115644), 4-{[(6-chloro-5-fluoropyrid-3-yl)methyl](methyl) amino}furan-2(5H)-one (known from WO 2007/115643), 4-{[(5,6-dichloropyrid-3-yl)methyl](2-fluoroethyl) amino}furan-2(5H)-one (known from WO 2007/115646), 4-{[(6-chloro-5-fluoropyrid-3-yl)methyl](cyclopropyl) amino}furan-2(5H)-one (known from WO 2007/115643), 4-{[(6-chloropyrid-3-yl)methyl](cyclopropyl)amino}furan-2(5H)-one (known from EP0539588), 4-{[(6-chloropyrid-3-yl)methyl](methyl)amino-furan-2(5H)-one (known from EP0539588), [1-(6-chloropyridin-3-yl)ethyl](methypoxido-λ⁴-sulfanylidenecyanamide (known from WO 2007/149134) and its diastereomers {[(1R)-1-(6-chloropyridin-3-yl)ethyl] (methyl)oxido-λ⁶-sulfanylidene}cyanamide and {[(1S)-1-(6-chloropyridin-3-yl)ethyl](methyl)oxido-λ⁶-sulfanylidene}cyanamide (likewise known from WO 2007/149134) and sulfoxaflor (likewise known from WO 2007/149134), 1-[2-fluoro-4-methyl-5-[(2,2,2-trifluoroethyl) sulfinyl]phenyl]-3-(trifluoromethyl)-1H-1,2,4-triazole-5-amine (known from WO 2006/043635), [(3S,4αR,12R,12αS,12βS)-3-[(cyclopropylcarbonyl)oxy]-6,12-dihydroxy-4,12β-dimethyl-11-oxo-9-(pyridin-3-yl)-1,3,4,4α,5,6,6α,12,12α,12β-decahydro-2H,11H-benzo[f]pyrano[4,3-b] chromen-4-yl]methylcyclopropanecarboxylate (known from WO 2006/129714), 2-cyano-3-(difluoromethoxy)-N,N-dimethylbenzenesulfonamide (known from WO2006/056433), 2-cyano-3-(difluoromethoxy)-N-methylbenzenesulfonamide (known from WO2006/100288), 2-cyano-3-(difluoromethoxy)-N-ethylbenzenesulfonamide (known from WO2005/035486), 4-(difluoromethoxy)-N-ethyl-N-methyl-1,2-benzothiazole-3-amine 1,1-dioxide (known from WO2007/057407), N-[1-(2,3-dimethylphenyl)-2-(3,5-dimethylphenyl)ethyl]-4,5-dihydro-1,3-thiazole-2-amine (known from WO2008/104503), {1'-[(2E)-3-(4-chlorophenyl)prop-2-en-1-yl]-5-fluorospiro[indol-3,4'-piperidin]-1 (2H)-yl}(2-chloropyridin-4-yl)methanone (known from WO2003/106457), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diazaspiro[4.5]dec-3-en-4-yl ethyl carbonate (known from WO2009/049851), 4-(but-2-yn-1-yloxy)-6-(3,5-dimethylpiperidin-1-yl)-5-fluoropyrimidine (known from WO2004/099160), (2,2,3,3,4,4,5,5-octafluoropentyl)(3,3,3-trifluoropropyl)malononitrile (known from WO2005/063094), (2,2,3,3,4,4,5,5-octafluoropentyl)(3,3,4,4,4-pentafluorobutyl)malononitrile (known from WO2005/063094), 8-[2-(cyclopropylmethoxy)-4-(trifluoromethyl)phenoxy]-3-[6-(trifluoromethyl)pyridazin-3-yl]-3-azabicyclo[3.2.1]octane (known from WO2007/040280/282), 2-ethyl-7-methoxy-3-methyl-6-[(2,2,3,3-tetrafluoro-2,3-dihydro-1,4-benzodioxin-6-yl)oxy]quinolin-4-yl methyl carbonate (known from JP2008110953), 2-ethyl-7-methoxy-3-methyl-6-[(2,2,3,3-tetrafluoro-2,3-dihydro-1,4-benzodioxin-6-yl) oxy]quinolin-4-yl acetate (known from JP2008110953), PF1364 (Chemical Abstracts No 1204776-60-2, known from JP2010018586), 5-[5-(3,5-dichlorophenyl)-5-(trifluoromethyl)-4,5-dihydro-1,2-oxazol-3-yl]-2-(1H-1,2,4-triazol-1-yl)benzonitrile (known from WO2007/075459), 5-[5-(2-chloropyridin-4-yl)-5-(trifluoromethyl)-4,5-dihydro-1,2-oxazol-3-yl]-2-(1H-1,2,4-triazol-1-yl)benzonitrile (known from WO2007/075459), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (known from WO2005/085216).

Safeners are preferably selected from the group consisting of:

S1) compounds of the formula (S1)

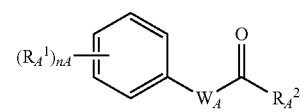

(S1)

where the symbols and indices have the following meanings:
$n_A$ is a natural number from 0 to 5, preferably 0 to 3;

$R_A^1$ is halogen, $(C_1-C_4)$alkyl, $(C_1-C_4)$alkoxy, nitro or $(C_1-C_4)$haloalkyl;

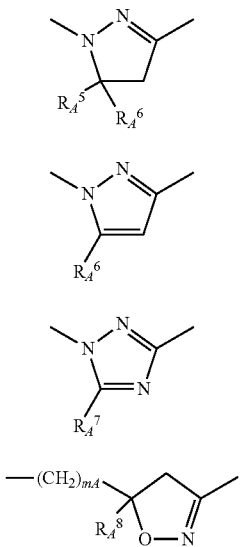

$W_A$ is an unsubstituted or substituted divalent heterocyclic radical from the group of the partially unsaturated or aromatic five-membered heterocycles having 1 to 3 ring heteroatoms from the N and O group, where at least one nitrogen atom and at most one oxygen atom is present in the ring, preferably a radical from the group of $(W_A^1)$ to $(W_A^4)$;

$m_A$ is 0 or 1;

$R_A^2$ is $OR_A^3$, $SR_A^3$ or $NR_A^3R_A^4$ or a saturated or unsaturated 3- to 7-membered heterocycle having at least one nitrogen atom and up to 3 heteroatoms, preferably from the group of O and S, which is joined to the carbonyl group in (S1) via the nitrogen atom and is unsubstituted or substituted by radicals from the group of $(C_1-C_4)$alkyl, $(C_1-C_4)$alkoxy or optionally substituted phenyl, preferably a radical of the formula $OR_A^3$, $NHR_A^4$ or $N(CH_3)_2$, especially of the formula $OR_A^3$;

$R_A^3$ is hydrogen or an unsubstituted or substituted aliphatic hydrocarbyl radical, preferably having a total of 1 to 18 carbon atoms;

$R_A^4$ is hydrogen, $(C_1-C_8)$alkyl, $(C_1-C_8)$alkoxy or substituted or unsubstituted phenyl;

$R_A^5$ is H, $(C_1-C_8)$alkyl, $(C_1-C_8)$haloalkyl, $(C_1-C_4)$alkoxy$(C_1-C_8)$alkyl, cyano or $COOR_A^9$ in which $R_A^9$ is hydrogen, $(C_1-C_8)$alkyl, $(C_1-C_8)$haloalkyl, $(C_1-C_4)$alkoxy-$(C_1-C_4)$alkyl, $(C_1-C_8)$hydroxyalkyl, $(C_3-C_{12})$cycloalkyl or tri-$(C_1-C_4)$-alkylsilyl;

$R_A^6$, $R_A^7$, $R_A^8$ are the same or different and are each hydrogen, $(C_1-C_8)$alkyl, $(C_1-C_8)$haloalkyl, $(C_3-C_{12})$cycloalkyl or substituted or unsubstituted phenyl;

preferably:

a) compounds of the dichlorophenylpyrazoline-3-carboxylic acid (S1$^a$) type, preferably compounds such as 1-(2,4-dichlorophenyl)-5-(ethoxycarbonyl)-5-methyl-2-pyrazoline-3-carboxylic acid, ethyl 1-(2,4-dichlorophenyl)-5-(ethoxycarbonyl)-5-methyl-2-pyrazoline-3-carboxylate (S1-1) ("mefenpyr-diethyl"), and related compounds as described in WO-A-91/07874;

b) derivatives of dichlorophenylpyrazolecarboxylic acid (S1$^b$), preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4) and related compounds as described in EP-A-333 131 and EP-A-269 806;

c) derivatives of 1,5-diphenylpyrazole-3-carboxylic acid (S1$^c$), preferably compounds such as ethyl 1-(2,4-dichlorophenyl)-5-phenylpyrazole-3-carboxylate (S1-5), methyl 1-(2-chlorophenyl)-5-phenylpyrazole-3-carboxylate (S1-6) and related compounds as described in EP-A-268 554, for example;

d) compounds of the triazolecarboxylic acid type (S1$^d$), preferably compounds such as fenchlorazole(-ethyl ester), i.e. ethyl 1-(2,4-dichlorophenyl)-5-trichloromethyl-(1H)-1,2,4-triazole-3-carboxylate (S1-7), and related compounds as described in EP-A-174 562 and EP-A-346 620;

e) compounds of the 5-benzyl- or 5-phenyl-2-isoxazoline-3-carboxylic acid type or of the 5,5-diphenyl-2-isoxazoline-3-carboxylic acid type (S1$^e$), preferably compounds such as ethyl 5-(2,4-dichlorobenzyl)-2-isoxazoline-3-carboxylate (S1-8) or ethyl 5-phenyl-2-isoxazoline-3-carboxylate (S1-9) and related compounds as described in WO-A-91/08202, or 5,5-diphenyl-2-isoxazoline-3-carboxylic acid (S1-10) or ethyl 5,5-diphenyl-2-isoxazoline-3-carboxylate (S1-11) ("isoxadifen-ethyl") or n-propyl 5,5-diphenyl-2-isoxazoline-3-carboxylate (S1-12) or ethyl 5-(4-fluorophenyl)-5-phenyl-2-isoxazoline-3-carboxylate (S1-13), as described in patent application WO-A-95/07897.

S2) Quinoline derivatives of the formula (S2)

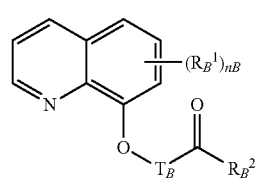

where the symbols and indices have the following meanings:

$R_B^1$ is halogen, $(C_1-C_4)$alkyl, $(C_1-C_4)$alkoxy, nitro or $(C_1-C_4)$haloalkyl;

$n_B$ is a natural number from 0 to 5, preferably 0 to 3;

$R_B^2$ is $OR_B^3$, $SR_B^3$ or $NR_B^3R_B^4$ or a saturated or unsaturated 3- to 7-membered heterocycle having at least one nitrogen atom and up to 3 heteroatoms, preferably from the group of O and S, which is joined via the nitrogen atom to the carbonyl group in (S2) and is unsubstituted or substituted by radicals from the group of $(C_1-C_4)$alkyl, $(C_1-C_4)$alkoxy or optionally substituted phenyl, preferably a radical of the formula $OR_B^3$, $NHR_B^4$ or $N(CH_3)_2$, especially of the formula $OR_B^3$;

$R_B^3$ is hydrogen or an unsubstituted or substituted aliphatic hydrocarbyl radical preferably having a total of 1 to 18 carbon atoms;

$R_B^4$ is hydrogen, $(C_1-C_6)$alkyl, $(C_1-C_6)$alkoxy or substituted or unsubstituted phenyl;

$T_B$ is a ($C_1$ or $C_2$)-alkanediyl chain which is unsubstituted or substituted by one or two $(C_1-C_4)$alkyl radicals or by $[(C_1-C_3)$-alkoxy]carbonyl;

preferably:

a) compounds of the 8-quinolinoxyacetic acid type (S2$^a$), preferably 1-methylhexyl (5-chloro-8-quinolinoxy)acetate ("cloquintocet-mexyl") (S2-1), 1,3-dimethylbut-1-yl (5-chloro-8-quinolinoxy)acetate (S2-2), 4-allyloxybutyl (5-chloro-8-quinolinoxy)acetate (S2-3), 1-allyloxyprop-2-yl (5-chloro-8-quinolinoxy)acetate (S2-4), ethyl (5-chloro-8-quinolinoxy)acetate (S2-5), methyl (5-chloro-8-quinolinoxy)acetate (S2-6), allyl (5-chloro-8-quinolinoxy)acetate (S2-7), 2-(2-propylideneiminoxy)-1-ethyl (5-chloro-8-quinolinoxy)acetate (S2-8), 2-oxoprop-1-yl (5-chloro-8-quinolinoxy)acetate (S2-9) and related compounds, as described in EP-A-86 750, EP-A-94 349 and EP-A-191 736 or EP-A-0 492 366, and also (5-chloro-8-quinolinoxy)acetic acid (S2-10), hydrates and salts thereof, for example the lithium, sodium, potassium, calcium, magnesium, aluminum, iron, ammonium, quaternary ammonium, sulfonium or phosphonium salts thereof, as described in WO-A-2002/34048;

b) compounds of the (5-chloro-8-quinolinoxy)malonic acid type (S2$^b$), preferably compounds such as diethyl (5-chloro-8-quinolinoxy)malonate, diallyl (5-chloro-8-quinolinoxy)malonate, methyl ethyl (5-chloro-8-quinolinoxy)malonate and related compounds, as described in EP-A-0 582 198.

S3) Compounds of the formula (S3)

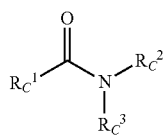

(S3)

where the symbols and indices have the following meanings:

$R_C^1$ is $(C_1-C_4)$alkyl, $(C_1-C_4)$haloalkyl, $(C_2-C_4)$alkenyl, $(C_2-C_4)$haloalkenyl, $(C_3-C_7)$cycloalkyl, preferably dichloromethyl;

$R_C^2$, $R_C^3$ are the same or different and are each hydrogen, $(C_1-C_4)$alkyl, $(C_2-C_4)$alkenyl, $(C_2-C_4)$alkynyl, $(C_1-C_4)$haloalkyl, $(C_2-C_4)$haloalkenyl, $(C_1-C_4)$alkylcarbamoyl$(C_1-C_4)$alkyl, $(C_2-C_4)$alkenylcarbamoyl$(C_1-C_4)$alkyl, $(C_1-C_4)$alkoxy$(C_1-C_4)$alkyl, dioxolanyl$(C_1-C_4)$alkyl, thiazolyl, furyl, furylalkyl, thienyl, piperidyl, substituted or unsubstituted phenyl, or $R_C^2$ and $R_C^3$ together form a substituted or unsubstituted heterocyclic ring, preferably an oxazolidine, thiazolidine, piperidine, morpholine, hexahydropyrimidine or benzoxazine ring; preferably: active compounds of the dichloroacetamide type, which are frequently used as pre-emergence safeners (soil-acting safeners), for example "dichlormid" (N,N-diallyl-2,2-dichloroacetamide) (S3-1), "R-29148" (3-dichloroacetyl-2,2,5-trimethyl-1,3-oxazolidine) from Stauffer (S3-2), "R-28725" (3-dichloroacetyl-2,2-dimethyl-1,3-oxazolidine) from Stauffer (S3-3), "benoxacor" (4-dichloroacetyl-3,4-dihydro-3-methyl-2H-1,4-benzoxazine) (S3-4), "PPG-1292" (N-allyl-N-[(1,3-dioxolan-2-yl)methyl]dichloroacetamide) from PPG Industries (S3-5), "DKA-24" (N-allyl-N-[(allylaminocarbonyl)methyl]dichloroacetamide) from Sagro-Chem (S3-6), "AD-67" or "MON 4660" (3-dichloroacetyl-1-oxa-3-azaspiro[4,5]decane) from Nitrokemia or Monsanto (S3-7), "TI-35" (1-dichloroacetylazepane) from TRI-Chemical RT (S3-8), "diclonon" (dicyclonone) or "BAS145138" or "LAB145138" (S3-9) ((RS)-1-dichloroacetyl-3,3,8a-trimethylperhydropyrrolo[1,2-a]pyrimidin-6-one) from BASF, "furilazole" or "MON 13900" ((RS)-3-dichloroacetyl-5-(2-furyl)-2,2-dimethyloxazolidine) (S3-10); and the (R) isomer thereof (S3-11).

S4) N-Acylsulfonamides of the formula (S4) and salts thereof

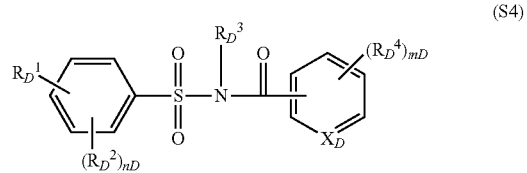

(S4)

where the symbols and indices have the following meanings:

$X_D$ is CH or N;

$R_D^1$ is CO—$NR_D^5 R_D^6$ or NHCO—$R_D^7$;

$R_D^2$ is halogen, $(C_1-C_4)$haloalkyl, $(C_1-C_4)$haloalkoxy, nitro, $(C_1-C_4)$alkyl, $(C_1-C_4)$alkoxy, $(C_1-C_4)$alkylsulfonyl, $(C_1-C_4)$alkoxycarbonyl or $(C_1-C_4)$alkylcarbonyl;

$R_D^3$ is hydrogen, $(C_1-C_4)$alkyl, $(C_2-C_4)$alkenyl or $(C_2-C_4)$alkynyl;

$R_D^4$ is halogen, nitro, $(C_1-C_4)$alkyl, $(C_1-C_4)$haloalkyl, $(C_1-C_4)$haloalkoxy, $(C_3-C_6)$cycloalkyl, phenyl, $(C_1-C_4)$alkoxy, cyano, $(C_1-C_4)$alkylthio, $(C_1-C_4)$alkylsulfinyl, $(C_1-C_4)$alkylsulfonyl, $(C_1-C_4)$alkoxycarbonyl or $(C_1-C_4)$alkylcarbonyl;

$R_D^5$ is hydrogen, $(C_1-C_6)$alkyl, $(C_3-C_6)$cycloalkyl, $(C_2-C_6)$alkenyl, $(C_2-C_6)$alkynyl, $(C_5-C_6)$cycloalkenyl, phenyl or 3- to 6-membered heterocyclyl containing $v_D$ heteroatoms from the group of nitrogen, oxygen and sulfur, where the seven latter radicals are substituted by $v_D$ substituents from the group of halogen, $(C_1-C_6)$alkoxy, $(C_1-C_6)$haloalkoxy, $(C_1-C_2)$alkylsulfinyl, $(C_1-C_2)$alkylsulfonyl, $(C_3-C_6)$cycloalkyl, $(C_1-C_4)$alkoxycarbonyl, $(C_1-C_4)$alkylcarbonyl and phenyl and, in the case of cyclic radicals, also $(C_1-C_4)$alkyl and $(C_1-C_4)$haloalkyl;

$R_D^6$ is hydrogen, $(C_1-C_6)$alkyl, $(C_2-C_6)$alkenyl or $(C_2-C_6)$alkynyl, where the three latter radicals are substituted by $V_D$ radicals from the group of halogen, hydroxyl, $(C_1-C_4)$alkyl, $(C_1-C_4)$alkoxy and $(C_1-C_4)$alkylthio, or $R_D^5$ and $R_D^6$ together with the nitrogen atom which bears them form a pyrrolidinyl or piperidinyl radical;

$R_D^7$ is hydrogen, $(C_1-C_4)$alkylamino, di-$(C_1-C_4)$alkylamino, $(C_1-C_6)$alkyl, $(C_3-C_6)$cycloalkyl, where the 2 latter radicals are substituted by $v_D$ substituents from the group of halogen, $(C_1-C_4)$alkoxy, $(C_1-C_6)$haloalkoxy and $(C_1-C_4)$alkylthio and, in the case of cyclic radicals, also $(C_1-C_4)$alkyl and $(C_1-C_4)$haloalkyl;

$n_D$ is 0, 1 or 2;

$m_D$ is 1 or 2;

$v_D$ is 0, 1, 2 or 3;

among these, preference is given to compounds of the N-acylsulfonamide type, for example of the formula (S4$^a$) below, which are known, for example, from WO-A-97/45016

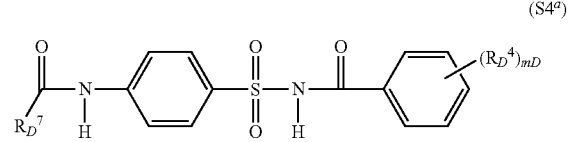

(S4$^a$)

in which $R_D^7$ is $(C_1-C_6)$alkyl, $(C_3-C_6)$cycloalkyl, where the 2 latter radicals are substituted by $v_D$ substituents from the group of halogen, $(C_1-C_4)$alkoxy, $(C_1-C_6)$haloalkoxy and $(C_1-C_4)$alkylthio and, in the case of cyclic radicals, also $(C_1-C_4)$alkyl and $(C_1-C_4)$haloalkyl;

$R_D^4$ is halogen, $(C_1-C_4)$alkyl, $(C_1-C_4)$alkoxy, $CF_3$;

$m_D$ is 1 or 2;

$v_D$ is 0, 1, 2 or 3;

and also to acylsulfamoylbenzamides, for example of the formula (S4$^b$) below, which are known, for example, from WO-A-99/16744,

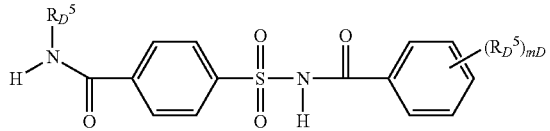

(S4$^b$)

for example those in which $R_D^5$=cyclopropyl and $(R_D^4)$=2-OMe ("cyprosulfamide", S4-1),
$R_D^5$=cyclopropyl and $(R_D^4)$=5-$C_{1-2}$-OMe (S4-2),
$R_D^5$=ethyl and $(R_D^4)$=2-OMe (S4-3),
$R_D^5$=isopropyl and $(R_D^4)$=5-$C_{1-2}$-OMe (S4-4) and
$R_D^5$=isopropyl and $(R_D^4)$=2-OMe (S4-5)

and to compounds of the N-acylsulfamoylphenylurea type, of the formula (S4$^c$), which are known, for example, from EP-A-365484,

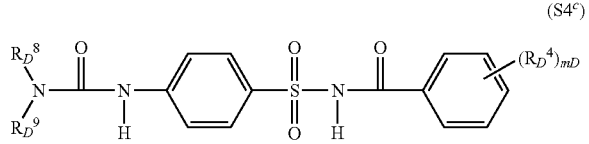

(S4$^c$)

in which $R_D^8$ and $R_D^9$ are each independently hydrogen, $(C_1-C_8)$alkyl, $(C_3-C_8)$cycloalkyl, $(C_3-C_6)$alkenyl, $(C_3-C_6)$alkynyl,
$R_D^4$ is halogen, $(C_1-C_4)$alkyl, $(C_1-C_4)$alkoxy, $CF_3$,
$m_D$ is 1 or 2;

for example

1-[4-(N-2-methoxybenzoylsulfamoyl)phenyl]-3-methylurea, 1-[4-(N-2-methoxybenzoylsulfamoyl)phenyl]-3,3-dimethylurea, 1-[4-(N-4,5-dimethylbenzoylsulfamoyl)phenyl]-3-methylurea.

S5) Active compounds from the class of the hydroxyaromatics and aromatic-aliphatic carboxylic acid derivatives (S5), for example ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicyclic acid, 2-hydroxycinnamic acid, 2,4-dichlorocinnamic acid, as described in WO-A-2004/084631, WO-A-2005/015994, WO-A-2005/016001.

S6) Active compounds from the class of the 1,2-dihydroquinoxalin-2-ones (S6), for example 1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-(2-methylsulfonylaminoethyl)-3-(2-thienyl)-1,2-dihydroquinoxalin-2-one, as described in WO-A-2005/112630.

S7) Compounds of the formula (S7), as described in WO-A-1998/38856,

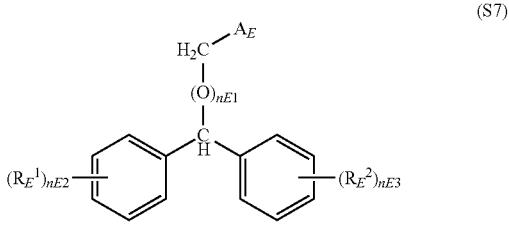

(S7)

where the symbols and indices have the following meanings:
$R_E^1$, $R_E^2$ are each independently halogen, $(C_1-C_4)$alkyl, $(C_1-C_4)$alkoxy, $(C_1-C_4)$haloalkyl, $(C_1-C_4)$alkylamino, di$(C_1-C_4)$alkylamino, nitro;
$A_E$ is $COOR_E^3$ or $COSR_E^4$
$R_E^3$, $R_E^4$ are each independently hydrogen, $(C_1-C_4)$alkyl, $(C_2-C_6)$alkenyl, $(C_2-C_4)$alkynyl, cyanoalkyl, $(C_1-C_4)$haloalkyl, phenyl, nitrophenyl, benzyl, halobenzyl, pyridinylalkyl and alkylammonium,
$n_E^1$ is 0 or 1
$n_E^2$, $n_E^3$ are each independently of one another 0, 1 or 2,
preferably diphenylmethoxyacetic acid, ethyl diphenylmethoxyacetate, methyl diphenylmethoxyacetate (CAS reg. no. 41858-19-9) (S7-1).

S8) Compounds of the formula (S8), as described in WO-A-98/27049,

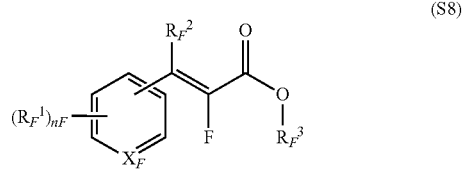

(S8)

in which $X_F$ is CH or N,
$n_F$ in the case that $X_F$=N is an integer from 0 to 4 and
in the case that $X_F$=CH is an integer from 0 to 5,
$R_F^1$ is halogen, $(C_1-C_4)$alkyl, $(C_1-C_4)$haloalkyl, $(C_1-C_4)$alkoxy, $(C_1-C_4)$haloalkoxy, nitro, $(C_1-C_4)$alkylthio, $(C_1-C_4)$alkylsulfonyl, $(C_1-C_4)$alkoxycarbonyl, optionally substituted phenyl, optionally substituted phenoxy,
$R_F^2$ is hydrogen or $(C_1-C_4)$alkyl
$R_F^3$ is hydrogen, $(C_1-C_8)$alkyl, $(C_2-C_4)$alkenyl, $(C_2-C_4)$alkynyl, or aryl, where each of the aforementioned carbon-containing radicals is unsubstituted or substituted by one or more, preferably up to three identical or different radicals from the group consisting of halogen and alkoxy, or salts thereof,
preferably compounds in which
$X_F$ is CH,
$n_F$ is an integer from 0 to 2,
$R_F^1$ is halogen, $(C_1-C_4)$alkyl, $(C_1-C_4)$haloalkyl, $(C_1-C_4)$alkoxy, $(C_1-C_4)$haloalkoxy,
$R_F^2$ is hydrogen or $(C_1-C_4)$alkyl
$R_F^3$ is hydrogen, $(C_1-C_8)$alkyl, $(C_2-C_4)$alkenyl, $(C_2-C_4)$alkynyl, or aryl, where each of the aforementioned carbon-containing radicals is unsubstituted or substituted by one or more, preferably up to three identical or different radicals from the group consisting of halogen and alkoxy, or salts thereof.

S9) Active compounds from the class of the 3-(5-tetrazolyl-carbonyl)-2-quinolones (S9), for example 1,2-dihydro-4-hydroxy-1-ethyl-3-(5-tetrazolylcarbonyl)-2-quinolone (CAS reg. no.: 219479-18-2), 1,2-dihydro-4-hydroxy-1-methyl-3-(5-tetrazolylcarbonyl)-2-quinolone (CAS reg. no. 95855-00-8), as described in WO-A-1999/000020.

S10) Compounds of the formulae (S10$^a$) or (S10$^b$)
as described in WO-A-2007/023719 and WO-A-2007/023764,

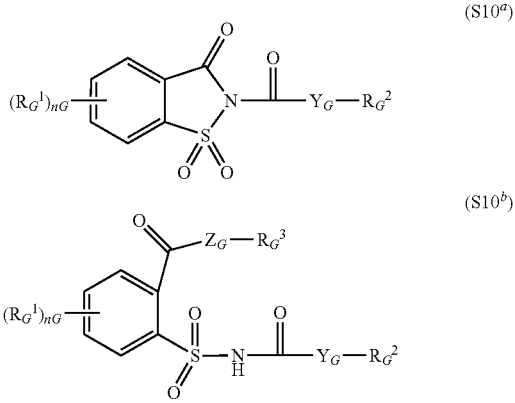

in which
$R_G^1$ is halogen, $(C_1-C_4)$-alkyl, methoxy, nitro, cyano, $CF_3$, $OCF_3$,
$Y_G$, $Z_G$ are each independently of one another O or S,
$n_G$ is an integer from 0 to 4,
$R_G^2$ is $(C_1-C_{16})$-alkyl, $(C_2-C_6)$-alkenyl, $(C_3-C_6)$-cycloalkyl, aryl; benzyl, halobenzyl,
$R_G^3$ is hydrogen or $(C_1-C_6)$-alkyl.

S11) Active compounds of the oxyimino compounds type (S11), which are known as seed-dressing compositions, for example "oxabetrinil" ((Z)-1,3-dioxolan-2-yl-methoxyimino(phenyl)acetonitrile) (S11-1), which is known as a seed-dressing safener for millet/sorghum, against damage by metolachlor, "fluxofenim" (1-(4-chlorophenyl)-2,2,2-trifluoro-1-ethanone O-(1,3-dioxolan-2-ylmethyl)oxime) (S11-2), which is known as a seed-dressing safener for millet/sorghum against damage by metolachlor, and "cyometrinil" or "CGA-43089" ((Z)-cyanomethoxyimino(phenyl)acetonitrile) (S11-3), which is known as a seed-dressing safener for millet/sorghum against damage by metolachlor.

S12) Active compounds from the class of the isothiochromanones (S12), for example methyl [(3-oxo-1H-2-benzothiopyran-4(3H)-ylidene)methoxy]acetate (CAS reg. no. 205121-04-6) (S12-1) and related compounds from WO-A-1998/13361.

S13) One or more compounds from group (S13): "naphthalic anhydride" (1,8-naphthalenedicarboxylic anhydride) (S13-1), which is known as a seed-dressing safener for corn against damage by thiocarbamate herbicides, "fenclorim" (4,6-dichloro-2-phenylpyrimidine) (S13-2), which is known as a safener for pretilachlor in sown rice, "flurazole" (benzyl 2-chloro-4-trifluoromethyl-1,3-thiazole-5-carboxylate) (S13-3), which is known as a seed-dressing safener for millet/sorghum against damage by alachlor and metolachlor, "CL 304415" (CAS reg. no. 31541-57-8) (4-carboxy-3,4-dihydro-2H-1-benzopyran-4-acetic acid) (S13-4) from American Cyanamid, which is known as a safener for corn against damage by imidazolinones, "MG 191" (CAS reg. no. 96420-72-3) (2-dichloromethyl-2-methyl-1,3-dioxolane) (S13-5) from Nitrokemia, which is known as a safener for corn, "MG-838" (CAS reg. no. 133993-74-5) (2-propenyl 1-oxa-4-aza-spiro[4.5]decane-4-carbodithioate) (S13-6) from Nitrokemia, "disulfoton" (O,O-diethyl S-2-ethylthioethyl phosphorodithioate) (S13-7), "dietholate" (O,O-diethyl O-phenylphosphorothioate) (S13-8), "mephenate" (4-chlorophenyl methylcarbamate) (S13-9).

S14) Active compounds which, in addition to herbicidal action against harmful plants, also have safener action on crop plants such as rice, for example "dimepiperate" or "MY-93" (S-1-methyl-1-phenylethylpiperidine-1-carbothioate), which is known as a safener for rice against damage by the herbicide molinate, "daimuron" or "SK 23" (1-(1-methyl-1-phenylethyl)-3-p-tolylurea), which is known as a safener for rice against damage by the herbicide imazosulfuron, "cumyluron"="JC-940" (3-(2-chlorophenylmethyl)-1-(1-methyl-1-phenylethyl)urea, see JP-A-60087254), which is known as a safener for rice against damage by some herbicides, "methoxyphenone" or "NK 049" (3,3'-dimethyl-4-methoxybenzophenone), which is known as a safener for rice against damage by some herbicides, "CSB" (1-bromo-4-(chloromethylsulfonyl)benzene) from Kumiai, (CAS reg. no. 54091-06-4), which is known as a safener against damage by some herbicides in rice.

S15) Compounds of the formula (S15) or tautomers thereof as described in WO-A-2008/131861 and WO-A-2008/131860

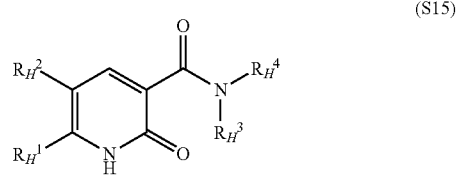

in which
$R_H^1$ is a $(C_1-C_6)$-haloalkyl radical and
$R_H^2$ is hydrogen or halogen and
$R_H^3$, $R_H^4$ are each independently of one another hydrogen, $(C_1-C_{16})$alkyl, $(C_2-C_{16})$alkenyl or $(C_2-C_{16})$alkynyl, where each of the latter 3 radicals is unsubstituted or substituted by one or more radicals from the group of halogen, hydroxyl, cyano, $(C_1-C_4)$alkoxy, $(C_1-C_4)$haloalkoxy, $(C_1-C_4)$alkylthio, $(C_1-C_4)$alkylamino, di[$(C_1-C_4)$alkyl]amino, [$(C_1-C_4)$alkoxy]carbonyl, [$(C_1-C_4)$haloalkoxy]carbonyl, $(C_3-C_6)$cycloalkyl which is unsubstituted or substituted, phenyl which is unsubstituted or substituted, and heterocyclyl which is unsubstituted or substituted, or $(C_3-C_6)$cycloalkyl, $(C_4-C_6)$cycloalkenyl, $(C_3-C_6)$cycloalkyl which is fused on one side of the ring to a 4 to 6-membered saturated or unsaturated carbocyclic ring, or $(C_4-C_6)$cycloalkenyl which is fused on one side of the ring to a 4 to 6-membered saturated or unsaturated carbocyclic ring, where each of the latter 4 radicals is unsubstituted or substituted by one or more radicals from the group of halogen, hydroxyl, cyano, (C1-C4)alkyl, (C1-C4)haloalkyl, (C1-C4)alkoxy, (C1-C4)haloalkoxy, (C1-C4)alkylthio, (C1-C4) alkylamino, di[(C1-C4)alkyl]amino, [(C1-C4)alkoxy]carbonyl, [(C1-C4)haloalkoxyl]-carbonyl, (C3-C6) cycloalkyl which is unsubstituted or substituted, phenyl which is unsubstituted or substituted, and heterocyclyl which is unsubstituted or substituted,
or
$R_H^3$ is $(C_1-C_4)$-alkoxy, $(C_2-C_4)$-alkenyloxy, $(C_2-C_6)$-alkynyloxy or $(C_2-C_4)$-haloalkoxy and $R_H^4$ is hydrogen or $(C_1-C_4)$-alkyl or $R_H^3$ and $R_H^4$ together with the directly bonded nitrogen atom are a four- to eight-membered heterocyclic ring which, as well as the nitrogen atom, may also contain further ring heteroatoms, preferably up to two further ring heteroatoms from the group of N, O and S, and which is unsubstituted or substituted by one or more radicals from the group of halogen, cyano, nitro, $(C_1-C_4)$alkyl, $(C_1-C_4)$haloalkyl, $(C_1-C_4)$alkoxy, $(C_1-C_4)$haloalkoxy and $(C_1-C_4)$alkylthio.

S16) Active compounds which are used primarily as herbicides but also have safener action on crop plants, for example (2,4-dichlorophenoxy)acetic acid (2,4-D), (4-chlorophenoxy)acetic acid, (R,S)-2-(4-chloro-o-tolyloxy)propionic acid (mecoprop), 4-(2,4-dichlorophenoxy)butyric acid (2,4-DB), (4-chloro-o-tolyloxy)acetic acid (MCPA), 4-(4-chloro-o-tolyloxy)butyric acid, 4-(4-chlorophenoxy)butyric acid, 3,6-dichloro-2-methoxybenzoic acid (dicamba), 1-(ethoxycarbonyl)ethyl 3,6-dichloro-2-methoxybenzoate (lactidichlor-ethyl).

Substances which Influence Plant Maturity:

Combination partners usable for the compounds of the formula (I) in mixture formulations or in tank mixes are, for example, known active compounds based on inhibition of, for example, 1-aminocyclopropane-1-carboxylate synthase, 1-aminocyclopropane-1-carboxylate oxidase and the ethylene receptors, for example ETR1, ETR2, ERS1, ERS2 or EIN4, as described, for example, in Biotechn. Adv. 2006, 24, 357-367; Bot. Bull. Acad. Sin. 199, 40, 1-7 or Plant Growth Reg. 1993, 13, 41-46 and literature cited therein.

Examples of known substances which influence plant maturity and can be combined with the compounds of the formula (I) include the active compounds which follow (the compounds are designated either by the "common name" according to the International Organization for Standardization (ISO) or by the chemical name or by the code number) and always encompass all use forms, such as acids, salts, esters and isomers, such as stereoisomers and optical isomers. In this list, one or else, in some cases, more than one application form is mentioned by way of example:

rhizobitoxine, 2-aminoethoxyvinylglycine (AVG), methoxyvinylglycine (MVG), vinylglycine, aminooxyacetic acid, sinefungin, S-adenosylhomocysteine, 2-keto-4-methyl thiobutyrate, 2-(methoxy)-2-oxoethyl (isopropyl idene)aminooxyacetate, 2-(hexyloxy)-2-oxoethyl (isopropylidene) aminooxyacetate, 2-(isopropyloxy)-2-oxoethyl (cyclohexylidene)aminooxyacetate, putrescine, spermidine, spermine, 1,8-diamino-4-aminoethyloctane, L-canaline, daminozide, methyl 1-aminocyclopropyl-1-carboxylate, N-methyl-1-aminocyclopropyl-1-carboxylic acid, 1-aminocyclopropyl-1-carboxamide, substituted 1-aminocyclopropyl-1-carboxylic acid derivatives as described in DE3335514, EP30287, DE2906507 or U.S. Pat. No. 5,123,951, 1-aminocyclopropyl-1-hydroxamic acid, 1-methylcyclopropene, 3-methylcyclopropene, 1-ethylcyclopropene, 1-n-propylcyclopropene, 1-cyclopropenylmethanol, carvone, eugenol, sodium cycloprop-1-en-1-ylacetate, sodium cycloprop-2-en-1-ylacetate, sodium 3-(cycloprop-2-en-1-yl)propanoate, sodium 3-(cycloprop-1-en-1-yl)propanoate, jasmonic acid, methyl jasmonate, ethyl jasmonate.

Substances which Influence Plant Health and Germination:

Examples of combination partners usable for the compounds of the formula (I) in mixture formulations or in tankmixes include known active ingredients which influence plant health (the compounds are designated by the "common name" according to the International Organization for Standardization (ISO) or by the chemical name or by the code number and always encompass all use forms, such as acids, salts, esters and isomers, such as stereoisomers and optical isomers): sarcosine, phenylalanine, tryptophan, N'-methyl-1-phenyl-1-N,N-diethylaminomethanesulfonamide, apio-galacturonans as described in WO2010017956, 4-oxo-4-[(2-phenylethyl)amino]butanoic acid, 4-{[2-(1H-indol-3-yl)ethyl]amino}-4-oxobutanoic acid, 4-[(3-methylpyridin-2-yl)amino]-4-oxobutanoic acid, allantoin, 5-aminolevulic acid, (2S,3R)-2-(3,4-dihydroxyphenyl)-3,4-dihydro-2H-chromene-3,5,7-triol and structurally related catechols as described in WO2010122956, 2-hydroxy-4-(methylsulfanyl)butanoic acid, (3E,3αR,8βS)-3-({[(2R)-4-methyl-5-oxo-2,5-dihydrofuran-2-yl]oxy}methylene)-3,3α,4,8β-tetrahydro-2H-indeno[1,2-b]furan-2-one and analogous lactones as described in EP2248421, abscisic acid, (2Z,4E)-5-[6-ethynyl-1-hydroxy-2,6-dimethyl-4-oxocyclohex-2-en-1-yl]-3-methylpenta-2,4-dienoic acid, methyl (2Z,4E)-5-[6-ethynyl-1-hydroxy-2,6-dimethyl-4-oxocyclohex-2-en-1-yl]-3-methylpenta-2,4-dienoate, 4-phenylbutyric acid, sodium 4-phenylbutanoate, potassium 4-phenylbutanoate.

Herbicides or Plant Growth Regulators:

Combination partners usable for the compounds of the formula (I) in mixture formulations or in tankmixes are, for example, known active compounds based on inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoendesaturase, photosystem I, photosystem II, protoporphyrinogen oxidase, or which act as plant growth regulators, as described, for example, in Weed Research 26 (1986) 441-445 or "The Pesticide Manual", 14th edition, The British Crop Protection Council and the Royal Soc. of Chemistry, 2006 and literature cited therein.

Examples of known herbicides or plant growth regulators which can be combined with compounds of the formula (I) include the active compounds which follow (the compounds are designated by the "common name" according to the International Organization for Standardization (ISO) or by the chemical name or by the code number) and always encompass all use forms, such as acids, salts, esters and isomers, such as stereoisomers and optical isomers. In this list, one or else, in some cases, more than one application form is mentioned by way of example:

acetochlor, acibenzolar, acibenzolar-S-methyl, acifluorfen, acifluorfen-sodium, aclonifen, alachlor, allidochlor, alloxydim, alloxydim-sodium, ametryne, amicarbazone, amidochlor, amidosulfuron, aminocyclopyrachlor, aminopyralid, amitrole, ammonium sulfamate, ancymidol, anilofos, asulam, atrazine, azafenidin, azimsulfuron, aziprotryne, beflubutamid, benazolin, benazolin-ethyl, bencarbazone, benfluralin, benfuresate, bensulide, bensulfuron, bensulfuron-methyl, bentazone, benzfendizone, benzobicyclon, benzolenap, benzofluor, benzoylprop, bicyclopyrone, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat-chloride, chlornitrofen, chlorophthalim, chlorthal-dimethyl, chlortoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dimefuron, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat-dibromide, dithiopyr, diuron, DNOC, eglinazine-ethyl, endothal, EPTC, esprocarb, ethalfluralin, ethametsulfuron, ethametsulfuron-methyl, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]phenyl]ethanesulfonamide, F-7967, i.e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoprop, fenoxaprop, fenoxaprop-P, fenoxaprop-ethyl, fenoxaprop-P-ethyl, fenoxasulfone, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, fluorochloridone, fluoroxypyr, fluoroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, glufosinate-ammonium, glufosinate-P, glufosinate-P-ammonium, glufosinate-P-sodium, glyphosate, glyphosate-isopropylammonium, H-9201, i.e. O-(2,4-dimethyl-6-nitrophenyl) O-ethyl isopropylphosphoramidothioate, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl)ethyl (2,4-dichlorophenoxy)acetate, imazamethabenz, imazamethabenz-methyl, imazamox, imazamox-ammonium, imazapic, imazapyr, imazapyr-isopropylammonium, imazaquin, imazaquin-ammonium, imazethapyr, imazethapyr-ammonium, imazosulfuron, inabenfide, indanofan, indaziflam, indoleacetic acid (IAA), 4-indol-3-ylbutyric acid (IBA), iodosulfuron, iodosulfuron-methyl-sodium, ioxynil, ipfencarbazone, isocarbamid, isopropalin, isoproturon, isouron, isoxaben, isoxachlortole, isoxaflutole, isoxapyrifop, KUH-043, i.e. 3-{([5-(difluoromethyl)-1-methyl-3-(trifluoromethyl)-1H-pyrazol-4-yl]methyl}sulfonyl)-5,5-dimethyl-4,5-dihydro-1,2-oxazole, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat-chloride, mesosulfuron, mesosulfuron-methyl, mesotrione, methabenzthiazuron, metam, metamifop, metamitron, metazachlor, metazasulfuron, methazole, methiopyrsulfuron, methiozolin, methoxyphenone, methyldymron, 1-methylcyclopropene, methyl isothiocyanate, metobenzuron, metobromuron, metolachlor, S-metolachlor, metosulam, metoxuron, metribuzin, metsulfuron, metsulfuron-methyl, molinate, monalide, monocarbamide, monocarbamide dihydrogensulfate, monolinuron, monosulfuron, monosulfuron ester, monuron, MT-128, i.e. 6-chloro-N-[(2E)-3-chloroprop-2-en-1-yl]-5-methyl-N-phenylpyridazine-3-amine, MT-5950, i.e. N-[3-chloro-4-(1-methylethyl)phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolate-sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazole, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazole, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyrisulfuron, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, secbumeton, sethoxydim, siduron, simazine, simetryn, SN-106279, i.e. methyl (2R)-2-({7-[2-chloro-4-(trifluoromethyl)phenoxy]-2-naphthyl}oxy)propanoate, sulcotrione, sulfallate (CDEC), sulfentrazone, sulfometuron, sulfometuron-methyl, sulfosate (glyphosate-trimesium), sulfosulfuron, SYN-523, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, tebutam, tebuthiuron, tecnazene, tefuryltrione, tembotrione, tepraloxydim, terbacil, terbucarb, terbuchlor, terbumeton, terbuthylazine, terbutryn, thenylchlor, thiafluamide, thiazafluoron, thiazopyr, thidiazimin, thidiazuron, thiencarbazone, thiencarbazone-methyl, thifensulfuron, thifensulfuron-methyl, thiobencarb, thiocarbazil, topramezone, tralkoxydim, triallate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0862, i.e. 3,4-dichloro-N-{2-[(4,6-dimethoxypyrimidin-2-yl)oxy]benzyl}aniline, and the following compounds:

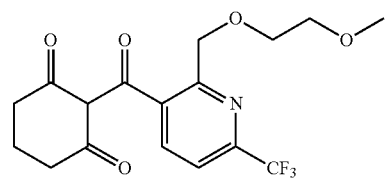

-continued

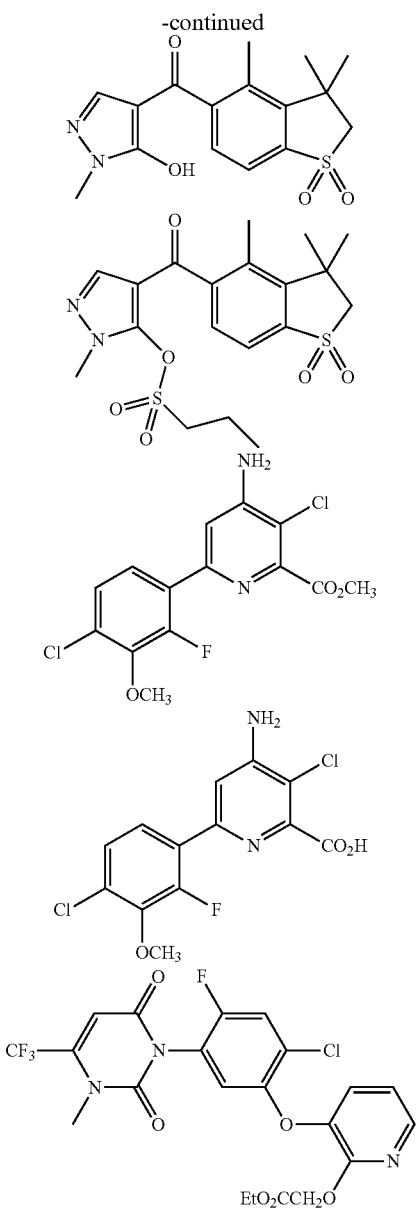

The invention is to be illustrated by the biological examples which follow, but without restricting it thereto.

BIOLOGICAL EXAMPLES

Seeds of monocotyledonous and dicotyledonous crop plants were laid out in sandy loam in wood-fiber pots, covered with soil and cultivated in a greenhouse under good growth conditions. The test plants were treated at the early leaf stage (BBCH10-BBCH13). To ensure uniform water supply before commencement of stress, the potted plants were supplied with the maximum amount of water immediately beforehand by dam irrigation and, after application, transferred into plastic inserts in order to prevent subsequent, excessively rapid drying. The compounds according to the invention, formulated in the form of wettable powders (WP), wettable granules (WG), suspension concentrates (SC) or emulsion concentrates (EC), were sprayed onto the green parts of the plants as an aqueous suspension at an equivalent water application rate of 600 l/ha with addition of 0.2% wetting agent (agrotin).

Substance application is followed immediately by stress treatment of the plants (cold or drought stress). For cold stress treatment, the plants were kept under the following controlled conditions:

"day": 12 hours with illumination at 8° C.
"night": 12 hours without illumination at 1° C.

Drought stress was induced by gradual drying out under the following conditions:

"day": 14 hours with illumination at 26° C.
"night": 10 hours without illumination at 18° C.

The duration of the respective stress phases was guided mainly by the state of the untreated (=treated with blank formulation but without test compound), stressed control plants and thus varied from crop to crop. It was ended (by re-irrigating or transfer to a greenhouse with good growth conditions) as soon as irreversible damage was observed on the untreated, stressed control plants. In the case of dicotyledonous crops, for example oilseed rape and soybeans, the duration of the drought stress phase varied between 3 and 5 days; in the case of monocotyledonous crops, for example wheat, barley or corn, it varied between 6 and 10 days. The duration of the cold stress phase varied between 12 and 14 days.

The end of the stress phase was followed by an approx. 5-7-day recovery phase, during which the plants were once again kept under good growth conditions in a greenhouse. In order to rule out any influence of the effects observed by any fungicidal action of the test compounds, it was additionally ensured that the tests proceeded without fungal infection and without infection pressure.

After the recovery phase had ended, the intensities of damage were rated visually in comparison to untreated, unstressed controls of the same age (in the case of drought stress) or the same growth stage (in the case of cold stress). The intensity of damage was first recorded as a percentage (100%=plants have died, 0%=like control plants). These values were then used to calculate the efficacy of the test compounds (=percentage reduction in the intensity of damage as a result of substance application) by the following formula:

$$EF = \frac{(DV_{us} - DV_{ts}) \times 100}{DV_{us}}$$

EF: efficacy (%)
$DV_{us}$: damage value of the untreated, stressed control
$DV_{ts}$: damage value of the plants treated with test compound The tables below list mean values in each case from three results of the same test.

Efficacies of selected compounds of the formula (I) under drought stress:

TABLE A1

| No. | Substance | Dosage | Unit | EF (BRSNS) |
|---|---|---|---|---|
| 1 | I.1-2 | 250 | g/ha | >5 |
| 2 | I.1-4 | 250 | g/ha | >5 |
| 3 | I.1-8 | 250 | g/ha | >5 |
| 4 | I.1-10 | 250 | g/ha | >5 |
| 5 | I.1-16 | 250 | g/ha | >5 |
| 6 | I.1-20 | 250 | g/ha | >5 |
| 7 | I.1-22 | 250 | g/ha | >5 |
| 8 | I.1-23 | 250 | g/ha | >5 |
| 9 | I.1-46 | 250 | g/ha | >5 |
| 10 | I.1-60 | 250 | g/ha | >5 |
| 11 | I.1-68 | 250 | g/ha | >5 |

TABLE A1-continued

| No. | Substance | Dosage | Unit | EF (BRSNS) |
|---|---|---|---|---|
| 12 | I.1-72 | 250 | g/ha | >5 |
| 13 | I.1-74 | 250 | g/ha | >5 |
| 14 | I.1-113 | 250 | g/ha | >5 |
| 15 | I.1-114 | 250 | g/ha | >5 |
| 16 | I.1-116 | 250 | g/ha | >5 |
| 17 | I.1-141 | 250 | g/ha | >5 |
| 18 | I.1-142 | 250 | g/ha | >5 |
| 19 | I.1-144 | 25 | g/ha | >5 |
| 20 | I.1-230 | 250 | g/ha | >5 |
| 21 | I.1-232 | 250 | g/ha | >5 |
| 22 | I.1-318 | 250 | g/ha | >5 |
| 23 | I.1-460 | 250 | g/ha | >5 |
| 24 | I.1-564 | 250 | g/ha | >5 |
| 25 | I.2-18 | 250 | g/ha | >5 |

TABLE A2

| No. | Substance | Dosage | Unit | EF (ZEAMX) |
|---|---|---|---|---|
| 1 | I.1-10 | 250 | g/ha | >5 |
| 2 | I.1-14 | 25 | g/ha | >5 |
| 3 | I.1-20 | 250 | g/ha | >5 |
| 4 | I.1-23 | 250 | g/ha | >5 |
| 5 | I.1-46 | 250 | g/ha | >5 |
| 6 | I.1-71 | 250 | g/ha | >5 |
| 7 | I.1-84 | 250 | g/ha | >5 |
| 8 | I.1-92 | 250 | g/ha | >5 |
| 9 | I.1-141 | 250 | g/ha | >5 |
| 10 | I.1-142 | 250 | g/ha | >5 |
| 11 | I.1-232 | 250 | g/ha | >5 |
| 12 | I.1-440 | 25 | g/ha | >5 |
| 13 | I.1-457 | 250 | g/ha | >5 |
| 14 | I.1-564 | 250 | g/ha | >5 |
| 15 | I.2-14 | 25 | g/ha | >5 |
| 16 | I.2-18 | 25 | g/ha | >5 |

TABLE A3

| No. | Substance | Dosage | Unit | EF (TRZAS) |
|---|---|---|---|---|
| 1 | I.1-2 | 250 | g/ha | >5 |
| 2 | I.1-4 | 250 | g/ha | >5 |
| 3 | I.1-8 | 250 | g/ha | >5 |
| 4 | I.1-10 | 250 | g/ha | >5 |
| 5 | I.1-16 | 250 | g/ha | >5 |
| 6 | I.1-20 | 250 | g/ha | >5 |
| 7 | I.1-22 | 250 | g/ha | >5 |
| 8 | I.1-23 | 250 | g/ha | >5 |
| 9 | I.1-46 | 250 | g/ha | >5 |
| 10 | I.1-60 | 250 | g/ha | >5 |
| 11 | I.1-86 | 250 | g/ha | >5 |
| 12 | I.1-92 | 250 | g/ha | >5 |
| 13 | I.1-113 | 250 | g/ha | >5 |
| 14 | I.1-114 | 250 | g/ha | >5 |
| 15 | I.1-116 | 250 | g/ha | >5 |
| 16 | I.1-122 | 25 | g/ha | >5 |
| 17 | I.1-124 | 250 | g/ha | >5 |
| 18 | I.1-141 | 250 | g/ha | >5 |
| 19 | I.1-142 | 250 | g/ha | >5 |
| 20 | I.1-144 | 25 | g/ha | >5 |
| 21 | I.1-230 | 250 | g/ha | >5 |
| 22 | I.1-317 | 25 | g/ha | >5 |
| 23 | I.1-442 | 25 | g/ha | >5 |
| 24 | I.1-444 | 250 | g/ha | >5 |
| 25 | I.1-457 | 25 | g/ha | >5 |

TABLE A3-continued

| No. | Substance | Dosage | Unit | EF (TRZAS) |
|---|---|---|---|---|
| 26 | I.1-458 | 25 | g/ha | >5 |
| 27 | I.1-460 | 250 | g/ha | >5 |

In the above tables:

BRSNS = *Brassica napus*

TRZAS = *Triticum aestivum*

ZEAMX = *Zea mays*

Similar results were also achieved with further compounds of the formula (I), also in the case of application to different plant species.

The invention claimed is:

1. A substituted 5-(cyclohex-2-en-1-yl)penta-2,4-diene and/or 5-(cyclohex-2-en-1-yl)pent-2-en-4-yne of formula (I) and/or a salt thereof

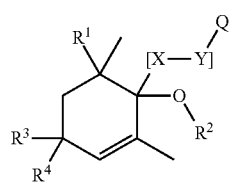
(I)

where

[X—Y] represents the moieties

[X-Y]$^1$

[X-Y]$^2$

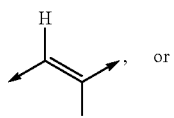
, or

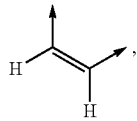
[X-Y]$^3$

Q represents the moieties Q-1 to Q-4

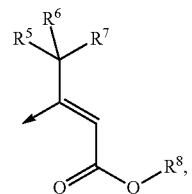
Q-1

-continued

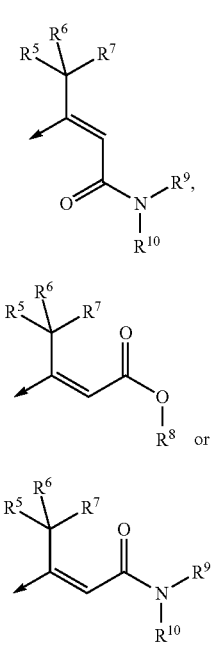

where $R^5$, $R^6$, $R^7$, $R^8$, $R^9$ and $R^{10}$ are each as defined below and where the arrow represents a bond to the respective [X—Y] grouping;

$R^1$ represents alkyl, alkenyl, alkynyl, alkenylalkyl, alkynylalkyl, alkoxyalkyl, hydroxyalkyl, haloalkyl, haloalkenyl, haloalkynyl, haloalkoxyalkyl, alkoxyhaloalkyl, haloalkoxyhaloalkyl, or alkylthioalkyl, $R^2$ represents hydrogen, alkyl, alkenyl, alkenylalkyl, alkoxyalkyl, alkylcarbonyl, arylcarbonyl, heteroarylcarbonyl, cycloalkylcarbonyl, alkoxycarbonyl, alkenyloxycarbonyl, aryloxyalkyl, arylalkoxycarbonyl, arylalkoxyalkyl, arylalkyl, alkoxyalkoxyalkyl, alkylthioalkyl, trialkylsilyl, alkyl(bisalkyl)silyl, alkyl(bisaryl)silyl, aryl(bisalkyl)silyl, cycloalkyl(bisalkyl)silyl, halo(bisalkyl)silyl, trialkylsilylalkoxyalkyl, or trialkylsilylalkyl, $R^3$ and $R^4$ independently of one another represent alkoxy, alkoxyalkoxy, cycloalkylalkoxy, haloalkoxy, alkylthio, haloalkylthio, arylalkoxy, or arylalkylthio or $R^3$ and $R^4$ together with the atom to which they are attached form an oxo group, hydroxyimino group, alkoxyimino group, cycloalkoxyimino group, cycloalkylalkoximino group, arylalkoxyimino group or a 5- to 7-membered heterocyclic ring which is optionally substituted further, $R^5$ and $R^6$ independently of one another represent hydrogen, halogen, alkyl, or haloalkyl, $R^7$ represents halogen, alkyl, haloalkyl, haloalkoxy, haloalkoxyalkyl, haloalkoxyhaloalkyl, alkoxyhaloalkyl, alkynyloxyhaloalkyl, alkenyloxyhaloalkyl, alkylthio, haloalkylthio, aryl, arylalkyl, heteroaryl, or heteroarylalkyl, or $R^6$ and $R^7$ together with the atoms to which they are bonded form a fully saturated 3- to 6-membered ring optionally interrupted by heteroatoms and optionally with further substitution, $R^8$ represents hydrogen, alkyl, alkoxyalkyl, cycloalkyl, cycloalkylalkyl, aryl, arylalkyl, heteroarylalkyl, bisarylalkyl, trisarylalkyl, alkenyl, alkenylalkyl, cycloalkenylalkyl, alkynylalkyl, trialkylsilylalkoxyalkyl, alkoxyalkoxyalkyl, alkylthioalkyl, haloalkyl, arylsulfonylalkyl, trialkylsilyl, alkyl(bisaryl)silyl, alkyl(bisalkyl)silyl, or bisalkylaminoalkyl, $R^9$ represents hydrogen, alkyl, cycloalkyl, halogen, alkenylalkyl, alkynylalkyl, haloalkyl, alkynyl, alkenyl, cyanoalkyl, cycloalkylalkyl, arylalkyl, heteroarylalkyl, alkylcarbonyl, alkoxycarbonyl, alkenyloxycarbonyl, alkenylalkyloxycarbonyl, arylalkyloxycarbonyl, cycloalkoxycarbonyl, cycloalkylalkoxycarbonyl, alkylsulfonyl, arylsulfonyl, cycloalkylsulfonyl, alkylsulfinyl, arylsulfinyl, cycloalkylsulfinyl, alkoxycarbonylalkyl, hydroxycarbonylalkyl, arylalkoxycarbonylalkyl, cycloalkylalkoxycarbonylalkyl, alkoxycarbonylcycloalkyl, hydroxycarbonylcycloalkyl, arylalkoxycarbonylcycloalkyl, alkenyloxycarbonylcycloalkyl, aminocarbonylcycloalkyl, alkylaminocarbonylcycloalkyl, cycloalkylaminocarbonylcycloalkyl, alkoxycarbonylcycloalkenyl, hydroxycarbonylcycloalkenyl, bisalkylaminoalkyl, hydroxycarbonylheterocyclyl, alkoxycarbonylheterocyclyl, alkenyloxycarbonylheterocyclyl, alkenylalkoxycarbonylheterocyclyl, arylalkoxycarbonylheterocyclyl, cycloalkoxycarbonylheterocyclyl, cycloalkylalkoxycarbonylheterocyclyl, aminocarbonylheterocyclyl, alkylaminocarbonylheterocyclyl, bisalkylaminocarbonylheterocyclyl, cycloalkylaminocarbonylheterocyclyl, arylalkylaminocarbonylheterocyclyl, alkenylaminocarbonylheterocyclyl, hydroxycarbonylheterocyclylalkyl, alkoxycarbonylheterocyclylalkyl, hydroxycarbonylcycloalkylalkyl, alkoxycarbonylcycloalkylalkyl, hydroxy, or alkoxy, and $R^{10}$ represents hydrogen, alkyl, cycloalkyl, halogen, alkylalkenyl, halogenalkyl, alkynyl, alkenyl, cyanoalkyl, arylalkyl, heteroarylalkyl, alkylcarbonyl, alkoxycarbonyl, alkylsulfonyl, arylsulfonyl, cycloalkylsulfonyl, alkylsulfinyl, arylsulfinyl, cycloalkylsulfinyl, or alkoxycarbonylalkyl, or $R^9$ and $R^{10}$ together with the nitrogen to which they are attached form an optionally halogen-, alkyl-, haloalkyl-, alkoxy-, alkoxycarbonyl-, cycloalkoxycarbonyl-, cycloalkylalkoxycarbonyl-, alkenyloxycarbonyl-, hydroxycarbonyl-, aminocarbonyl-, alkylaminocarbonyl-, cycloalkylaminocarbonyl-, or arylalkylaminocarbonyl-substituted three- to eight-membered ring which is optionally interrupted by O, S or N, or $R^9$ and $R^{10}$ together are part of an optionally substituted sulfilimine or amidine group or form an iminophosphorane.

2. The substituted 5-(cyclohex-2-en-1-yl)penta-2,4-diene and/or 5-(cyclohex-2-en-1-yl)pent-2-en-4-yne of formula (I) as claimed in claim 1, and/or a salt thereof in which

[X—Y] represents the moieties

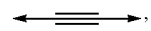

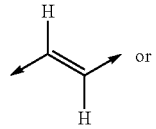

-continued

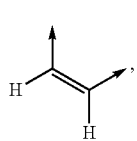

Q represents the moieties Q-1 to Q-4

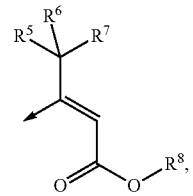

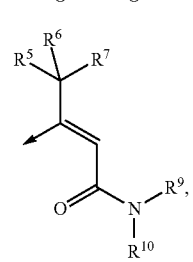

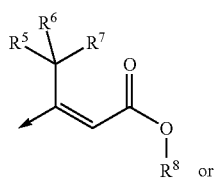

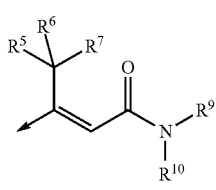

where $R^5$, $R^6$, $R^7$, $R^8$, $R^9$ and $R^{10}$ are each as defined below and where the arrow represents a bond to the respective [X—Y] grouping;

$R^1$ represents $(C_1$-$C_8)$-alkyl, $(C_2$-$C_8)$-alkenyl, $(C_2$-$C_8)$-alkynyl, $(C_2$-$C_8)$-alkenyl-$(C_1$-$C_8)$-alkyl, $(C_2$-$C_8)$-alkynyl-$(C_1$-$C_8)$-alkyl, $(C_1$-$C_8)$-alkoxy-$(C_1$-$C_8)$-alkyl, hydroxy-$(C_1$-$C_8)$-alkyl, $(C_1$-$C_8)$-haloalkyl, $(C_2$-$C_8)$-haloalkenyl, $(C_2$-$C_8)$-haloalkynyl, $(C_1$-$C_8)$-haloalkoxy-$(C_1$-$C_8)$-alkyl, $(C_3$-$C_8)$-cycloalkyl, $(C_1$-$C_8)$-alkoxy-$(C_1$-$C_8)$-haloalkyl, $(C_1$-$C_8)$-haloalkoxy-$(C_1$-$C_8)$-haloalkyl, or $(C_1$-$C_8)$-alkylthio-$(C_1$-$C_8)$-alkyl, $R^2$ represents hydrogen, $(C_1$-$C_8)$-alkyl, $(C_2$-$C_8)$-alkenyl, $(C_2$-$C_8)$-alkenyl-$(C_1$-$C_8)$-alkyl, $(C_1$-$C_8)$-alkoxy-$(C_1$-$C_8)$-alkyl, $(C_1$-$C_8)$-alkylcarbonyl, arylcarbonyl, heteroarylcarbonyl, $(C_3$-$C_8)$-cycloalkylcarbonyl, $(C_1$-$C_8)$-alkoxycarbonyl, $(C_2$-$C_8)$-alkenyloxycarbonyl, aryl-$(C_1$-$C_8)$-alkoxycarbonyl, aryl-$(C_1$-$C_8)$-alkoxy-$(C_1$-$C_8)$-alkyl, aryloxy-$(C_1$-$C_8)$-alkyl, aryl-$(C_1$-$C_8)$-alkyl, $(C_1$-$C_8)$-alkoxy-$(C_1$-$C_8)$-alkoxy-$(C_1$-$C_8)$-alkyl, $(C_1$-$C_8)$-alkylthio-$(C_1$-$C_8)$-alkyl, tri-$(C_1$-$C_8)$-alkylsilyl, $(C_1$-$C_8)$-alkyl-(bis-$(C_1$-$C_8)$-alkyl)silyl, $(C_1$-$C_8)$-alkyl(bisaryl)silyl, aryl(bis-$(C_1$-$C_8)$-alkyl)silyl, $(C_3$-$C_8)$-cycloalkyl-(bis-$(C_1$-$C_6)$-alkyl)silyl, halo(bis-$(C_1$-$C_8)$-alkyl)silyl, tri-$(C_1$-$C_8)$-alkylsilyl-$(C_1$-$C_8)$-alkoxy-$(C_1$-$C_8)$-alkyl, or tri-$(C_1$-$C_8)$-alkylsilyl-$(C_1$-$C_8)$-alkyl, $R^3$ and $R^4$ independently of one another represent $(C_1$-$C_8)$-alkoxy, $(C_1$-$C_8)$-alkoxy-$(C_1$-$C_8)$-alkoxy, $(C_3$-$C_8)$-cycloalkyl-$(C_1$-$C_8)$-alkoxy, $(C_1$-$C_8)$-haloalkoxy, $(C_1$-$C_8)$-alkylthio, $(C_1$-$C_8)$-haloalkylthio, aryl-$(C_1$-$C_8)$-alkoxy, aryl-$(C_1$-$C_8)$-alkylthio or $R^3$ and $R^4$ together with the atom to which they are attached form an oxo group, hydroxyimino group, $(C_1$-$C_8)$-alkoxyimino group, $(C_3$-$C_8)$-cycloalkoxyimino group, $(C_3$-$C_8)$-cycloalkyl-$(C_1$-$C_8)$-alkoximino group, aryl-$(C_1$-$C_8)$-alkoxyimino group or a 5- to 7-membered heterocyclic ring which is optionally substituted further, $R^5$ and $R^6$ independently of one another represent hydrogen, halogen, $(C_1$-$C_8)$-alkyl, or $(C_1$-$C_8)$-haloalkyl, $R^7$ represents halogen, $(C_1$-$C_8)$-alkyl, $(C_1$-$C_8)$-haloalkyl, $(C_1$-$C_8)$-haloalkoxy, $(C_1$-$C_8)$-haloalkoxy-$(C_1$-$C_8)$-alkyl, $(C_1$-$C_8)$-haloalkoxy-$(C_1$-$C_8)$-haloalkyl, $(C_1$-$C_8)$-alkoxy-$(C_1$-$C_8)$-haloalkyl, $(C_1$-$C_8)$-alkynyloxy-$(C_1$-$C_8)$-haloalkyl, $(C_1$-$C_8)$-alkenyloxy-$(C_1$-$C_8)$-haloalkyl, $(C_1$-$C_8)$-alkylthio, $(C_1$-$C_8)$-haloalkylthio, optionally substituted phenyl, aryl-$(C_1$-$C_8)$-alkyl, heteroaryl, or heteroaryl-$(C_1$-$C_8)$-alkyl, or $R^6$ and $R^7$ together with the atoms to which they are bonded form a fully saturated 3- to 6-membered ring optionally interrupted by heteroatoms and optionally with further substitution, $R^8$ represents hydrogen, $(C_1$-$C_8)$-alkyl, $(C_1$-$C_8)$-alkoxy-$(C_1$-$C_8)$-alkyl, $(C_3$-$C_8)$-cycloalkyl, $(C_3$-$C_8)$-cycloalkyl-$(C_1$-$C_8)$-alkyl, optionally substituted phenyl, aryl-$(C_1$-$C_8)$-alkyl, heteroaryl-$(C_1$-$C_8)$-alkyl, bisaryl-$(C_1$-$C_8)$-alkyl, trisaryl-$(C_1$-$C_8)$-alkyl, $(C_2$-$C_8)$-alkenyl, $(C_2$-$C_8)$-alkenyl-$(C_1$-$C_8)$-alkyl, $(C_4$-$C_8)$-cycloalkenyl-$(C_1$-$C_8)$-alkyl, $(C_2$-$C_8)$-alkynyl-$(C_1$-$C_8)$-alkyl, tri-$(C_1$-$C_8)$-alkylsilyl-$(C_1$-$C_8)$-alkoxy-$(C_1$-$C_8)$-alkyl, $(C_1$-$C_8)$-alkoxy-$(C_1$-$C_8)$-alkoxy-$(C_1$-$C_8)$-alkyl, $(C_1$-$C_8)$-alkylthio-$(C_1$-$C_8)$-alkyl, $(C_1$-$C_8)$-haloalkyl, arylsulfonyl-$(C_1$-$C_8)$-alkyl, tri-$(C_1$-$C_8)$-alkylsilyl, $(C_1$-$C_8)$-alkyl-(bisaryl)silyl, $(C_1$-$C_8)$-alkyl-(bis-$(C_1$-$C_8)$-alkyl)silyl, or bis-$(C_1$-$C_8)$-alkylamino-$(C_1$-$C_8)$-alkyl, $R^9$ represents hydrogen, $(C_1$-$C_8)$-alkyl, $(C_3$-$C_8)$-cycloalkyl, halogen, $(C_2$-$C_8)$-alkenyl-$(C_1$-$C_8)$-alkyl, $(C_2$-$C_8)$-alkynyl-$(C_1$-$C_8)$-alkyl, $(C_1$-$C_8)$-haloalkyl, $(C_2$-$C_8)$-alkynyl, $(C_2$-$C_8)$-alkenyl, cyano-$(C_1$-$C_8)$-alkyl, $(C_3$-$C_8)$-cycloalkyl-$(C_1$-$C_8)$-alkyl, aryl-$(C_1$-$C_8)$-alkyl, heteroaryl-$(C_1$-$C_8)$-alkyl, $(C_1$-$C_8)$-alkylcarbonyl, $(C_1$-$C_8)$-alkoxycarbonyl, $(C_2$-$C_8)$-alkenyloxycarbonyl, $(C_2$-$C_8)$-alkenyl-$(C_1$-$C_8)$-alkyloxycarbonyl, aryl-$(C_1$-$C_8)$-alkyloxycarbonyl, $(C_3$-$C_8)$-cycloalkoxycarbonyl, $(C_3$-$C_8)$-cycloalkyl-$(C_1$-$C_8)$-alkoxycarbonyl, $(C_1$-$C_8)$-alkylsulfonyl, arylsulfonyl, $(C_3$-$C_8)$-cycloalkylsulfonyl, $(C_1$-$C_8$-alkylsulfinyl, arylsulfinyl, $(C_3$-$C_8)$-cycloalkylsulfinyl, $(C_1$-$C_8)$-alkoxycarbonyl-$(C_1$-$C_8)$-alkyl, hydroxycarbonyl-$(C_1$-$C_8)$-alkyl, aryl-$(C_1$-$C_8)$-alkoxycarbonyl-$(C_1$-$C_8)$-alkyl, $(C_3$-$C_8)$-cycloalkyl-$(C_1$-$C_8)$-alkoxycarbonyl-$(C_1$-$C_8)$-alkyl, $(C_1$-$C_8)$-alkoxycarbonyl-$(C_3$-$C_8)$-cycloalkyl, hydroxycarbonyl-$(C_3$-$C_8)$-cycloalkyl, aryl-$(C_1$-$C_8)$-alkoxycarbonyl-$(C_3$-$C_8)$-cycloalkyl, $(C_2$-$C_8)$-alkenyloxycarbonyl-$(C_3$-$C_8)$-cycloalkyl, aminocarbonyl-$(C_3$-$C_8)$-cycloalkyl, $(C_1$-$C_8)$-alkylaminocarbonyl-$(C_3$-$C_8)$-cycloalkyl, $(C_3$-$C_8)$-cycloalkylaminocarbonyl-$(C_3$-$C_8)$-cycloalkyl, $(C_1$-$C_8)$-alkoxycarbonyl-$(C_4$-$C_8)$-cycloalkenyl, hydroxycarbonyl-($C_4$-$C_8$)-cycloalkenyl, bis-($C_1$-$C_8$)-alkylamino-($C_1$-$C_8$)-alkyl, hydroxycarbonylheterocyclyl, ($C_1$-$C_8$)-alkoxycarbonylheterocyclyl, ($C_2$-$C_8$)-alkenyloxycarbonylheterocyclyl, ($C_2$-$C_8$)-alkenyl-($C_1$-$C_8$)-alkoxycarbonylheterocyclyl, aryl-($C_1$-$C_8$)-alkoxycarbonylheterocyclyl, ($C_3$-$C_8$)-cycloalkoxycarbonylheterocyclyl, ($C_3$-$C_8$)-cycloalkyl-($C_1$-$C_8$)-alkoxycarbonylheterocyclyl, aminocarbonylheterocyclyl, ($C_1$-$C_8$)-alkylaminocarbonylheterocyclyl, bis-($C_1$-$C_8$)-alkylaminocarbonylheterocyclyl, ($C_3$-$C_8$)-cycloalkylaminocarbonylheterocyclyl, aryl-($C_1$-$C_8$)-alkylaminocarbonylheterocyclyl, ($C_2$-$C_8$)-alkenylaminocarbonylheterocyclyl, hydroxycarbonylheterocyclyl-($C_1$-$C_8$)-alkyl, ($C_1$-$C_8$)-alkoxycarbonylheterocyclyl-($C_1$-$C_8$)-alkyl, hydroxycarbonyl-($C_3$-$C_8$)-cycloalkyl-($C_1$-$C_8$)-alkyl, ($C_1$-$C_8$)-alkoxycarbonyl-($C_3$-$C_8$)-cycloalkyl-($C_1$-$C_8$)-alkyl, hydroxy, or ($C_1$-$C_8$)-alkoxy, and $R^{10}$ represents hydrogen, ($C_1$-$C_8$)-alkyl, ($C_3$-$C_8$)-cycloalkyl, halogen, ($C_1$-$C_8$)-alkyl-($C_1$-$C_8$)-alkenyl, ($C_1$-$C_8$)-haloalkyl, ($C_2$-$C_8$)-alkynyl, ($C_2$-$C_8$)-alkenyl, cyano-($C_1$-$C_8$)-alkyl, aryl-($C_1$-$C_8$)-alkyl, heteroaryl-($C_1$-$C_8$)-alkyl, ($C_1$-$C_8$)-alkylcarbonyl, ($C_1$-$C_8$)-alkoxycarbonyl, ($C_1$-$C_8$)-alkylsulfonyl, arylsulfonyl, ($C_3$-$C_8$)-cycloalkylsulfonyl, ($C_1$-$C_8$)-alkylsulfinyl, arylsulfinyl, ($C_3$-$C_8$)-cycloalkylsulfinyl, or ($C_1$-$C_8$)-alkoxycarbonyl-($C_1$-$C_8$)-alkyl, or $R^9$ and $R^{10}$ together with the nitrogen to which they are attached form an optionally halogen-, ($C_1$-$C_8$)-alkyl-, ($C_1$-$C_8$)-haloalkyl-, ($C_1$-$C_8$)-alkoxy-, ($C_1$-$C_8$)-alkoxycarbonyl-, ($C_3$-$C_8$)-cycloalkoxycarbonyl-, ($C_3$-$C_8$)-cycloalkyl-($C_1$-$C_8$)-alkoxycarbonyl-, ($C_2$-$C_8$)-alkenyloxycarbonyl-, hydroxycarbonyl-, aminocarbonyl-, ($C_1$-$C_8$)-alkylaminocarbonyl-, ($C_3$-$C_8$)-cycloalkylaminocarbonyl-, or aryl-($C_1$-$C_8$)-alkylaminocarbonyl-substituted three- to eight-membered ring which is optionally interrupted by O, S or N, or $R^9$ and $R^{10}$ together form an N-(bis-($C_1$-$C_6$)-alkyl)sulfanylidene, N-(aryl-($C_1$-$C_6$)-alkyl)-sulfanylidene, N-(bis-($C_3$-$C_7$)-cycloalkyl)sulfanylidene, N—(($C_1$-$C_6$)-alkyl-($C_3$-$C_7$)-cycloalkyl)sulfanylidene group or an N,N-di-($C_1$-$C_6$)-alkylformylidene group.

3. The substituted 5-(cyclohex-2-en-1-yl)penta-2,4-diene and/or 5-(cyclohex-2-en-1-yl)pent-2-en-4-yne of formula (I) as claimed in claim 1, and/or a salt thereof in which

[X—Y] represents the moieties

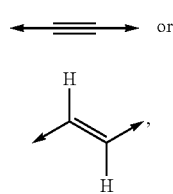

Q represents the moieties Q-1 to Q-3

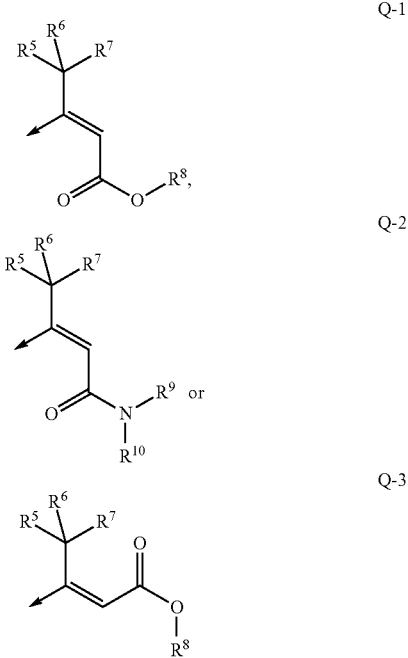

where $R^5$, $R^6$, $R^7$, $R^8$, $R^9$ and $R^{10}$ are each as defined below and where the arrow represents a bond to the respective [X—Y] grouping;

$R^1$ represents ($C_1$-$C_6$)-alkyl, ($C_2$-$C_6$)-alkenyl, ($C_2$-$C_6$)-alkynyl, ($C_2$-$C_6$)-alkenyl-($C_1$-$C_6$)-alkyl, ($C_2$-$C_6$)-alkynyl-($C_1$-$C_6$)-alkyl, ($C_1$-$C_6$)-alkoxy-($C_1$-$C_6$)-alkyl, hydroxy-($C_1$-$C_6$)-alkyl, ($C_1$-$C_6$)-haloalkyl, ($C_2$-$C_6$)-haloalkenyl, ($C_2$-$C_6$)-haloalkynyl, ($C_1$-$C_6$)-haloalkoxy-($C_1$-$C_6$)-alkyl, ($C_3$-$C_7$)-cycloalkyl, ($C_1$-$C_6$)-alkoxy-($C_1$-$C_6$)-haloalkyl, ($C_1$-$C_6$)-haloalkoxy-($C_1$-$C_6$)-haloalkyl, or ($C_1$-$C_6$)-alkylthio-($C_1$-$C_6$)-alkyl, $R^2$ represents hydrogen, tri-($C_1$-$C_6$)-alkylsilyl, ($C_1$-$C_6$)-alkyl-(bis-($C_1$-$C_6$)-alkyl)silyl, ($C_1$-$C_6$)-alkyl(bisaryl)silyl, aryl(bis-($C_1$-$C_6$)-alkyl)silyl, ($C_3$-$C_7$)-cycloalkyl(bis-($C_1$-$C_6$)-alkyl)silyl, halo(bis-($C_1$-$C_6$)-alkyl)silyl, tri-($C_1$-$C_6$)-alkylsilyl-($C_1$-$C_6$)-alkoxy-($C_1$-$C_6$)-alkyl, or tri-($C_1$-$C_6$)-alkylsilyl-($C_1$-$C_6$)-alkyl, $R^3$ and $R^4$ independently of one another represent ($C_1$-$C_6$)-alkoxy, ($C_1$-$C_6$)-alkylthio or $R^3$ and $R^4$ together with the atom to which they are attached form an oxo group, hydroxyimino group, ($C_1$-$C_6$)-alkoxyimino group, ($C_3$-$C_6$)-cycloalkoxyimino group, ($C_3$-$C_6$)-cycloalkyl-($C_1$-$C_6$)-alkoximino group, aryl-($C_1$-$C_6$)-alkoxyimino group or a 5- to 7-membered heterocyclic ring which is optionally substituted further, $R^5$ and $R^6$ independently of one another represent hydrogen, halogen, ($C_1$-$C_8$)-alkyl, or ($C_1$-$C_6$)-haloalkyl, $R^7$ represents halogen, ($C_1$-$C_8$)-alkyl, ($C_1$-$C_8$)-haloalkyl, ($C_1$-$C_8$)-haloalkoxy, ($C_1$-$C_8$)-haloalkoxy-($C_1$-$C_8$)-alkyl, ($C_1$-$C_8$)-haloalkoxy-($C_1$-$C_8$)-haloalkyl, ($C_1$-$C_8$)-alkoxy-($C_1$-$C_8$)-haloalkyl, ($C_1$-$C_8$)-alkynyloxy-($C_1$-$C_8$)-haloalkyl, ($C_1$-$C_8$)-alkenyloxy-($C_1$-$C_8$)-haloalkyl, ($C_1$-$C_6$)-alkylthio, ($C_1$-$C_6$)-haloalkylthio, optionally substituted phenyl, aryl-($C_1$-$C_6$)-alkyl, heteroaryl, or heteroaryl-($C_1$-$C_6$)-alkyl, or $R^6$ and $R^7$ together with the atoms to which they are bonded form a fully saturated 3- to 6-membered ring optionally interrupted by heteroatoms and optionally with further substitution, R⁸ represents hydrogen, $(C_1-C_6)$-alkyl, $(C_1-C_6)$-alkoxy-$(C_1-C_6)$-alkyl, $(C_3-C_7)$-cycloalkyl, $(C_3-C_7)$-cycloalkyl-$(C_1-C_6)$-alkyl, optionally substituted phenyl, aryl-$(C_1-C_6)$-alkyl, heteroaryl-$(C_1-C_6)$-alkyl, bisaryl-$(C_1-C_6)$-alkyl, trisaryl-$(C_1-C_6)$-alkyl, $(C_2-C_6)$-alkenyl, $(C_2-C_6)$-alkenyl-$(C_1-C_6)$-alkyl, $(C_4-C_7)$-cycloalkenyl-$(C_1-C_6)$-alkyl, $(C_2-C_6)$-alkynyl-$(C_1-C_6)$-alkyl, tri-$(C_1-C_6)$-alkylsilyl-$(C_1-C_6)$-alkoxy-$(C_1-C_6)$-alkyl, $(C_1-C_6)$-alkoxy-$(C_1-C_6)$-alkoxy-$(C_1-C_6)$-alkyl, $(C_1-C_6)$-alkylthio-$(C_1-C_6)$-alkyl, $(C_1-C_6)$-haloalkyl, arylsulfonyl-$(C_1-C_6)$-alkyl, tri-$(C_1-C_6)$-alkylsilyl, $(C_1-C_6)$-alkyl-(bisaryl)silyl, $(C_1-C_6)$-alkyl-(bis-$(C_1-C_6)$-alkyl)silyl, or bis-$(C_1-C_6)$-alkylamino-$(C_1-C_6)$-alkyl, R⁹ represents hydrogen, $(C_1-C_6)$-alkyl, $(C_3-C_7)$-cycloalkyl, halogen, $(C_2-C_6)$-alkenyl-$(C_1-C_6)$-alkyl, $(C_2-C_6)$-alkynyl-$(C_1-C_6)$-alkyl, $(C_1-C_6)$-haloalkyl, $(C_2-C_6)$-alkynyl, $(C_2-C_6)$-alkenyl, cyano-$(C_1-C_6)$-alkyl, $(C_3-C_7)$-cycloalkyl-$(C_1-C_6)$-alkyl, aryl-$(C_1-C_6)$-alkyl, heteroaryl-$(C_1-C_6)$-alkyl, $(C_1-C_6)$-alkylcarbonyl, $(C_1-C_6)$-alkoxycarbonyl, $(C_2-C_6)$-alkenyloxycarbonyl, $(C_2-C_6)$-alkenyl-$(C_1-C_6)$-alkyloxycarbonyl, aryl-$(C_1-C_6)$-alkyloxycarbonyl, $(C_3-C_7)$-cycloalkoxycarbonyl, $(C_3-C_6)$-cycloalkyl-$(C_1-C_6)$-alkoxycarbonyl, $(C_1-C_6)$-alkylsulfonyl, arylsulfonyl, $(C_3-C_7)$-cycloalkylsulfonyl, $(C_1-C_6)$-alkylsulfinyl, arylsulfinyl, $(C_3-C_7)$-cycloalkylsulfinyl, $(C_1-C_6)$-alkoxycarbonyl-$(C_1-C_6)$-alkyl, hydroxycarbonyl-$(C_1-C_6)$-alkyl, aryl-$(C_1-C_6)$-alkoxycarbonyl-$(C_1-C_6)$-alkyl, $(C_3-C_7)$-cycloalkyl-$(C_1-C_6)$-alkoxycarbonyl-$(C_1-C_6)$-alkyl, $(C_1-C_6)$-alkoxycarbonyl-$(C_3-C_6)$-cycloalkyl, hydroxycarbonyl-$(C_3-C_6)$-cycloalkyl, aryl-$(C_1-C_6)$-alkoxycarbonyl-$(C_1-C_6)$-cycloalkyl, $(C_2-C_6)$-alkenyloxycarbonyl-$(C_3-C_6)$-cycloalkyl, aminocarbonyl-$(C_3-C_7)$-cycloalkyl, $(C_1-C_6)$-alkylaminocarbonyl-$(C_3-C_7)$-cycloalkyl, $(C_3-C_7)$-cycloalkylaminocarbonyl-$(C_3-C_7)$-cycloalkyl, $(C_1-C_6)$-alkoxycarbonyl-$(C_4-C_7)$-cycloalkenyl, hydroxycarbonyl-$(C_4-C_7)$-cycloalkenyl, bis-$(C_1-C_6)$-alkylamino-$(C_1-C_6)$-alkyl, hydroxycarbonylheterocyclyl, $(C_1-C_6)$-alkoxycarbonylheterocyclyl, $(C_2-C_6)$-alkenyloxycarbonylheterocyclyl, $(C_2-C_6)$-alkenyl-$(C_1-C_6)$-alkoxycarbonylheterocyclyl, aryl-$(C_1-C_6)$-alkoxycarbonylheterocyclyl, $(C_3-C_7)$-cycloalkoxycarbonylheterocyclyl, $(C_3-C_7)$-cycloalkyl-$(C_1-C_6)$-alkoxycarbonylheterocyclyl, aminocarbonylheterocyclyl, $(C_1-C_6)$-alkylaminocarbonylheterocyclyl, bis-$(C_1-C_6)$-alkylaminocarbonylheterocyclyl, $(C_3-C_7)$-cycloalkylaminocarbonylheterocyclyl, aryl-$(C_1-C_6)$-alkylaminocarbonylheterocyclyl, $(C_2-C_6)$-alkenylaminocarbonylheterocyclyl, hydroxycarbonylheterocyclyl-$(C_1-C_6)$-alkyl, $(C_1-C_6)$-alkoxycarbonylheterocyclyl-$(C_1-C_6)$-alkyl, hydroxycarbonyl-$(C_3-C_7)$-cycloalkyl-$(C_1-C_6)$-alkyl, $(C_1-C_6)$-alkoxycarbonyl-$(C_3-C_7)$-cycloalkyl-$(C_1-C_6)$-alkyl, hydroxy, or $(C_1-C_6)$-alkoxy, and R¹⁰ represents hydrogen, $(C_1-C_6)$-alkyl, $(C_3-C_7)$-cycloalkyl, $(C_1-C_6)$-alkyl-$(C_1-C_6)$-alkenyl, $(C_1-C_6)$-haloalkyl, $(C_2-C_6)$-alkynyl, $(C_2-C_6)$-alkenyl, cyano-$(C_1-C_6)$-alkyl, aryl-$(C_1-C_6)$-alkyl, heteroaryl-$(C_1-C_6)$-alkyl, $(C_1-C_6)$-alkylcarbonyl, $(C_1-C_6)$-alkoxycarbonyl, $(C_1-C_6)$-alkylsulfonyl, arylsulfonyl, $(C_3-C_7)$-cycloalkylsulfonyl, $(C_1-C_6)$-alkylsulfinyl, arylsulfinyl, $(C_3-C_7)$-cycloalkylsulfinyl, or $(C_1-C_6)$-alkoxycarbonyl-$(C_1-C_6)$-alkyl, or R⁹ and R¹⁰ together with the nitrogen to which they are attached form an optionally fluorine-, chlorine-, bromine-, iodine-, $(C_1-C_6)$-alkyl-, $(C_1-C_6)$-haloalkyl-, $(C_1-C_6)$-alkoxy-, $(C_1-C_6)$-alkoxycarbonyl-, $(C_3-C_7)$-cycloalkoxycarbonyl-, $(C_3-C_7)$-cycloalkyl-$(C_1-C_6)$-alkoxycarbonyl-, $(C_2-C_6)$-alkenyloxycarbonyl-, hydroxycarbonyl-, aminocarbonyl-, $(C_1-C_6)$-alkylaminocarbonyl-, $(C_3-C_7)$-cycloalkylaminocarbonyl-, or aryl-$(C_1-C_6)$-alkylaminocarbonyl-substituted three- to eight-membered ring which is optionally interrupted by O, S or N, or R⁹ and R¹⁰ together form an N-(bis-$(C_1-C_6)$-alkyl)sulfanylidene, N-(aryl-$(C_1-C_6)$-alkyl)-sulfanylidene, N-(bis-$(C_3-C_7)$-cycloalkyl)sulfanylidene, N—(($C_1-C_6$)-alkyl-$(C_3-C_7)$-cycloalkyl)sulfanylidene group or an N,N-di-$(C_1-C_6)$-alkylformylidene group.

4. A compound of formula (I) and/or a salt thereof as claimed in claim 1 capable of being used for increasing tolerance to abiotic stress in a plant.

5. A compound of formula (I) and/or a salt thereof as claimed in claim 1 capable of being used in spray application to a plant and/or a plant part in combination with at least one active ingredient selected from the group consisting of insecticides, attractants, acaricides, fungicides, nematicides, herbicides, growth regulators, safeners, substances which influence plant maturity and bactericides.

6. The compound of formula (I) and/or a salt thereof as claimed in claim 1 capable of being used in spray application to a plant and/or a plant part in combination with a fertilizer.

7. The compound of formula (I) and/or a salt thereof as claimed in claim 1 capable of being used for application to a genetically modified cultivar, a seed thereof, and/or to a cultivated area on which a cultivar grows.

8. A spray solution for treating a plant, comprising an amount, effective for enhancing resistance of a plant to one or more abiotic stress factors, of at least one compound of formula (I) as claimed in claim 1 and/or a salt thereof.

9. A spray solution comprising at least one compound of formula (I) as claimed in claim 1 and/or a salt thereof capable of being used for enhancing resistance of a plan to one or more abiotic stress factors.

10. A compound of formula (II)

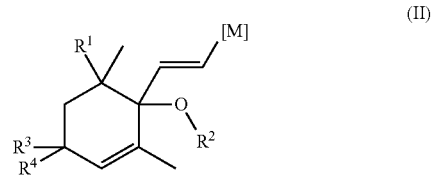

(II)

where

R¹ represents $(C_1-C_8)$-alkyl, $(C_2-C_8)$-alkenyl, $(C_2-C_8)$-alkynyl, $(C_2-C_8)$-alkenyl-$(C_1-C_8)$-alkyl, $(C_2-C_8)$-alkynyl-$(C_1-C_8)$-alkyl, $(C_1-C_8)$-alkoxy-$(C_1-C_8)$-alkyl, hydroxy-$(C_1-C_8)$-alkyl, $(C_1-C_8)$-haloalkyl, $(C_2-C_8)$-haloalkenyl, $(C_2-C_8)$-haloalkynyl, $(C_1-C_8)$-haloalkoxy-$(C_1-C_8)$-alkyl, $(C_3-C_8)$-cycloalkyl, $(C_1-C_8)$-alkoxy-$(C_1-C_8)$-haloalkyl, $(C_1-C_8)$-haloalkoxy-$(C_1-C_8)$-haloalkyl, or $(C_1-C_8)$-alkylthio-$(C_1-C_8)$-alkyl, R² represents hydrogen, $(C_1-C_8)$-alkyl, $(C_2-C_8)$-alkenyl, $(C_2-C_8)$-alkenyl-$(C_1-C_8)$-alkyl, $(C_1-C_8)$-alkoxy-$(C_1-C_8)$-alkyl, $(C_1-C_8)$-alkylcarbonyl, arylcarbonyl, heteroarylcarbonyl, $(C_3-C_8)$-cycloalkylcarbonyl, $(C_1-C_8)$-alkoxycarbonyl, $(C_2-C_8)$-alkenyloxycarbonyl, aryl-$(C_1-C_8)$-alkoxycarbonyl, aryl-$(C_1-C_8)$-alkoxy-$(C_1-C_8)$-alkyl, aryloxy-$(C_1-C_8)$-alkyl, aryl-$(C_1-C_8)$-alkyl, $(C_1-C_8)$-alkoxy-$(C_1-C_8)$-alkoxy-$(C_1-C_8)$-alkyl, $(C_1-C_8)$- alkylthio-($C_1$-$C_8$)-alkyl, tri-($C_1$-$C_8$)-alkylsilyl, ($C_1$-$C_8$)-alkyl-(bis-($C_1$-$C_8$)-alkyl)silyl, ($C_1$-$C_8$)-alkyl(bisaryl)silyl, aryl(bis-($C_1$-$C_8$)-alkyl)silyl, ($C_3$-$C_8$)-cycloalkyl-(bis-($C_1$-$C_6$)-alkyl)silyl, halo(bis-($C_1$-$C_8$)-alkyl)silyl, tri-($C_1$-$C_8$)-alkylsilyl-($C_1$-$C_8$)-alkoxy-($C_1$-$C_8$)-alkyl, or tri-($C_1$-$C_8$)-alkylsilyl-($C_1$-$C_8$)-alkyl, $R^3$ and $R^4$ independently of one another represent ($C_1$-$C_8$)-alkoxy, ($C_1$-$C_8$)-alkoxy-($C_1$-$C_8$)-alkoxy, ($C_3$-$C_8$)-cycloalkyl-($C_1$-$C_8$)-alkoxy, ($C_1$-$C_8$)-haloalkoxy, ($C_1$-$C_8$)-alkylthio, ($C_1$-$C_8$)-haloalkylthio, aryl-($C_1$-$C_8$)-alkoxy, aryl-($C_1$-$C_8$)-alkylthio or together with the atom to which they are attached form an oxo group or a 1,3-dioxolanyl, 1,3-dioxanyl, 1,3-dithiolanyl, 1,3-dithianyl, 1,3-oxathianyl, 5-alkyl-1,3,5-dithiazinyl, or 1,3-oxazolidinyl ring, which is optionally substituted further by ($C_1$-$C_6$)-alkyl, ($C_1$-$C_6$)-alkoxycarbonyl, ($C_3$-$C_6$)-cycloalkyl, spiro-($C_3$-$C_6$)-cycloalkyl, or spiro-oxetanyl and

[M] represents tris-[($C_1$-$C_6$)-alkyl]stannyl, tris-[($C_3$-$C_8$)-cycloalkyl]stannyl, tris-[($C_1$-$C_6$)-alkyl]germanyl, tris-[($C_3$-$C_8$)-cycloalkyl]germanyl, bis-(cyclopentadienyl)zirconyl, bis-(1,2,3,4,5-pentamethylcyclopentadienyl)zirconyl, bis-(cyclopentadienyl)hafnyl, bis-(1,2,3,4,5-pentamethylcyclopentadienyl)hafnyl, bis-(hydroxy)boryl, bis-[($C_1$-$C_6$)-alkoxy]-boryl, ($C_1$-$C_6$)-alkyl-1,3,2-dioxaborolan-2-yl, bis-[($C_1$-$C_6$)-alkyl]-1,3,2-dioxaborolan-2-yl, tetrakis-[($C_1$-$C_6$)-alkyl]-1,3,2-dioxaborolan-2-yl, 1,3,2-dioxaborinan-2-yl, bis-[($C_1$-$C_6$)-alkyl]-1,3,2-dioxaborinan-2-yl, ($C_1$-$C_6$)-alkyl-1,3,2-dioxaborinan-2-yl, tris-[($C_1$-$C_6$)-alkyl]-1,3,2-dioxaborinan-2-yl, 2,6,7-trioxa-1-boranuidabicyclo[2.2.2]-octanyl, ($C_1$-$C_6$)-alkyl-2,6,7-trioxa-1-boranuidabicyclo[2.2.2]octanyl, tris-[($C_1$-$C_6$)-alkyl]plumbanyl, tris-[($C_1$-$C_6$)-alkylcarbonyloxy]plumbanyl, tris-aryl-plumbanyl, bis-[($C_1$-$C_6$)-alkylcarbonyloxy]-arylplumbanyl, bis-[($C_1$-$C_6$)-alkyl]-alanyl, bis-[($C_1$-$C_6$)-cycloalkyl]-alanyl, dichloroalanyl, chloromagnesyl, bromomagnesyl, chlorozincyl, chlorohydrargyl, bromohydrargyl, ($C_1$-$C_6$)-alkylhydrargyl, ($C_3$-$C_6$)-cycloalkylhydrargyl, tris-[($C_1$-$C_6$)-alkyl]silyl, ($C_1$-$C_6$)-alkyl-[bis-($C_1$-$C_6$)-alkyl]silyl, ($C_1$-$C_6$)-alkyl-bis-(aryl)silyl, aryl-bis-[($C_1$-$C_6$)-alkyl)]silyl, or ($C_3$-$C_7$)-cycloalkyl-bis-[($C_1$-$C_6$)-alkyl]silyl.

11. A substituted 5-(cyclohex-2-en-1-yl)penta-2,4-diene of formula (I) as claimed in claim 1, and/or a salt thereof

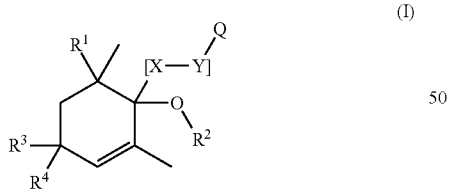

(I)

in which
[X—Y] represents the moieties

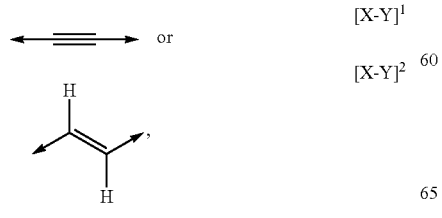

[X-Y]$^1$ or [X-Y]$^2$

Q represents the moiety

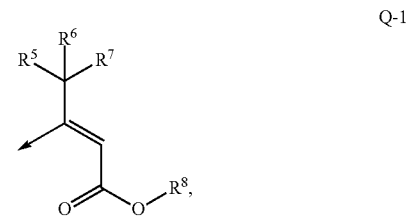

Q-1 where $R^5$, $R^6$, $R^7$, and $R^8$ are each as defined below and where the arrow represents a bond to the respective [X—Y] grouping;

$R^1$ represents ($C_1$-$C_6$)-alkyl, ($C_2$-$C_6$)-alkenyl, ($C_2$-$C_6$)-alkynyl, ($C_2$-$C_6$)-alkenyl-($C_1$-$C_6$)-alkyl, ($C_2$-$C_6$)-alkynyl-($C_1$-$C_6$)-alkyl, ($C_1$-$C_6$)-alkoxy-($C_1$-$C_6$)-alkyl, hydroxy-($C_1$-$C_6$)-alkyl, ($C_1$-$C_6$)-haloalkyl, ($C_2$-$C_6$)-haloalkenyl, ($C_2$-$C_6$)-haloalkynyl, ($C_1$-$C_6$)-haloalkoxy-($C_1$-$C_6$)-alkyl, ($C_3$-$C_7$)-cycloalkyl, ($C_1$-$C_6$)-alkoxy-($C_1$-$C_6$)-haloalkyl, ($C_1$-$C_6$)-haloalkoxy-($C_1$-$C_6$)-haloalkyl, or ($C_1$-$C_6$)-alkylthio-($C_1$-$C_6$)-alkyl, $R^2$ represents hydrogen, tri-($C_1$-$C_6$)-alkylsilyl, ($C_1$-$C_6$)-alkyl-(bis-($C_1$-$C_6$)-alkyl)silyl, ($C_1$-$C_6$)-alkyl(bisaryl)silyl, aryl(bis-($C_1$-$C_6$)-alkyl)silyl, ($C_3$-$C_7$)-cycloalkyl(bis-($C_1$-$C_6$)-alkyl)silyl, halo(bis-($C_1$-$C_6$)-alkyl)silyl, tri-($C_1$-$C_6$)-alkylsilyl-($C_1$-$C_6$)-alkoxy-($C_1$-$C_6$)-alkyl, or tri-($C_1$-$C_6$)-alkylsilyl-($C_1$-$C_6$)-alkyl, $R^3$ and $R^4$ together with the atom to which they are attached form an oxo group, or a 5-membered heterocyclic ring which is optionally substituted further, $R^5$ and $R^6$ independently of one another represent hydrogen, halogen, ($C_1$-$C_8$)-alkyl, or ($C_1$-$C_6$)-haloalkyl, $R^7$ represents halogen, ($C_1$-$C_8$)-alkyl, ($C_1$-$C_8$)-haloalkyl, ($C_1$-$C_8$)-haloalkoxy, ($C_1$-$C_8$)-haloalkoxy-($C_1$-$C_8$)-alkyl, ($C_1$-$C_8$)-haloalkoxy-($C_1$-$C_8$)-haloalkyl, ($C_1$-$C_8$)-alkoxy-($C_1$-$C_8$)-haloalkyl, ($C_1$-$C_8$)-alkynyloxy-($C_1$-$C_8$)-haloalkyl, ($C_1$-$C_8$)-alkenyloxy-($C_1$-$C_8$)-haloalkyl, ($C_1$-$C_6$)-alkylthio, ($C_1$-$C_6$)-haloalkylthio, optionally substituted phenyl, aryl-($C_1$-$C_6$)-alkyl, heteroaryl, or heteroaryl-($C_1$-$C_6$)-alkyl, or $R^6$ and $R^7$ together with the atoms to which they are bonded form a fully saturated 3- to 6-membered, and $R^8$ represents hydrogen, ($C_1$-$C_6$)-alkyl, ($C_1$-$C_6$)-alkoxy-($C_1$-$C_6$)-alkyl, ($C_3$-$C_7$)-cycloalkyl, ($C_3$-$C_7$)-cycloalkyl-($C_1$-$C_6$)-alkyl, optionally substituted phenyl, aryl-($C_1$-$C_6$)-alkyl, heteroaryl-($C_1$-$C_6$)-alkyl, bisaryl-($C_1$-$C_6$)-alkyl, trisaryl-($C_1$-$C_6$)-alkyl, ($C_2$-$C_6$)-alkenyl, ($C_2$-$C_6$)-alkenyl-($C_1$-$C_6$)-alkyl, ($C_4$-$C_7$)-cycloalkenyl-($C_1$-$C_6$)-alkyl, ($C_2$-$C_6$)-alkynyl-($C_1$-$C_6$)-alkyl, tri-($C_1$-$C_6$)-alkylsilyl-($C_1$-$C_6$)-alkoxy-($C_1$-$C_6$)-alkyl, ($C_1$-$C_6$)-alkoxy-($C_1$-$C_6$)-alkoxy-($C_1$-$C_6$)-alkyl, ($C_1$-$C_6$)-alkylthio-($C_1$-$C_6$)-alkyl, ($C_1$-$C_6$)-haloalkyl, arylsulfonyl-($C_1$-$C_6$)-alkyl, tri-($C_1$-$C_6$)-alkylsilyl, ($C_1$-$C_6$)-alkyl-(bisaryl)silyl, ($C_1$-$C_6$)-alkyl-(bis-($C_1$-$C_6$)-alkyl)silyl, or bis-($C_1$-$C_6$)-alkylamino-($C_1$-$C_6$)-alkyl.

12. A substituted 5-(cyclohex-2-en-1-yl)penta-2,4-diene of formula (I) as claimed in claim 1, and/or a salt thereof

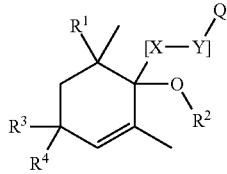
(I)

in which
[X—Y] represents the moieties

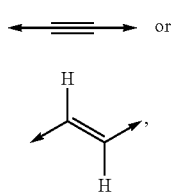 or

[X-Y]¹

[X-Y]²

Q represents the moiety

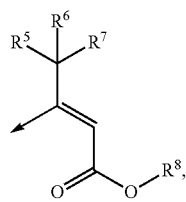
Q-1 where $R^5$, $R^6$, $R^7$, and $R^8$ are each as defined below and where the arrow represents a bond to the respective [X—Y] grouping;

$R^1$ represents $(C_1-C_6)$-alkyl, $R^2$ represents hydrogen, $R^3$ and $R^4$ together with the atom to which they are attached form an oxo group or a 5-membered heterocyclic ring which is optionally substituted further, $R^5$ and $R^6$ independently of one another represent hydrogen or halogen, $R^7$ represents halogen or $(C_1-C_8)$-alkyl, or $R^6$ and $R^7$ together with the atoms to which they are bonded form a fully saturated 3- to 6-membered ring, and $R^8$ represents hydrogen, $(C_1-C_6)$-alkyl, or $(C_1-C_6)$-haloalkyl.

13. A substituted 5-(cyclohex-2-en-1-yl)penta-2,4-diene as claimed in claim 1, and/or a salt thereof, having the formula

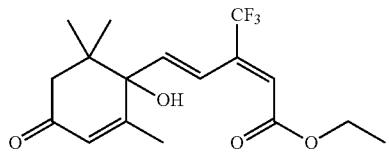

* * * * *